United States Patent
Yen et al.

(10) Patent No.: US 11,296,282 B2
(45) Date of Patent: *Apr. 5, 2022

(54) ORGANIC COMPOUND AND ORGANIC ELECTROLUMINESCENCE DEVICE USING THE SAME

(71) Applicants: Feng-Wen Yen, Taipei (TW); Wan-Shiuan Wu, Taipei (TW)

(72) Inventors: Feng-Wen Yen, Taipei (TW); Wan-Shiuan Wu, Taipei (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 117 days.

This patent is subject to a terminal disclaimer.

(21) Appl. No.: 16/592,766

(22) Filed: Oct. 4, 2019

(65) Prior Publication Data
US 2020/0203632 A1    Jun. 25, 2020

Related U.S. Application Data

(63) Continuation-in-part of application No. 16/221,626, filed on Dec. 17, 2018.

(51) Int. Cl.
| | |
|---|---|
| H01L 51/00 | (2006.01) |
| C07D 307/77 | (2006.01) |
| C07D 209/56 | (2006.01) |
| C09K 11/06 | (2006.01) |
| C09K 11/02 | (2006.01) |
| C07D 333/50 | (2006.01) |
| H01L 51/50 | (2006.01) |

(52) U.S. Cl.
CPC ........ *H01L 51/0073* (2013.01); *C07D 209/56* (2013.01); *C07D 307/77* (2013.01);
(Continued)

(58) Field of Classification Search
None
See application file for complete search history.

(56) References Cited

U.S. PATENT DOCUMENTS 9,120,748 B2    9/2015   Takashima et al.
9,172,046 B1 *  10/2015  Kim ..................... C09B 1/00
(Continued)

FOREIGN PATENT DOCUMENTS

KR    20120072784    * 12/2010   ......... H01L 51/0085
KR    101952393 B1      2/2019

OTHER PUBLICATIONS

Machine translation of KR-20120072784, translation generated Feb. 2021, 40 pages. (Year: 2021).*

*Primary Examiner* — Robert S Loewe

(57) ABSTRACT

An organic compound is described. An organic electroluminescence device comprises the organic compound, as a host of an emissive layer, as a dopant of an emissive layer, or as an electron transporting layer. The organic compound of the following formula may lower a driving voltage or increase a current efficiency or a half-life of the organic electroluminescence device.

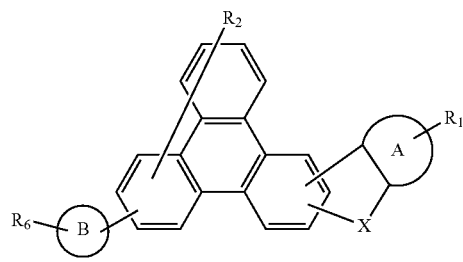

The same definition as described in the present invention.

4 Claims, 4 Drawing Sheets

(52) U.S. Cl.
CPC .......... *C07D 333/50* (2013.01); *C09K 11/025* (2013.01); *C09K 11/06* (2013.01); *H01L 51/0072* (2013.01); *H01L 51/0074* (2013.01); *C09K 2211/1018* (2013.01); *H01L 51/5012* (2013.01)

(56) References Cited

U.S. PATENT DOCUMENTS

| | | | |
|---|---|---|---|
| 2013/0048975 A1* | 2/2013 | Hong | C07D 409/10 257/40 |
| 2014/0231754 A1* | 8/2014 | Yen | C07D 333/22 257/40 |
| 2015/0255731 A1* | 9/2015 | Lee | H01L 51/0067 257/40 |
| 2016/0072073 A1* | 3/2016 | Lee | C07D 409/14 257/40 |
| 2016/0133853 A1* | 5/2016 | Cho | H01L 51/0059 257/40 |
| 2016/0141512 A1* | 5/2016 | Jung | H01L 51/0072 257/40 |
| 2019/0229275 A1* | 7/2019 | Lee | C07D 307/77 |
| 2020/0111971 A1* | 4/2020 | Yen | H01L 51/0054 |
| 2020/0190065 A1* | 6/2020 | Yen | H01L 51/0072 |
| 2020/0235306 A1* | 7/2020 | Yen | C07D 495/04 |
| 2020/0235320 A1* | 7/2020 | Yen | H01L 51/0059 |

\* cited by examiner

ORGANIC COMPOUND AND ORGANIC ELECTROLUMINESCENCE DEVICE USING THE SAME

This patent application is a Continuation-in-Part of U.S. patent application Ser. No. 16/221,626, filed Dec. 17, 2018.

FIELD

The present invention relates to an organic compound and a device comprising the same.

BACKGROUND

Organic electroluminescence (organic EL) devices, i.e., organic light-emitting diodes (OLEDs) that make use of organic compounds, are becoming increasingly desirable than before. The devices make use of thin organic films that emit light when voltage is applied across the device. They are becoming an interesting technology for use in applications such as flat panel displays, illumination, or backlighting.

One of the organic compounds, denoted H1 hereinafter, has the following structure:

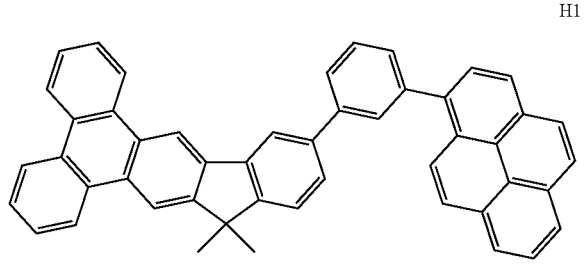 [SMILES: CC1(C)c2ccc(-c3cccc(-c4ccc5ccc6cccc7ccc4c5c67)c3)cc2-c2cc3c4ccccc4c4ccccc4c3cc21]

H1

As used herein, "top" means furthest away from the substrate, while "bottom" means closest to the substrate. Where a second layer is described as formed on or onto a first layer, the second layer is formed further away from substrate. There may be other layers between the second layer and the first layer, unless it is specified that the second layer is "in contact with" the first layer. For example, a cathode may be described as formed onto an anode, even though there are various organic layers in between.

SUMMARY

An organic compound has the following formula (1):

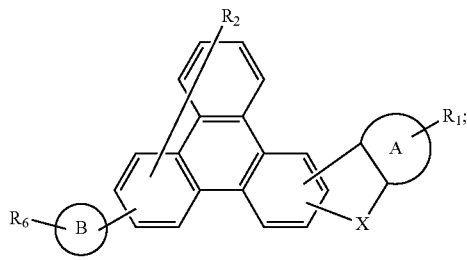

formula (1)

wherein X represents a divalent bridge selected from the group consisting of O, S, Se, $NR_3$ and $SiR_4R_5$;

wherein $R_6$ represents mono or di substitutions, or no substitution, each of the substitutions is selected from the group consisting of hydrogen, halogen, trifluoromethyl, cyano, nitro, silyl, and combinations thereof;

wherein $R_2$ represents mono to the maximum allowable substitution, or no substitution;

wherein ring A represents a monocyclic aromatic hydrocarbon or a polycyclic aromatic hydrocarbon having 2, 3 or 4 fused rings;

wherein ring B represents a chemical group selected from the group consisting of a monocyclic aromatic hydrocarbyl, a polycyclic aromatic hydrocarbyl having 2, 3, 4 or 5 fused rings, and combinations thereof; and wherein each of $R_1$ to $R_5$ is hydrogen or a substituent selected from the group consisting of alkyl, aryl, aralkyl, heteroaryl, and combinations thereof.

$R_2$ may represent mono, di, tri, tetra, penta, hexa, hepta, or octa substitutions. Each of $R_1$ to $R_5$ may be hydrogen or a substituent selected from the group consisting of alkyl having 20 or fewer carbon atoms, aryl having 30 or fewer carbon atoms, aralkyl having 30 or fewer carbon atoms, heteroaryl having 30 or fewer carbon atoms, and combinations thereof.

An organic EL device is also provided. The organic EL device may comprise an anode, a cathode and one or more organic layers formed between the anode and the cathode. At least one of the organic layers comprises the organic compound of formula (1).

DETAILED DESCRIPTION

Figure 1:
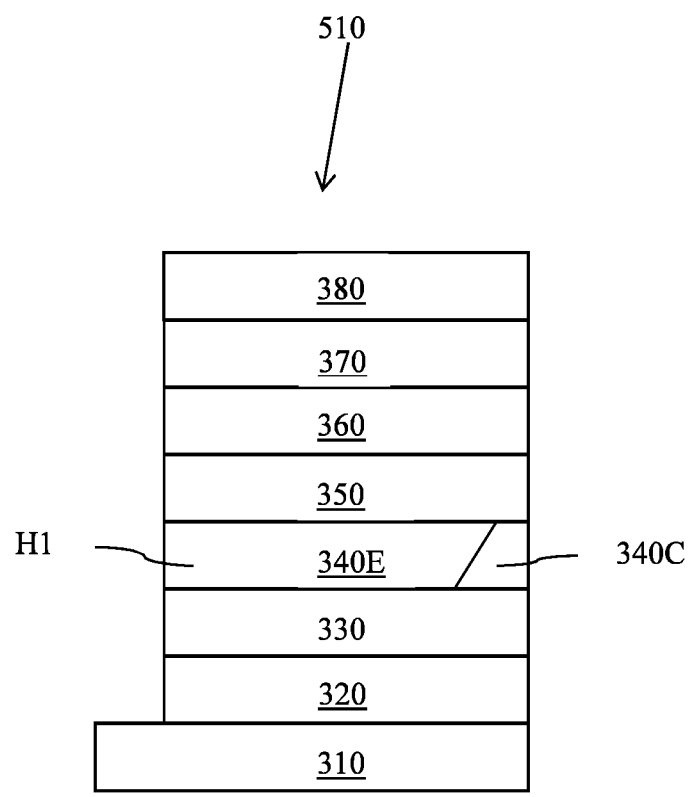
FIG. 1 is a cross-sectional view of a first organic EL device.

Plural embodiments of the present disclosure are disclosed through drawings. For the purpose of clear illustration, many practical details will be illustrated along with the description below. It should be understood that, however, these practical details should not limit the present disclosure. In other words, in embodiments of the present disclosure, these practical details are not necessary. In addition, for the purpose of simplifying the drawings, some conventional structures and components are simply and schematically depicted in the figures.

It is to be understood that although particular phrases used herein, such as "first", "second", "third", and so on, are used to describe different components, members, regions, layers, and/or sections, these components, members, regions, layers, and/or sections should not be limited by these terms. These phrases are used to distinguish one component, member, region, layer, or section from another component, member, region, layer, or section. In this way, a first component, member, region, layer, and/or section to be described below may be referred to as a second component, member, region, layer, and/or section, without departing from the spirit and scope of the present disclosure.

Spatially relative phrases, such as "onto", "on", "under", "below", "underlying", "beneath", "above", and so on used herein, are used for facilitating description of a relation between one component or feature and another component or feature depicted in the drawings. Therefore, it can be understood that, in addition to directions depicted in the drawings, the spatially relative terms mean to include all different orientations during usage or operations of the device. For example, it is assumed that a device in a figure is reversed upside down, a component described as being "under", "below", or "beneath" another component or feature is oriented "onto" or "on" the other component or feature. Therefore, these exemplary terms "under" and "below" may include orientations above and below. The device may be otherwise oriented (e.g., turned by 90 degrees, or other orientations), and the spatially relative terms used herein should be explained accordingly.

Accordingly, it may be understood that when a component or a layer is referred to as being "onto", "on", "connected to", or "coupled to" another component or another layer, it may be immediately on the other component or layer, or connected to or coupled to the other component or layer, or there may be one or more intermediate components or intermediate layers. Further, it can be understood that when a component or a layer is referred to as being "between" two components or two layers, it may be the only component or layer between the two components or layers, or there may be one or more intermediate components or intermediate layers.

Terminologies used herein are only for the purpose of describing particular embodiments, but not limiting the present disclosure. The singular form of "a" and "the" used herein may also include the plural form, unless otherwise indicated in the context. Accordingly, it can be understood that when there terms "include" or "comprise" are used in the specification, it clearly illustrates the existence of a specified feature, bulk, step, operation, component, and/or member, while not excluding the existence or addition of one or more features, bulks, steps, operations, components, members and/or groups thereof. "And/or" used herein includes any and all combinations of one or more related terms that are listed. When a leading word, such as "at least one of", is added ahead of a component list, it is to describe the entire component list, but not individual components among the list.

The terms "substituted" and "substitution" refer to a substituent bonded to the relevant position, e.g., a carbon or nitrogen. When $R_1$ represents no substitution, $R_1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms. A polycyclic aromatic hydrocarbyl may have two or more rings possible for being substituted. In this case, a long straight line may be drawn to pass through each of the rings in a formula. The following may be an example:

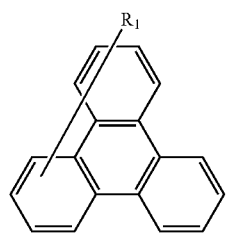

Occasionally, a single straight line cannot pass through all substitutable rings. In this case, two or more straight lines may be drawn to pass through each of the substitutable rings in a formula. The following may be an example:

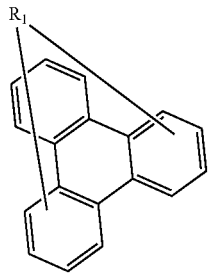

Generally, an organic EL device comprises at least one organic layer disposed between and electrically connected to an anode and a cathode. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the light emitting layer to form excitons and then emit light. When luminescent molecules absorb energy to achieve an excited state, the exciton may either be in a singlet state or a triplet state, depending on how the spins of the electrons and holes have been combined.

The term "hydrogen" refers to a —H radical.

The terms "halogen" and "halide" are used interchangeably and refer to fluorine, chlorine, bromine, or iodine.

The term "trifluoromethyl" refers to a —$CF_3$ radical.

The term "cyano" refers to a —C≡N radical.

The term "nitro" refers to a —$NO_2$ radical.

The term "silyl" refers to a —$Si(R_s)_3$ radical, wherein each $R_s$ can be same or different. $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combinations thereof. Preferred Rs is selected from the group consisting of alkyl, cycloalkyl, aryl, heteroaryl, and combinations thereof.

As used herein, "a first integer to a second integer" indicates a group comprising at least a first integer, a second integer, and all integers therebetween. For example, "1 to 4 atoms" indicates a group comprising 1, 2, 3 and 4 atoms; and "an integer of 0 to 3" indicates a group comprising 0, 1, 2, and 3.

As used herein, "combinations thereof" indicates that one or more members of the applicable list are combined to form a known or chemically stable arrangement that one of ordinary skill in the art can envision from the applicable list. For example, a monocyclic aromatic hydrocarbyl and a polycyclic aromatic hydrocarbyl can be combined by being joined through a direct bond, or can be combined to have two carbons common to two adjoining rings (the rings are "fused"); a halogen and alkyl can be combined to form a halogenated alkyl substituent; a halogen, alkyl, and aryl can be combined to form a halogenated arylalkyl; and an alkyl and deuterium can be combined to form a partial or fully deuterated alkyl group. In one instance, the term substitution includes a combination of two to four of the listed groups.

In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The term "alkyl" refers to and includes both straight and branched chain alkyl radicals. Preferred alkyl groups are those containing 30 or fewer carbon atoms, preferably 1 to 20 carbon atoms, more preferably 1 to 15 carbon atoms, and most preferably 1 to 12 carbon atoms. Suitable alkyl groups include methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates a monocyclic aromatic hydrocarbyl ring system, polycyclic aromatic hydrocarbyl ring systems, and combinations thereof. The polycyclic aromatic hydrocarbyl may have two, three, four or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Unless otherwise specified, preferred aryl groups are those containing 30 or fewer carbon atoms, preferably 6 to 30 carbon atoms, more preferably 6 to 20 carbon atoms, and most preferably 6 to 12 carbon atoms. Especially preferred is an aryl group having 6 carbons, 10 carbons or 12 carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "aromatic hydrocarbyl" or "ring hydrocarbon unit" are used interchangeably and refer to a monocyclic aromatic hydrocarbyl or a polycyclic aromatic hydrocarbyl consisting entirely of hydrogen and carbon.

The terms "aralkyl" or "arylalkyl" are used interchangeably and refer to an alkyl group that is substituted with an aryl group. Preferred aralkyl groups are those containing 30 or fewer carbon atoms, preferably 6 to 30 carbon atoms. Additionally, the aralkyl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, Se, N or Si are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing 30 or fewer carbon atoms, preferably 3 to 30 carbon atoms, more preferably 3 to 20 carbon atoms, and most preferably 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

The terms alkyl, aralkyl, heteroaryl, aryl, cycloalkyl, heteroalkyl, heterocycloalkyl, alkenyl, cycloalkenyl, heteroalkenyl, alkynyl, alkoxy, and heterocyclic group, as used herein, are independently unsubstituted, or independently substituted, with one or more general substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of hydrogen, halogen, trifluoromethyl, cyano, nitro, silyl, and combinations thereof.

In yet other instances, the more preferred general substituents are selected from the group consisting of hydrogen, alkyl, aralkyl, heteroaryl and combinations thereof.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —$SR_s$ radical.

The term "sulfinyl" refers to a —S(O)—$R_s$, radical.

The term "sulfonyl" refers to a —$SO_2$—$R_s$ radical.

The term "phosphino" refers to a —$P(R_s)_3$ radical, wherein each $R_s$ can be same or different.

It is to be understood that when a molecular fragment is described as being a substituent or otherwise attached to another moiety, its name may be written as if it were a fragment (e.g., phenyl, phenylene, naphthyl, dibenzofuryl, hydrocarbyl, aromatic linker, arylene) or as if it were the whole molecule (e.g., benzene, naphthalene, dibenzofuran, hydrocarbon, aromatic compound, aromatic hydrocarbon). As used herein, these different ways of designating a substituent or attached fragment are considered to be equivalent.

An organic compound is described to have the following formula (1):

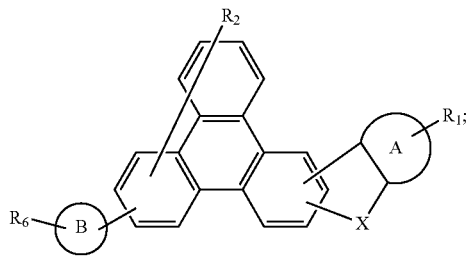

formula (1)

wherein X represents a divalent bridge selected from the group consisting of O, S, Se, $NR_3$ and $SiR_4R_5$;

wherein $R_6$ represents mono or di substitutions, or no substitution, each of the substitutions is selected from the group consisting of hydrogen, halogen, trifluoromethyl, cyano, nitro, silyl, and combinations thereof;

wherein $R_2$ represents mono to the maximum allowable substitution, or no substitution;

wherein ring A represents a monocyclic aromatic hydrocarbon or a polycyclic aromatic hydrocarbon having 2, 3 or 4 fused rings;

wherein ring B represents a chemical group selected from the group consisting of a monocyclic aromatic hydrocarbyl, a polycyclic aromatic hydrocarbyl having 2, 3, 4 or 5 fused rings, and combinations thereof; and wherein each of $R_1$ to $R_5$ is hydrogen or a substituent selected from the group consisting of alkyl, aryl, aralkyl, heteroaryl, and combinations thereof.

In one embodiment, $R_2$ represents mono, di, tri, tetra, penta, hexa, hepta, or octa substitutions.

In one embodiment, each of $R_1$ to $R_5$ may be hydrogen or a substituent selected from the group consisting of alkyl having 20 or fewer carbon atoms, aryl having 30 or fewer carbon atoms, aralkyl having 30 or fewer carbon atoms, heteroaryl having 30 or fewer carbon atoms, and combinations thereof.

In one embodiment, $R_1$ to $R_5$ may be hydrogen or be independently selected from the group consisting of alkyl having 1 to 30 carbon atoms, aryl having 6 to 30 carbon atoms, aralkyl having 7 to 30 carbon atoms and heteroaryl having 3 to 30 carbon atoms, and combinations thereof.

An organic EL device using the organic compound of formula (1) is also described. FIG. 1 is a cross-sectional view of the first organic EL device. Referring to FIG. 1, the first organic EL device 510 may comprise the organic compound of formula (1) as a dopant 340C of an emissive layer 340E.

Figure 2:
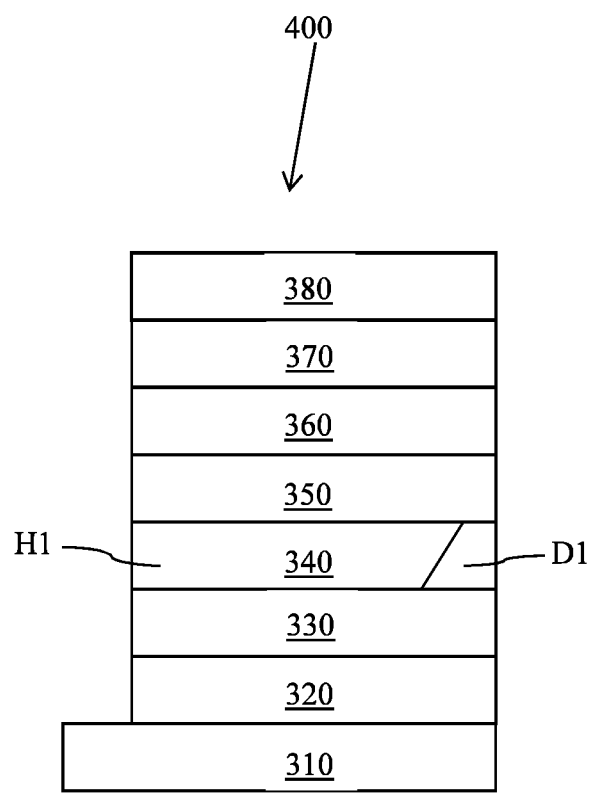
FIG. 2 is a cross-sectional view of an organic EL device without the host 340C of FIG. 1.

In a first embodiment of the present invention, FIG. 2 is a cross-sectional view of an organic EL device without the organic compound of formula (1) (without 340C of FIG. 1). Referring to FIG. 2, the organic EL device 400 may have a driving voltage of about 4.0 V, a current efficiency of about 5.2 cd/A, or a half-life of about 170 hours.

Referring to FIG. 1, by comprising the organic compound of formula (1) as the dopant 340C, the first organic EL device 510 may have a driving voltage lower than that of the organic EL device 400 (FIG. 2). Moreover, by comprising the organic compound of formula (1) as the dopant 340C, the first organic EL device 510 of FIG. 1 may have a current efficiency higher than that of the organic EL device 400 (FIG. 2). Furthermore, by comprising the organic compound of formula (1) as the dopant 340C, the first organic EL device 510 of FIG. 1 may have a half-life longer than that of the organic EL device 400 (FIG. 2).

As the dopant 340C of the first organic EL device 510 of FIG. 1, the organic compound of formula (1) may lower the driving voltage to be about 3.3 V to about 4.0 V. Moreover, the organic compound of formula (1) may increase the current efficiency to be about 5.2 cd/A to about 6.9 cd/A. Furthermore, the organic compound of formula (1) may increase the half-life to be about 170 hours to about 330 hours.

Figure 3:
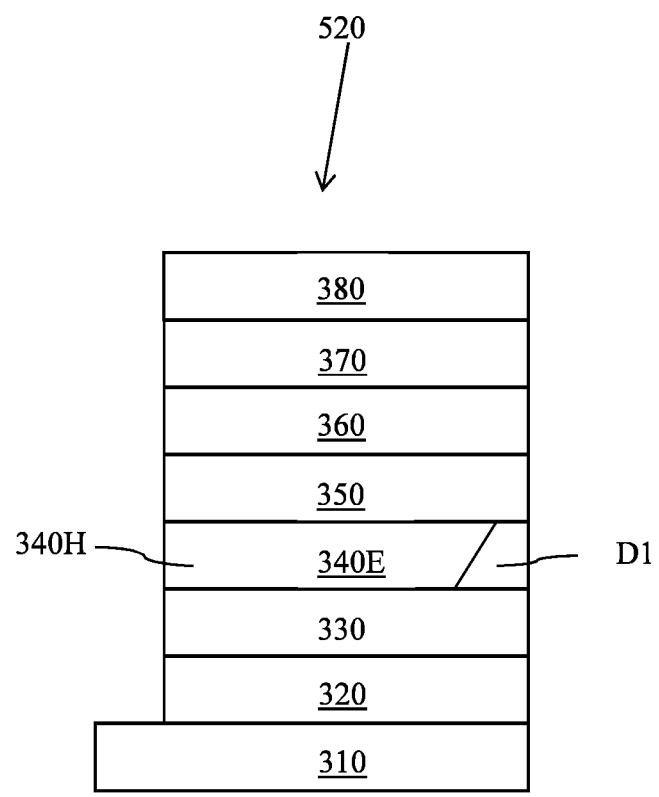
FIG. 3 is a cross-sectional view of a second organic EL device.

In a second embodiment of the present invention, a second organic EL device using the organic compound of formula (1) is disclosed. FIG. 3 is a cross-sectional view of the second organic EL device. Referring to FIG. 3, the second organic EL device 520 may comprise the organic compound of formula (1) as a host 340C of an emissive layer 340E.

In a first embodiment of the present invention, FIG. 2 is a cross-sectional view of an organic EL device without the organic compound of formula (1) (without 340C of FIG. 1). Referring to FIG. 2, the organic EL device 400 may have a driving voltage of about 4.0 V, a current efficiency of about 5.2 cd/A, or a half-life of about 170 hours.

Referring to FIG. 3, by comprising the organic compound of formula (1) as the host 340H, the second organic EL device 520 may have a driving voltage lower than that of the organic EL device 400 (FIG. 2). Moreover, by comprising the organic compound of formula (1) as the host 340C, the second organic EL device 520 of FIG. 3 may have a current efficiency higher than that of the organic EL device 400 (FIG. 2). Furthermore, by comprising the organic compound of formula (1) as a host 340C, the second organic EL device 520 of FIG. 3 may have a half-life longer than that of the organic EL device 400 (FIG. 2).

Referring to FIG. 3, as the host 340C of the second organic EL device 520, the organic compound of formula (1) may lower the driving voltage to be about 3.2 V to about 3.9 V. Moreover, the organic compound of formula (1) may increase the current efficiency to be about 5.3 cd/A to about 7.2 cd/A. Furthermore, the organic compound of formula (1) may increase the half-life to be about 180 hours to about 340 hours.

Figure 4:
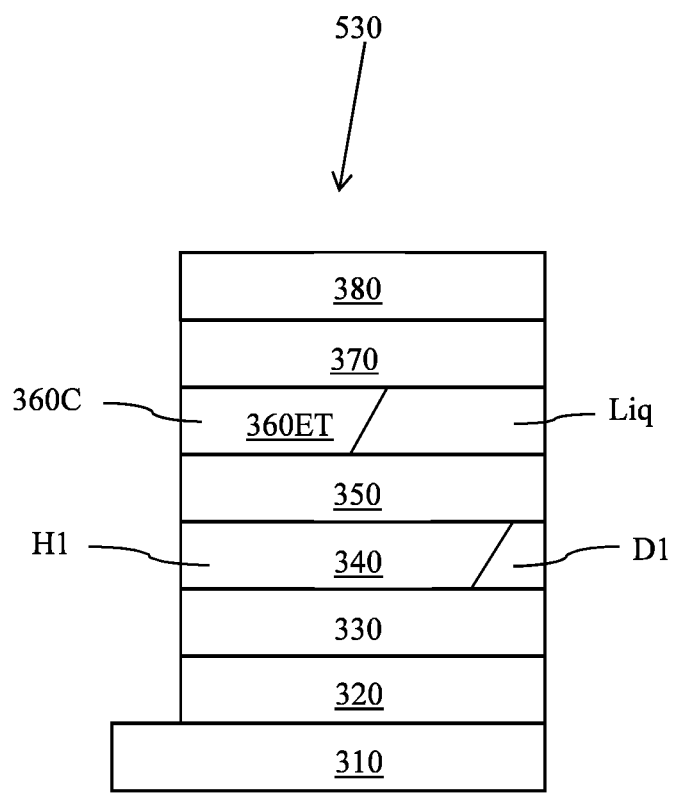
FIG. 4 is a cross-sectional view of a third organic EL device.

In a second embodiment of the present invention, a third organic EL device using the organic compound of formula (1) is disclosed. FIG. 4 is a cross-sectional view of the third organic EL device. Referring to FIG. 4, the third organic EL device 530 may comprise the organic compound of formula (1) as an electron transporting layer 360C.

In a first embodiment of the present invention, FIG. 2 is a cross-sectional view of an organic EL device without the organic compound of formula (1) (without 340C of FIG. 1). Referring to FIG. 2, the organic EL device 400 may have a driving voltage of about 4.0 V, a current efficiency of about 5.2 cd/A, or a half-life of about 170 hours.

Referring to FIG. 4, by comprising the organic compound of formula (1) as an electron transporting layer 360ET, the third organic EL device 530 may have a driving voltage lower than that of the organic EL device 400 (FIG. 2). Moreover, by comprising the organic compound of formula (1) as an electron transporting layer 360ET, the third organic EL device 530 of FIG. 4 may have a current efficiency higher than that of the organic EL device 400 (FIG. 2). Furthermore, by comprising the organic compound of formula (1) as an electron transporting layer 360ET, the third organic EL device 530 of FIG. 4 may have a half-life longer than that of the organic EL device 400 (FIG. 2).

Referring to FIG. 4, as an electron transporting layer 360C of the third organic EL device 530, the organic compound of formula (1) may lower the driving voltage to be about 3.2 V to about 4.0 V. Moreover, the organic compound of formula (1) may increase the current efficiency to be about 5.3 cd/A to about 7.1 cd/A. Furthermore, the organic compound of formula (1) may increase the half-life to be about 190 hours to about 360 hours.

Compounds of formula (1) of interest may be selected from the group consisting of the following:

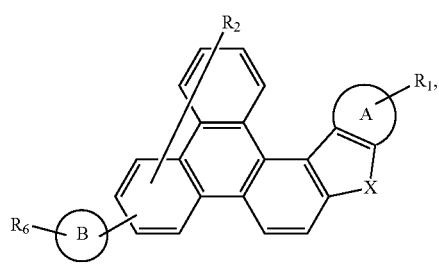

formula (2)

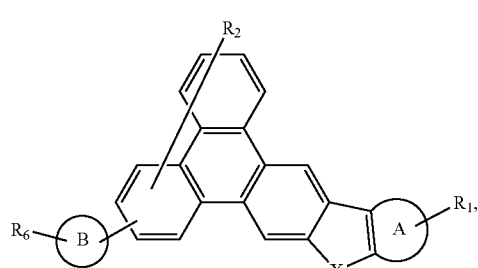

formula (3)

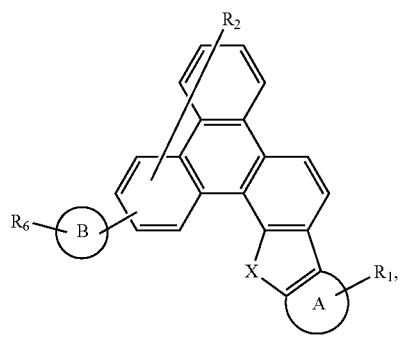

formula (4)

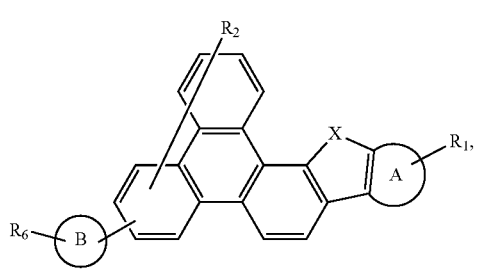

formula (5)

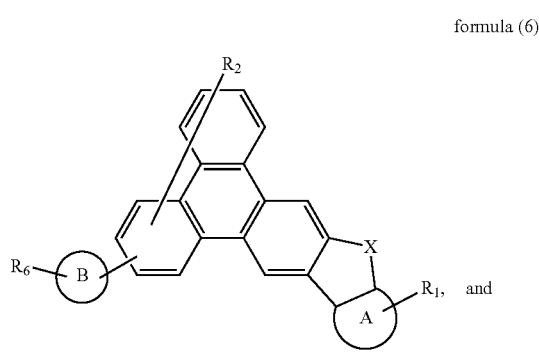

formula (6)

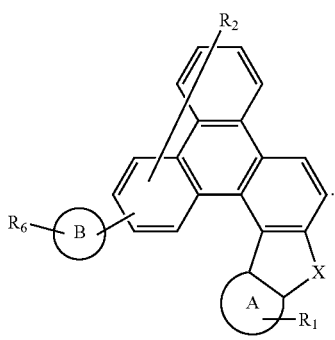

formula (7), and

In selected embodiments, ring A is selected from the group consisting of a phenyl group, a naphthyl group, an anthracenyl group, a phenanthrenyl group, a pyrenyl group, a chrysenyl group, a tetraphenyl group, a benzophenanthrenyl group, a triphenylenyl group, and combinations thereof.

In selected embodiments, ring A may represent one of the following substituents:

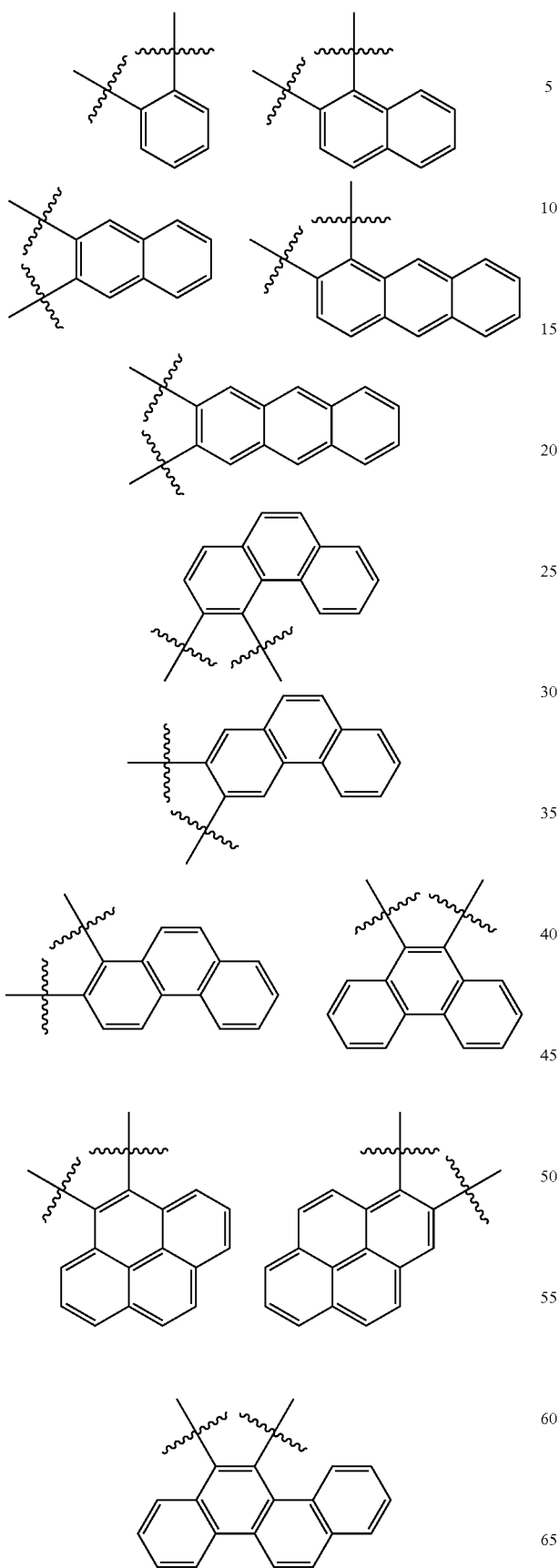
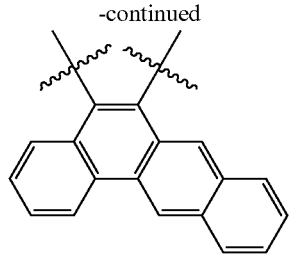
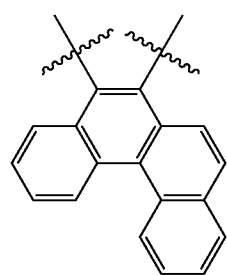
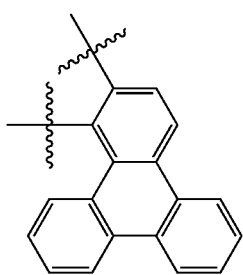
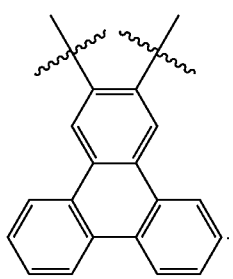
Compounds of formula (1) of interest may be selected from the group consisting of the following:
formula (2-1)
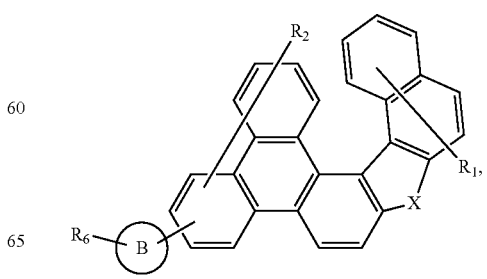

-continued
formula (2-2)
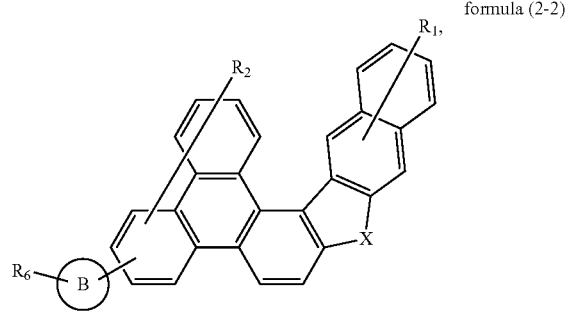
formula (2-3)
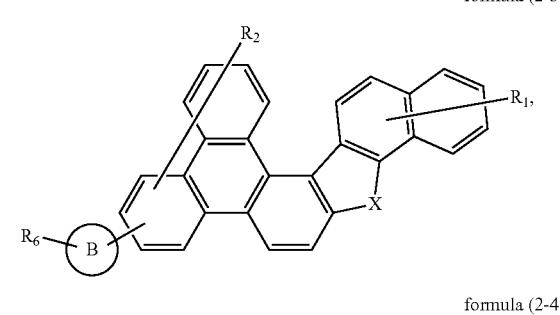
formula (2-4)
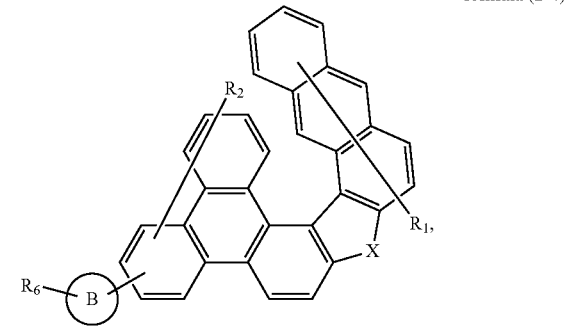
formula (2-5)
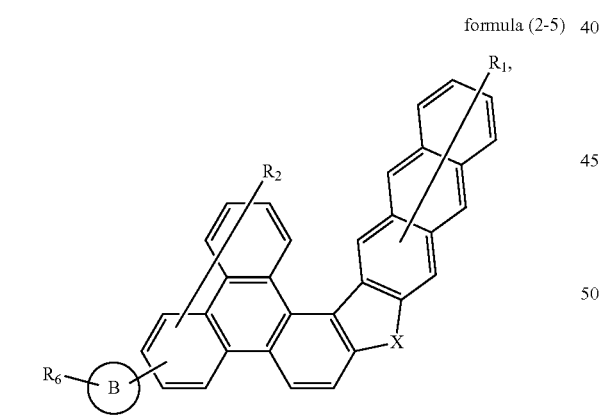
formula (2-6)
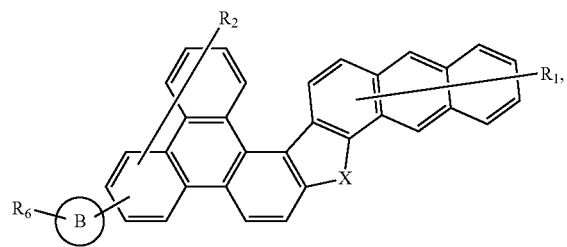
formula (2-7)
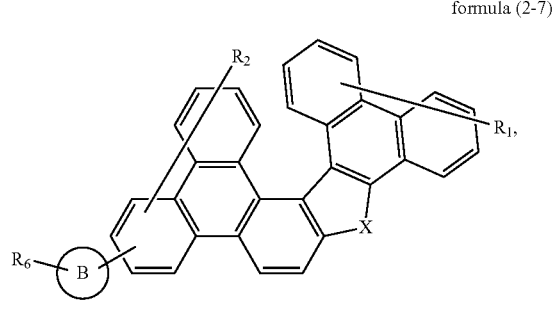
formula (2-8)
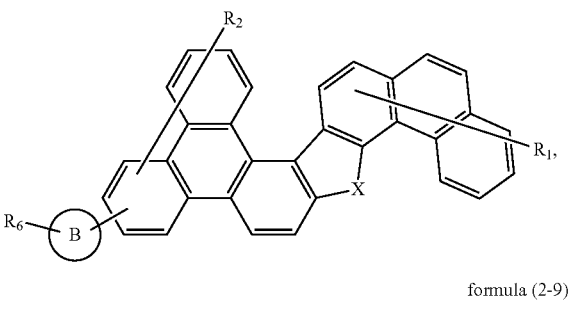
formula (2-9)
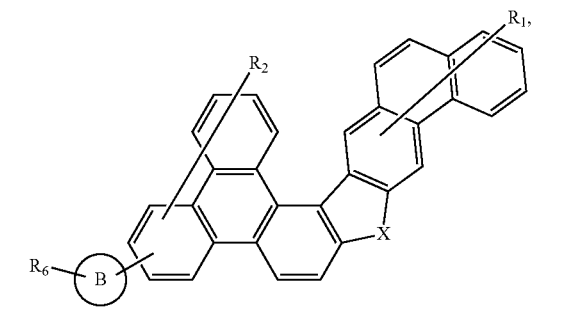
formula (2-10)
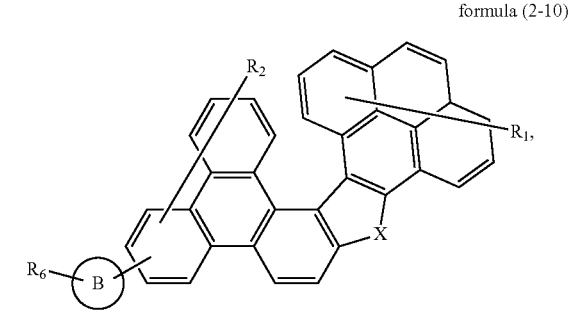
formula (2-11)
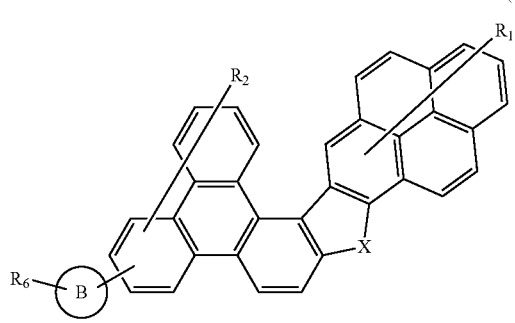

-continued
formula (2-12)
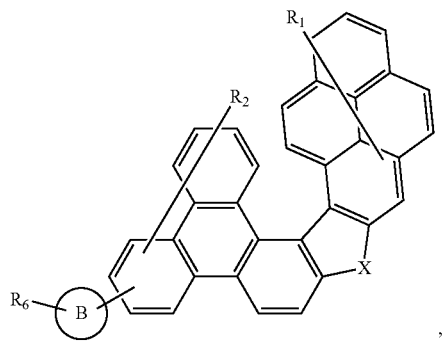
formula (2-13)
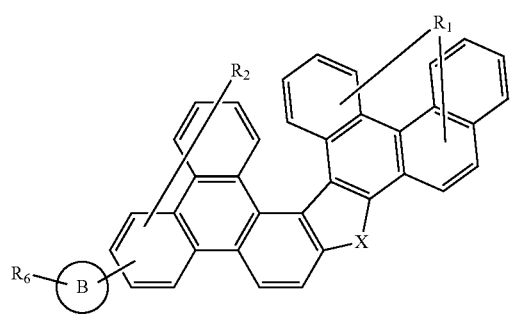
formula (2-14)
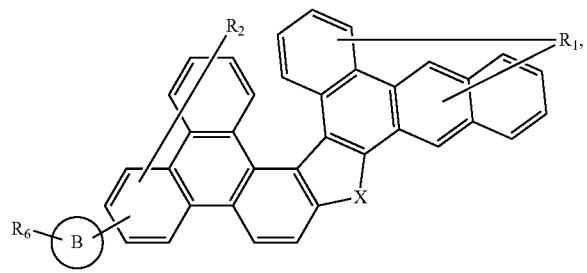
formula (2-15)
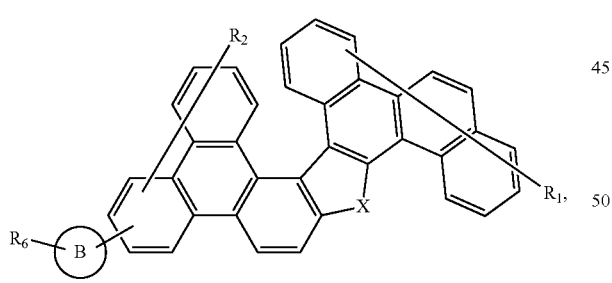
formula (2-16)
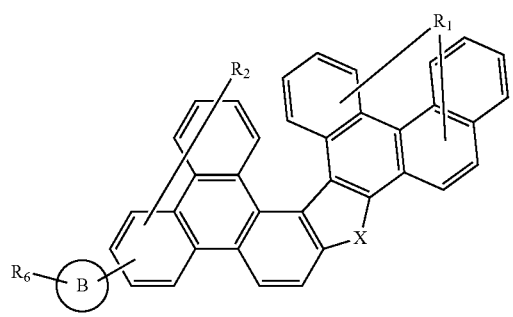
formula (2-17)
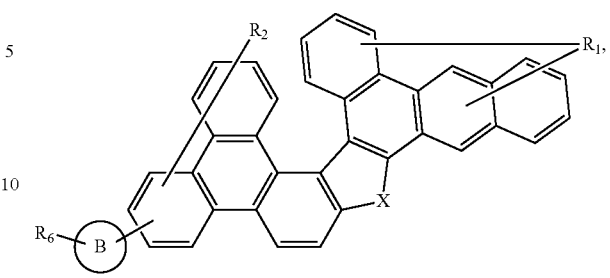
formula (2-18)
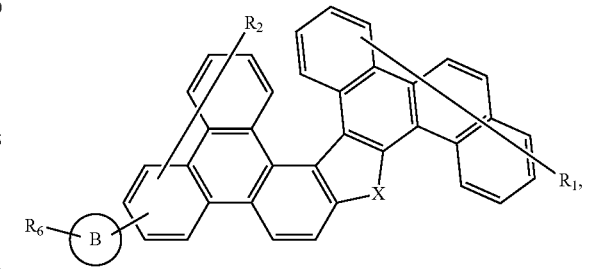
formula (2-19)
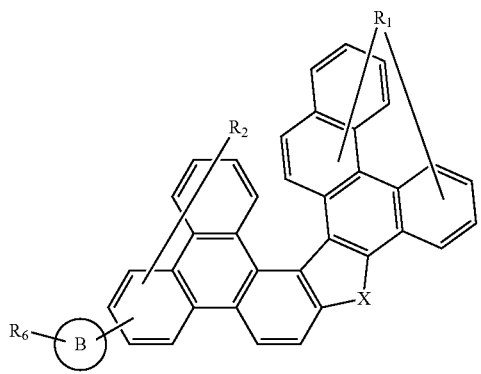
formula (2-20)
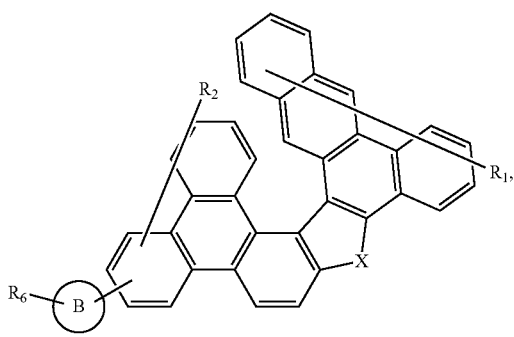

formula (2-21)
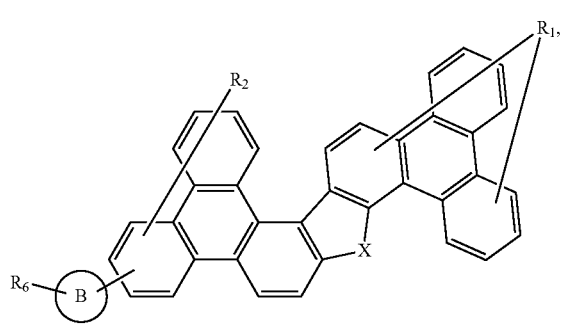
formula (2-22)
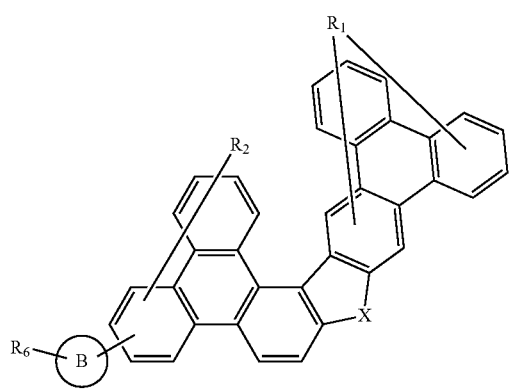
,
formula (2-23)
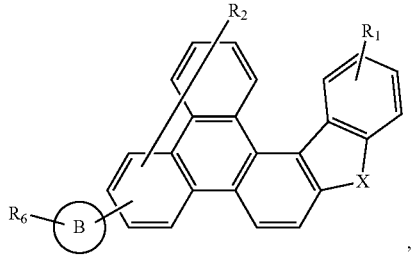
,
formula (3-1)
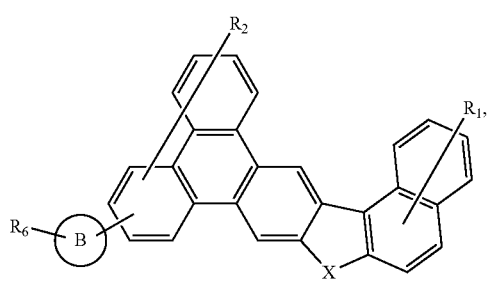
formula (3-2)
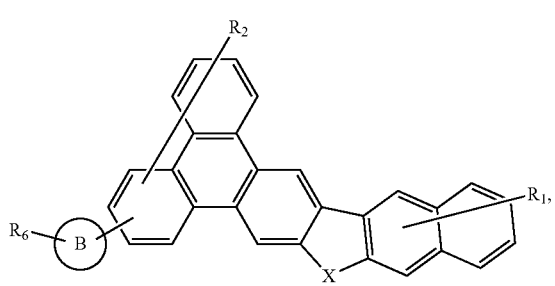
formula (3-3)
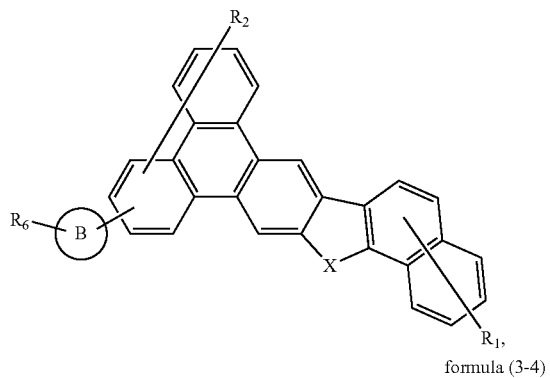
formula (3-4)
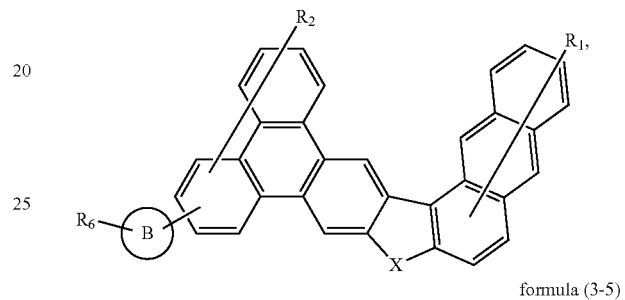
formula (3-5)
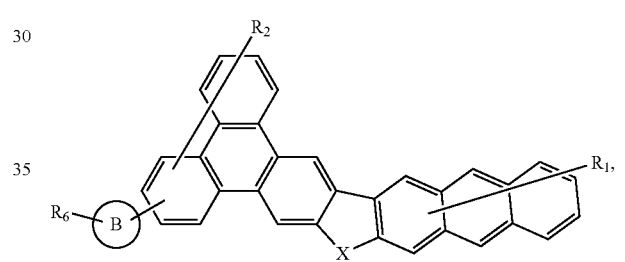
formula (3-6)
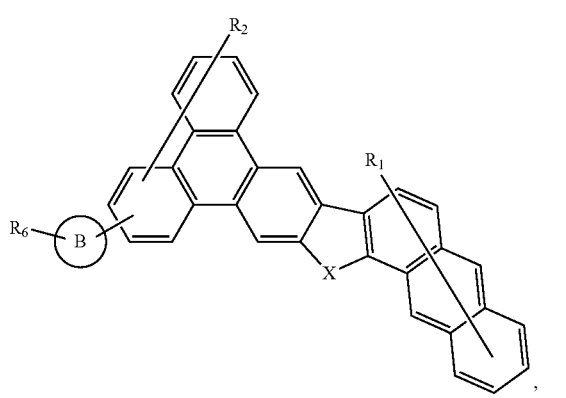
formula (3-7)
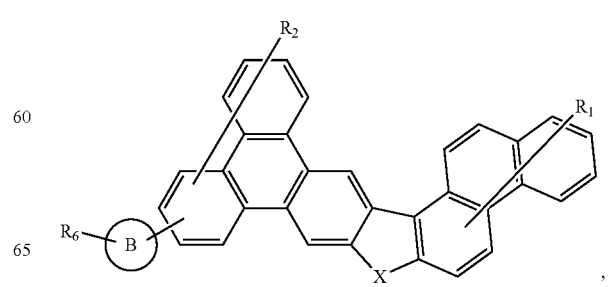
, formula (3-8)
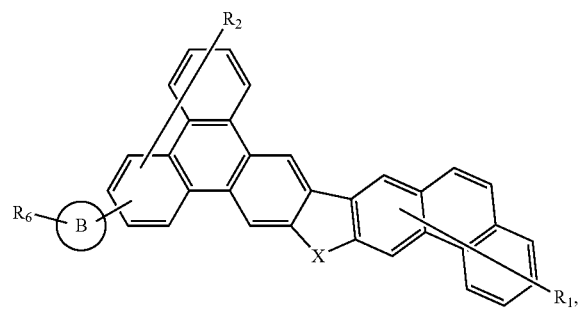
formula (3-9)
formula (3-10)
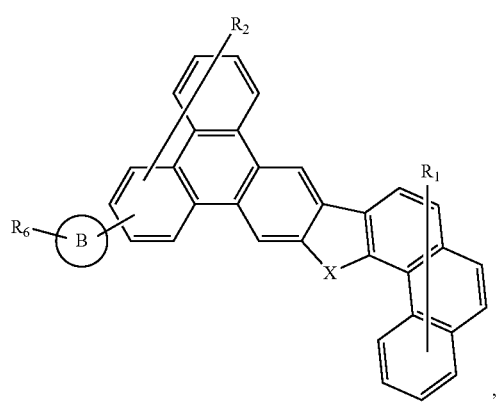
formula (3-11)
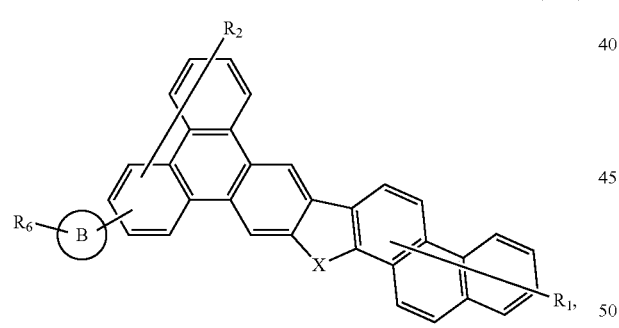
formula (3-12)
formula (3-13)
formula (3-14)
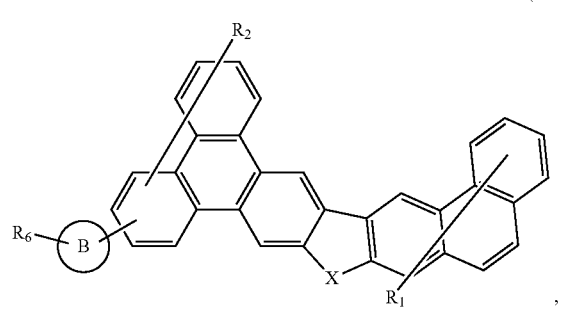
formula (3-15)

formula (3-16)
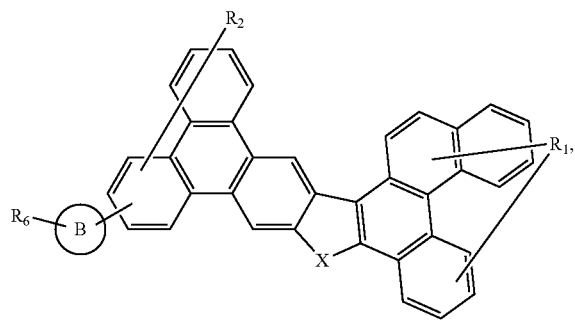
formula (3-17)
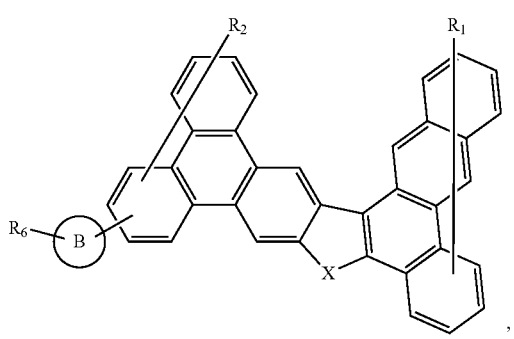
formula (3-18)
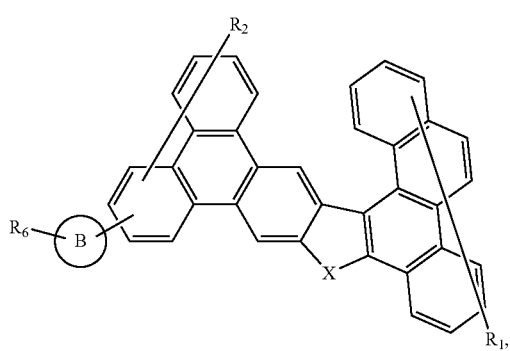
formula (3-19)
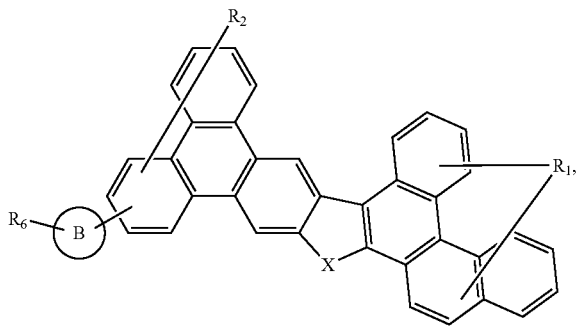
formula (3-20)
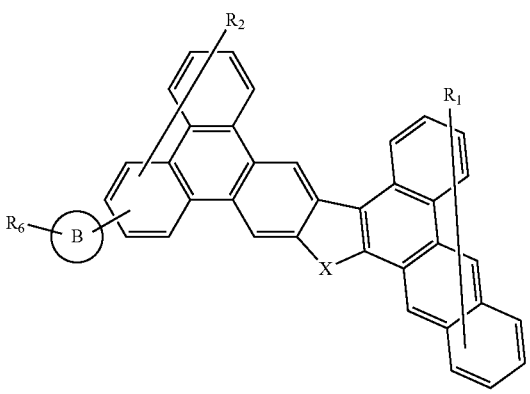
formula (3-21)
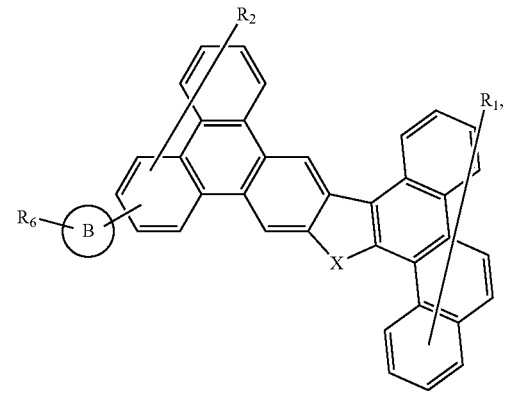
formula (3-22)
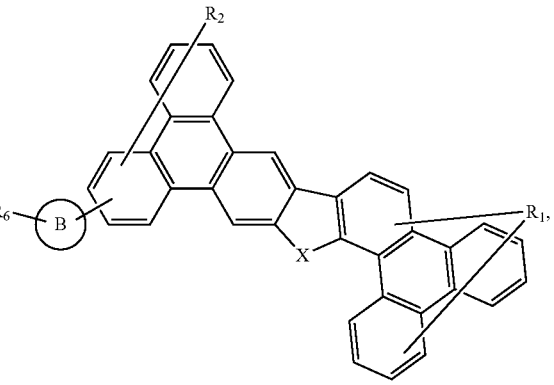
formula (3-23)
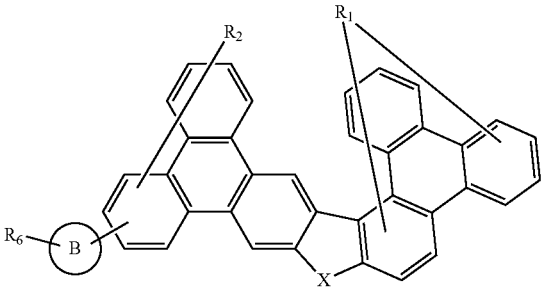

-continued
formula (3-24)
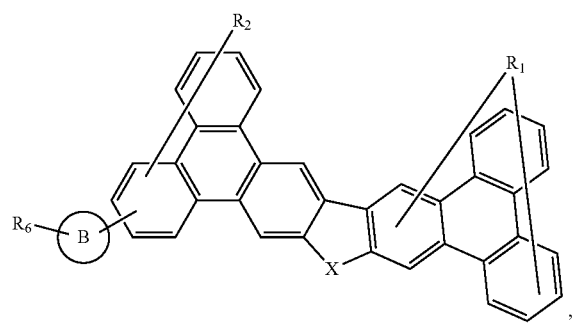
formula (3-25)
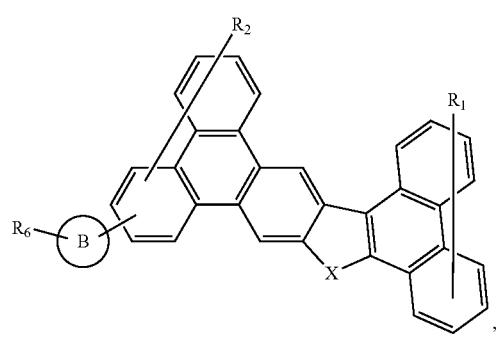
formula (3-26)
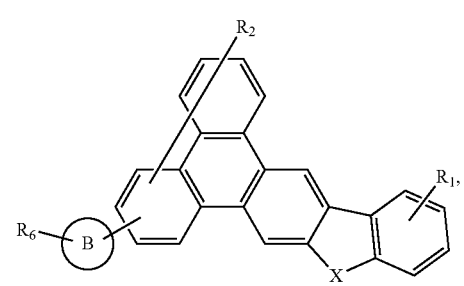
formula (4-1)
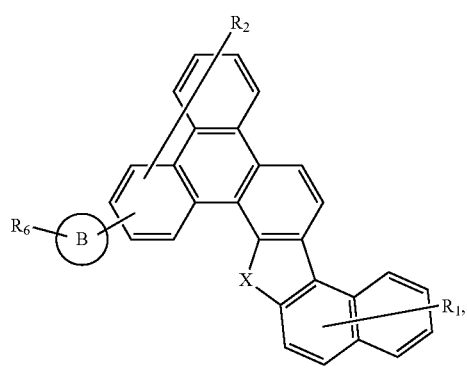
formula (4-2)
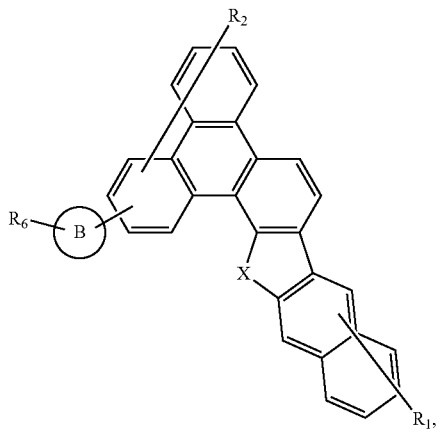
formula (4-3)
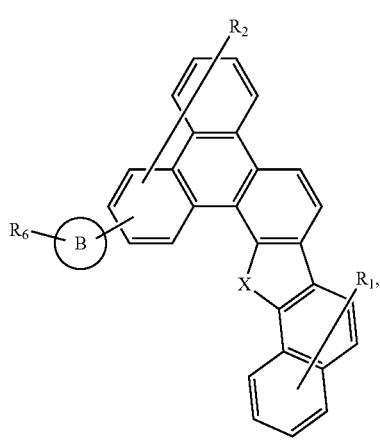
formula (4-4)
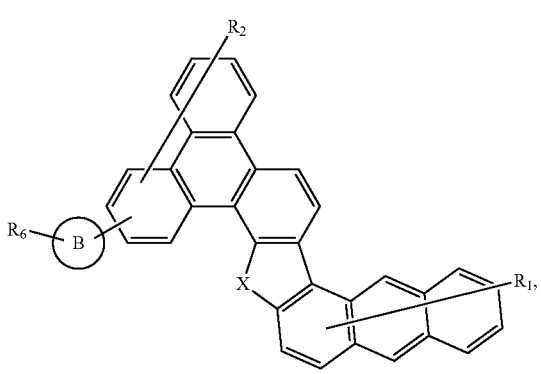

formula (4-5)
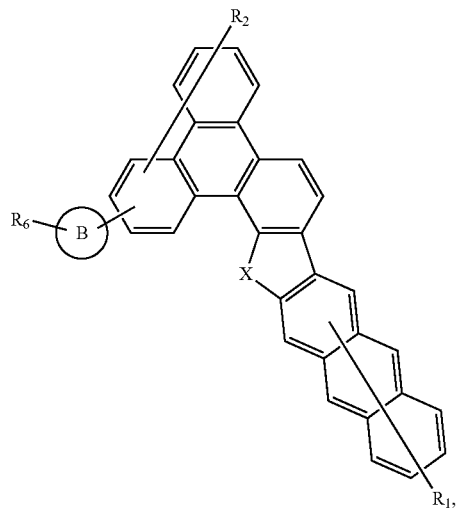
formula (4-6)
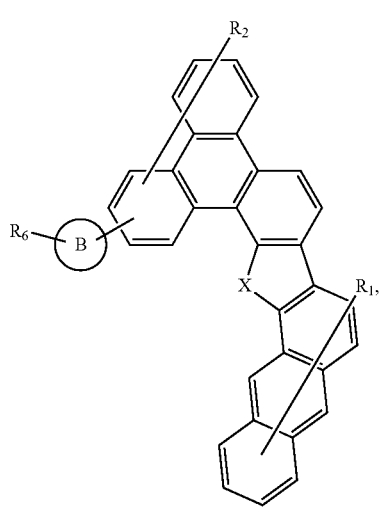
formula (4-7)
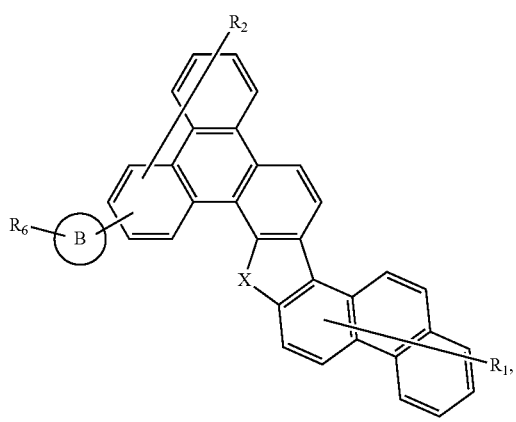
formula (4-8)
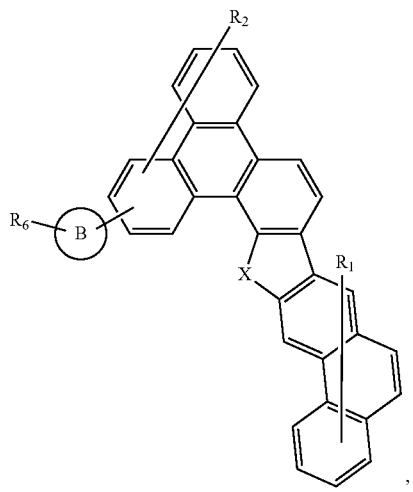
formula (4-9)
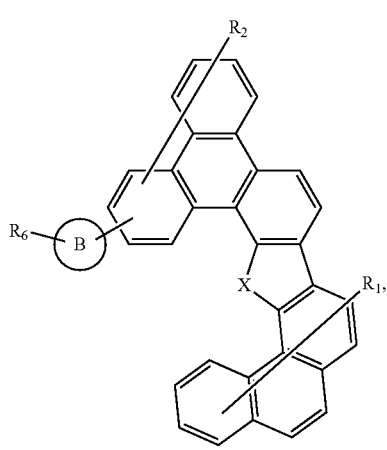
formula (4-10)
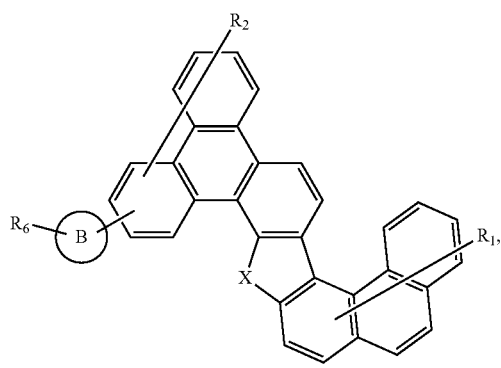

formula (4-11)
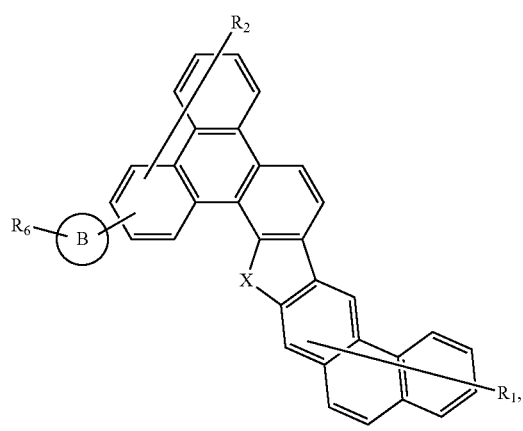
formula (4-12)
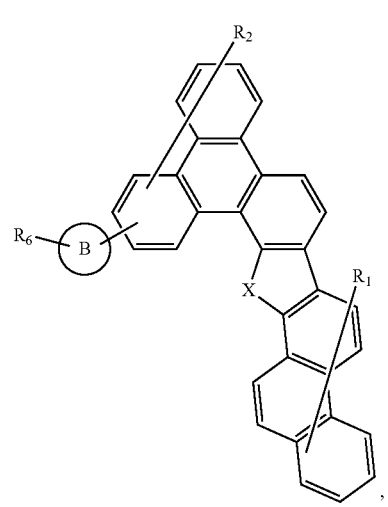
formula (4-13)
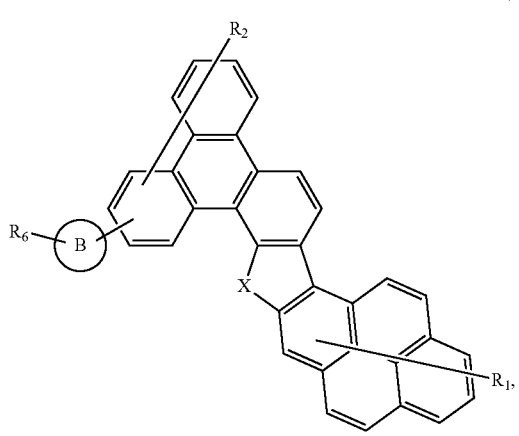
formula (4-14)
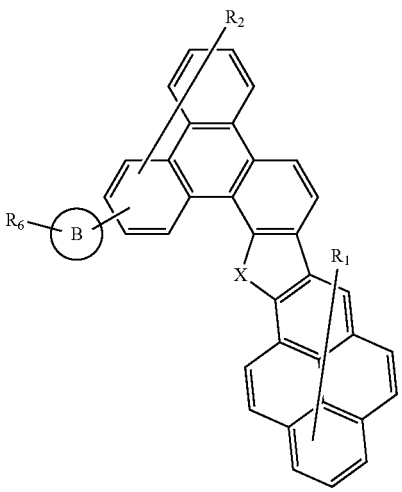
formula (4-15)
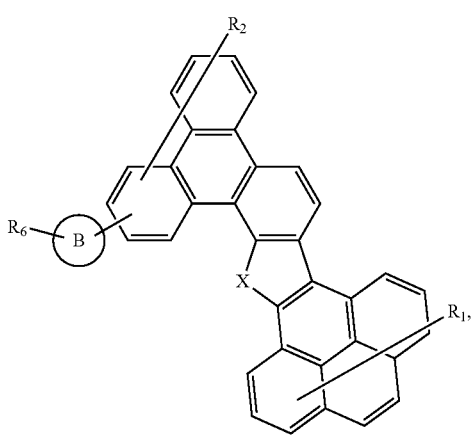
formula (4-16)
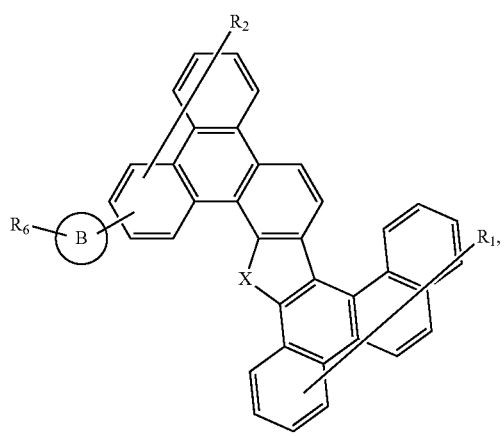

-continued
formula (4-17)
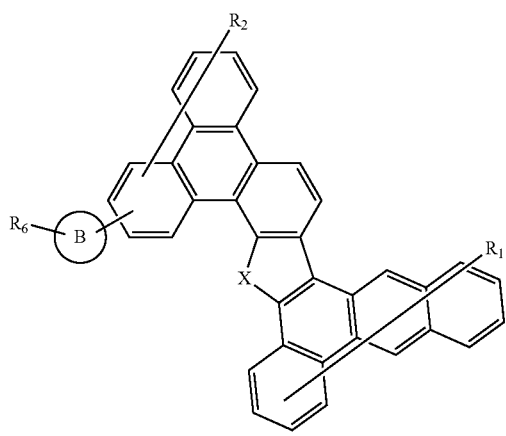
formula (4-18)
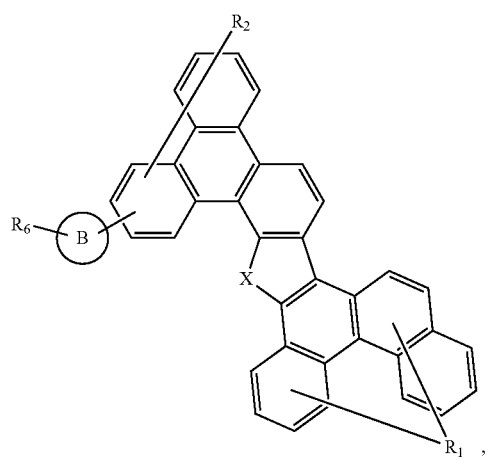
formula (4-19)
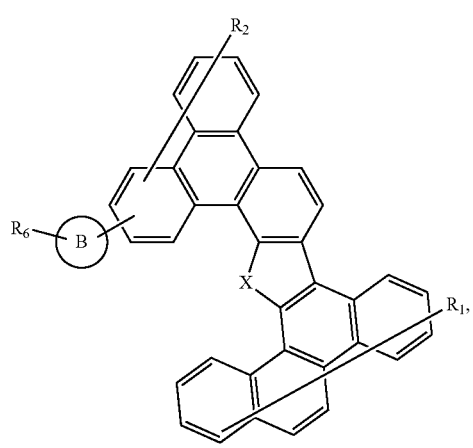
formula (4-20)
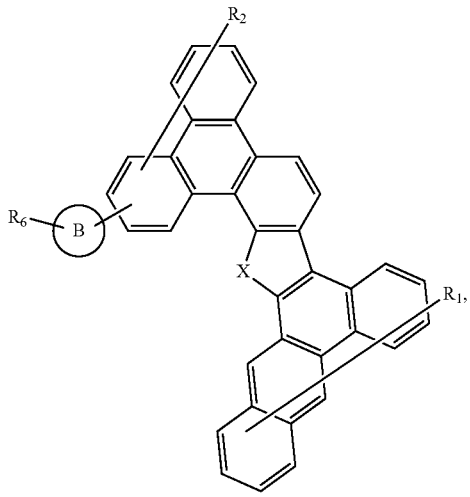
formula (4-21)
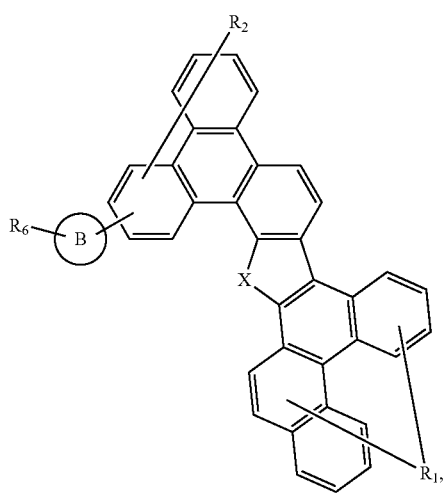
formula (4-22)
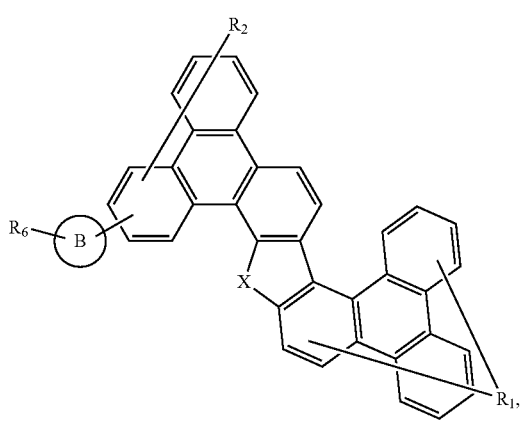

formula (4-23)
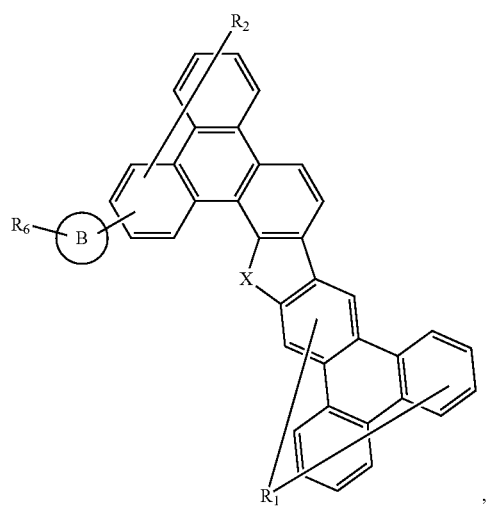
formula (4-24)
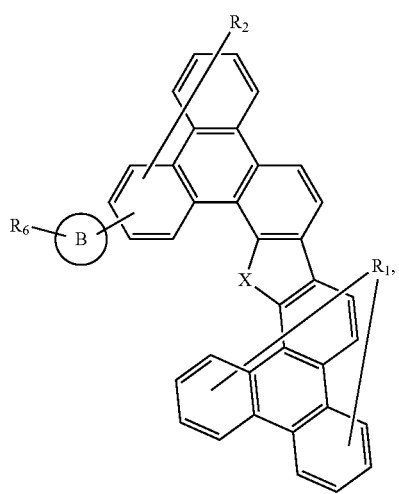
formula (4-25)
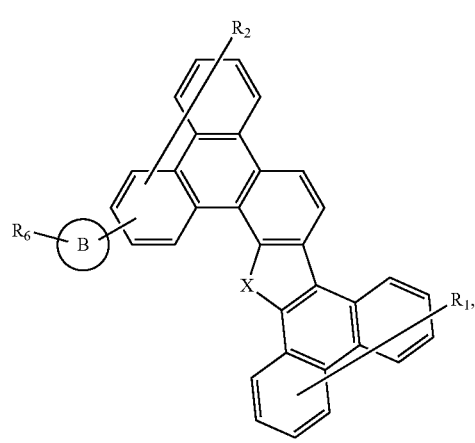
formula (4-26)
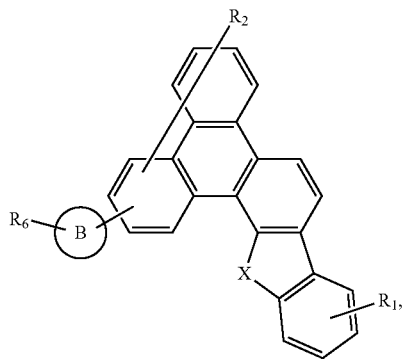
formula (5-1)
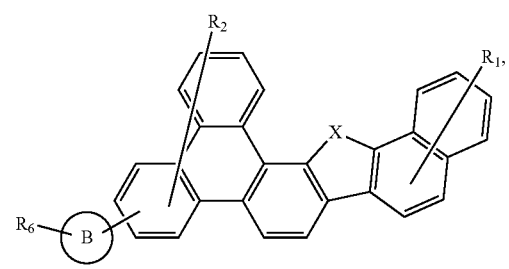
formula (5-2)
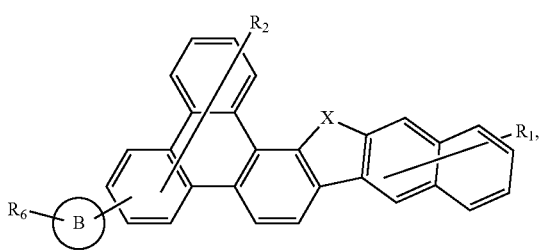
formula (5-3)
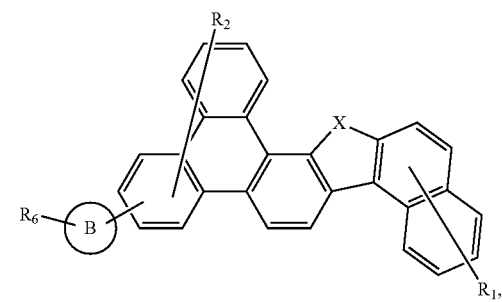
formula (5-4)
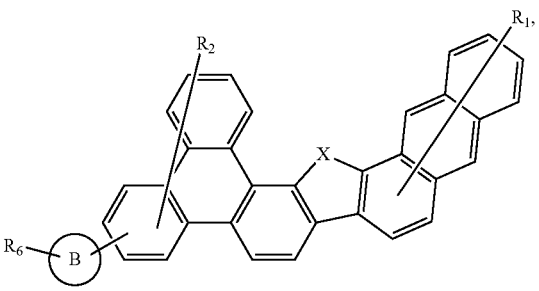

formula 5-5)
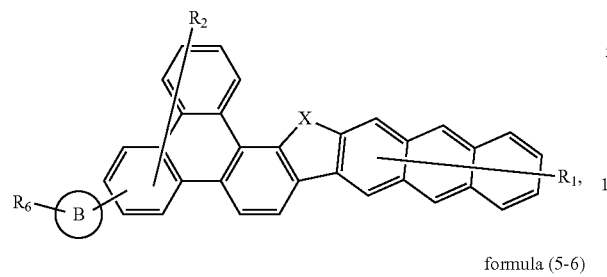
formula (5-6)
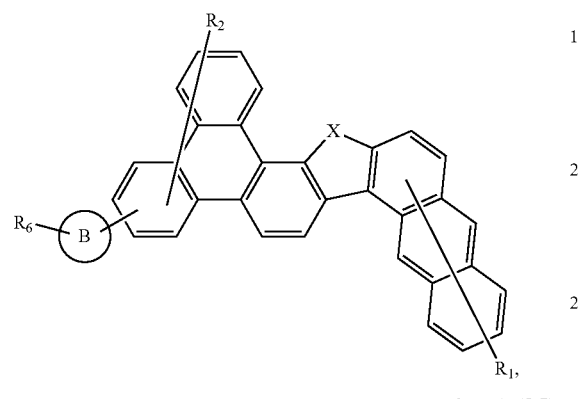
formula (5-7)
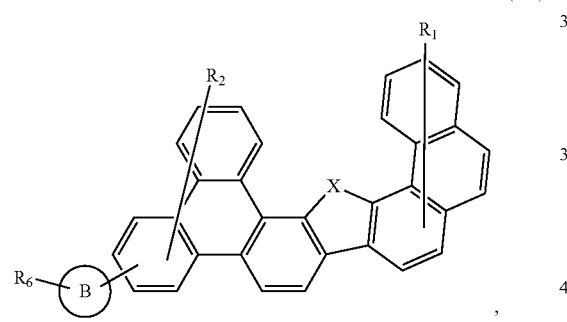
formula (5-8)
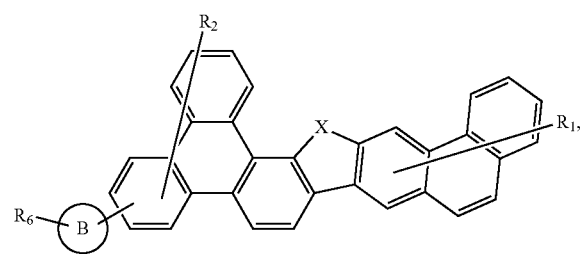
formula (5-9)
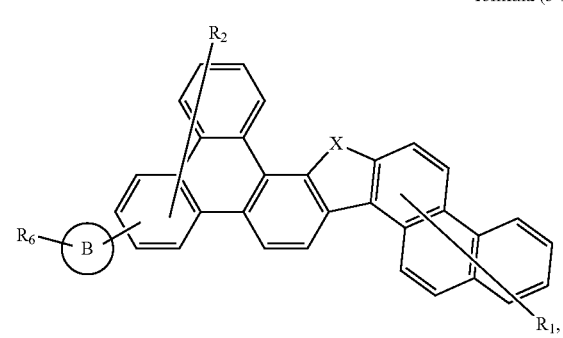
formula (5-10)
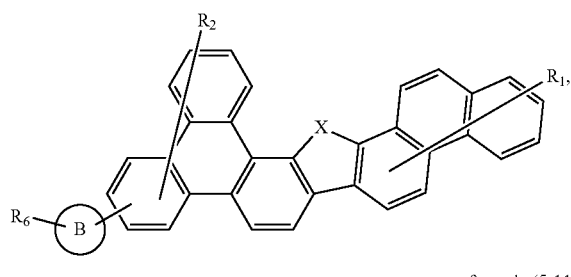
formula (5-11)
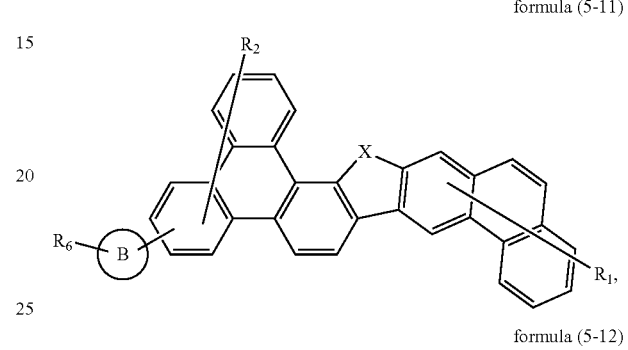
formula (5-12)
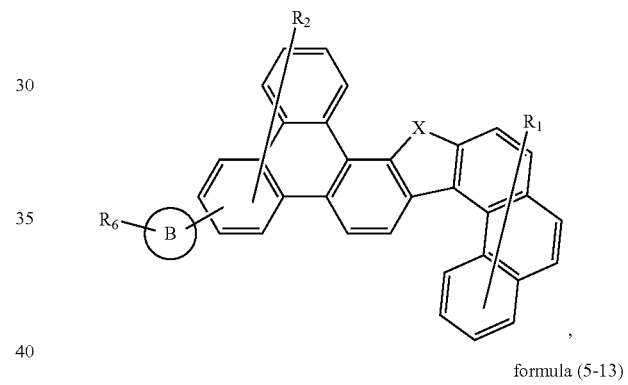
formula (5-13)
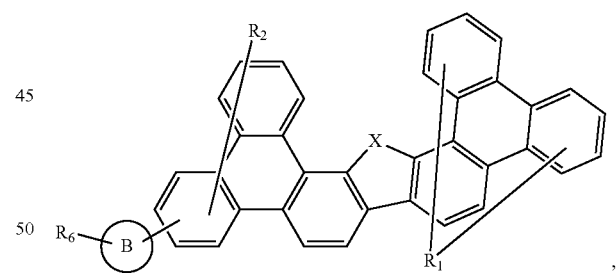
formula (5-14)

-continued
formula (5-15)
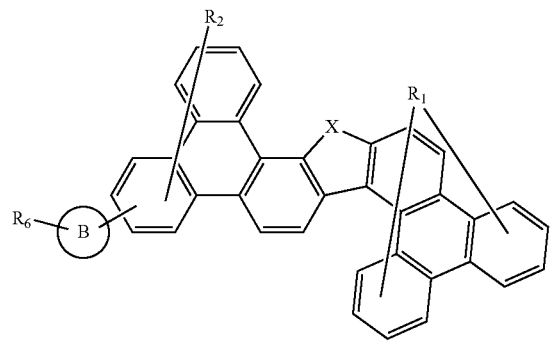
formula (5-16)
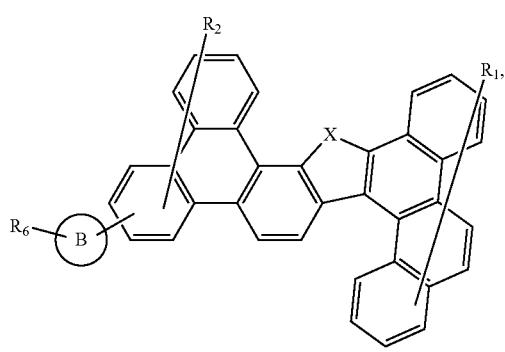
formula (5-17)
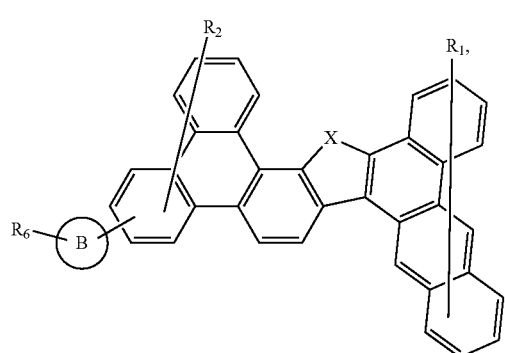
formula (5-18)
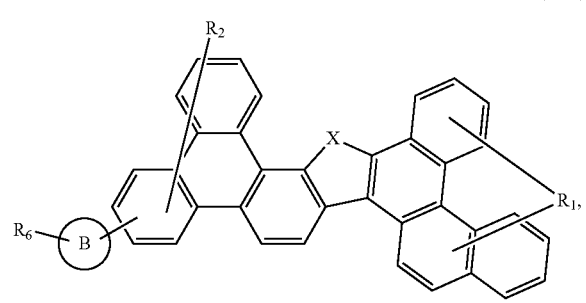
-continued
formula (5-19)
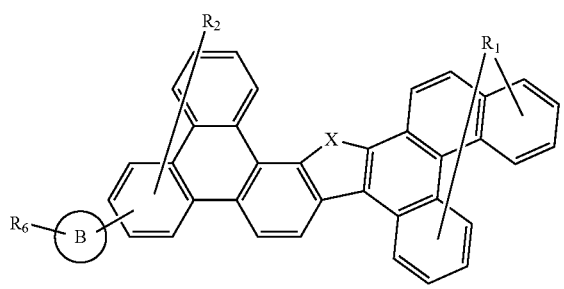
formula (5-20)
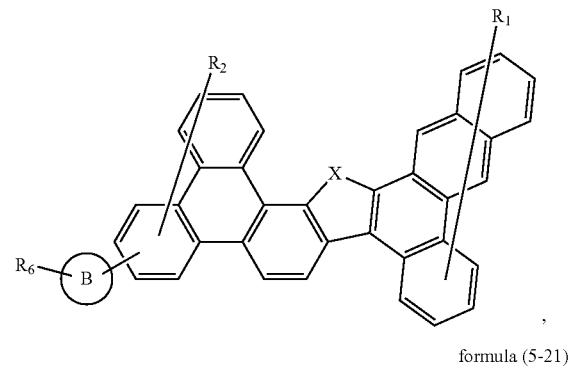
formula (5-21)
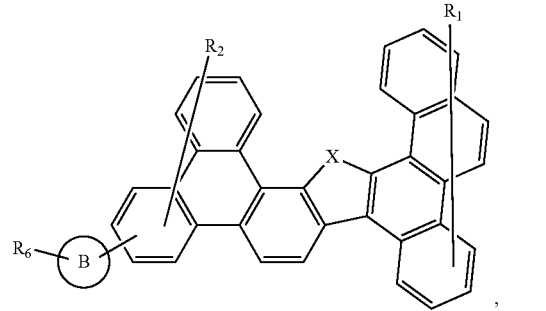
formula (5-22)
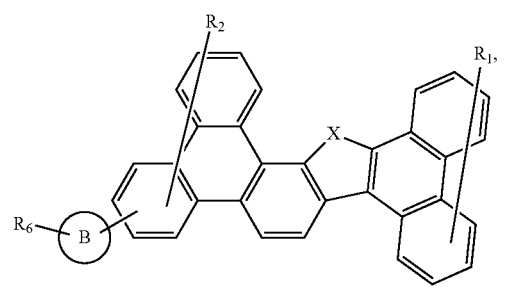
formula (5-23)

formula (6-1)
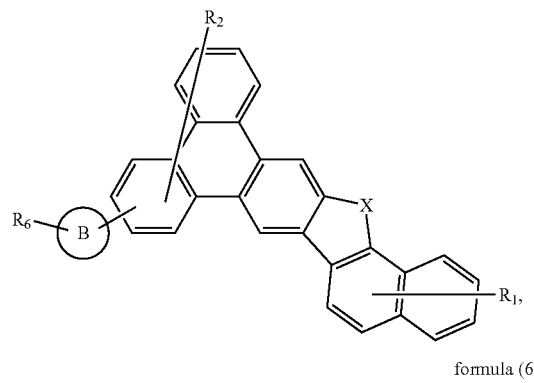
formula (6-2)
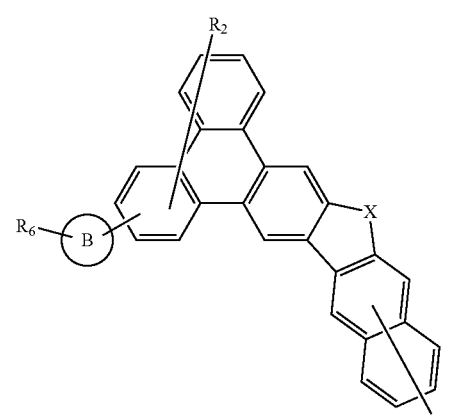
formula (6-3)
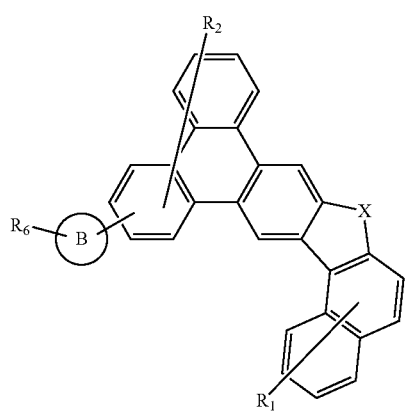
formula (6-4)
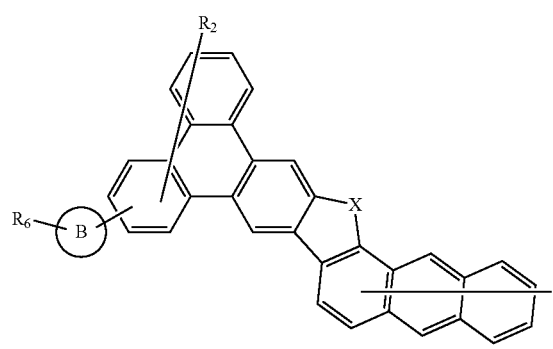
formula (6-5)
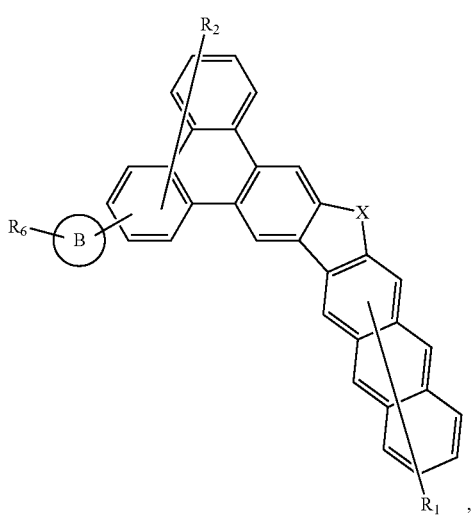
formula (6-6)
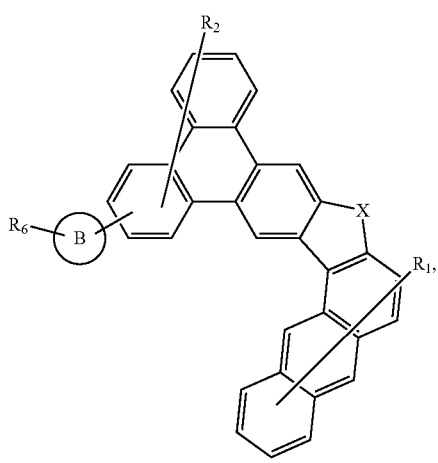
formula (6-7)
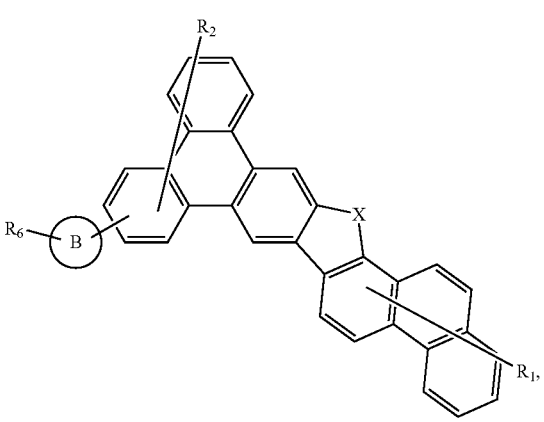

formula (6-8)
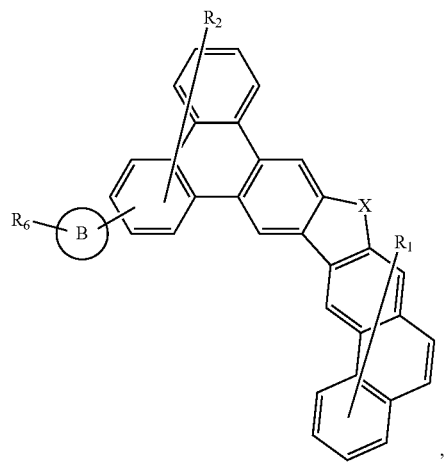
formula (6-9)
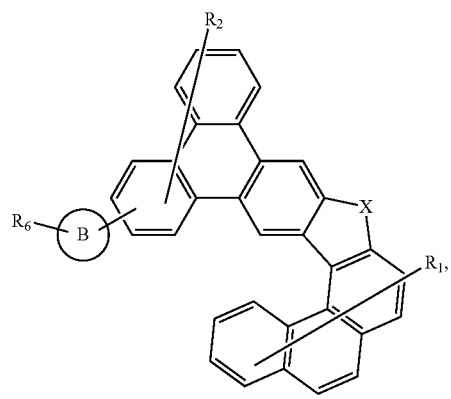
formula (6-10)
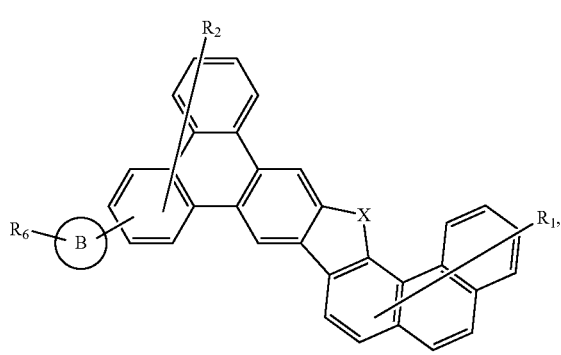
formula (6-11)
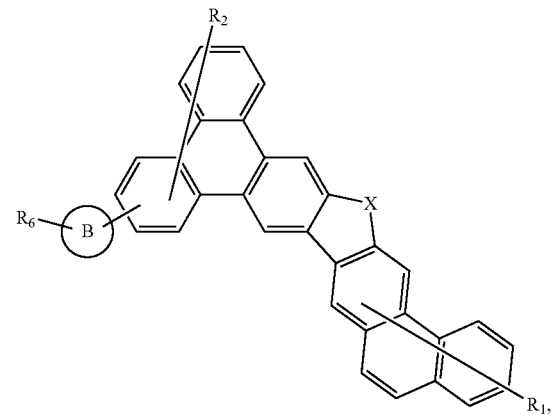
formula (6-12)
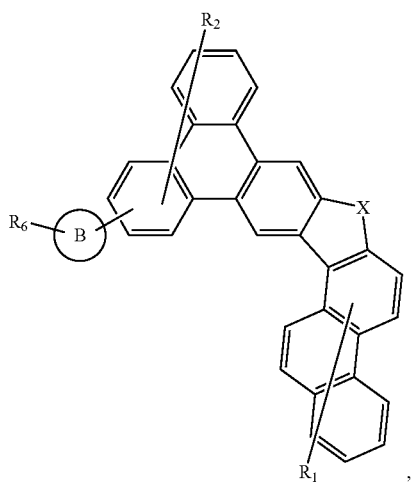
formula (6-13)
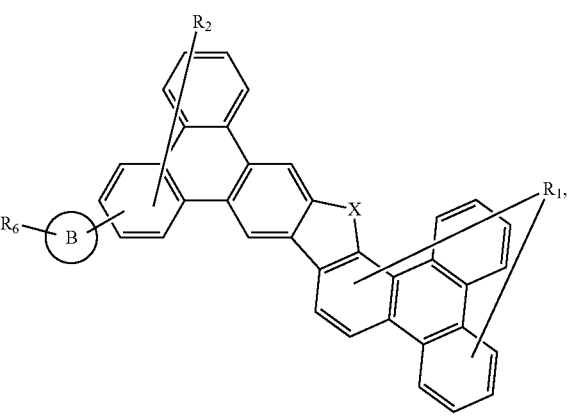

formula (6-14)
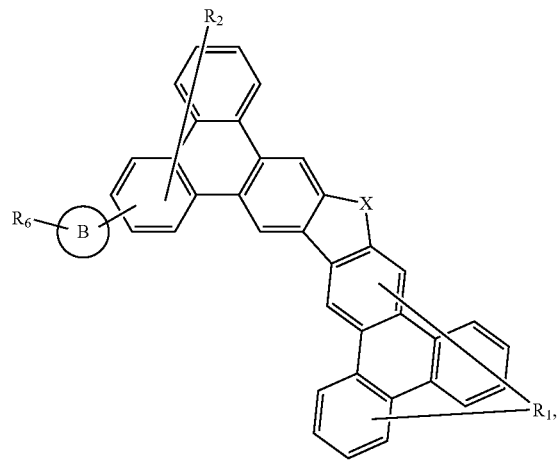
formula (6-15)
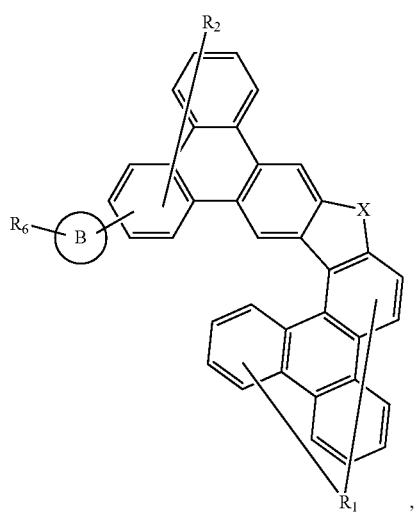
formula (6-16)
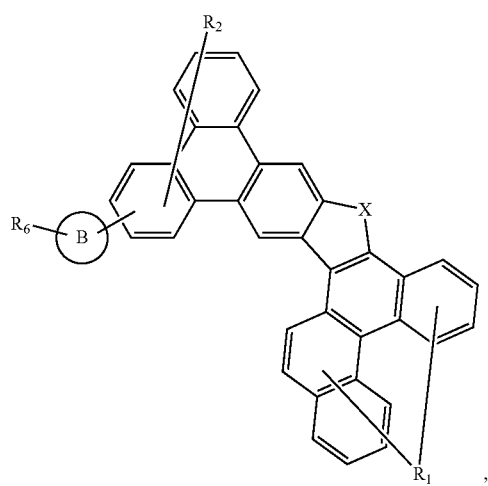
formula (6-17)
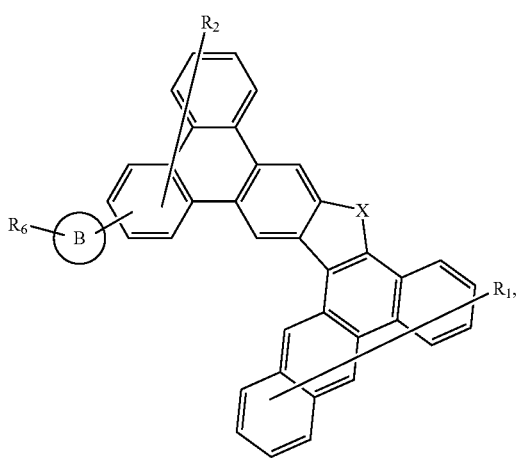
formula (6-18)
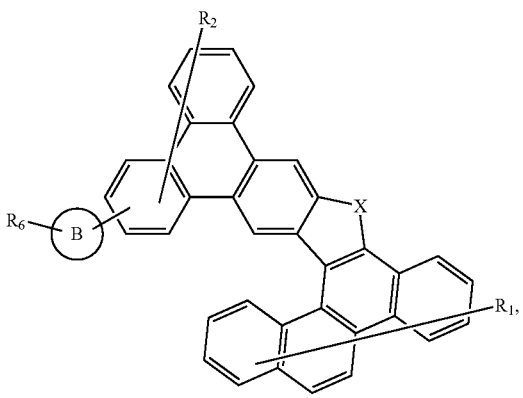
formula (6-19)
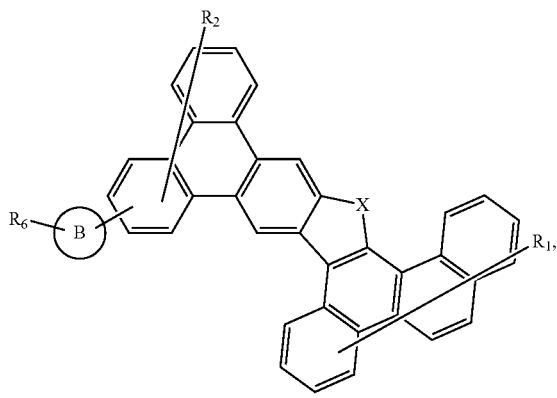

formula (6-20)
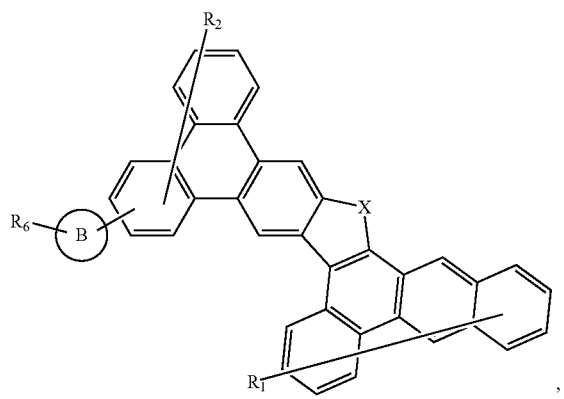
,
formula (6-21)
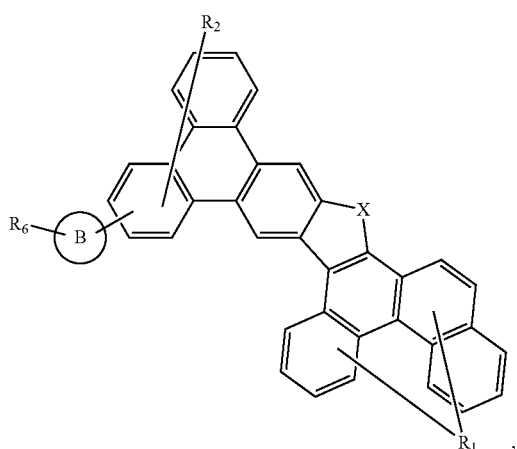
,
formula (6-22)
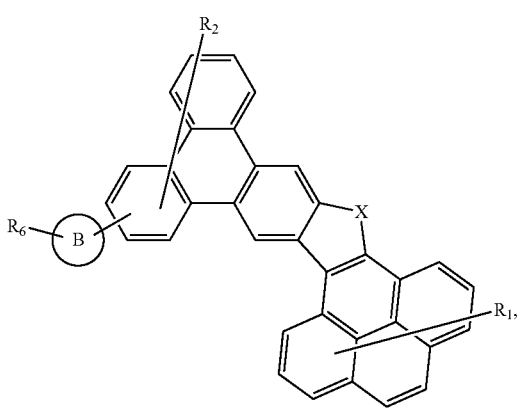
,
formula (6-23)
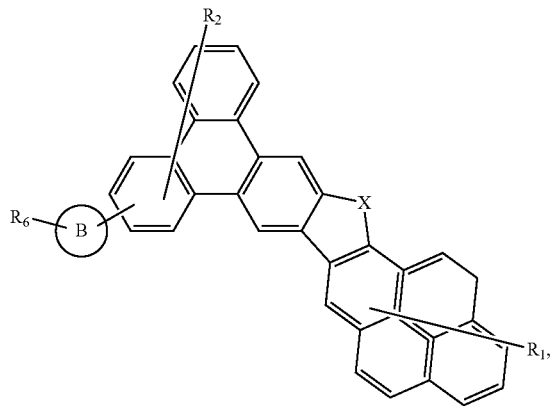
,
formula (6-24)
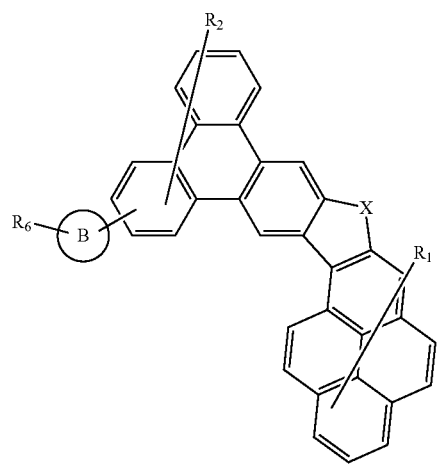
,
formula (6-25)
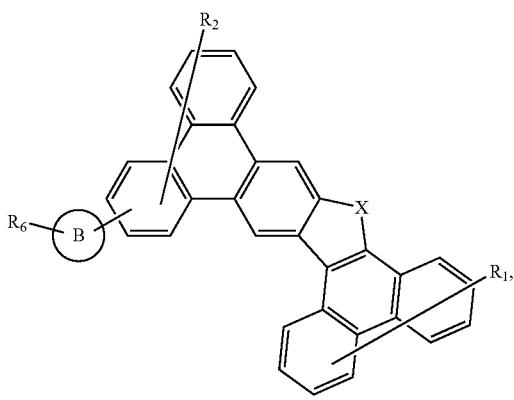
, formula (6-26)
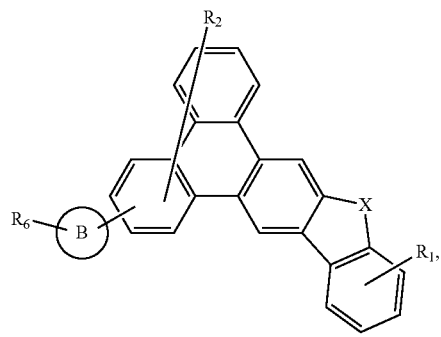
formula (7-1)
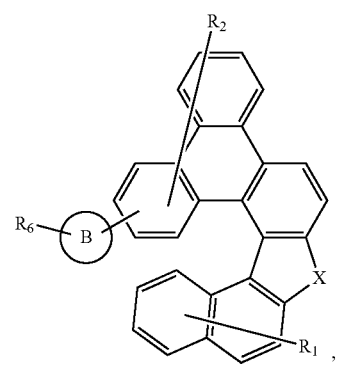
formula (7-2)
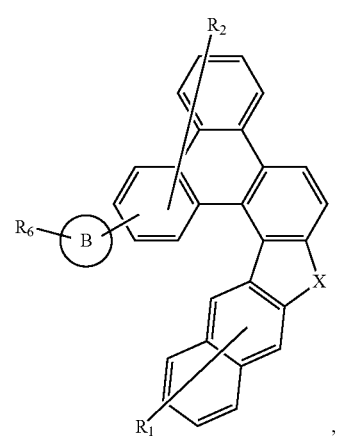
formula (7-3)
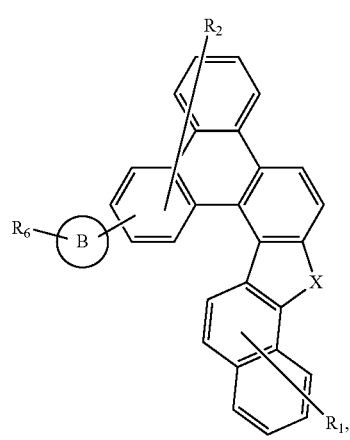
formula (7-4)
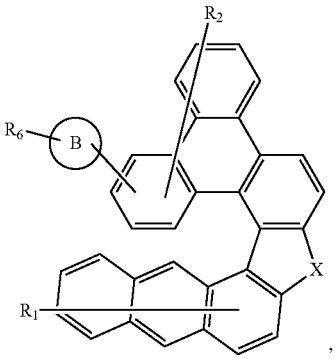
formula (7-5)
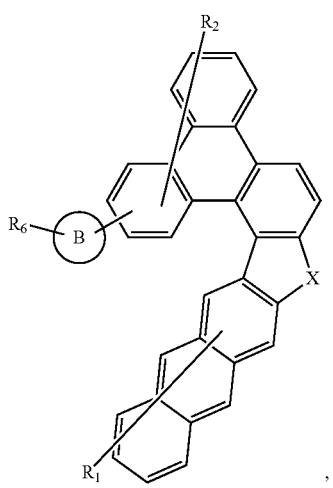
formula (7-6)
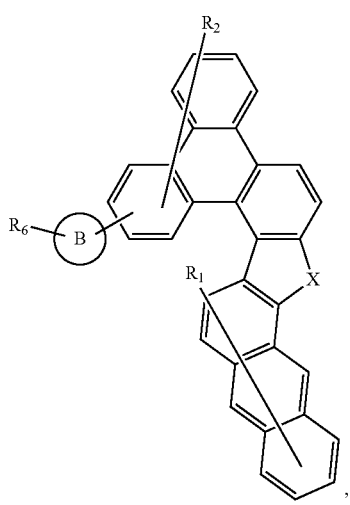

formula (7-7)
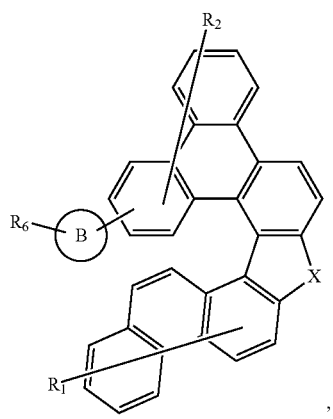
formula (7-8)
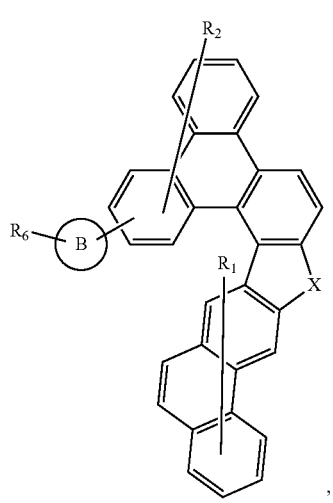
formula (7-9)
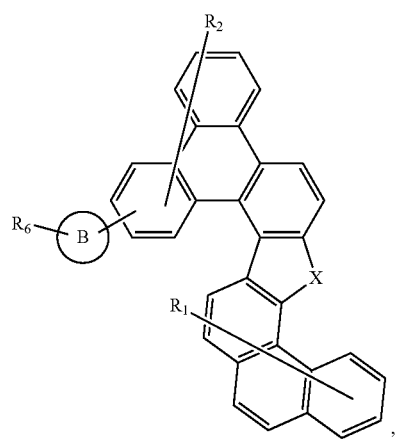
formula (7-10)
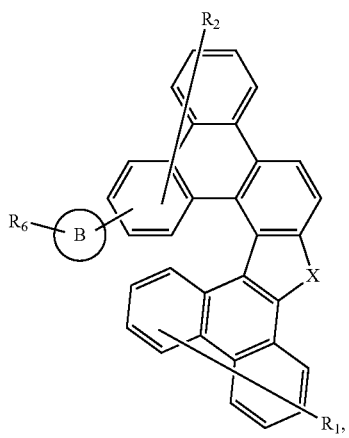
formula (7-11)
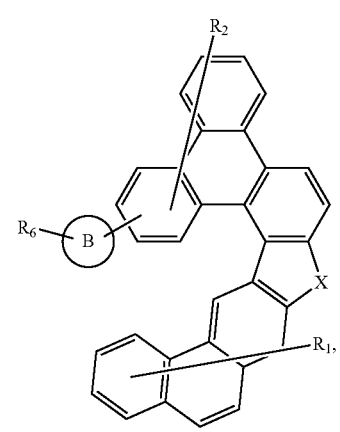
formula (7-12)
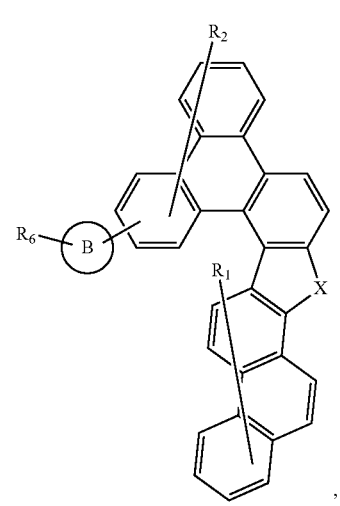

-continued
formula (7-13)
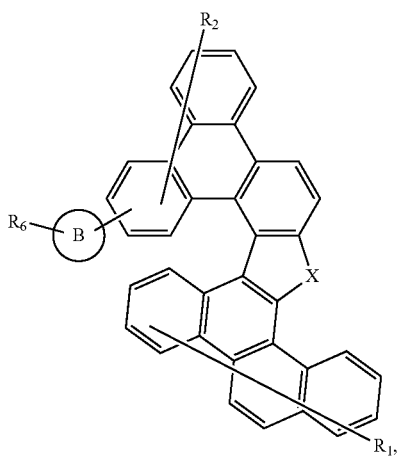
formula (7-14)
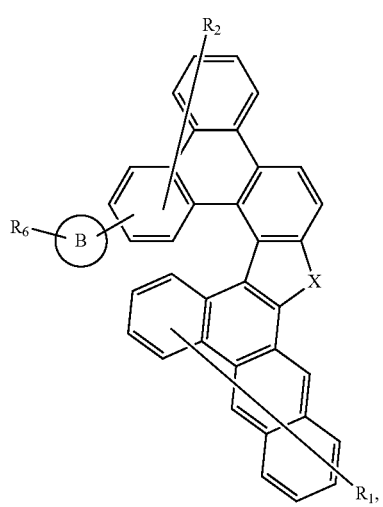
formula (7-15)
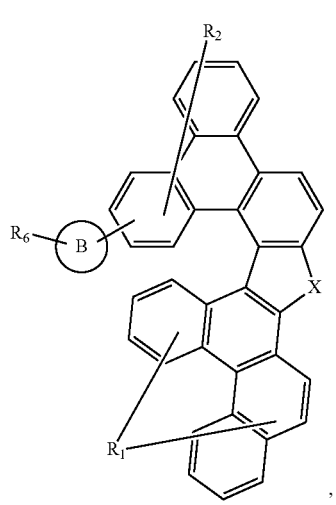
formula (7-16)
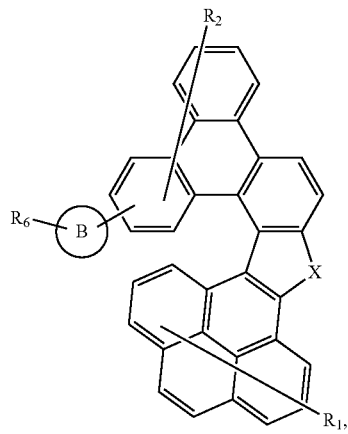
formula (7-17)
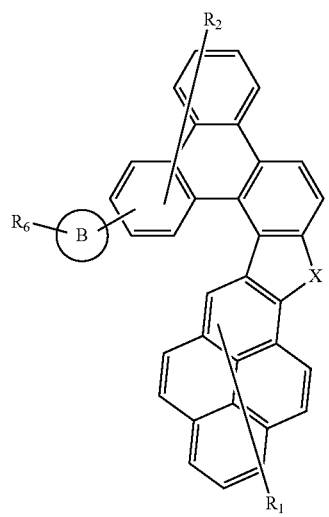
formula (7-18)
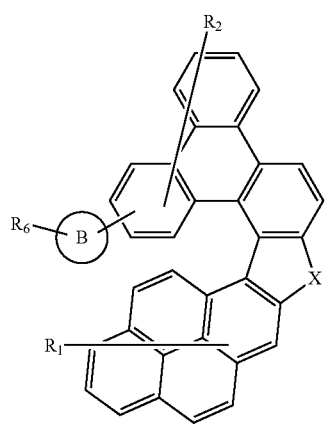

formula (7-19)
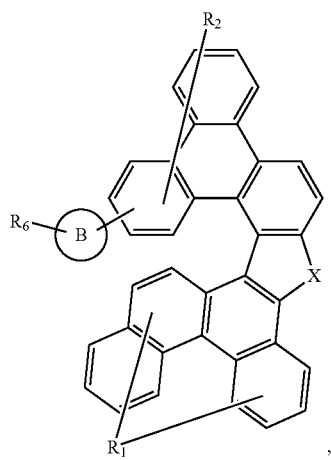
formula (7-20)
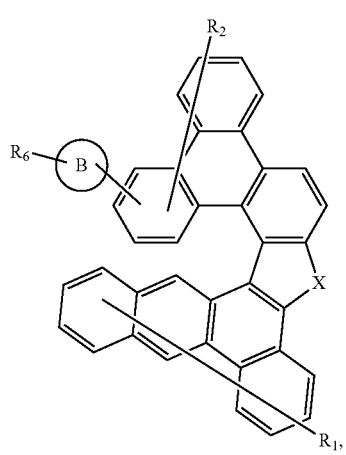
formula (7-21)
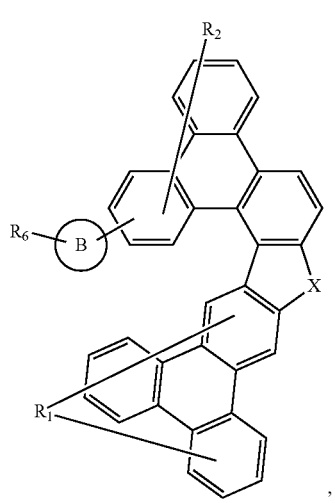
formula (7-22)
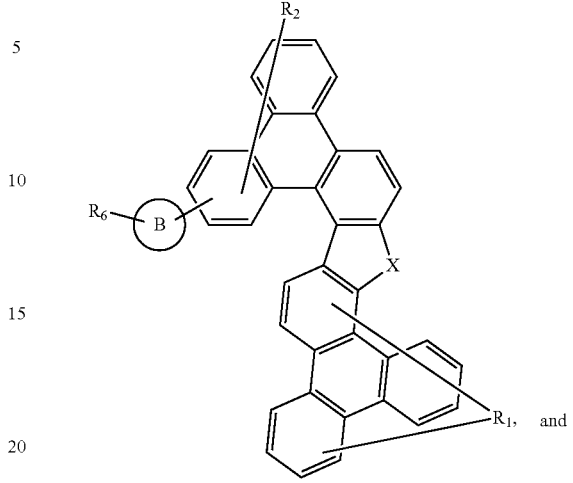, and
formula (7-23)
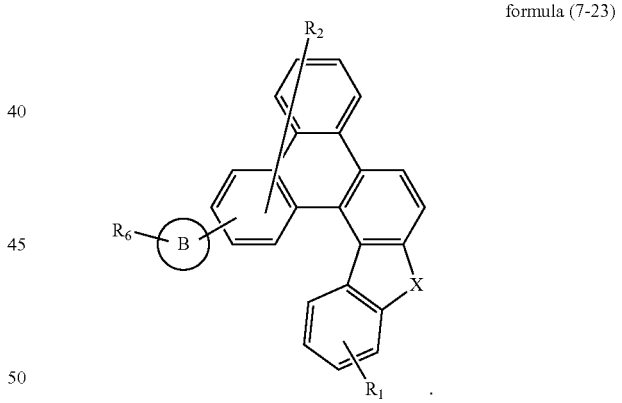
In one embodiment, the organic compound of the present invention may not have one of the following formulae:

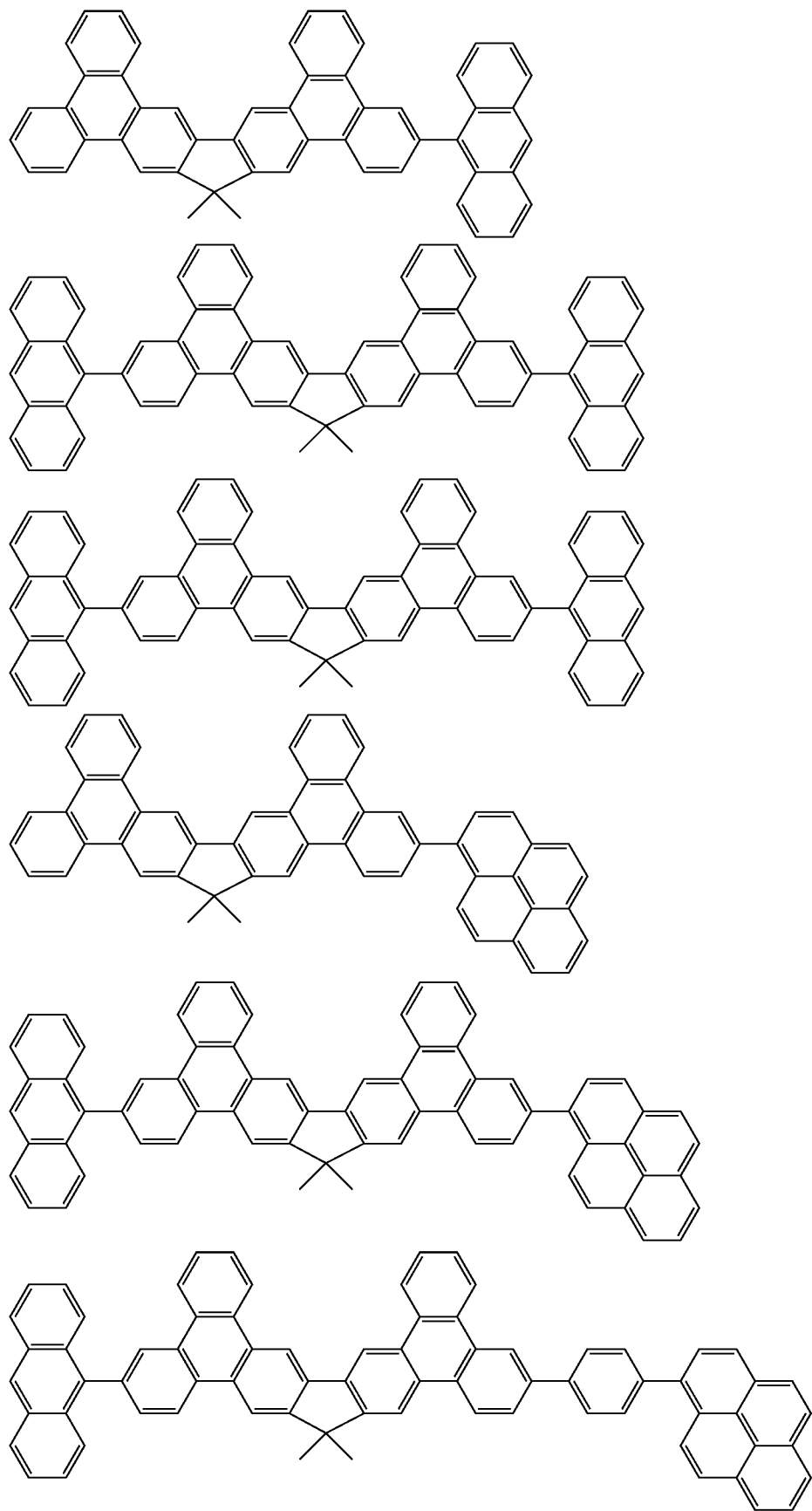

-continued

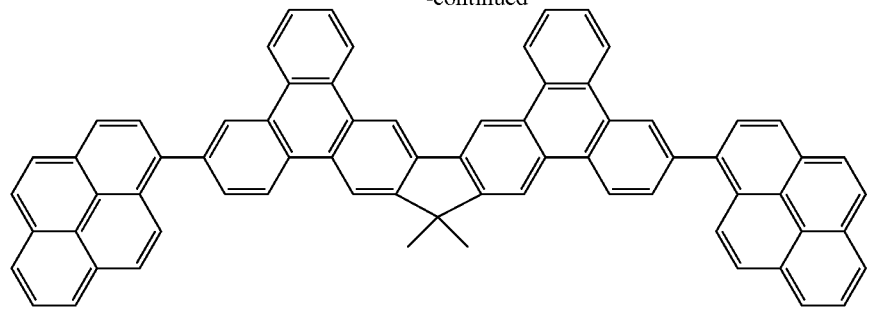

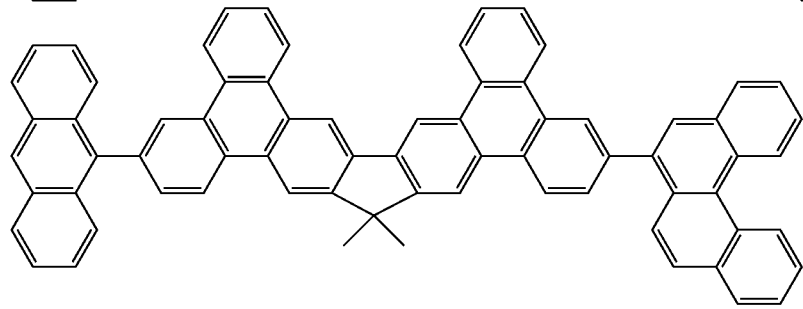

In one embodiment, the formula (3-24) does not comprise the following formulae:

formula (3-24-1)

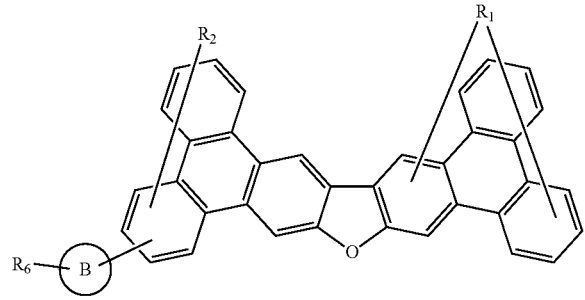

formula (3-24-2)

[formula 3-24-2 structure]

-continued formula (3-24-3)

[formula 3-24-3 structure]

formula (3-24-4)

[formula 3-24-4 structure]

In other words, the organic compound of the present invention may not have any one of the above four formulas.

In selected embodiments, ring B preferably comprises an unsubstituted aryl group having 6 to 50 carbon atoms.

In selected embodiments, ring B is an aromatic linker selected from the group consisting of a single aromatic hydrocarbyl, two joined aromatic hydrocarbyls, three joined aromatic hydrocarbyls, and four joined aromatic hydrocarbyls.

If ring B is a single aromatic hydrocarbyl, the single aromatic hydrocarbyl may be one of the following substituents:

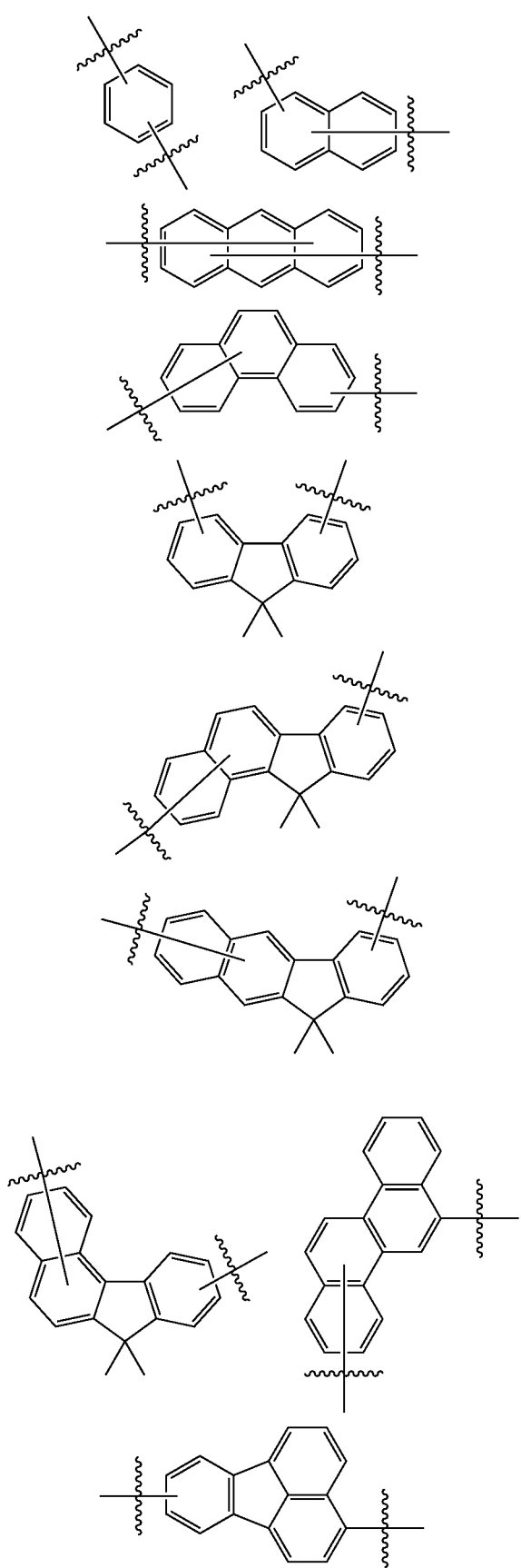
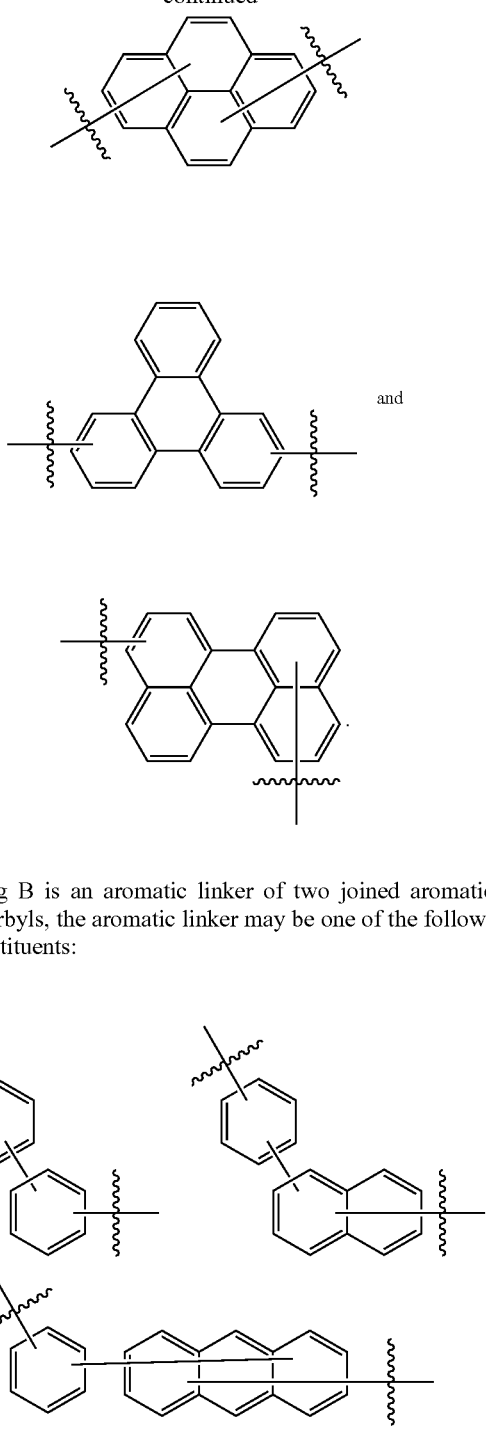
If ring B is an aromatic linker of two joined aromatic hydrocarbyls, the aromatic linker may be one of the following substituents:
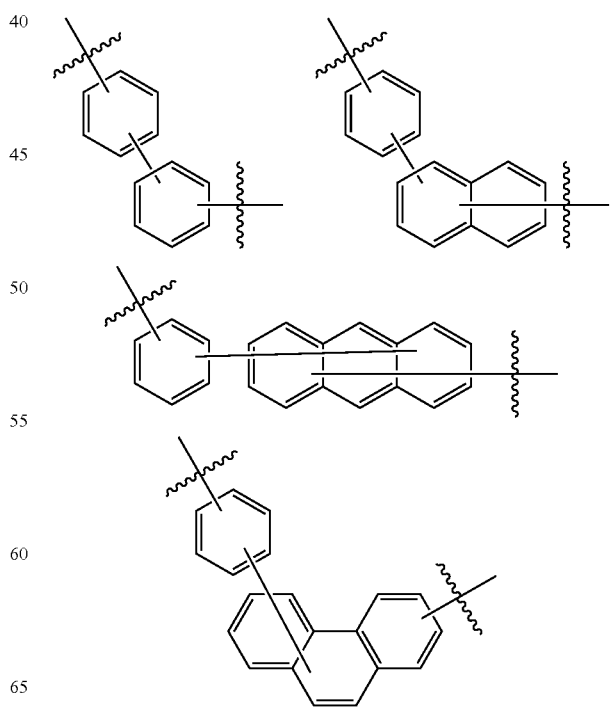

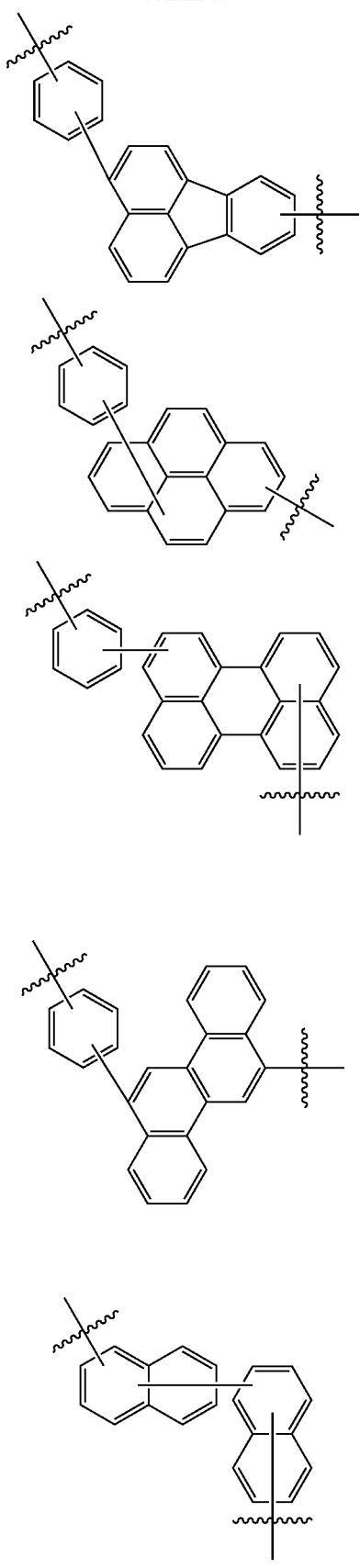
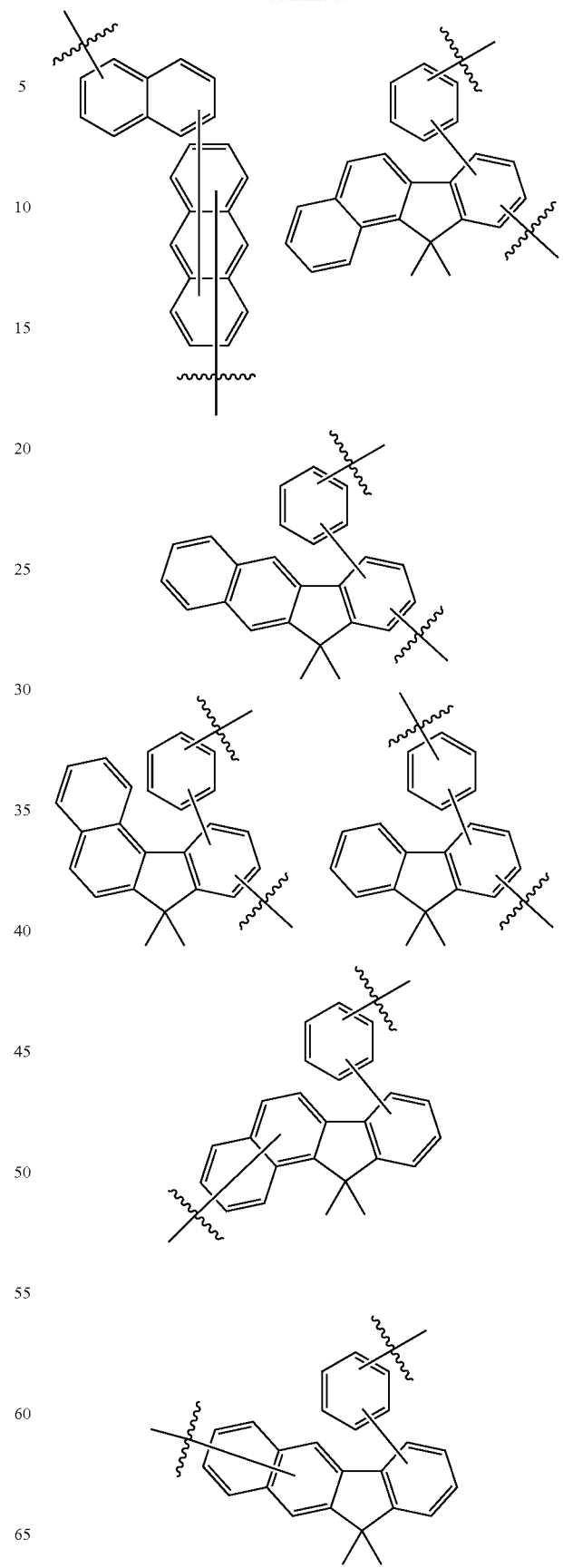

61
-continued
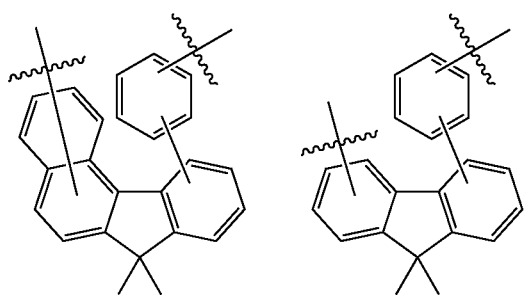
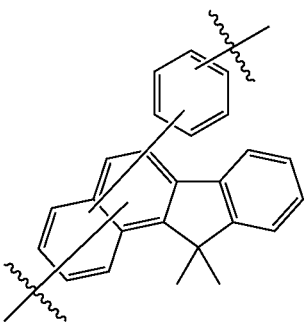
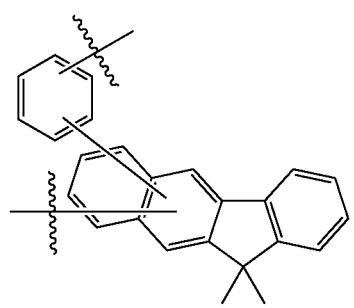
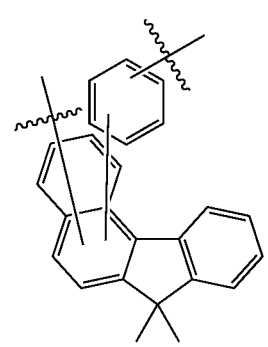
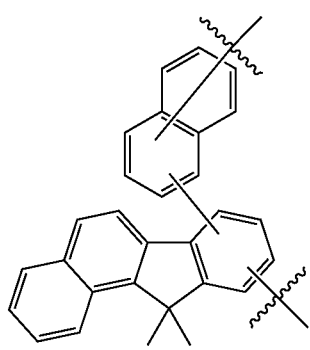
62
-continued
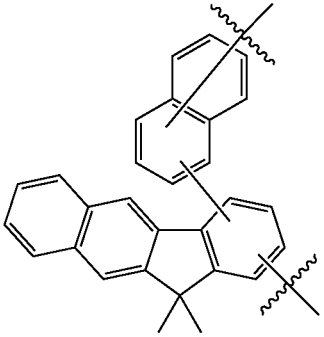
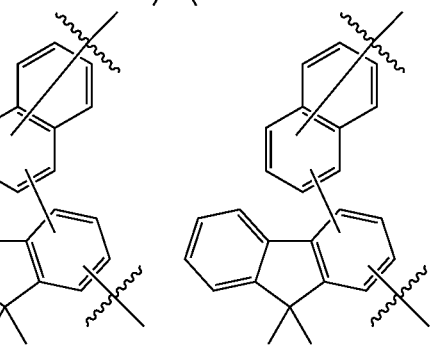
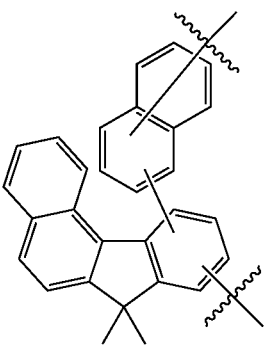
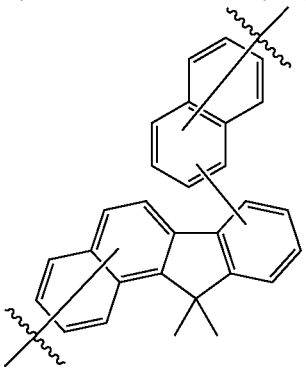
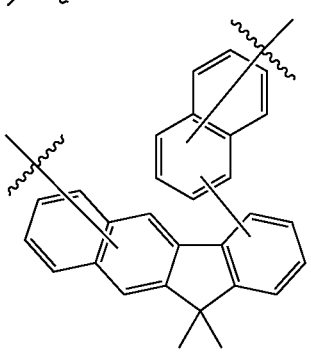
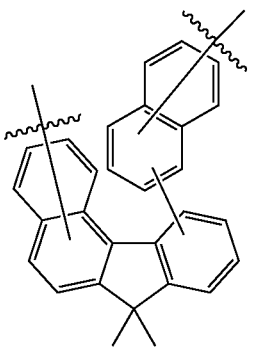
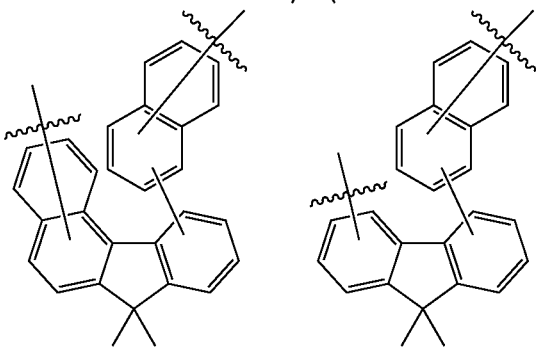

63
-continued
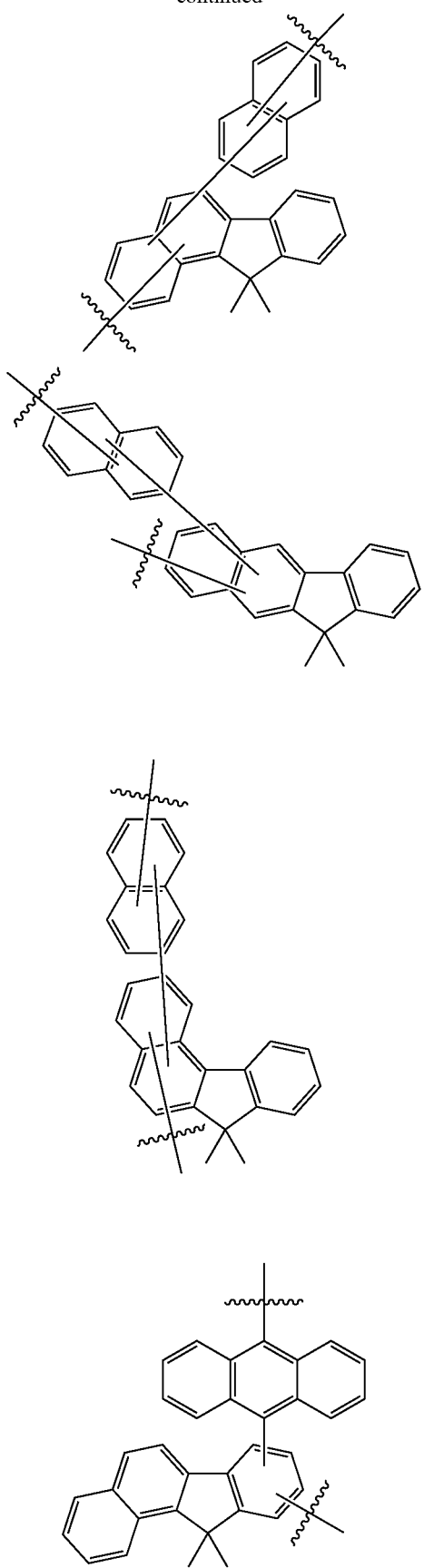
64
-continued
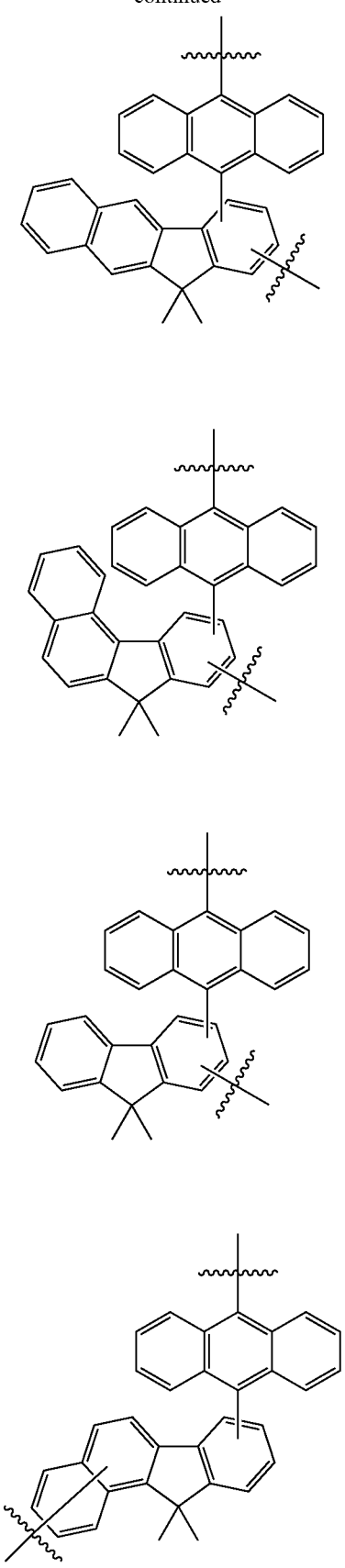

65
-continued
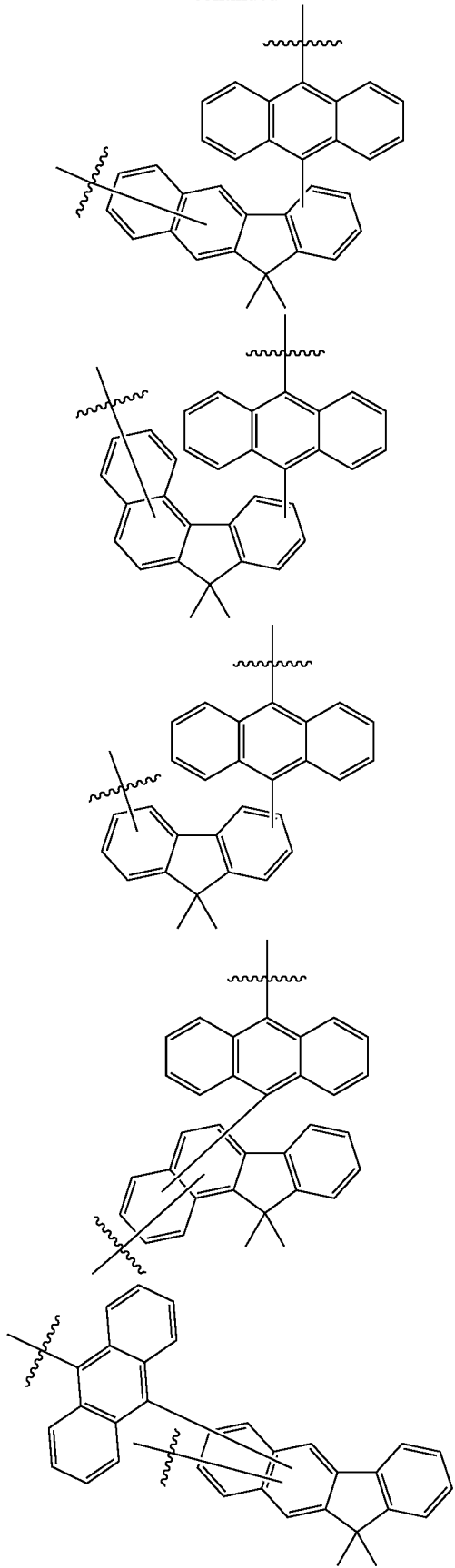
66
-continued
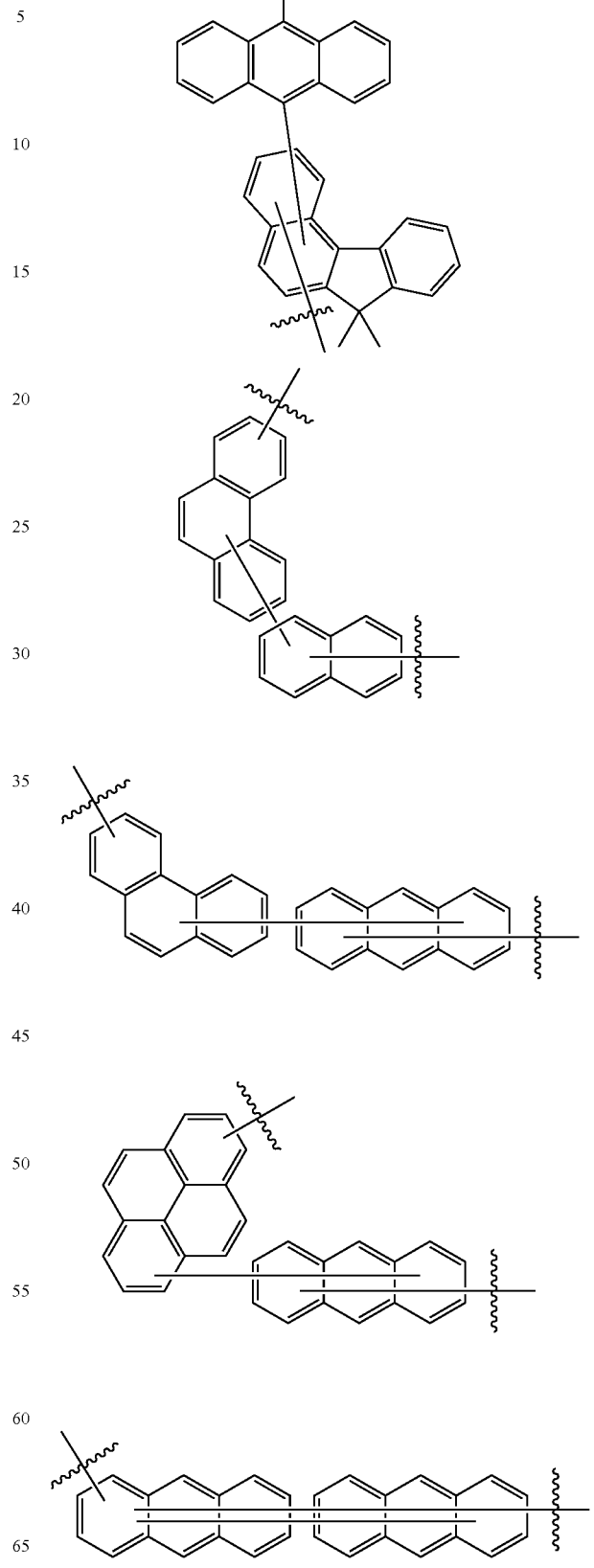

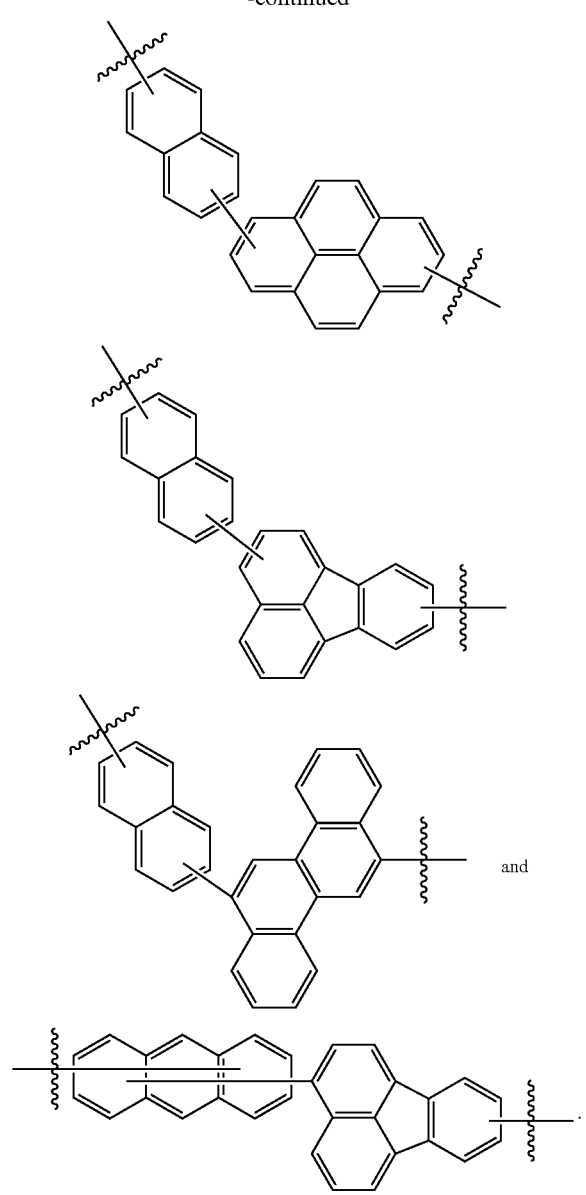
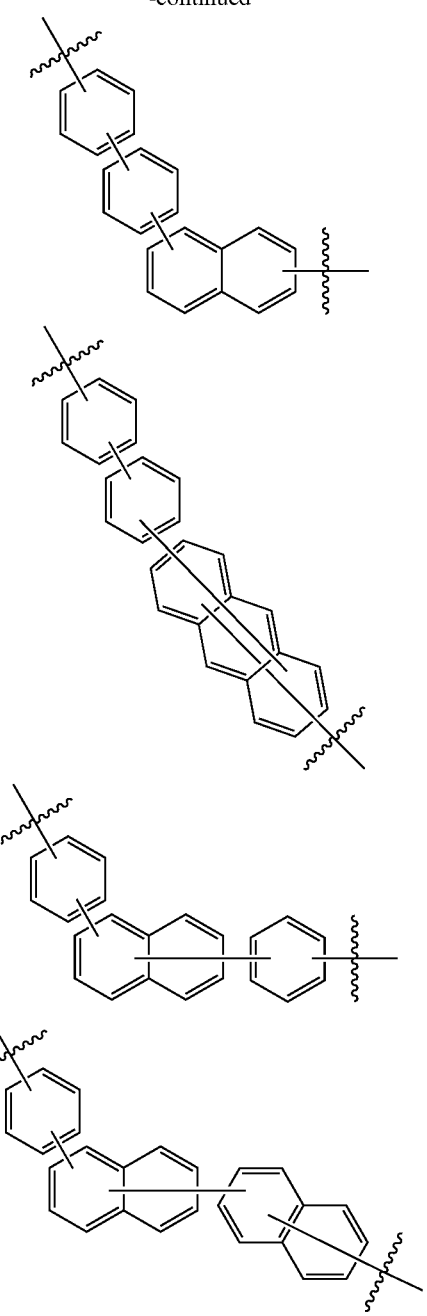
If ring B is an aromatic linker of three joined aromatic hydrocarbyls, the aromatic linker may be one of the following substituents:
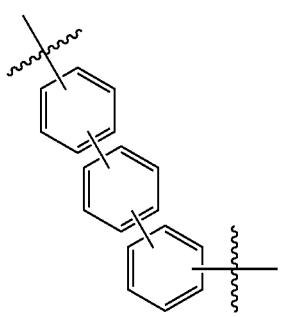
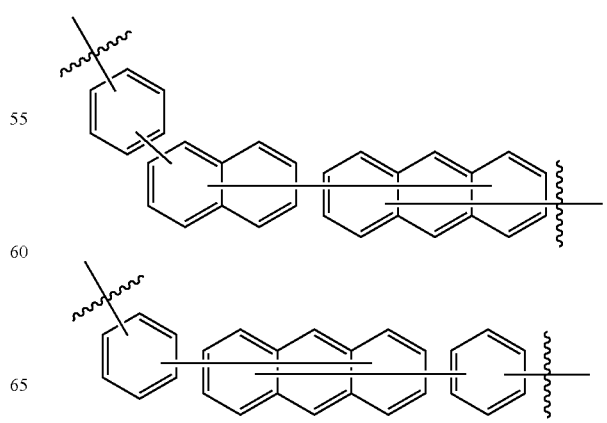

-continued
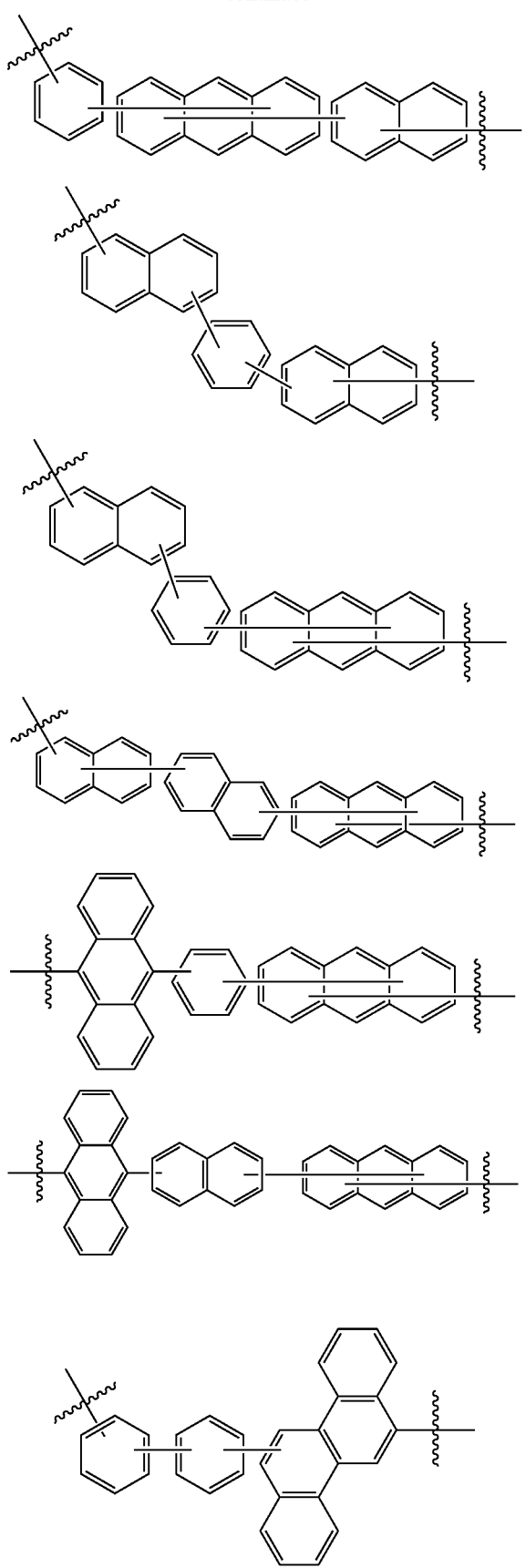
-continued
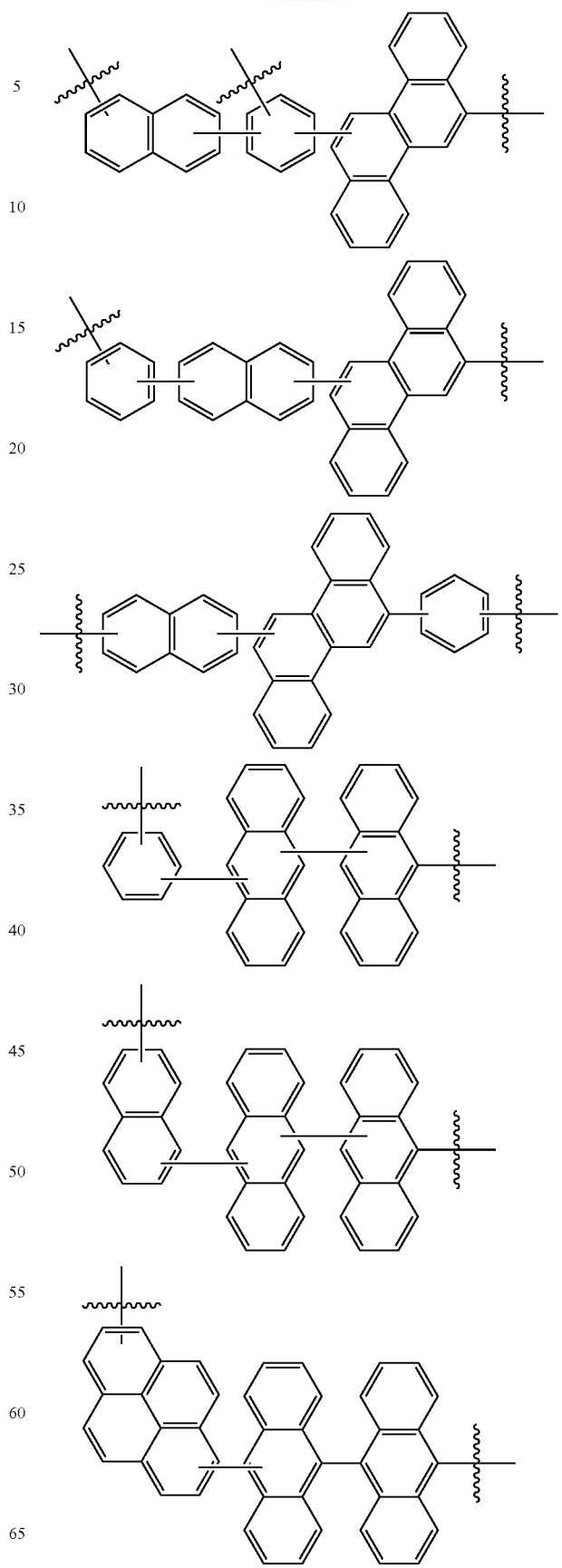

-continued
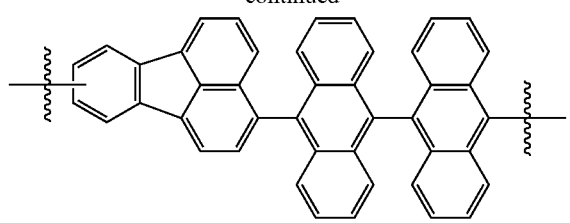
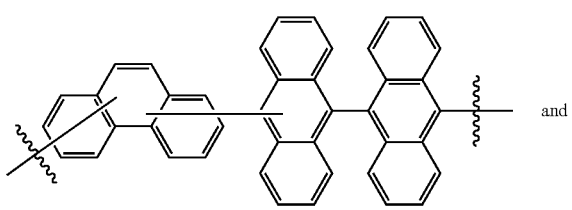
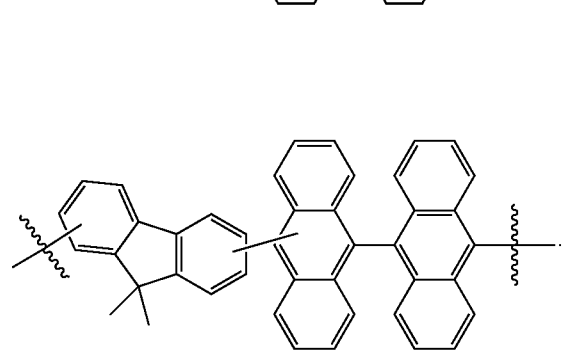
If ring B is an aromatic linker of four joined aromatic hydrocarbyls, the aromatic linker may be one of the following substituents:
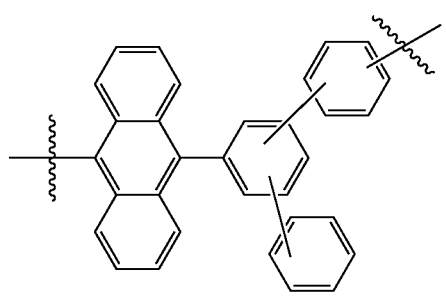
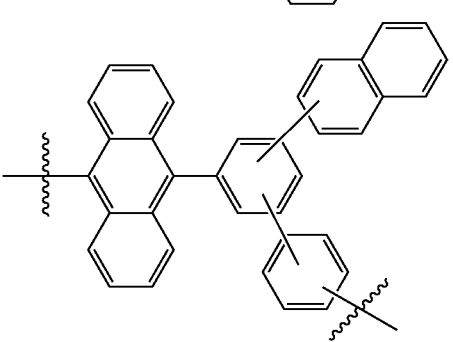
-continued
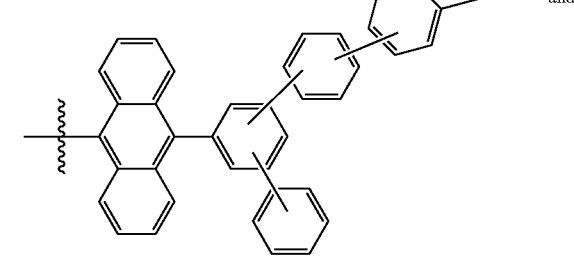
and
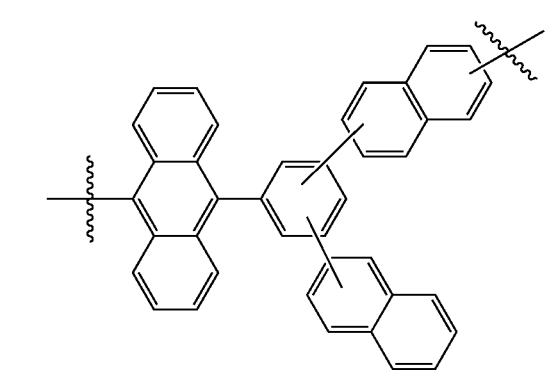
If ring B is an aromatic linker of five joined aromatic hydrocarbyls, the aromatic linker may be one of the following substituents:
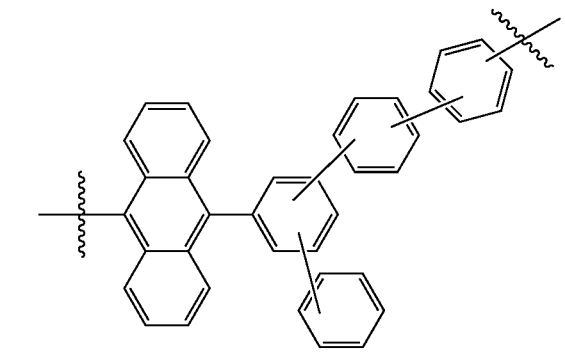
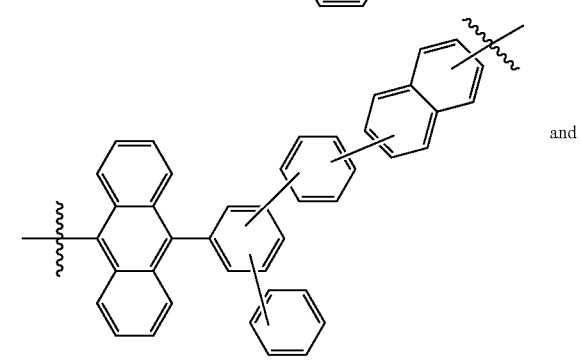
and

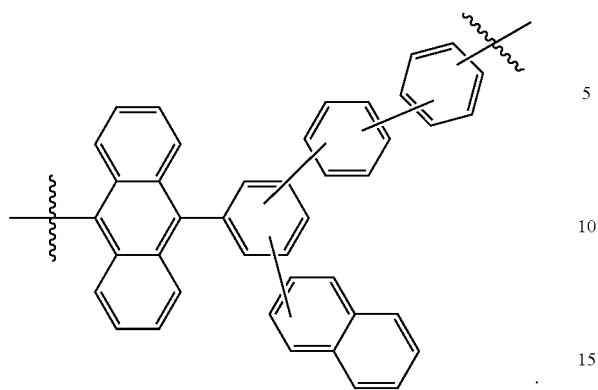
The selected compounds of formula (1) of interest may be selected from the group consisting of
Compound 1
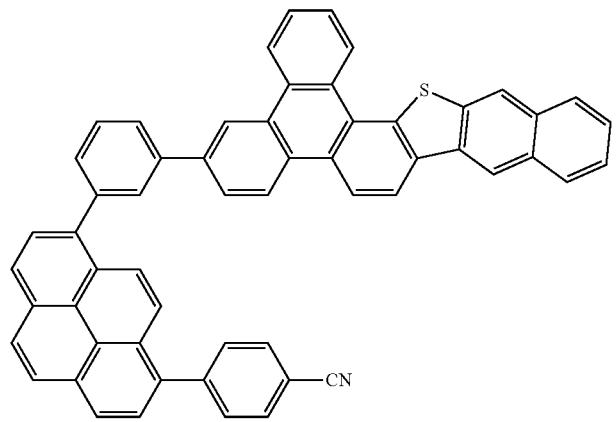
Compound 2
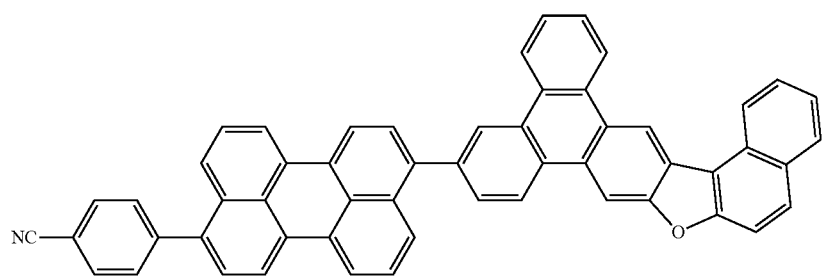
Compound 3
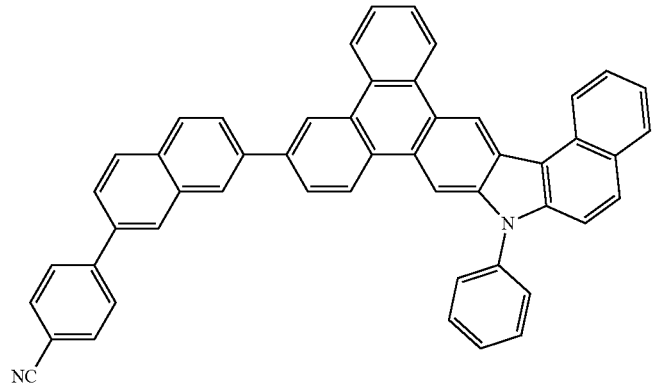

Compound 4
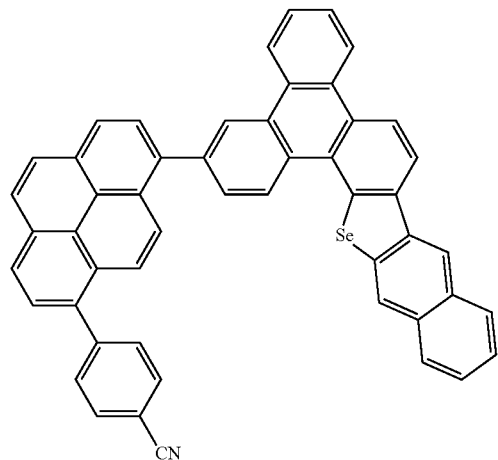
Compound 5
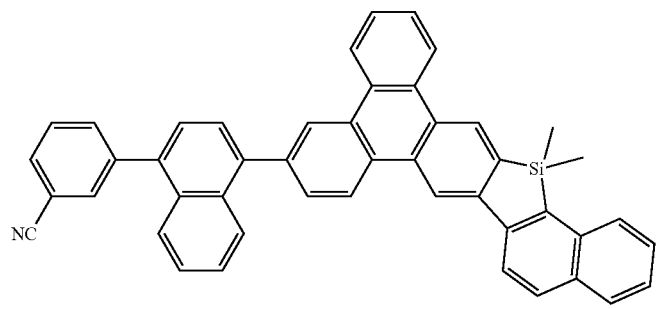
Compound 6
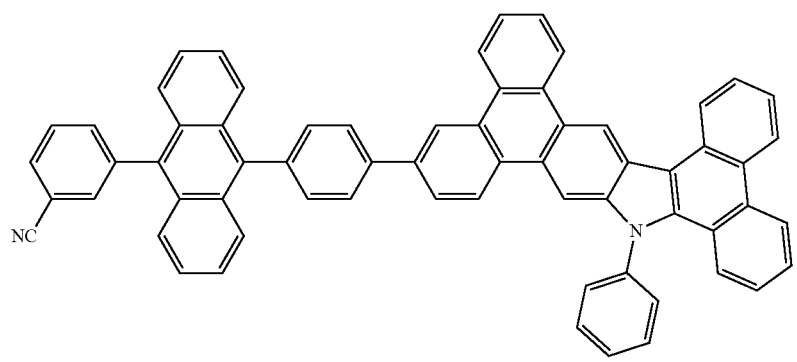
Compound 7
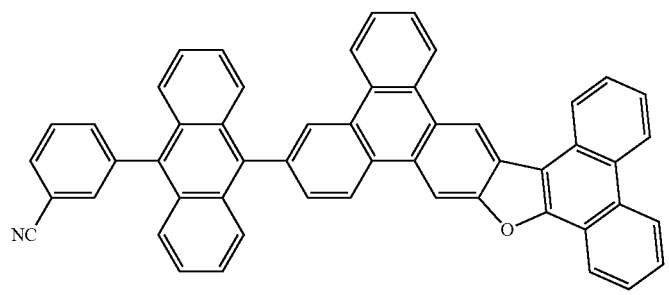

-continued
Compound 8
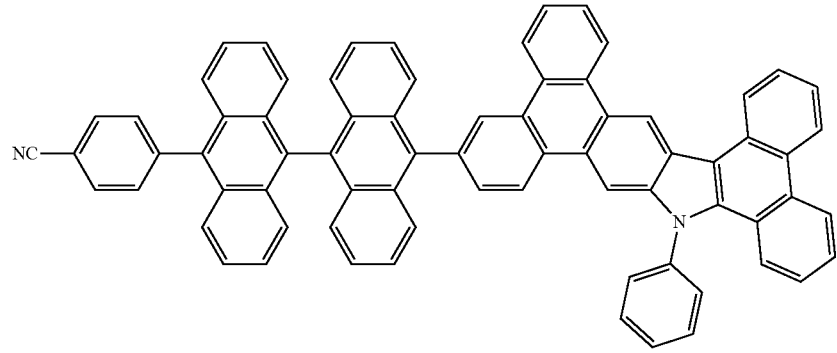
Compound 9
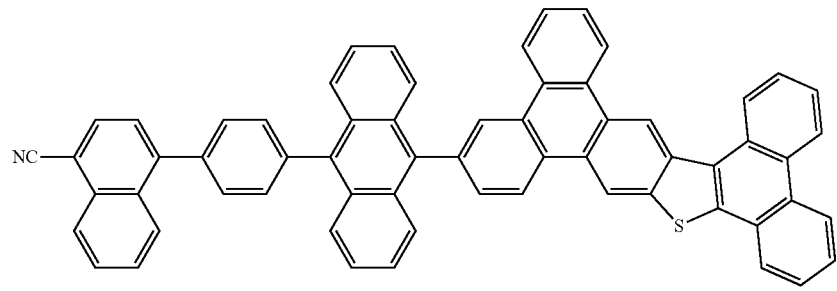
Compound 10
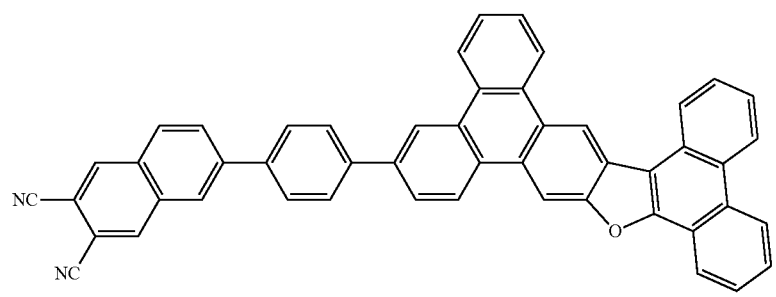
Compound 11
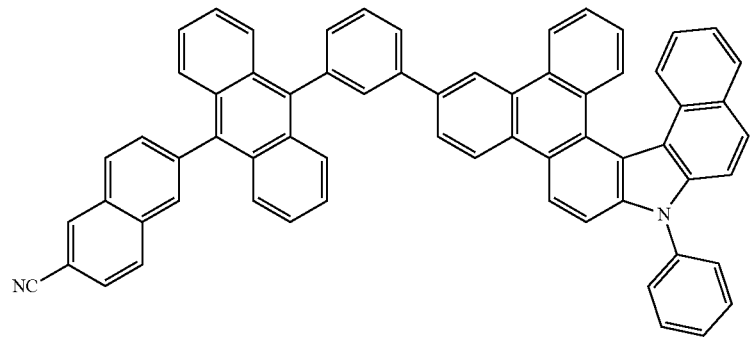
Compound 12
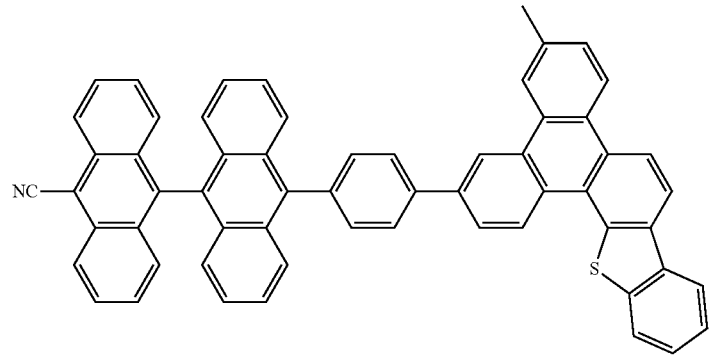

Compound 13
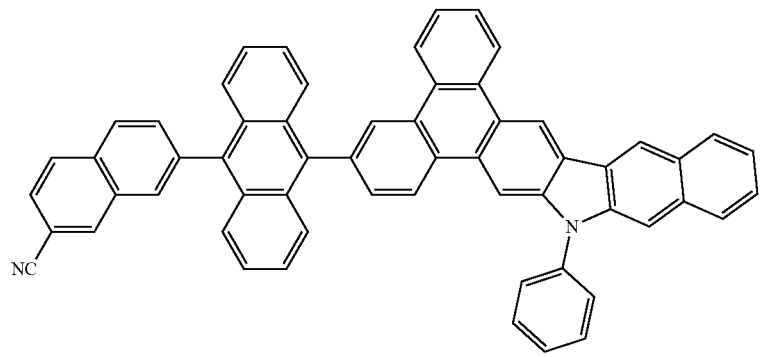
Compound 14
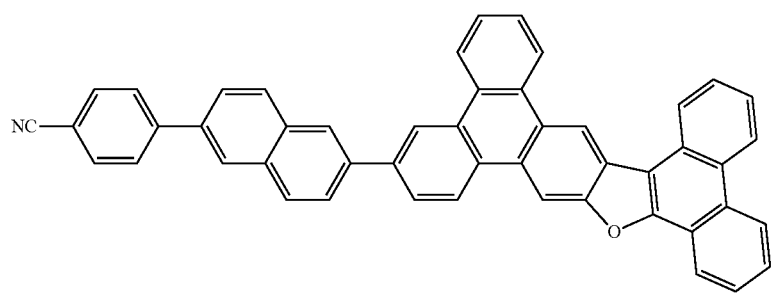
Compound 15
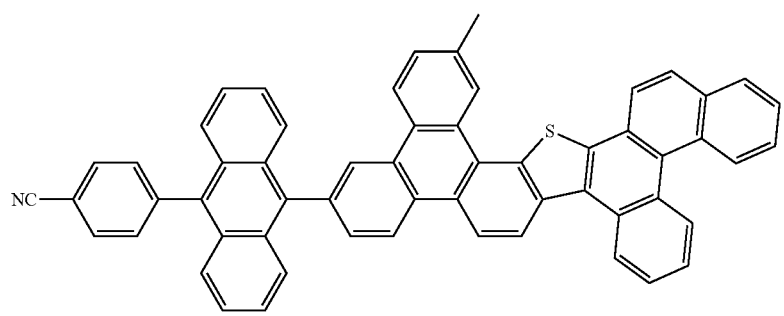
Compound 16
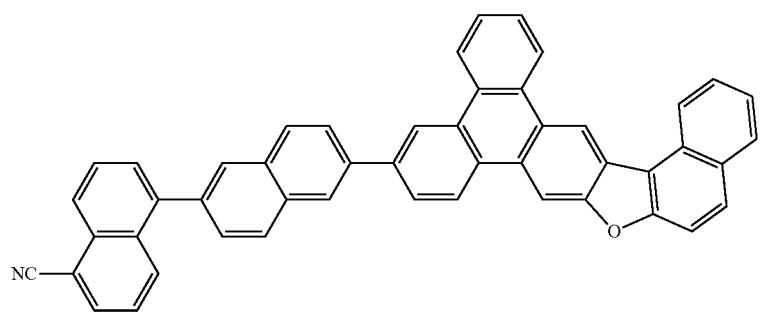

Compound 17
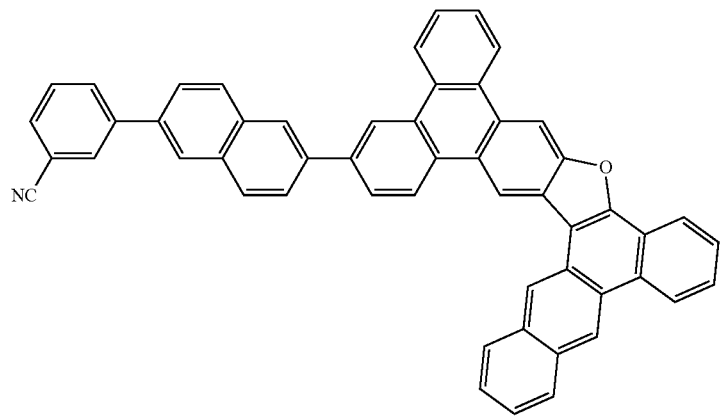
Compound 18
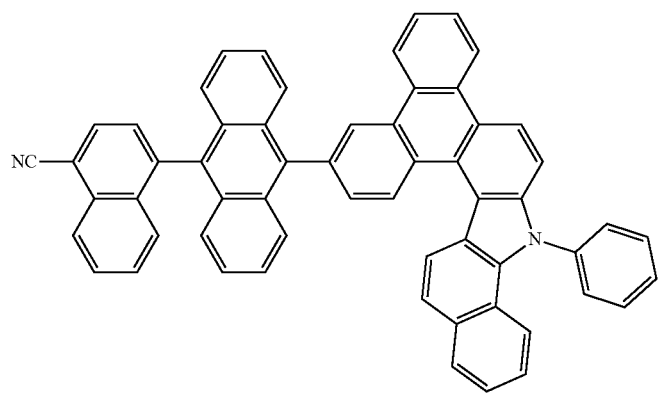
Compound 19
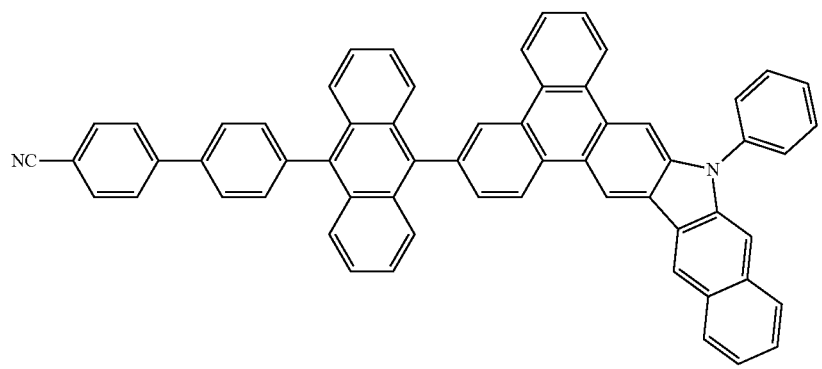
Compound 20
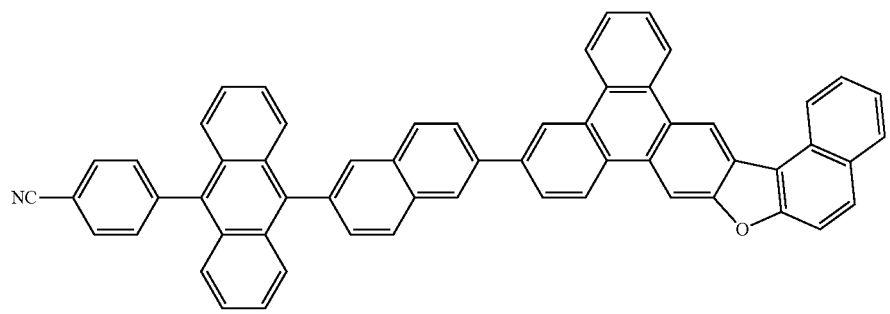

Compound 21
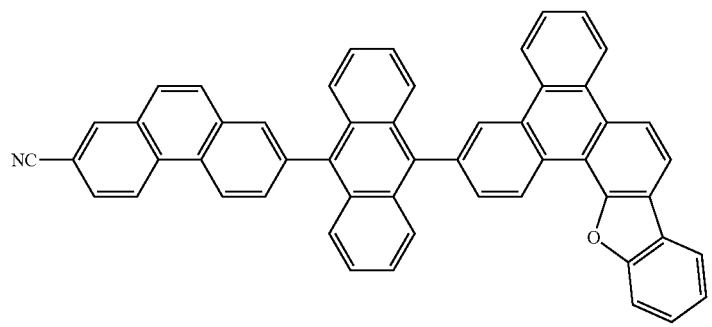
Compound 22
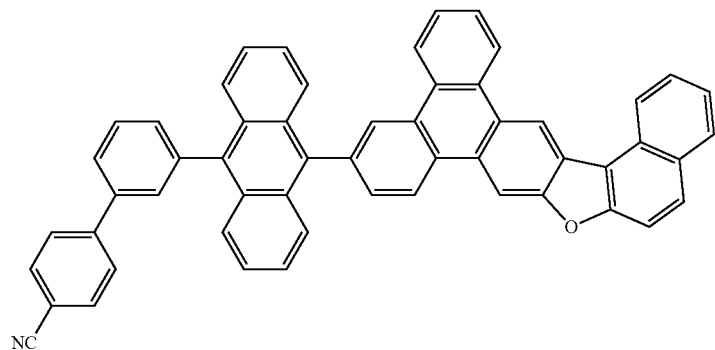
Compound 23
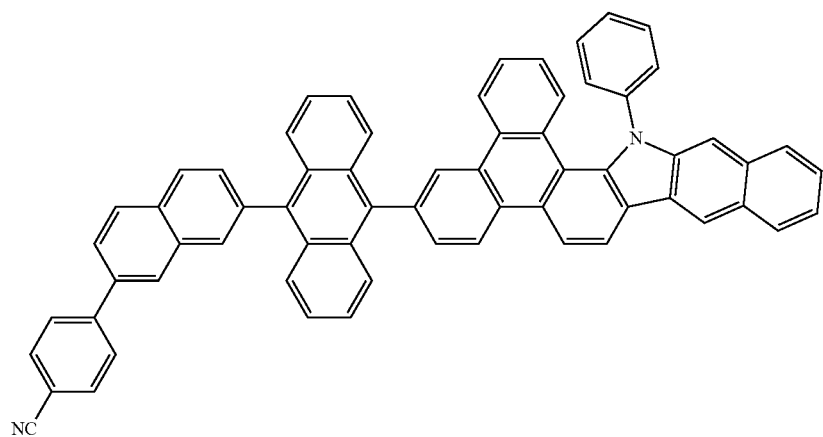
Compound 24
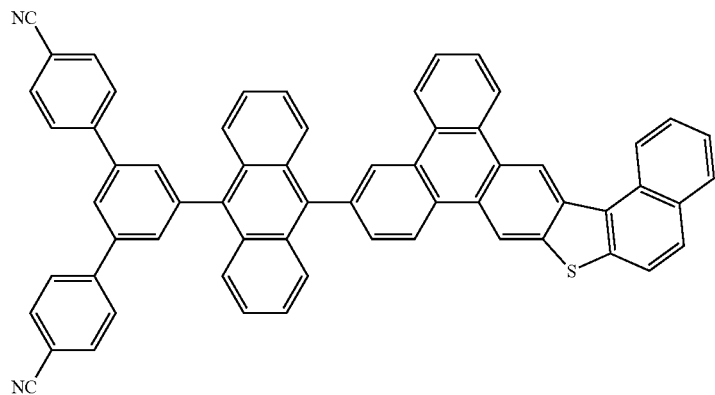

-continued
Compound 25
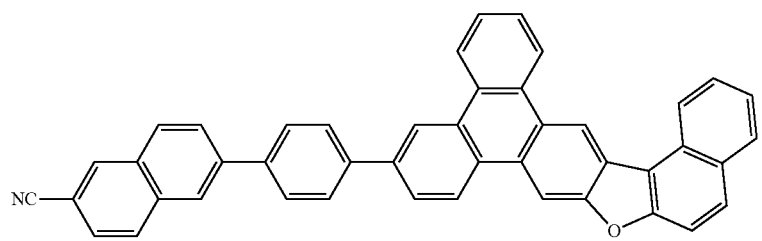
Compound 26
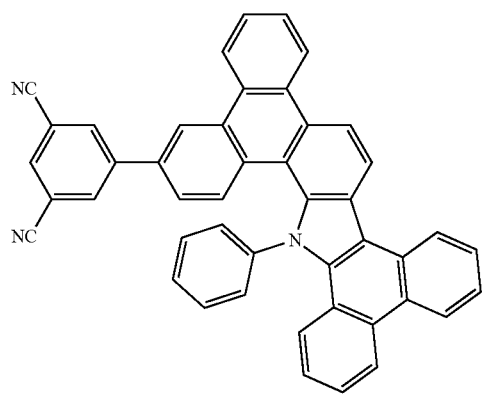
Compound 27
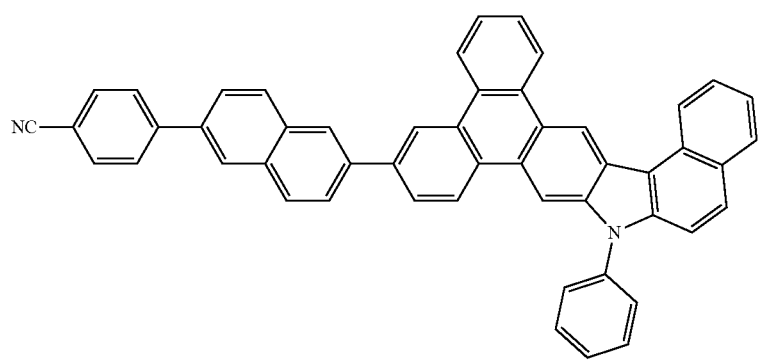
Compound 28
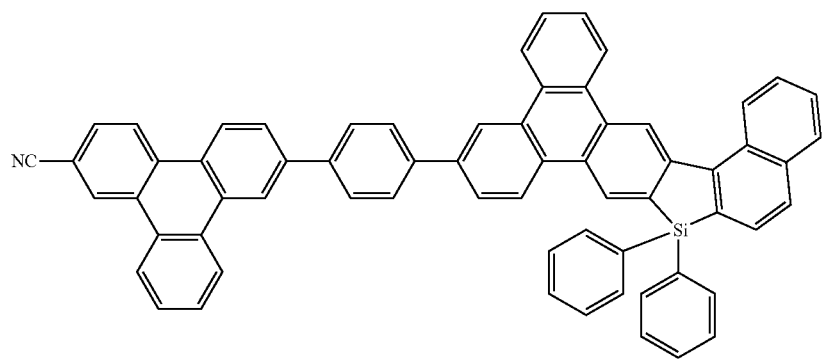
Compound 29
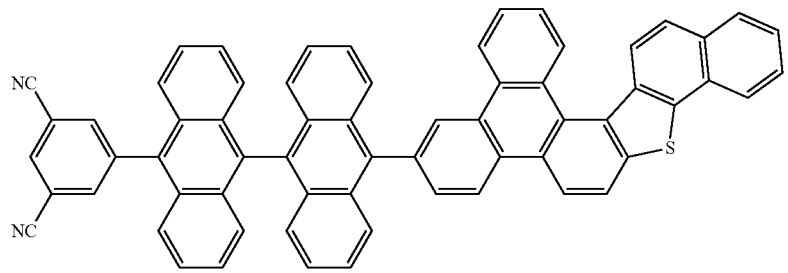

Compound 30
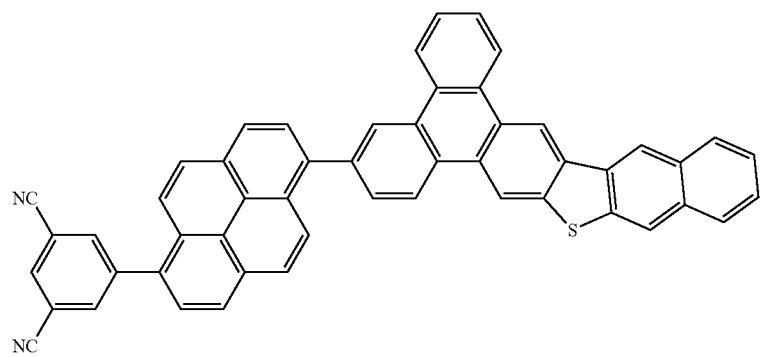
Compound 31
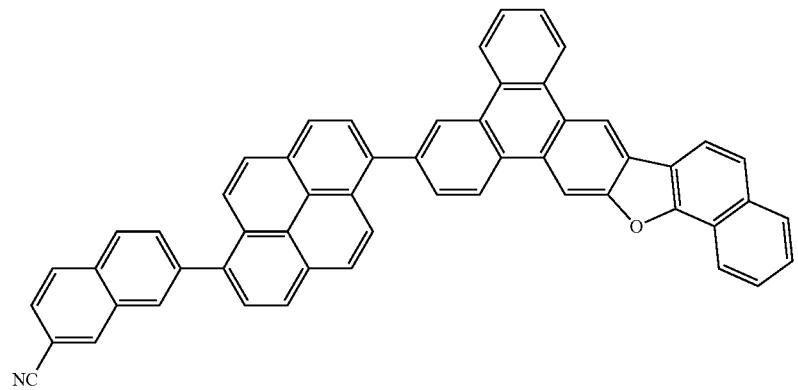
Compound 32
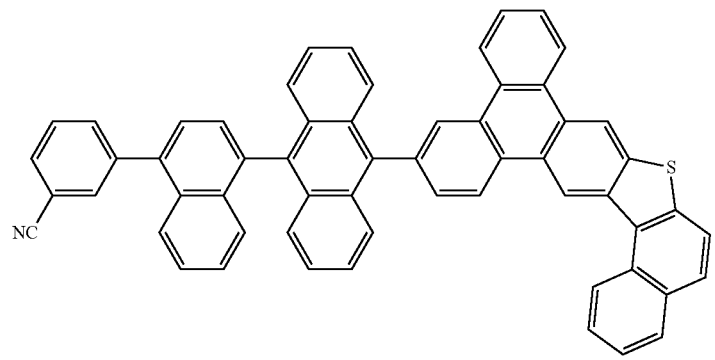
Compound 33
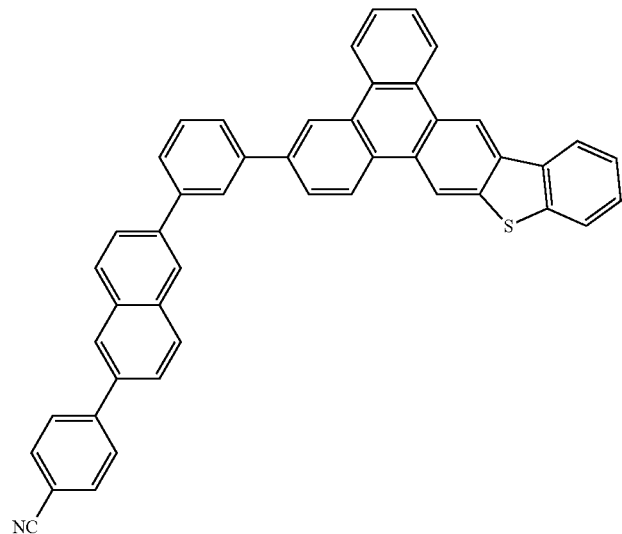

Compound 34
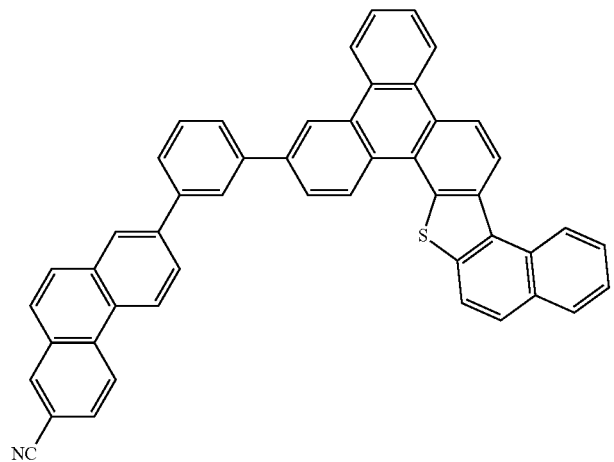
Compound 35
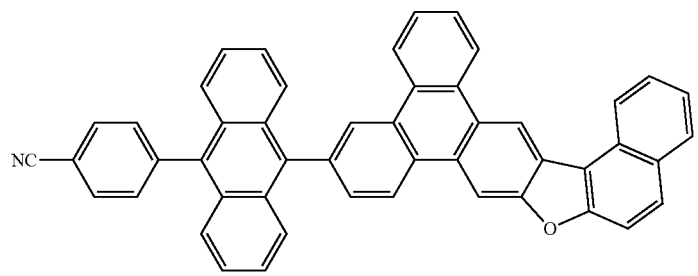
Compound 36
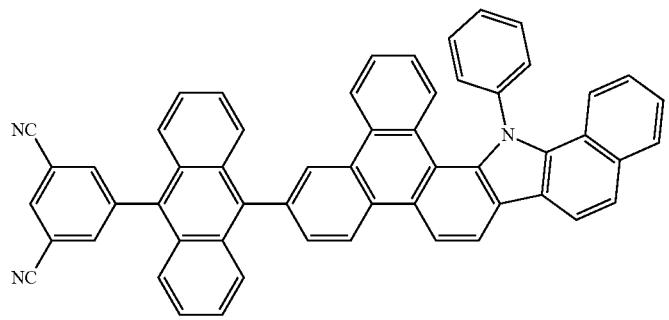
Compound 37
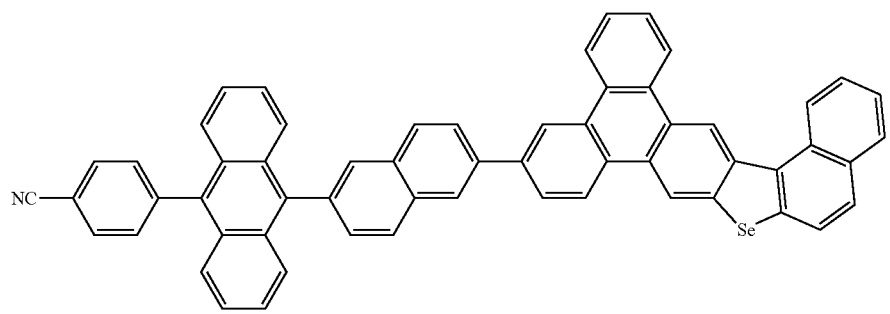
Compound 38
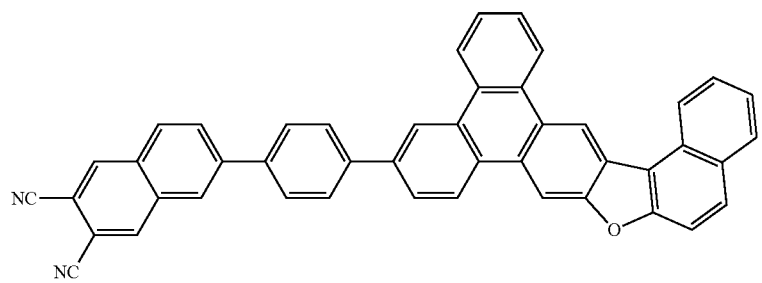

Compound 39
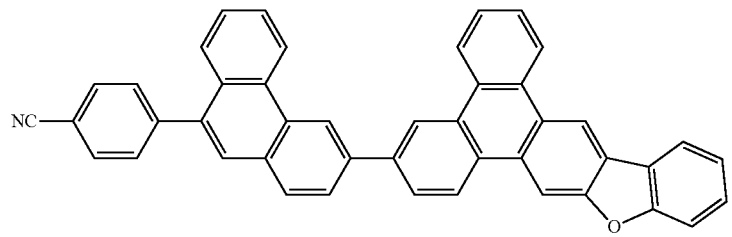
Compound 40
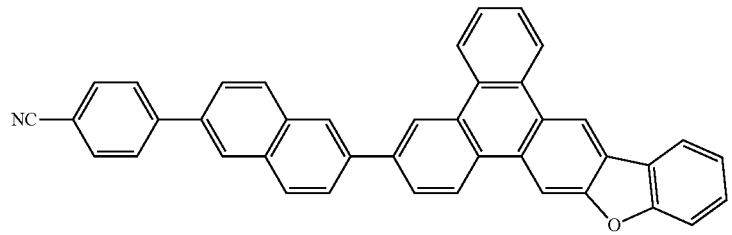
Compound 41
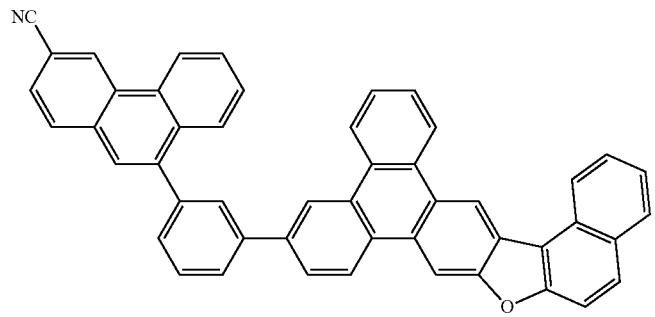
Compound 42
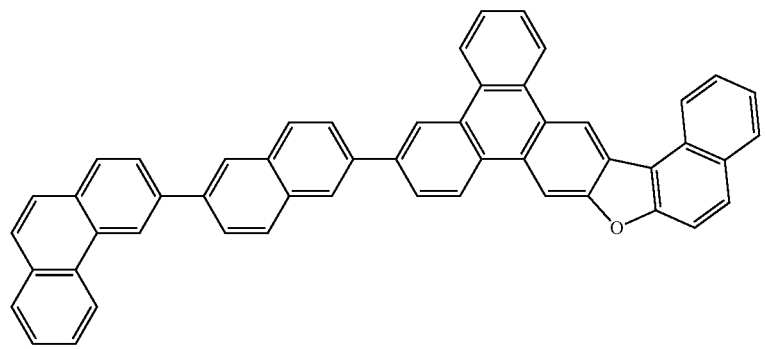
Compound 43
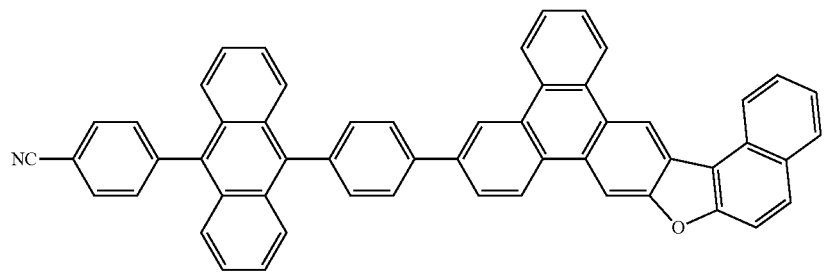

Compound 44
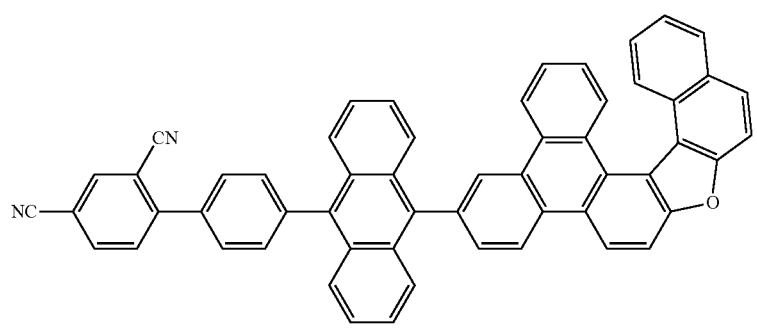
Compound 45
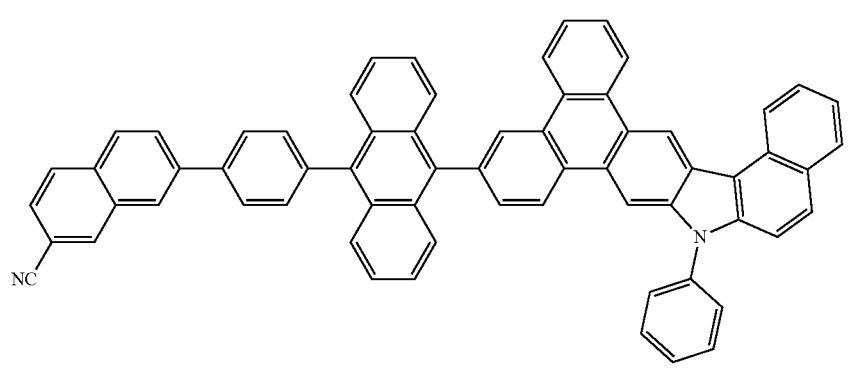
Compound 46
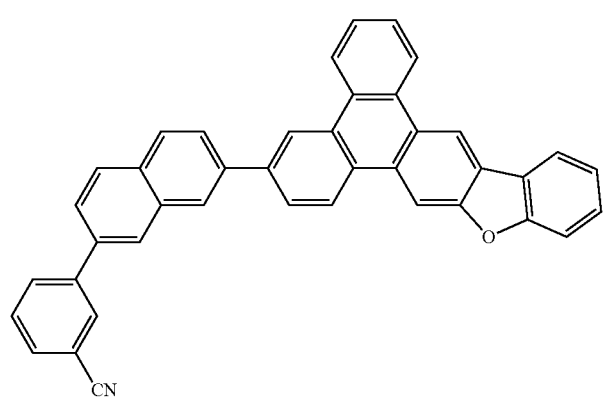
Compound 47
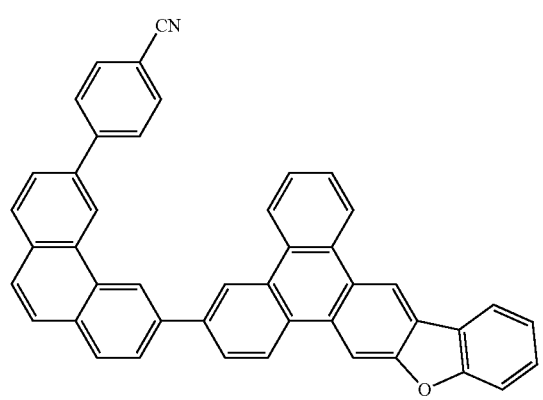

Compound 48
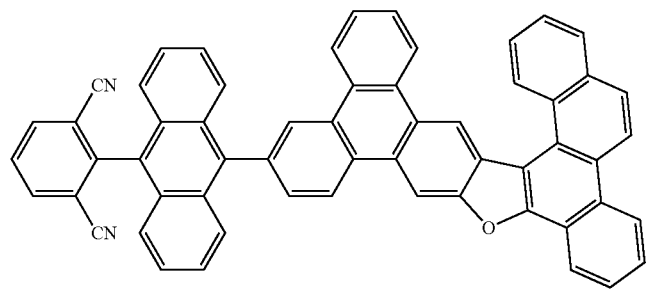
Compound 49
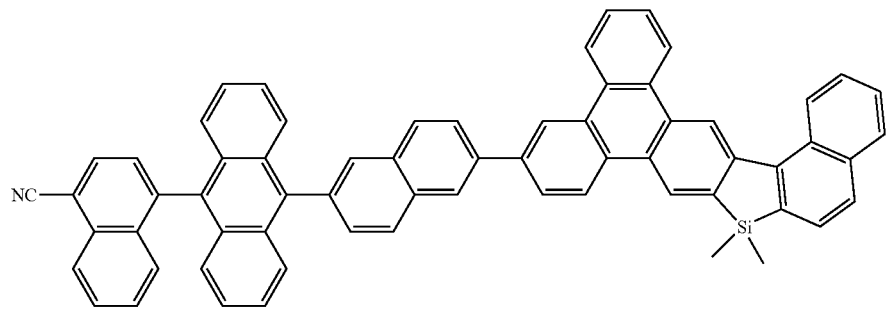
Compound 50
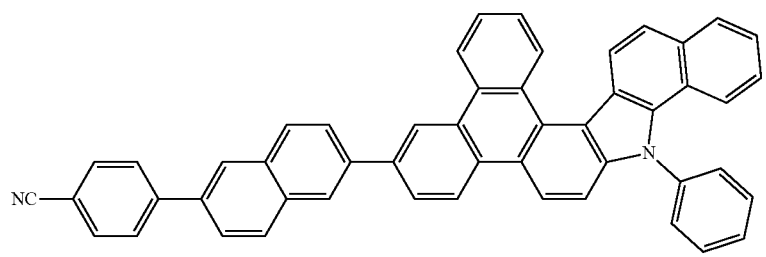
Compound 51
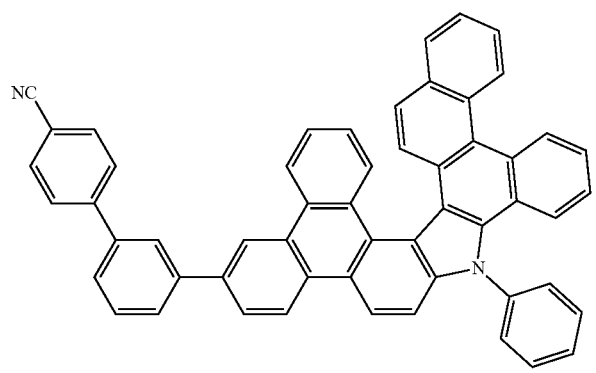
Compound 52
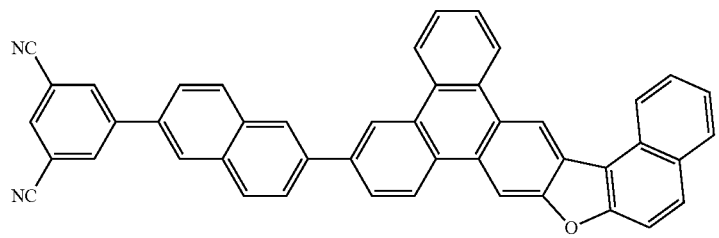

Compound 53
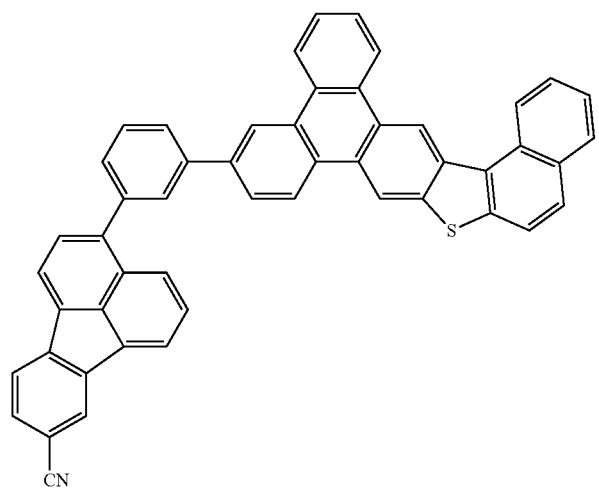
Compound 54
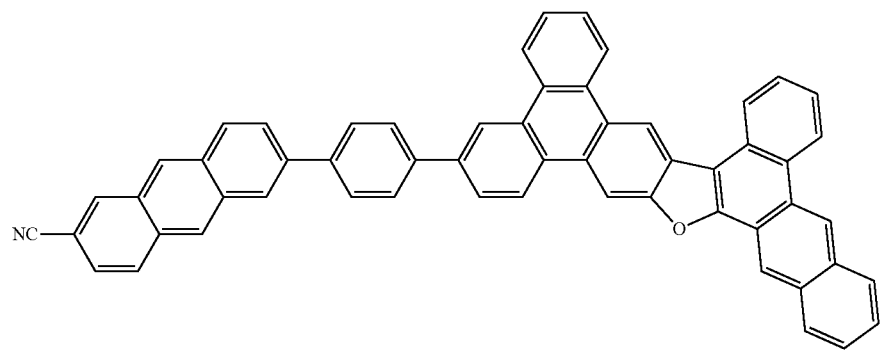
Compound 55
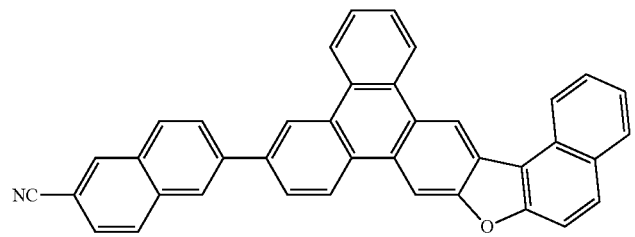
Compound 56
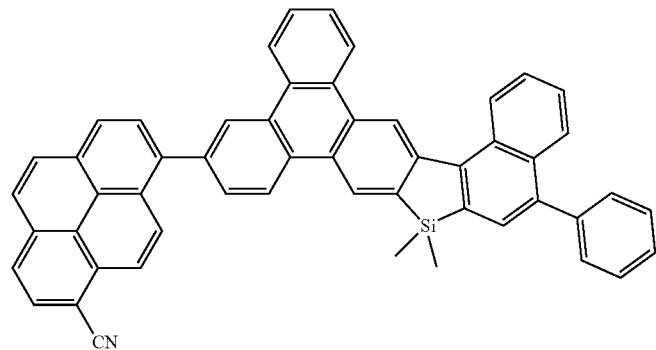

-continued
Compound 57
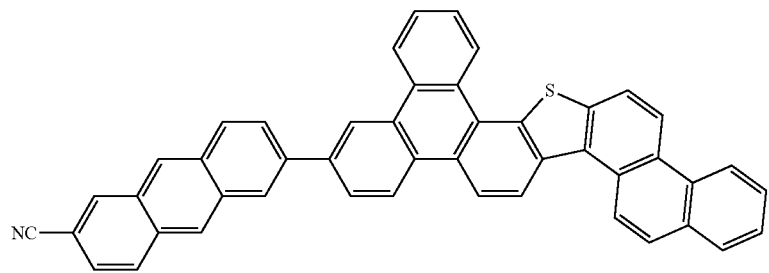
Compound 58
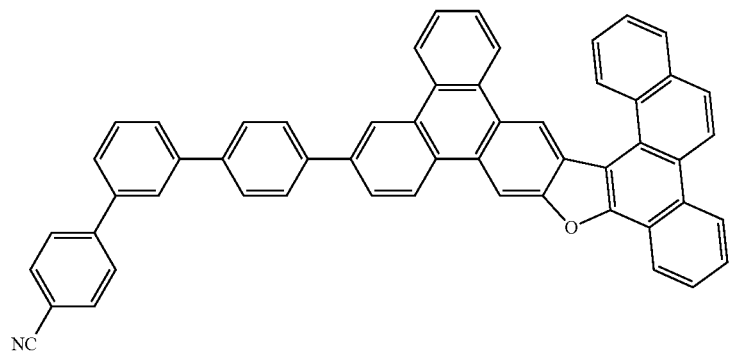
Compund 59
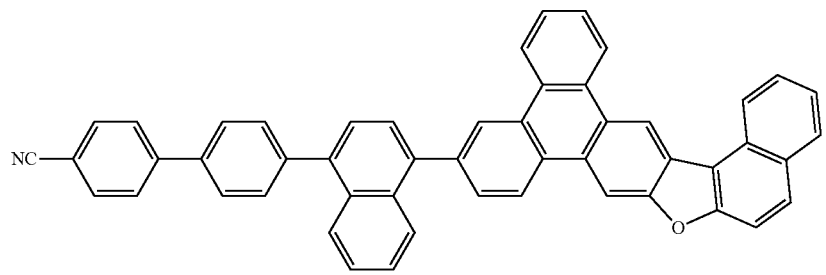
Compound 60
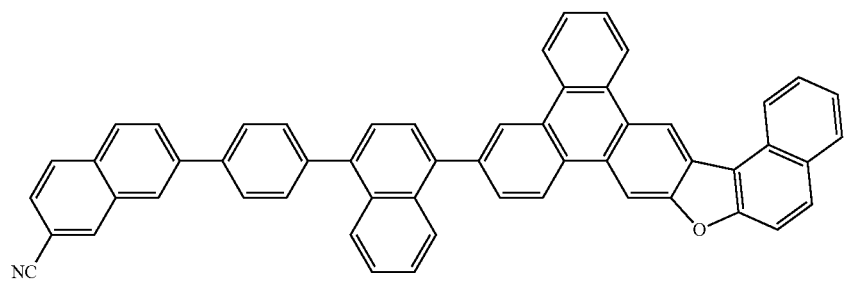
Compound 61
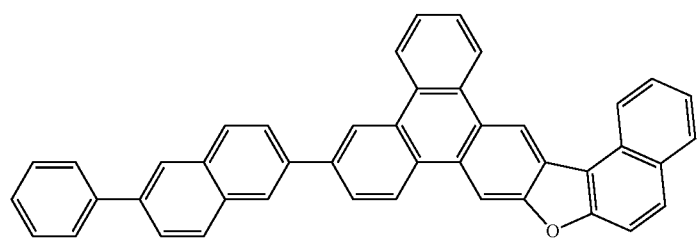

Compound 62
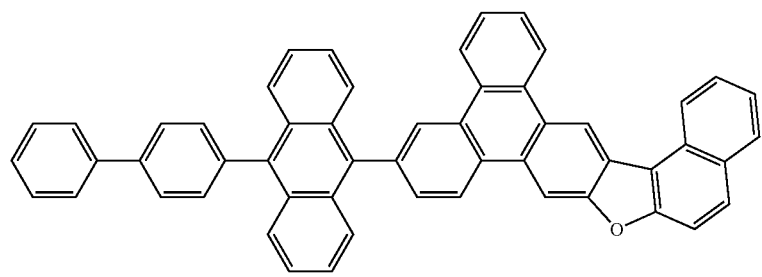
Compound 63
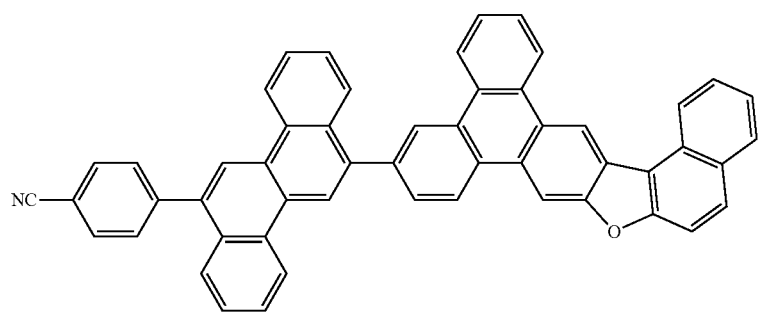
Compound 64
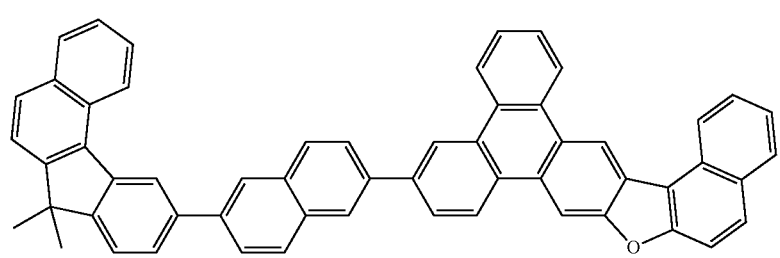
Compound 65
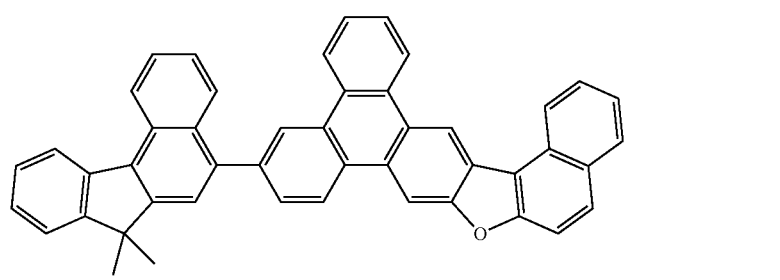
Compound 66
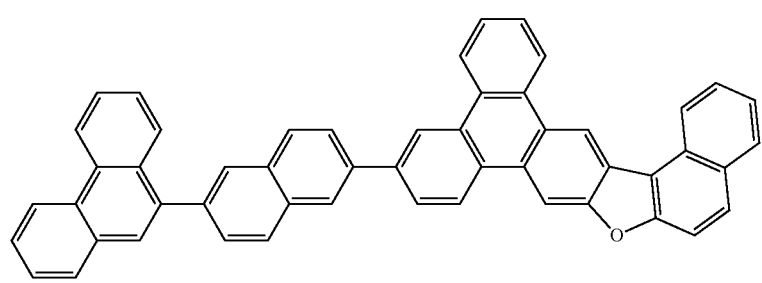
Compound 67
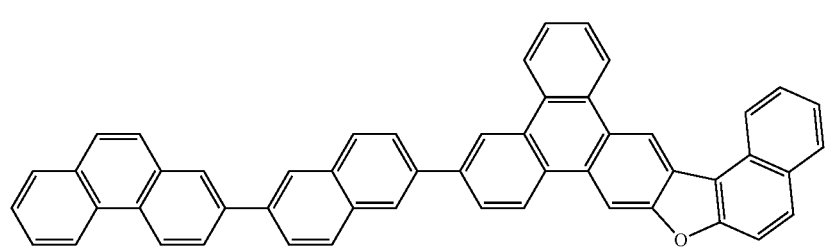

Compound 68
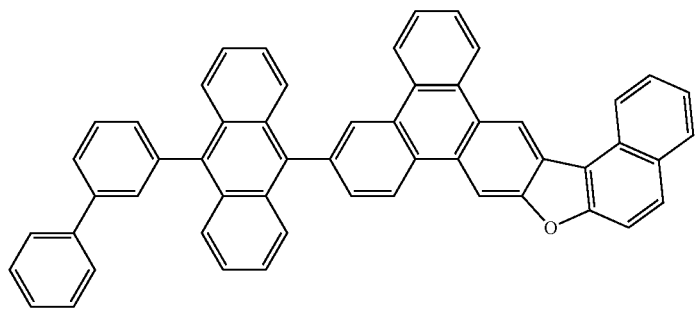
Compound 69
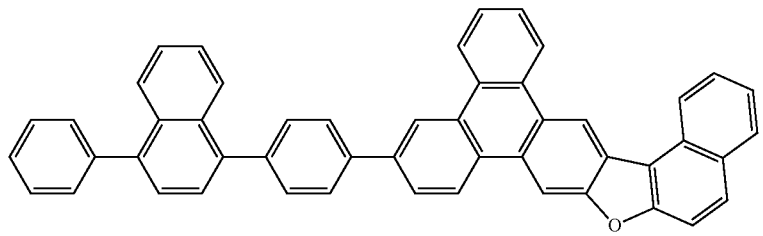
Compound 70
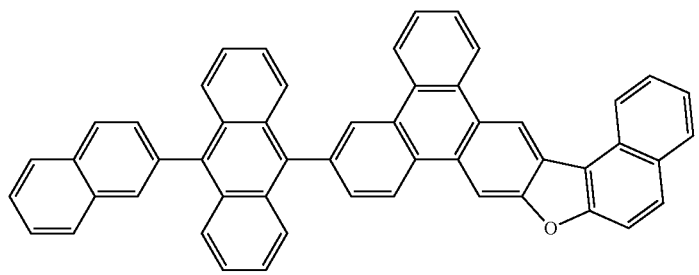
Compound 71
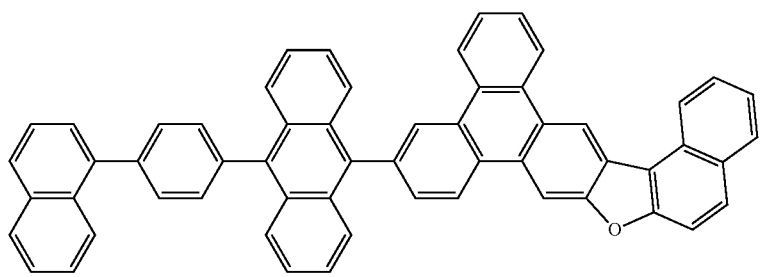
Compound 72
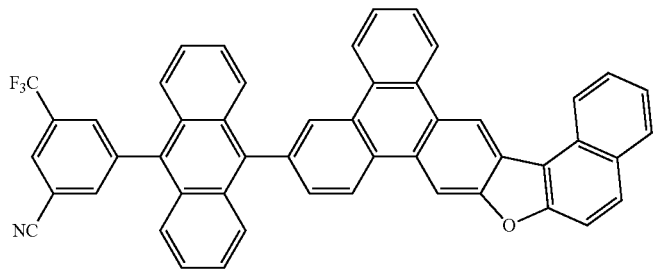

Compound 73
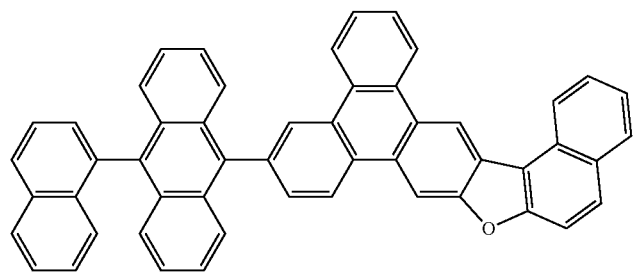
Compound 74
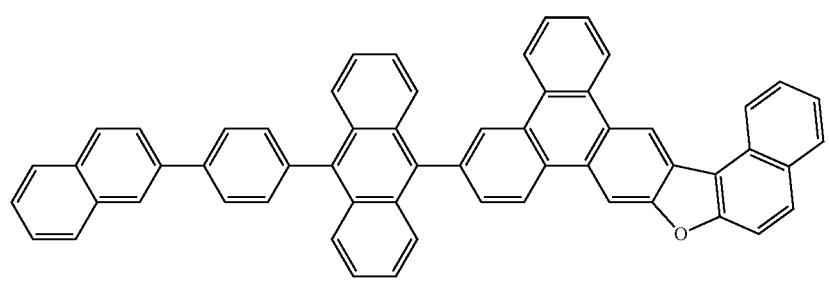
Compound 75
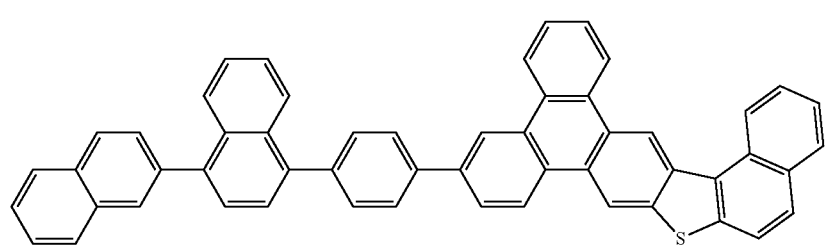
Compound 76
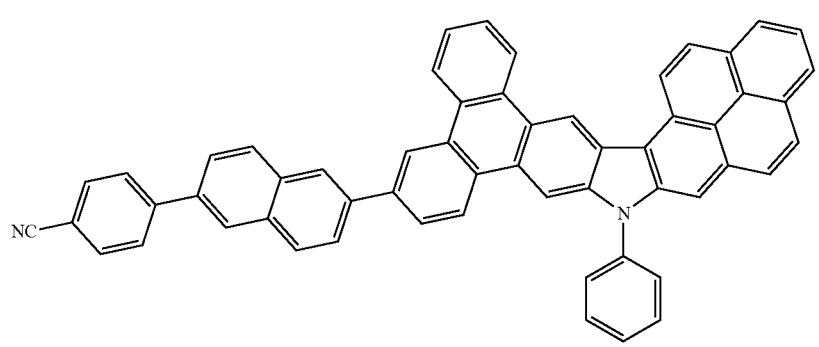
Compound 77
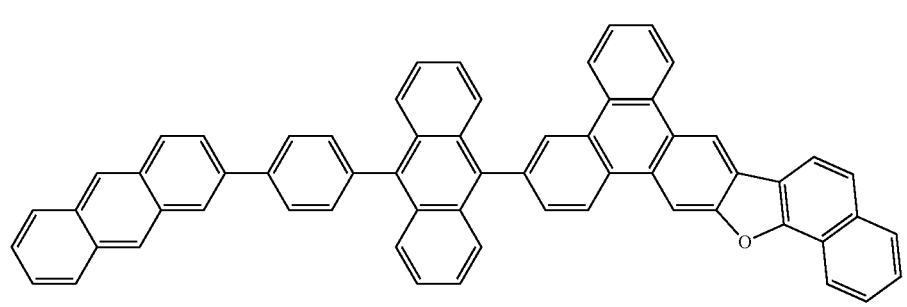

Compound 78
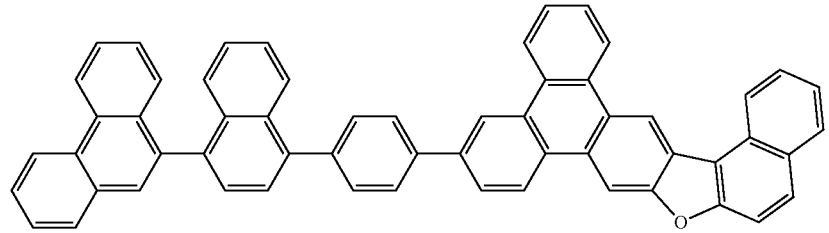
Compound 79
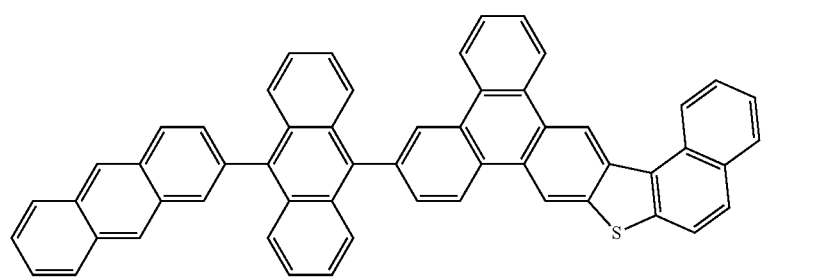
Compound 80
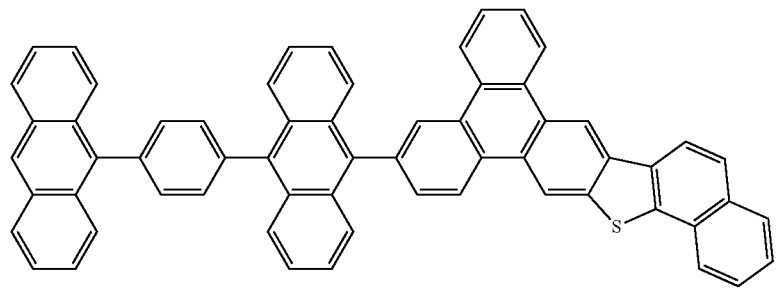
Compound 81
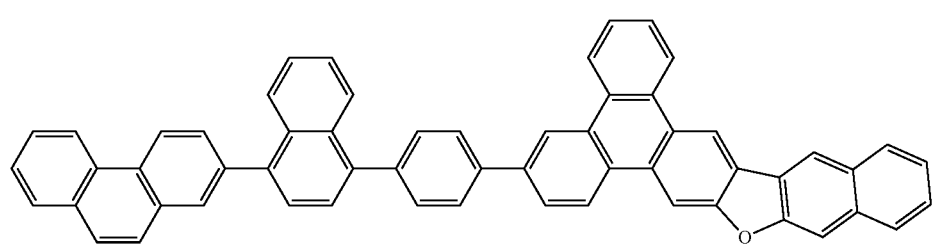
Compound 82
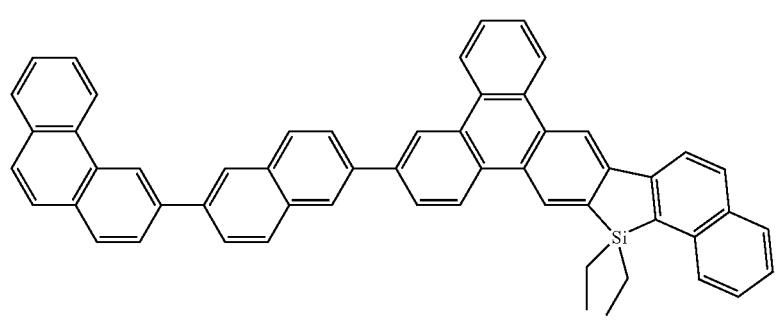
Compound 83
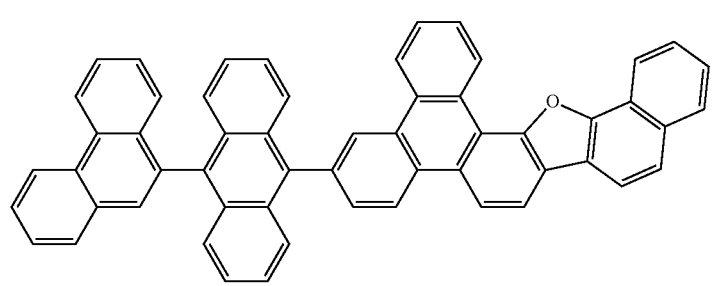

Compound 84
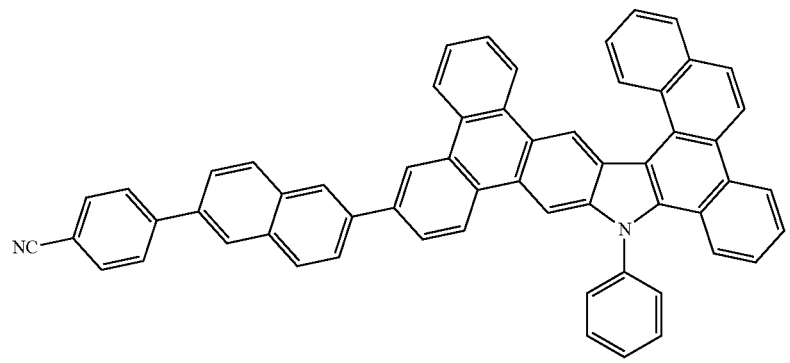
Compound 85
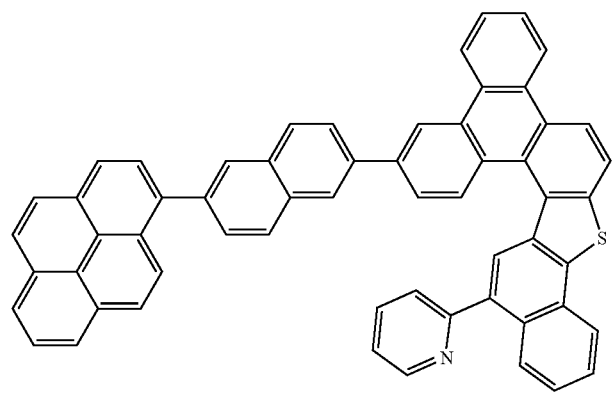
Compound 86
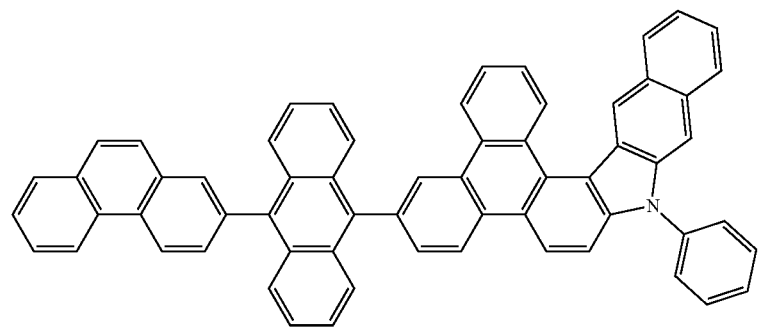
Compound 87
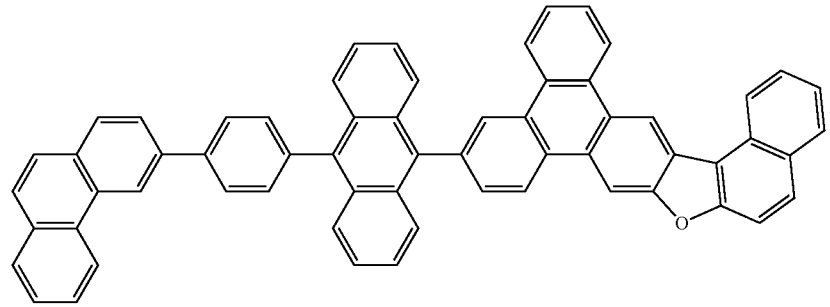

Compound 88
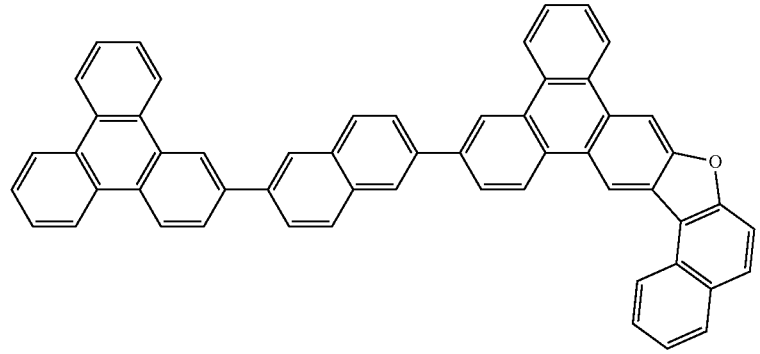
Compound 89
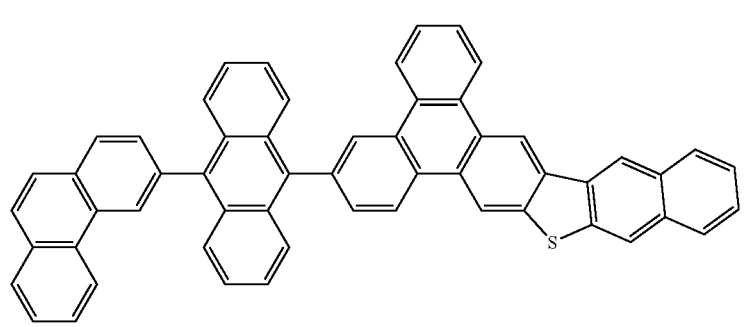
Compound 90
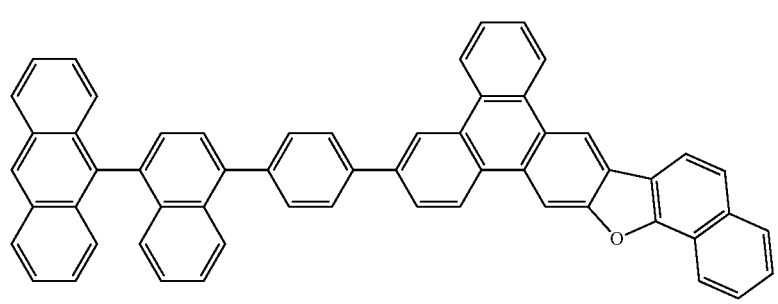
Compound 91
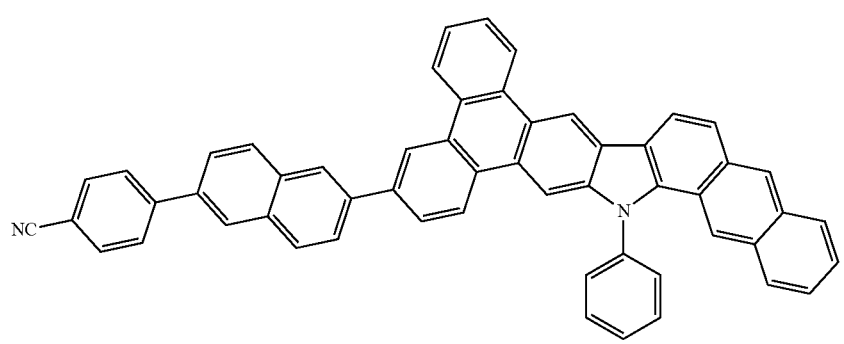

Compound 92
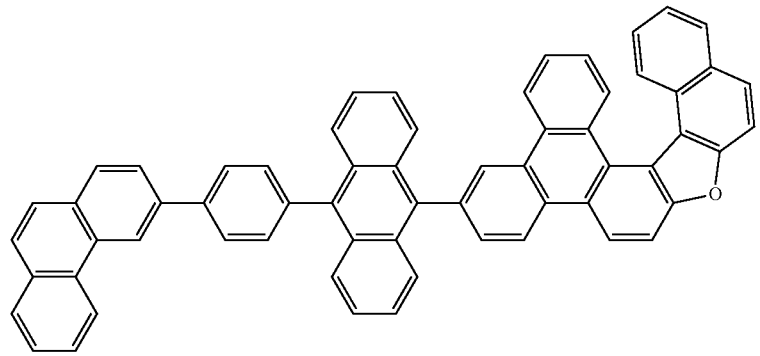
Compound 93
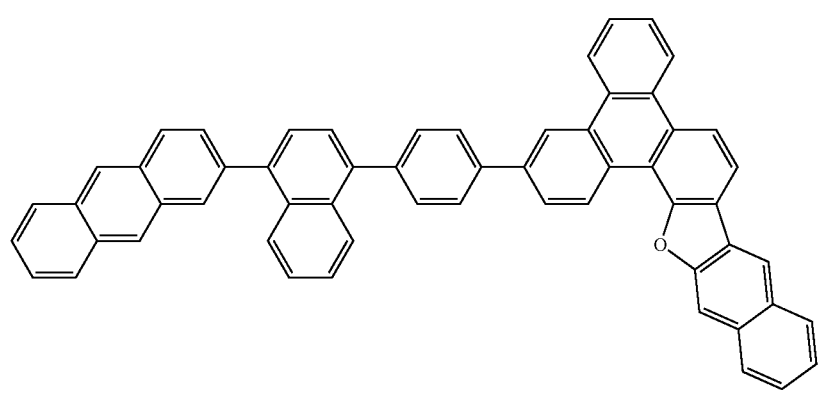
Compoud 94
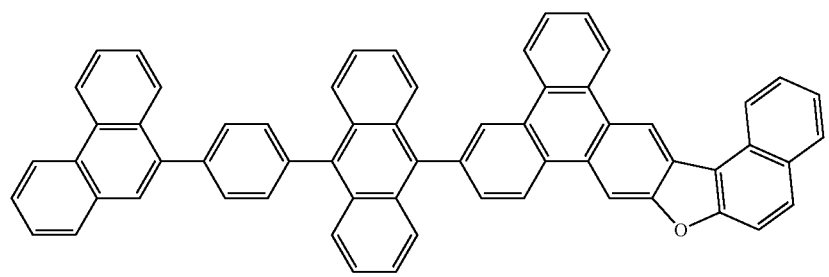
Compound 95
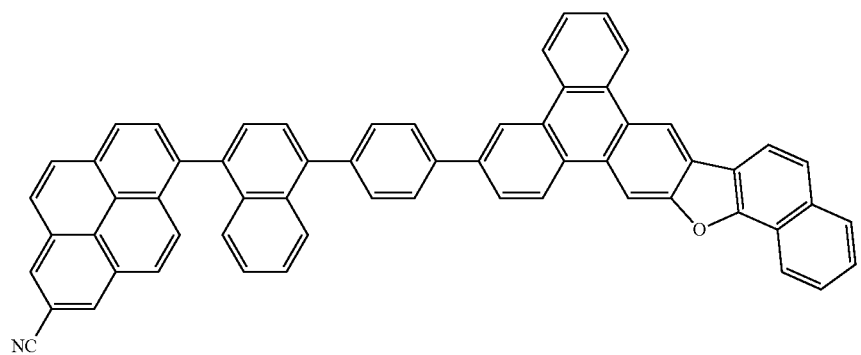

-continued
Compound 96
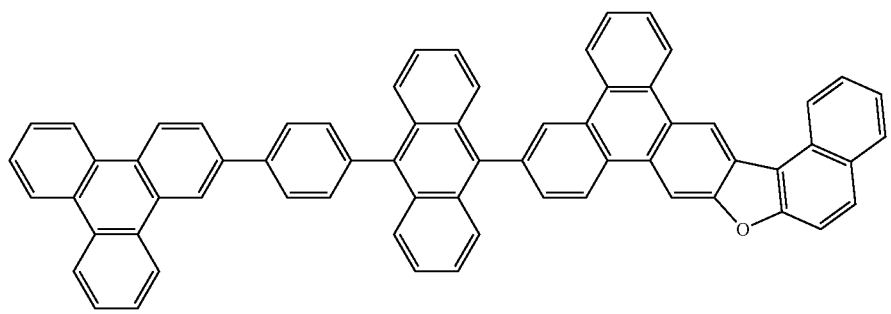
Compound 97
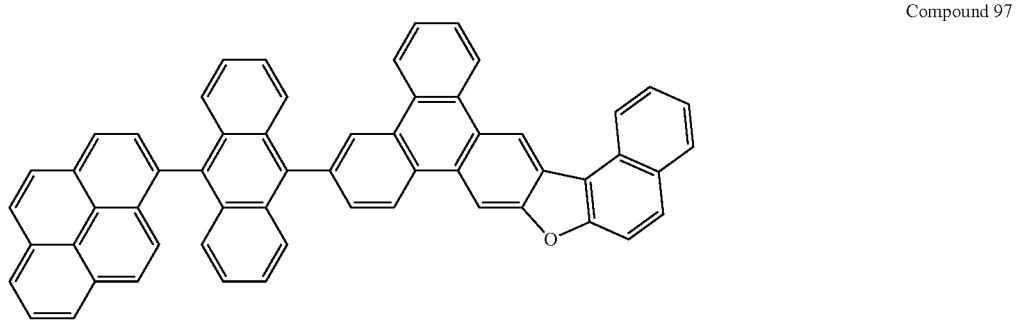
Compound 98
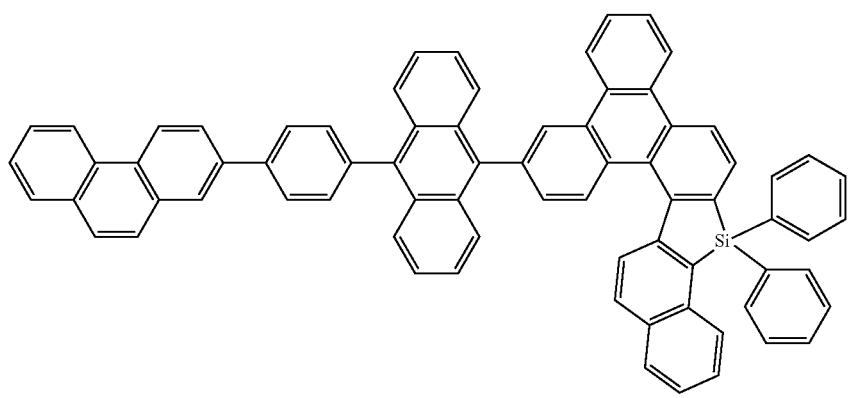
Compound 99
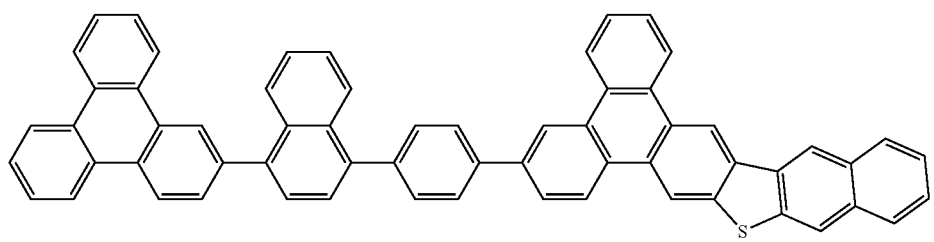
Compound 100
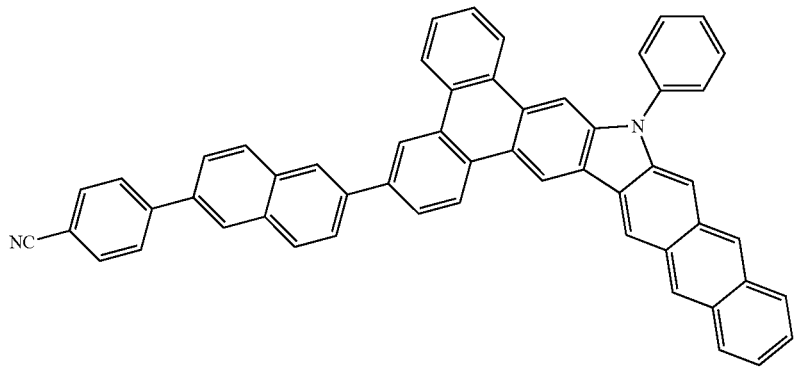

-continued
Compound 101
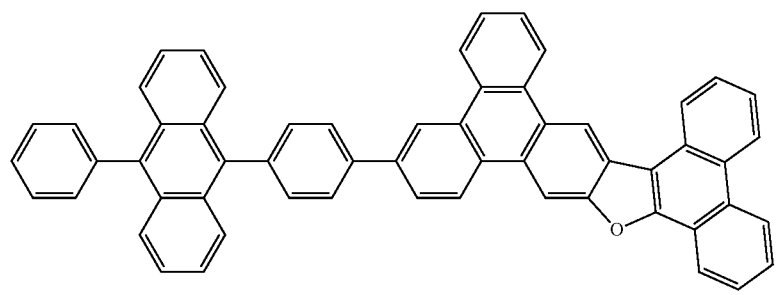
Compound 102
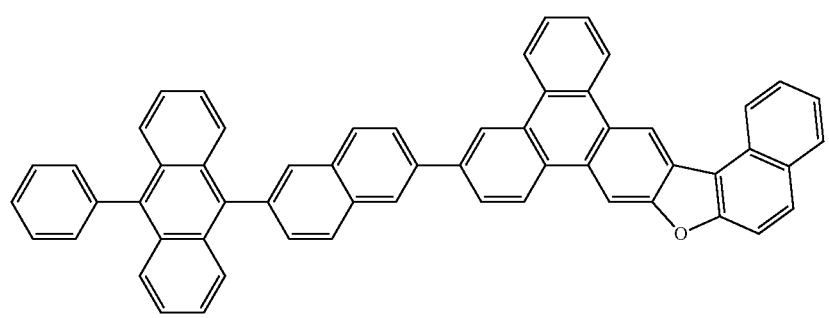
Compound 103
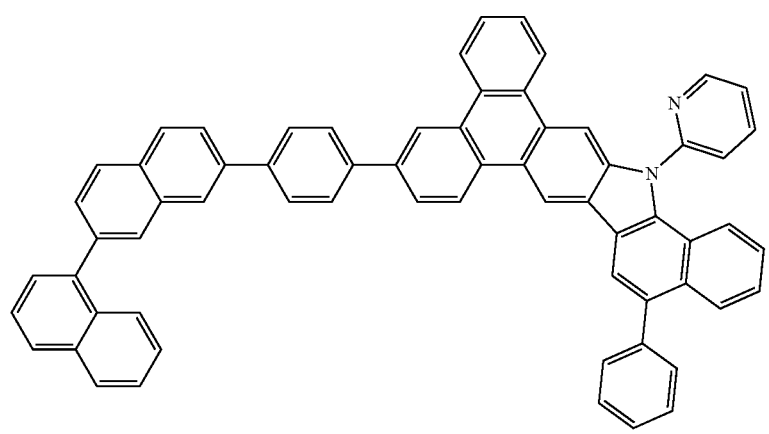
Compound 104
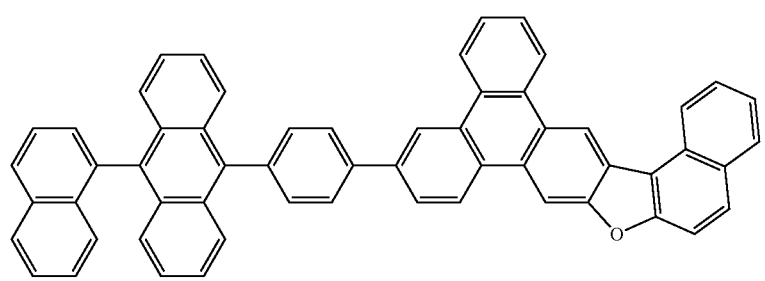
Compound 105
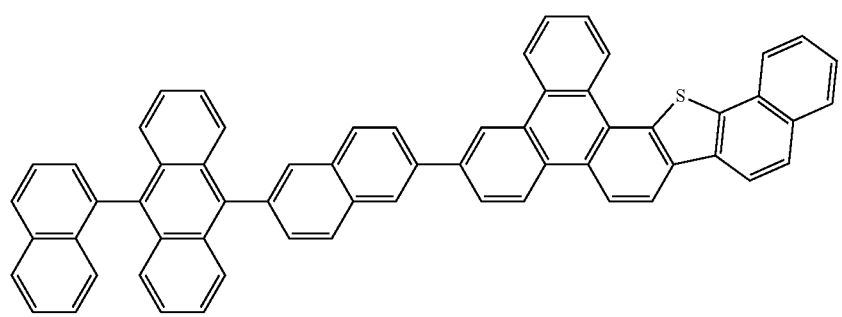

Compound 106
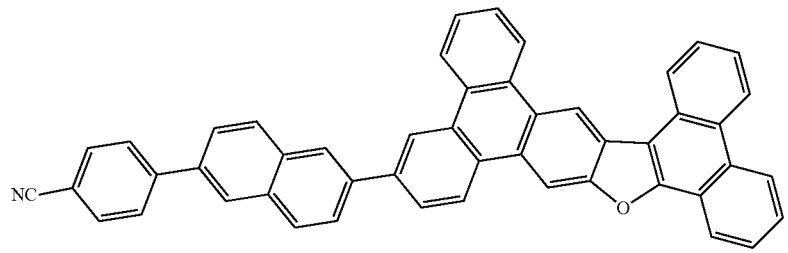
Compound 107
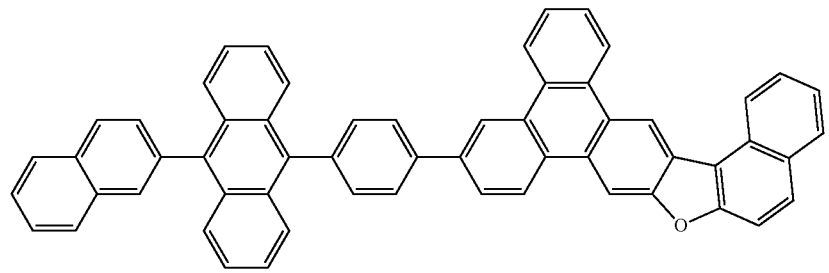
Compound 108
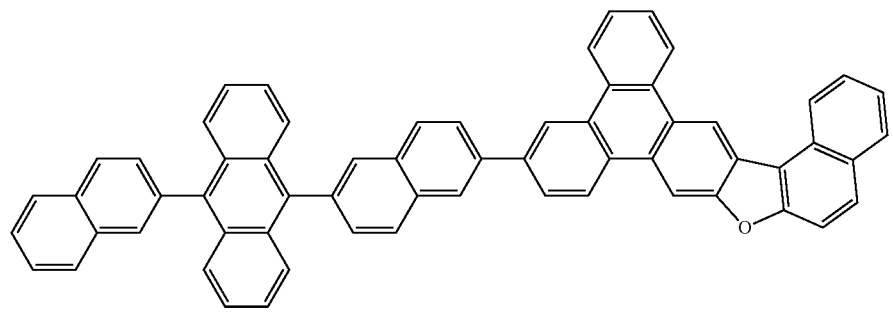
Compound 109
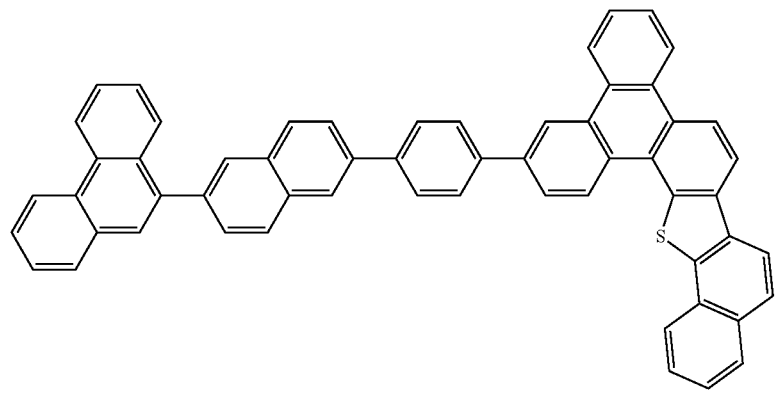
Compound 110
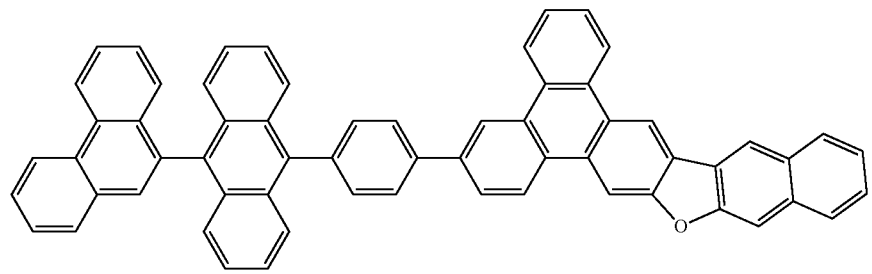

-continued
Compound 111
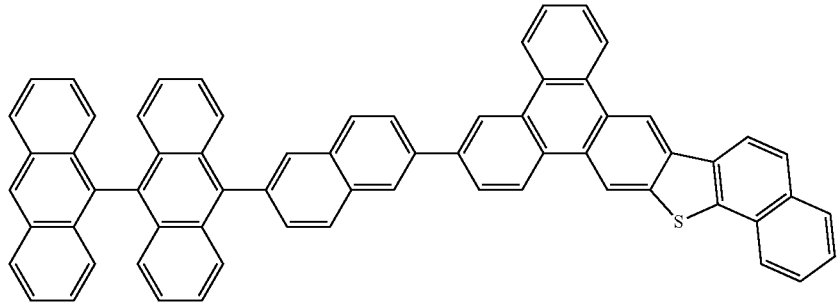
Compound 112
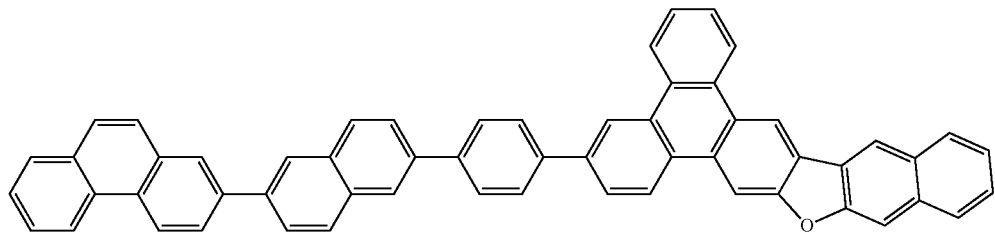
Compound 113
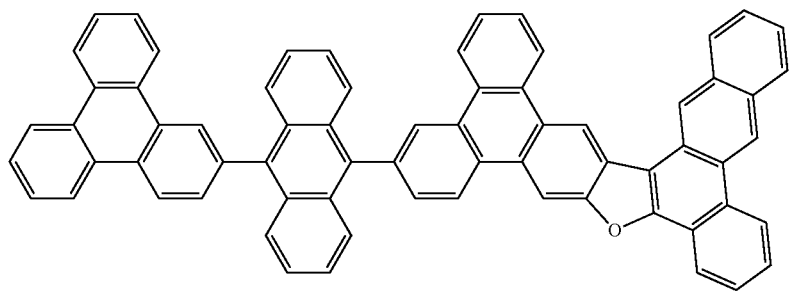
Compound114
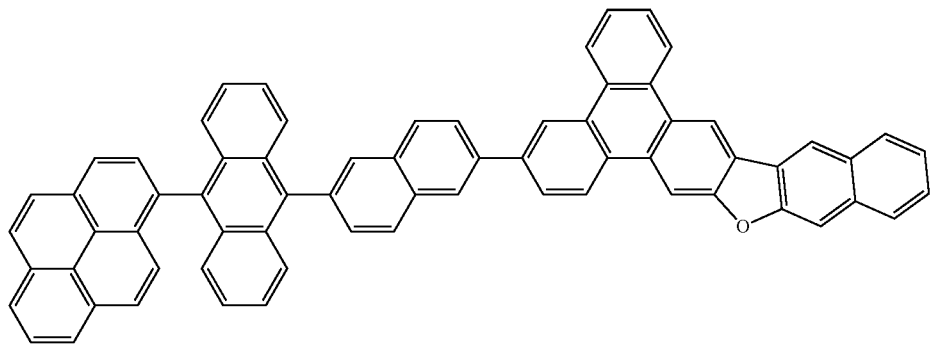
Compound 115
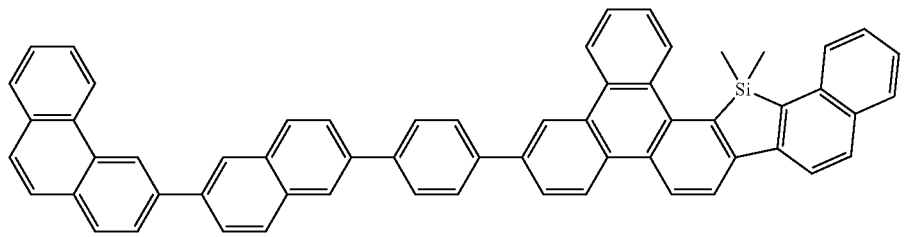

Compound 116
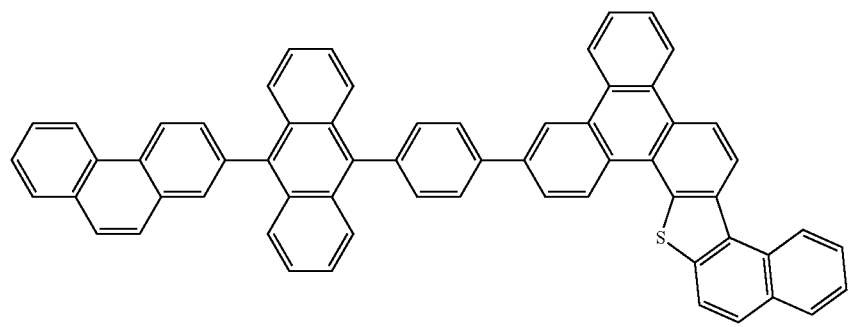
Compound 117
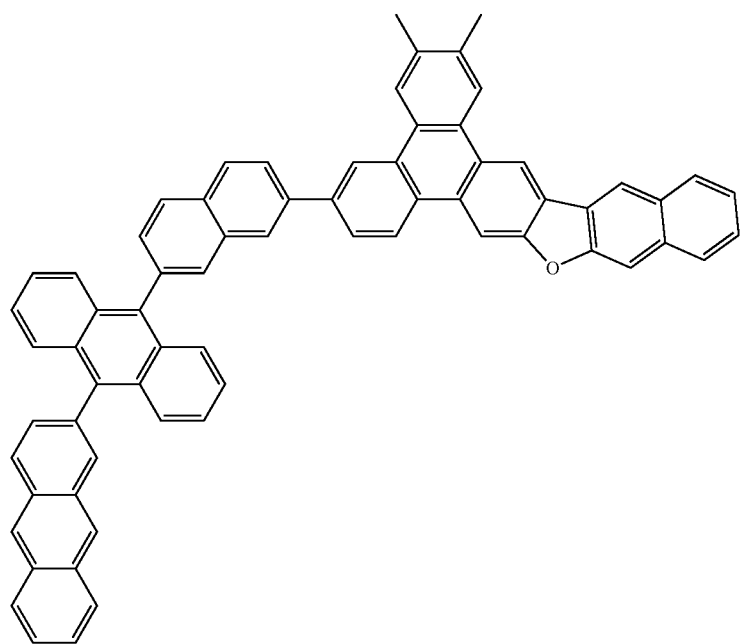
Compound 118
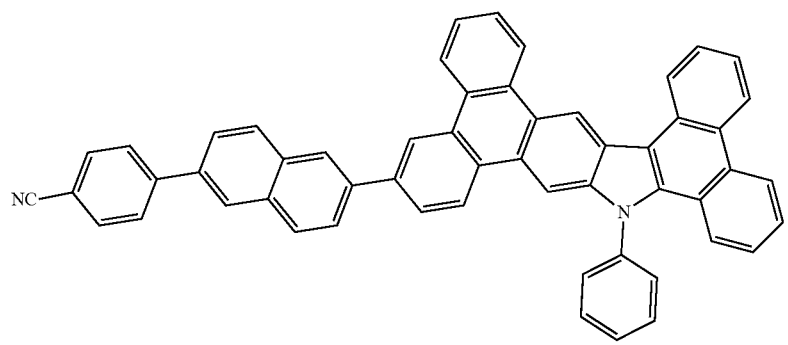

-continued
Compound 119
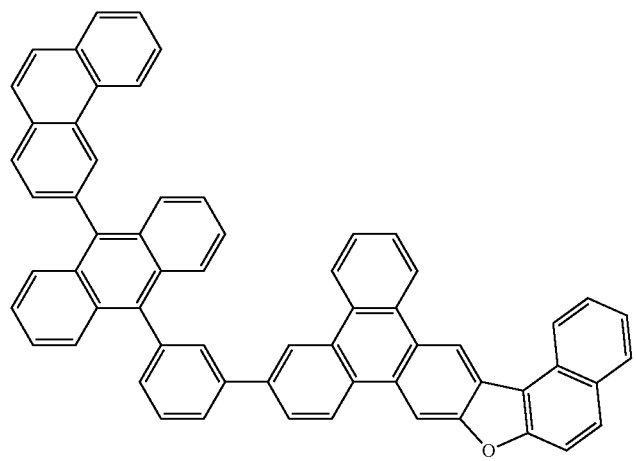
Compound 120
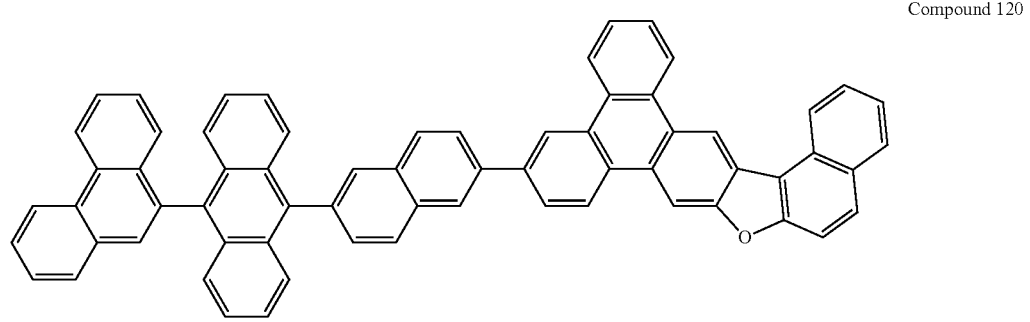
Compound 121
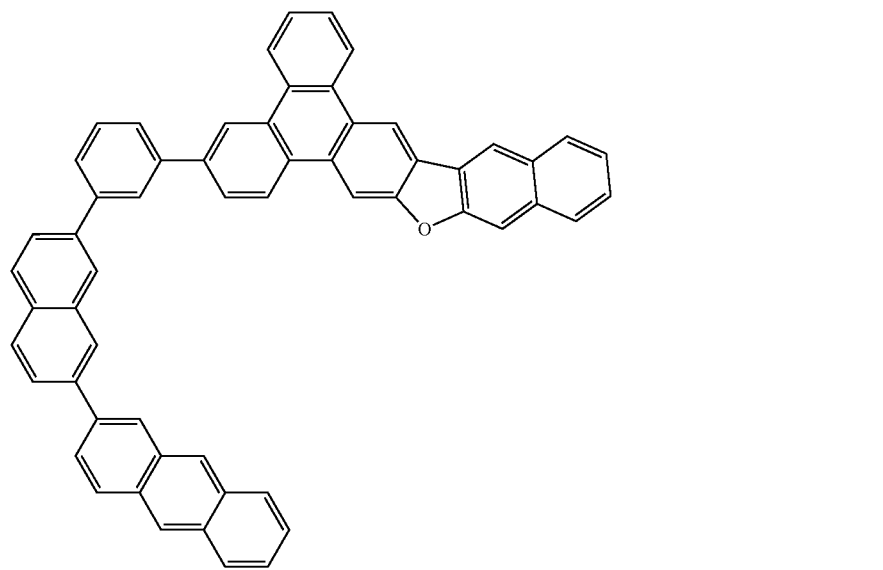

-continued
Compound 122
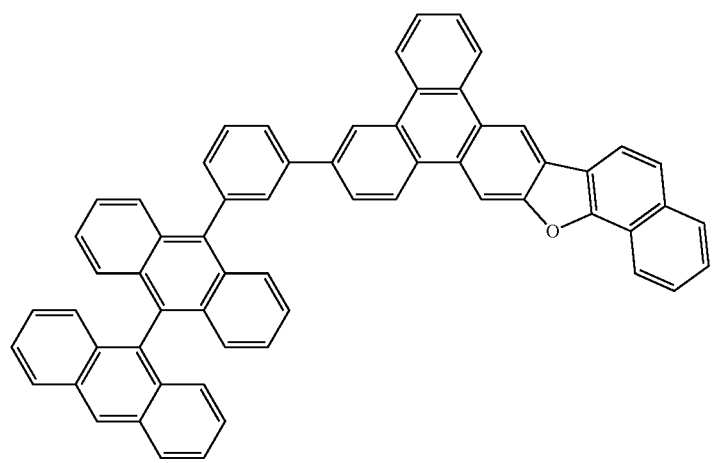
Compound 123
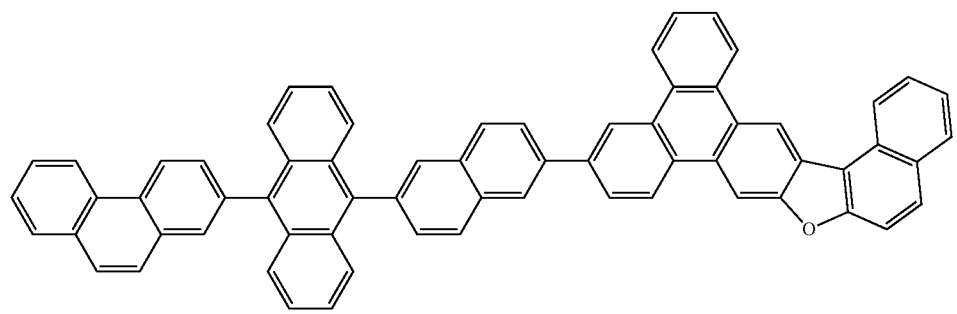
Compound 124
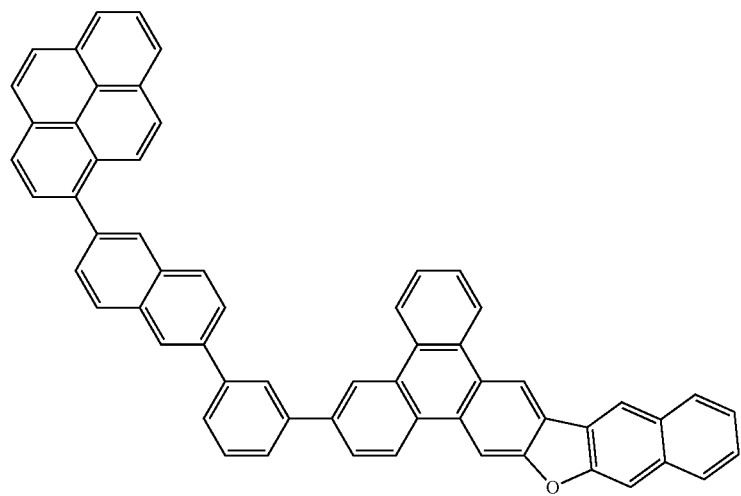

Compound 125
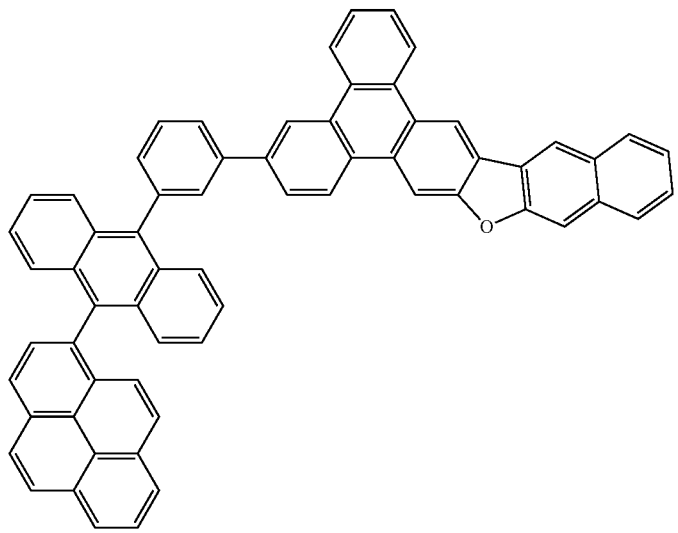
Compound 126
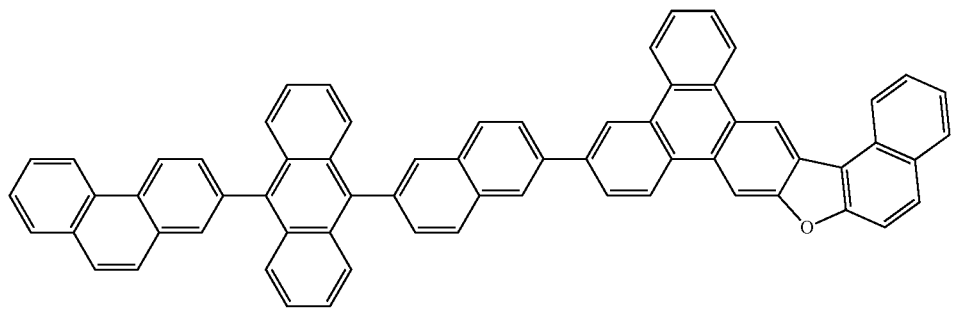
Compound 127
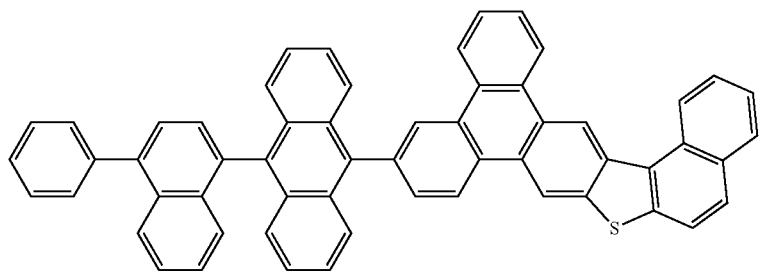
Compound 128
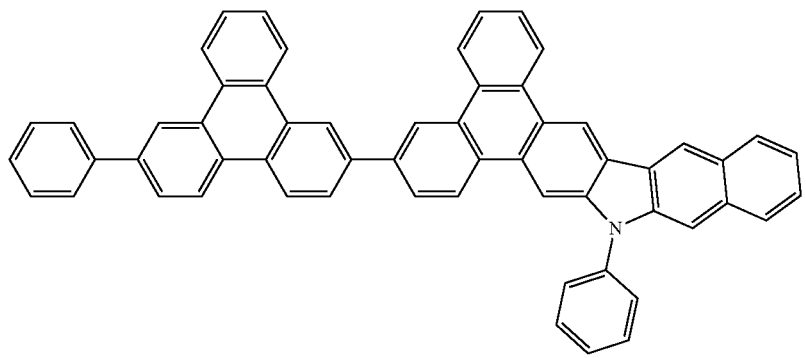

-continued
Compound 129
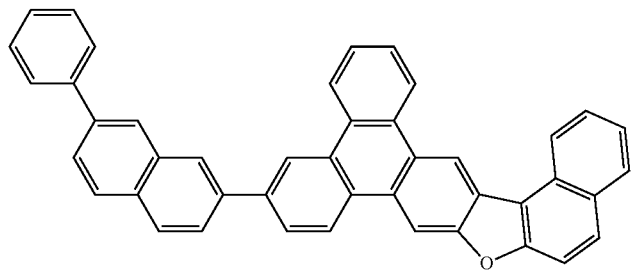
Compound 130
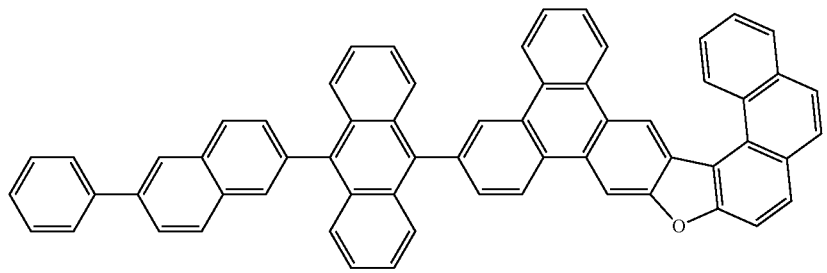
Compound 131
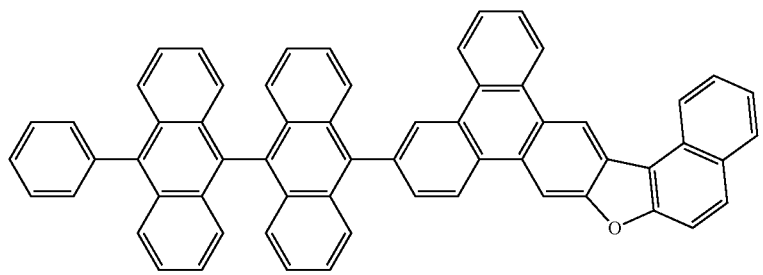
Compound 132
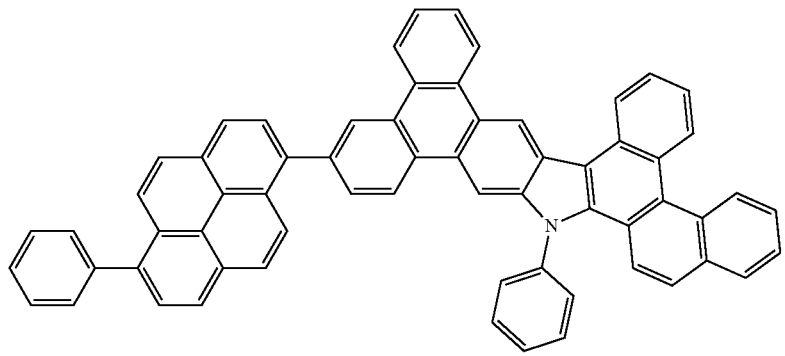
Compound 133
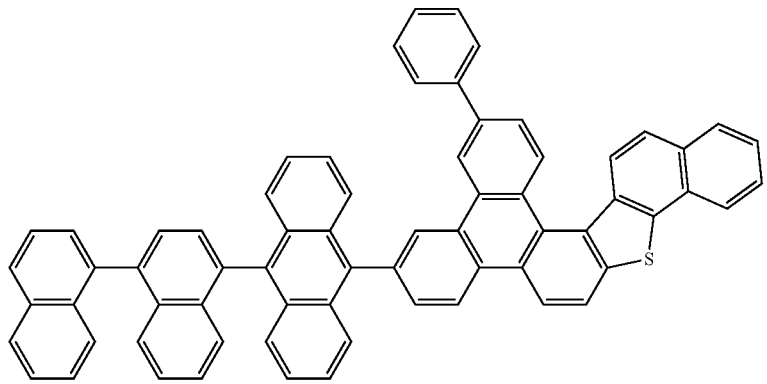

Compound 134
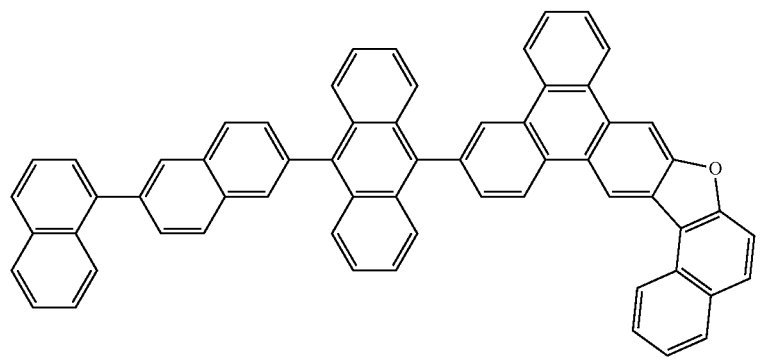
Compound 135
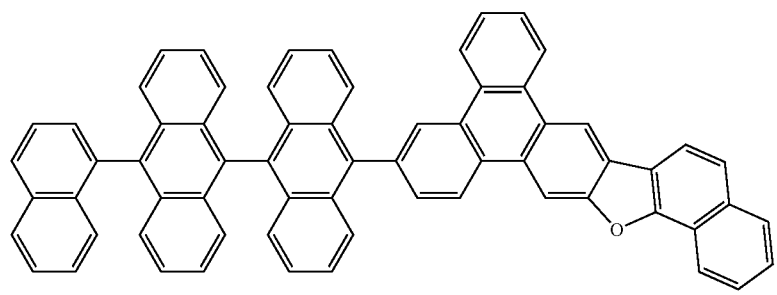
Compound 136
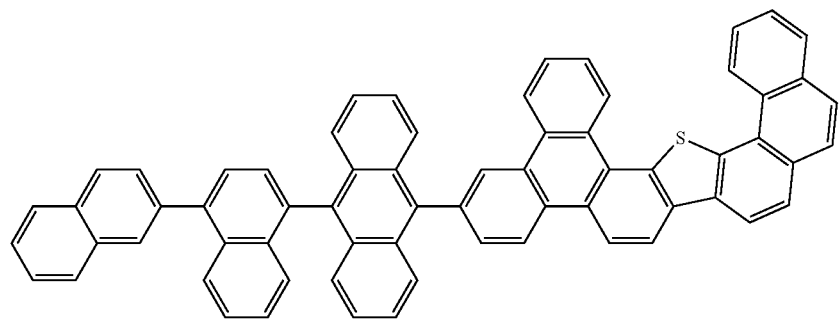
Compound 137
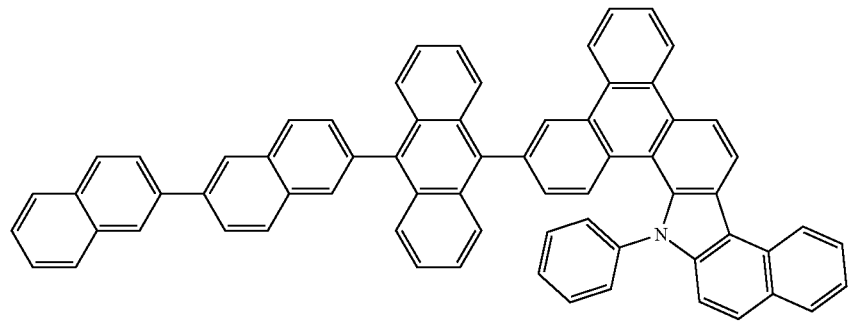
Compound 138
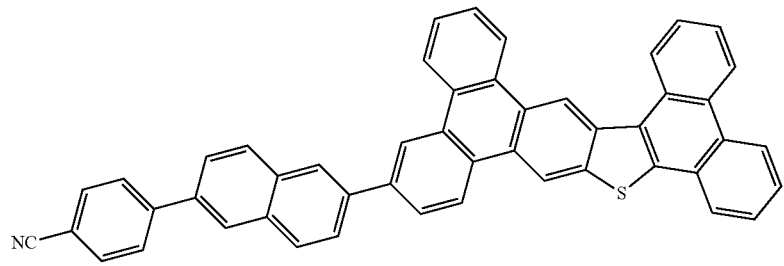

-continued
Compound 139
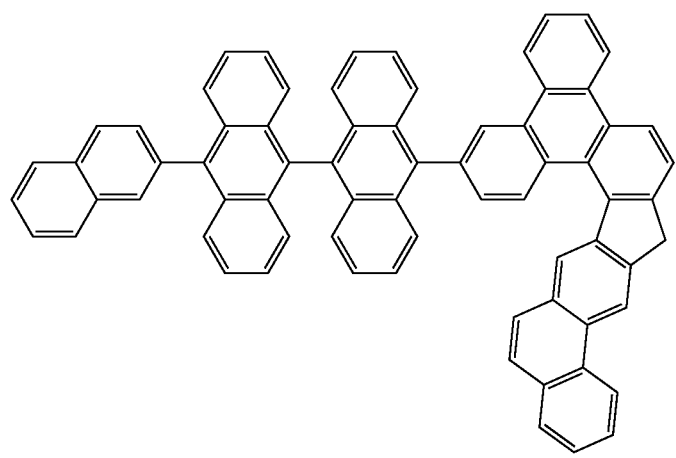
Compound 140
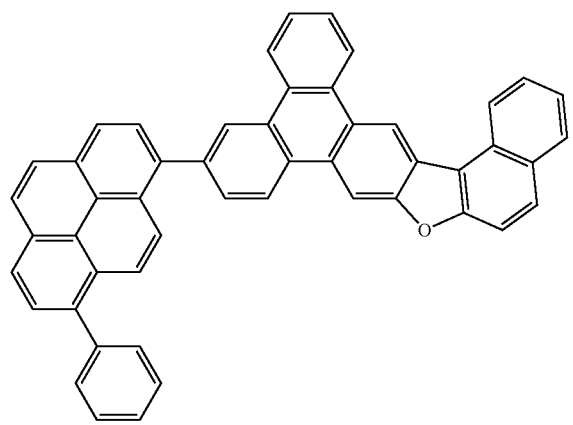
Compound 141
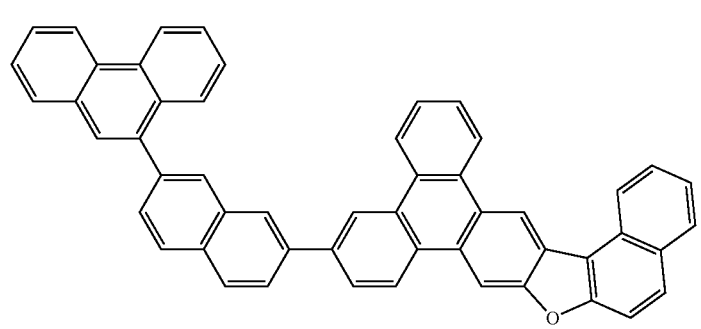
Compound 142
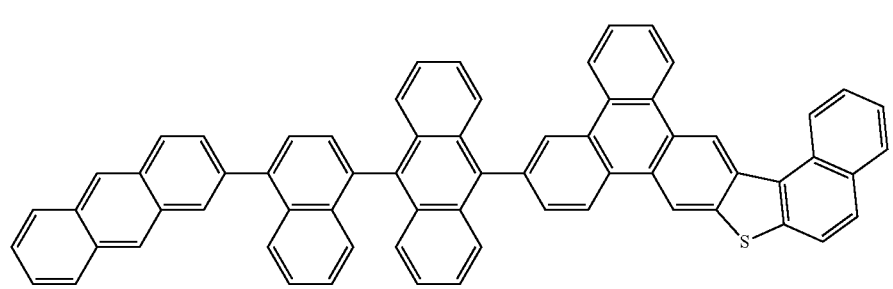

Compound 143
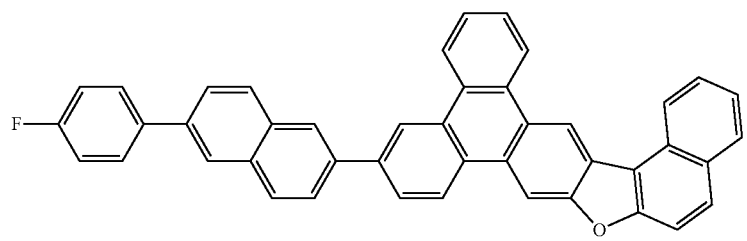
Compound 144
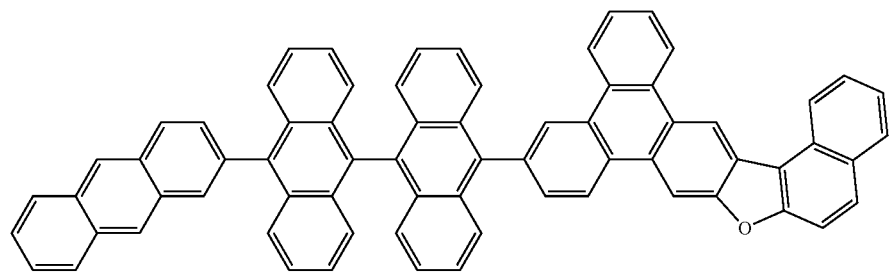
Compound 145
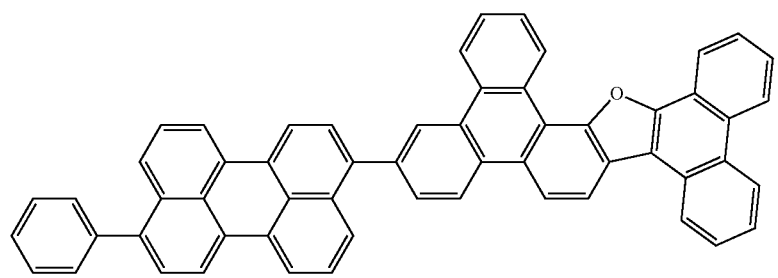
Compound 146
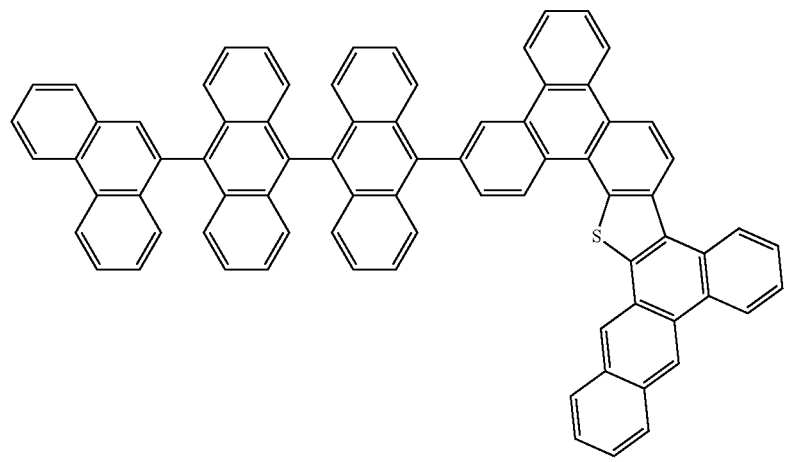
Compound 147
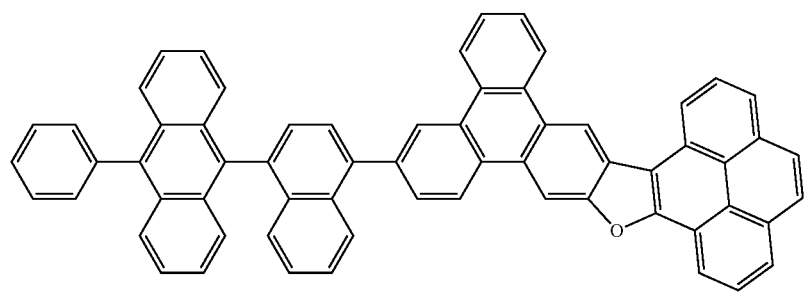

-continued
Compound 148
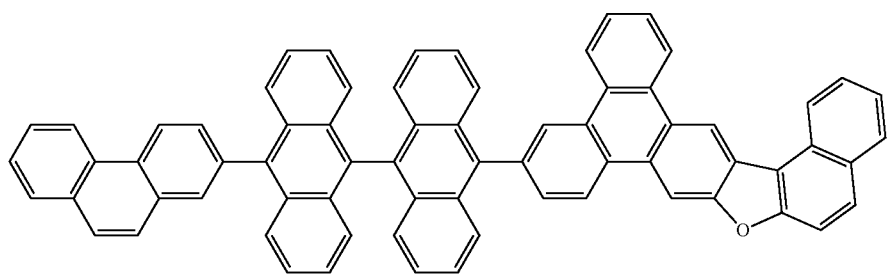
Compound 149
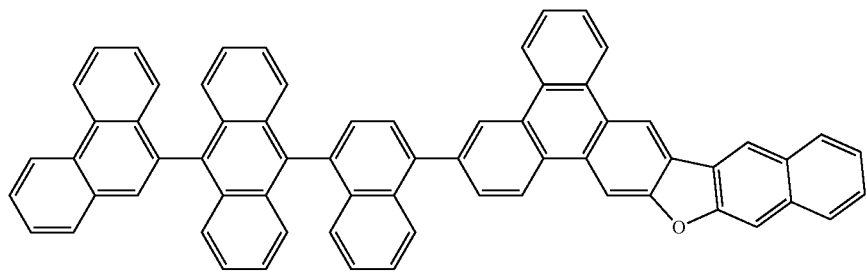
Compound 150
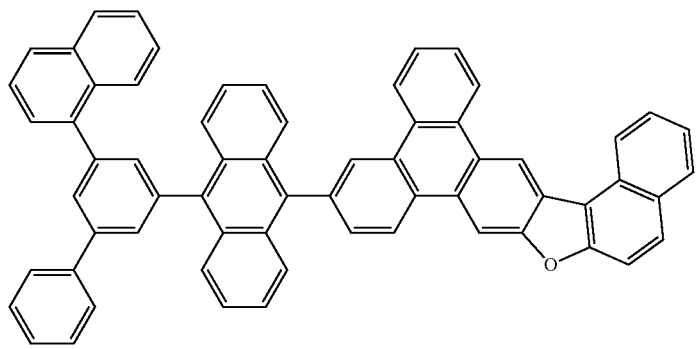
Compound 151
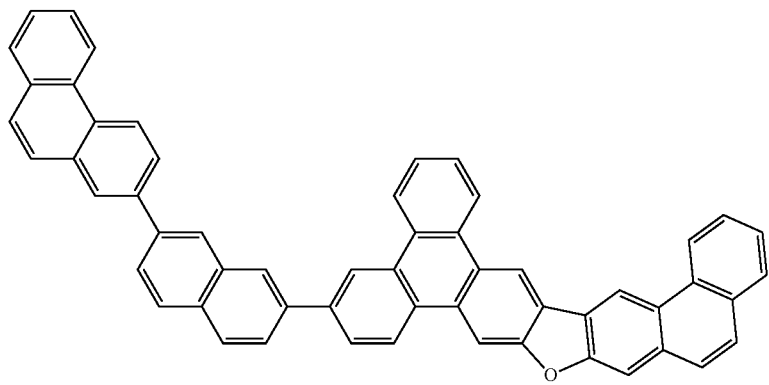
Compound 152
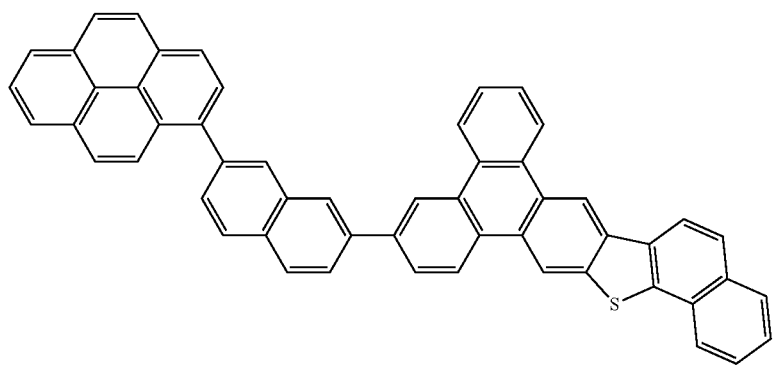

Compound 153
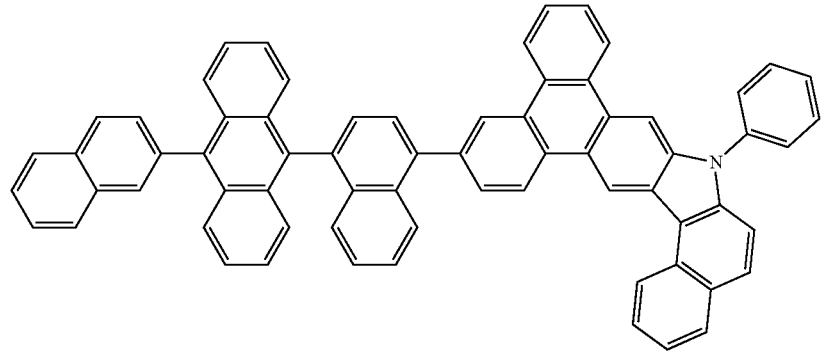
Compound 154
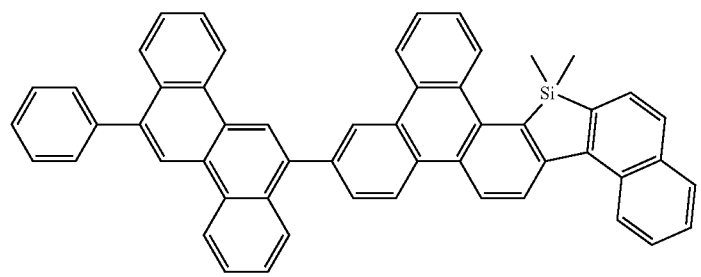
Compound 155
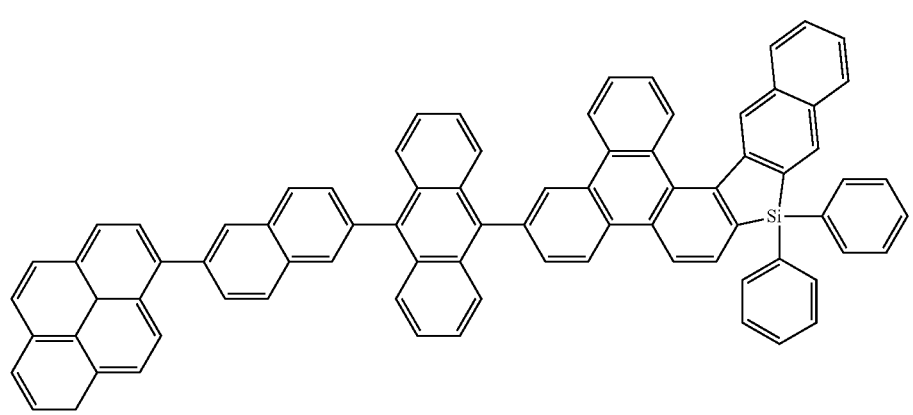
Compound 156
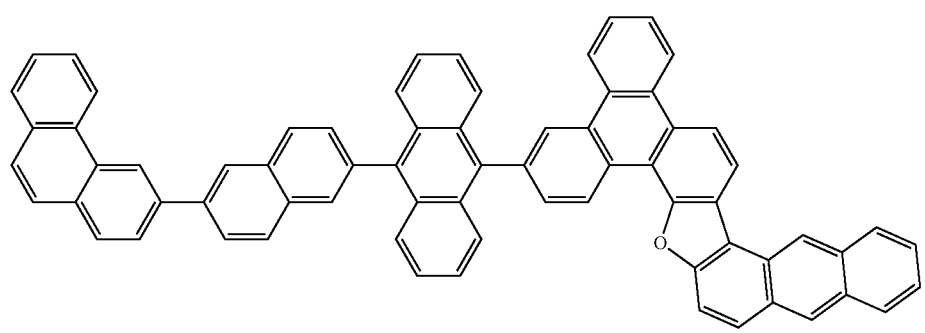

Compound 157
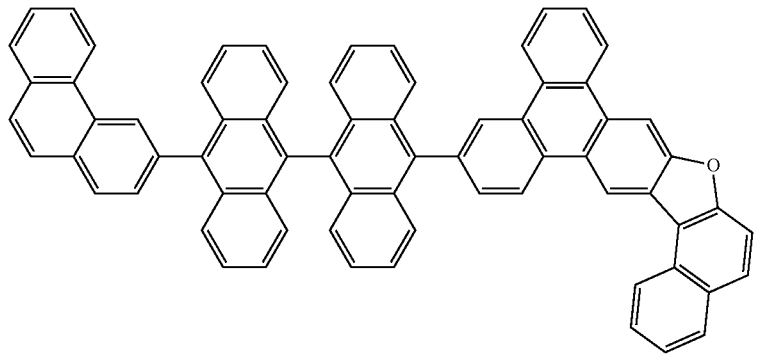
Compound 158
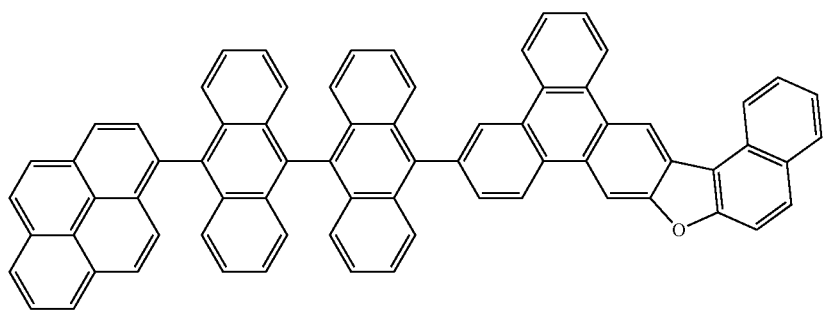
Compound 159
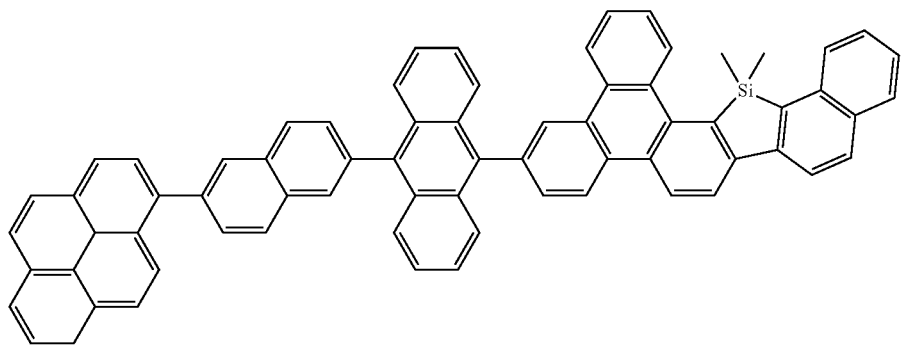
Compound 160
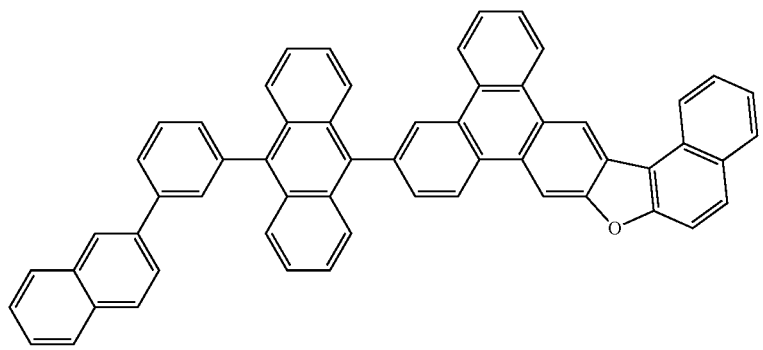

Compound 161
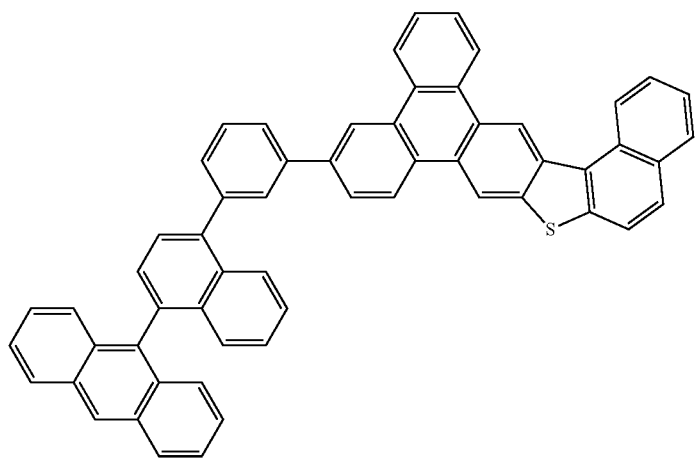
Compound 162
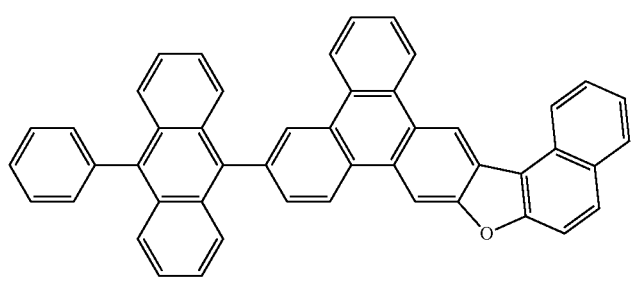
Compound 163
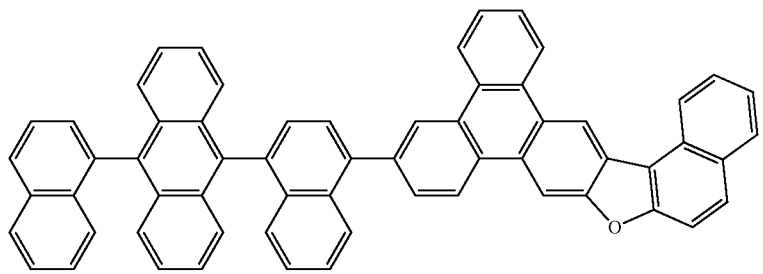
Compound 164
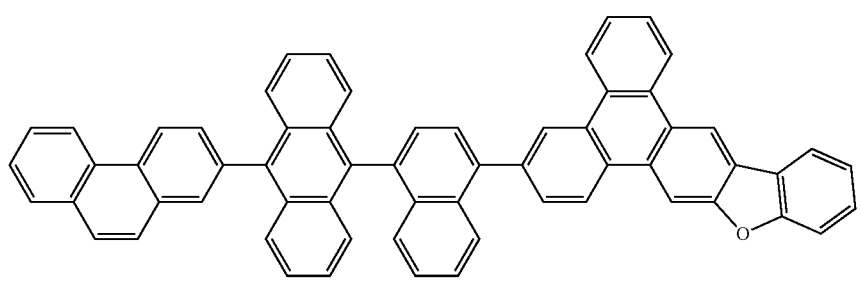
Compound 165
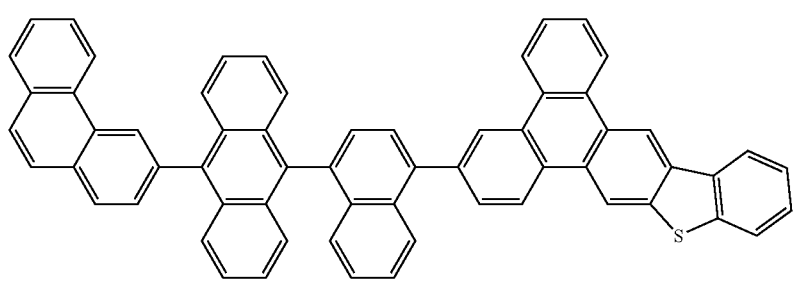

-continued
Compound 166
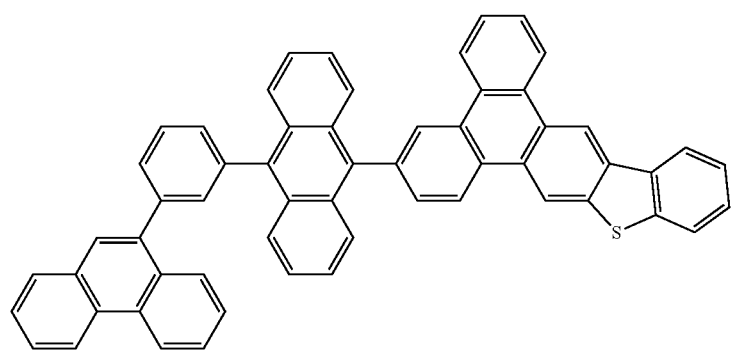
Compound 167
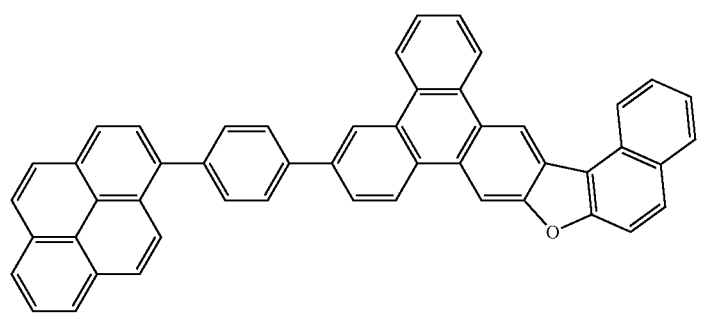
Compound 168
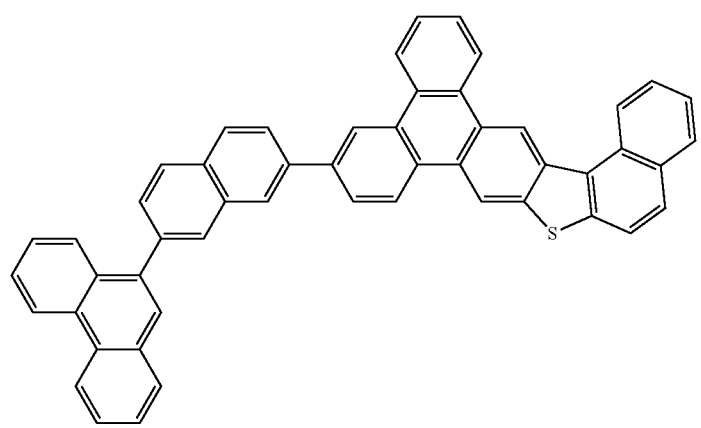
Compound 169
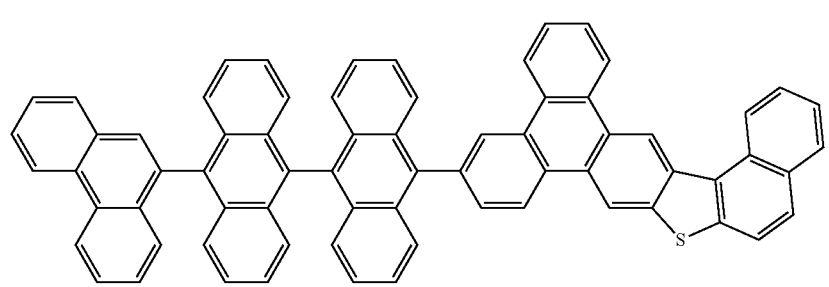

Compound 170
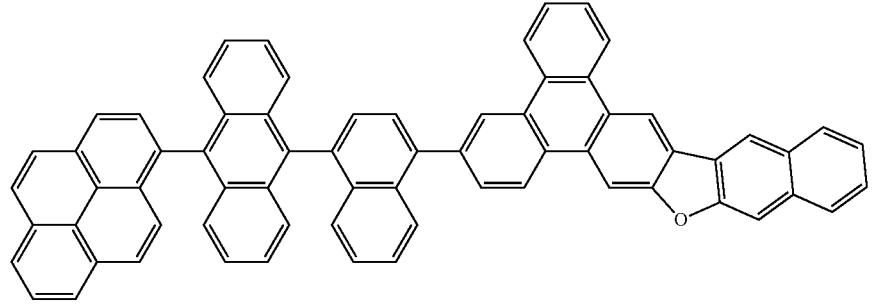
Compound 171
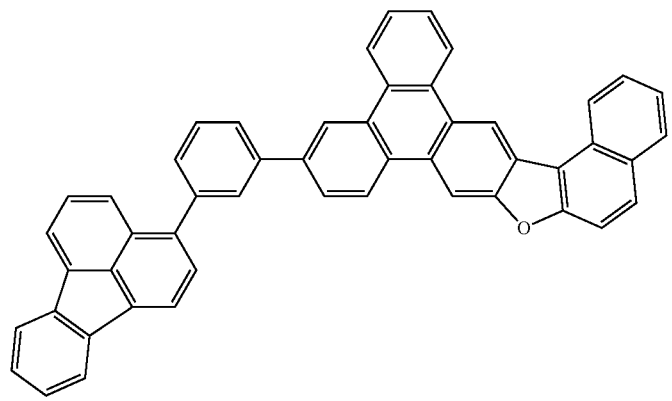
Compound 172
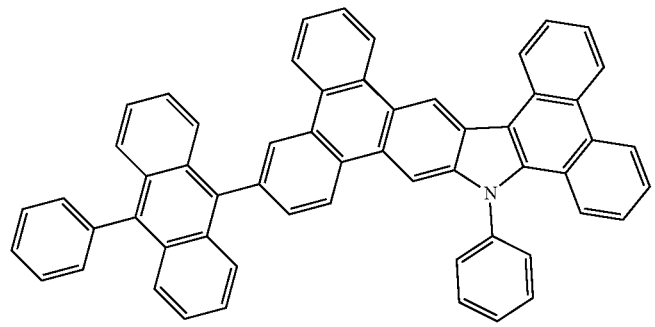
Compound 173
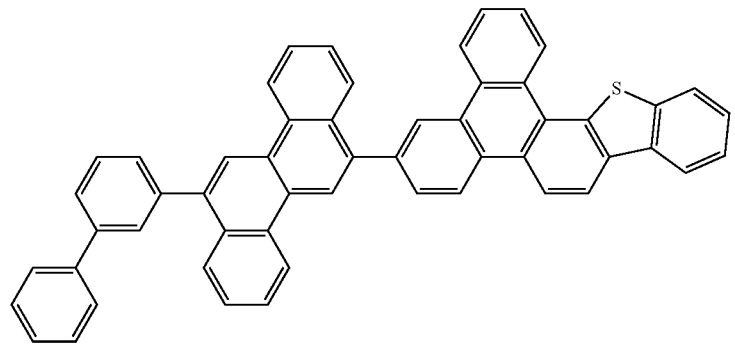

-continued
Compound 174
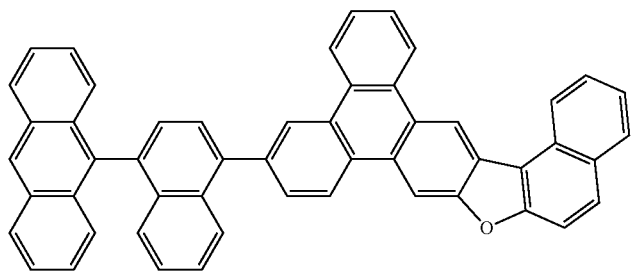
Compound 175
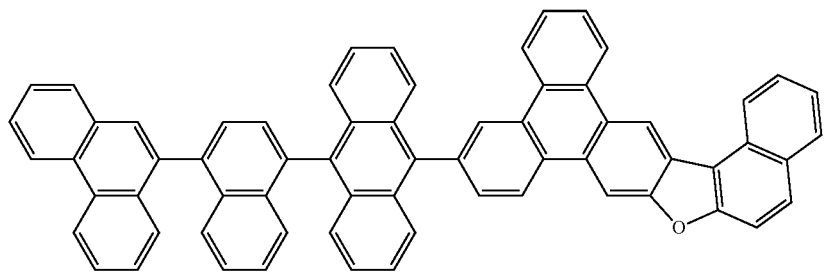
Compound 176
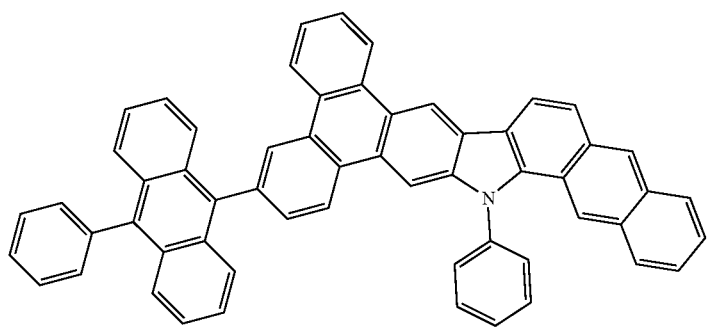
Compound 177
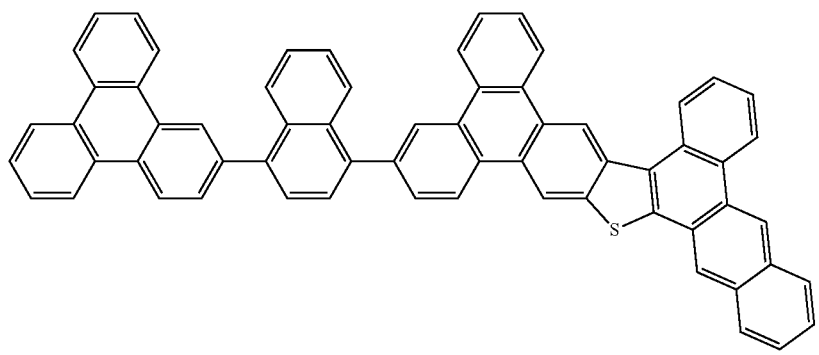
Compound 178
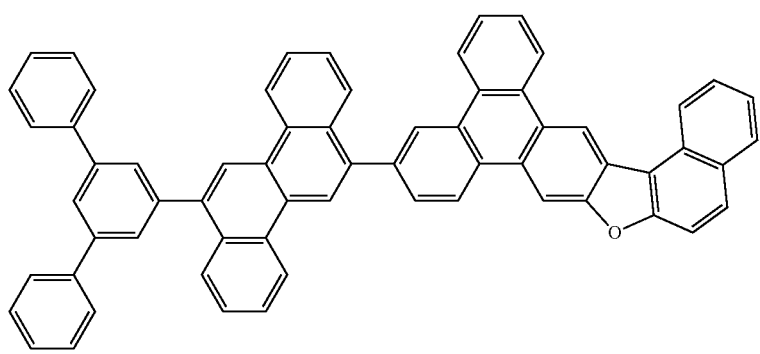

Compound 179
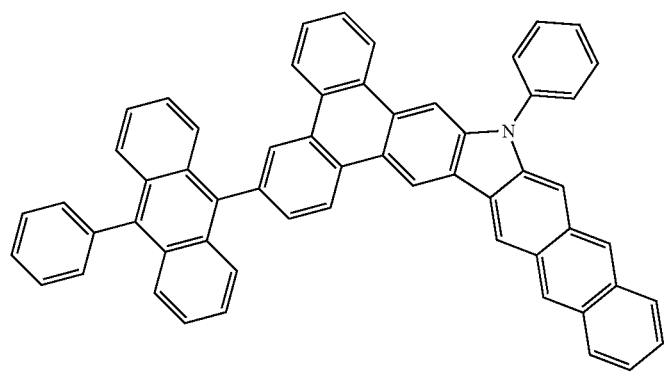
Compound 180
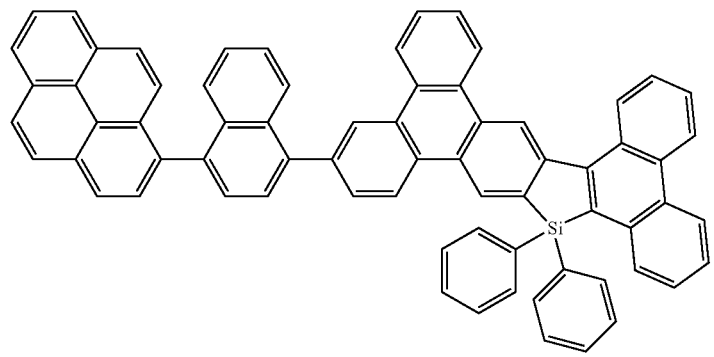
Compound 181
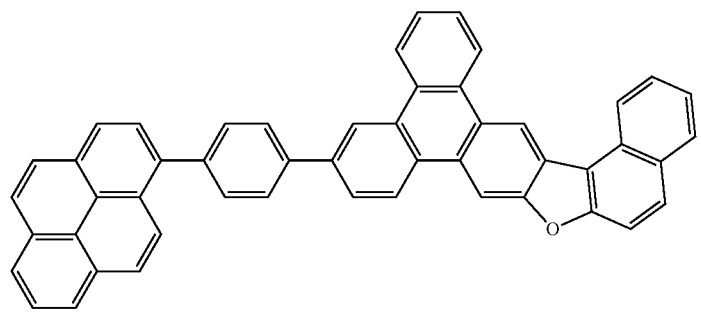
Compound 182
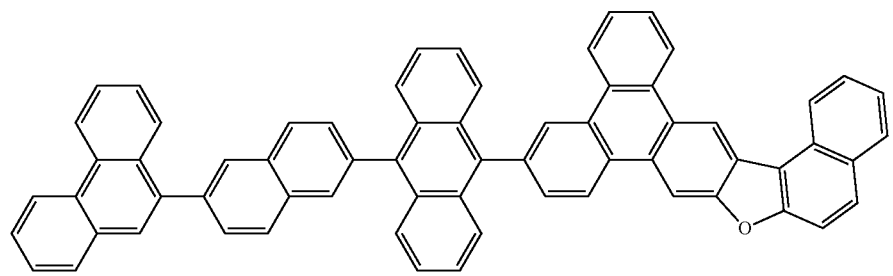

Compound 183
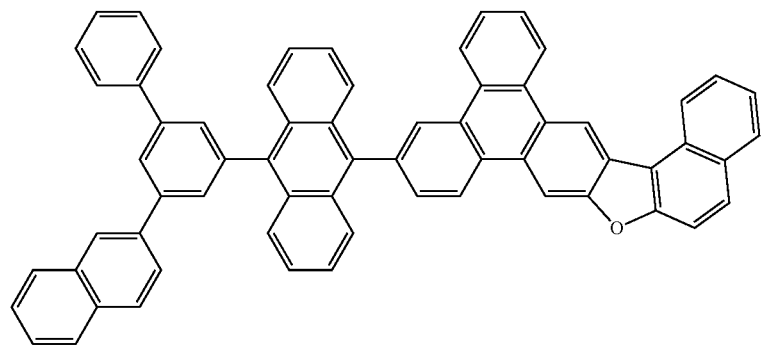
Compound 184
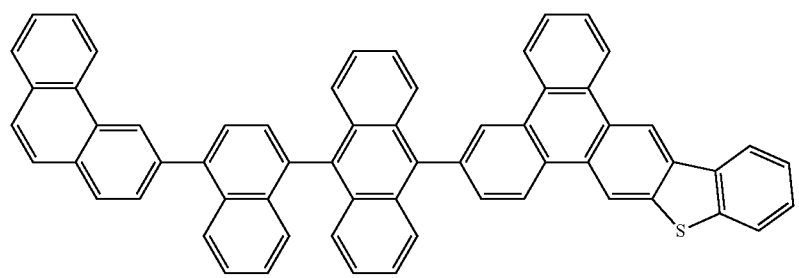
Compound 185
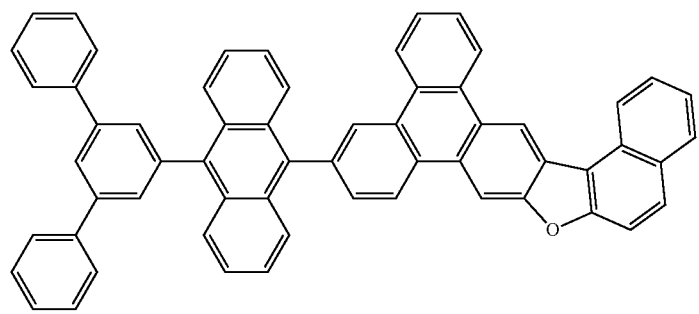
Compound 186
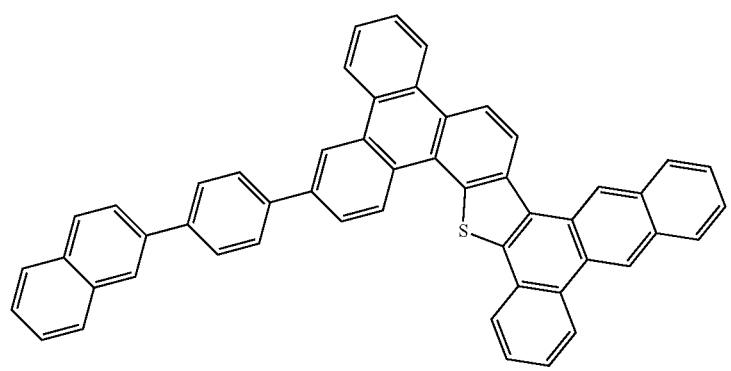

-continued
Compound 187
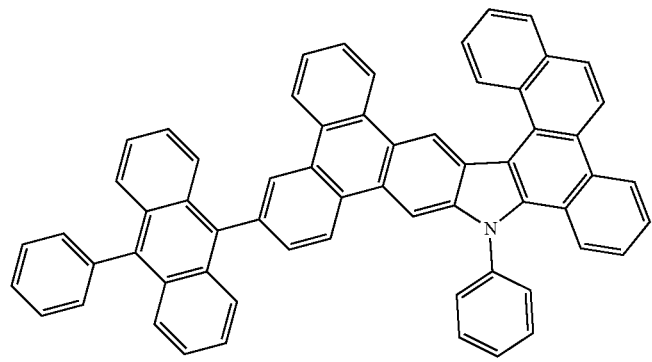
Compound 188
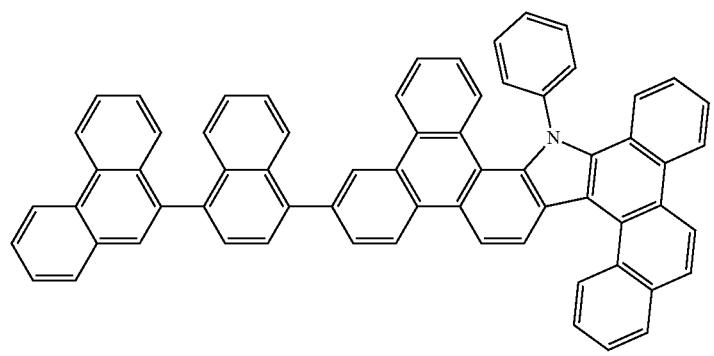
Compound 189
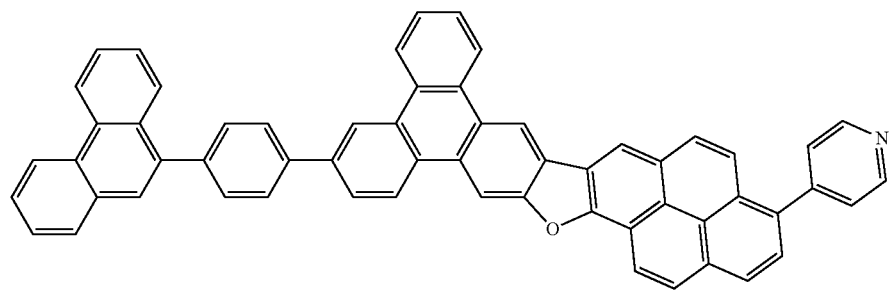
Compound 190
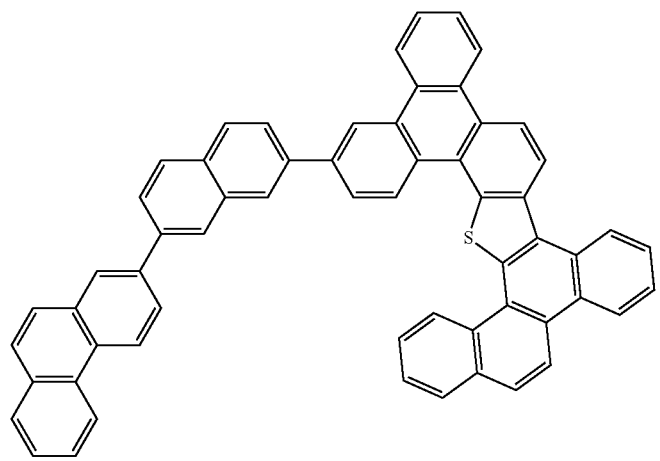

Compound 191
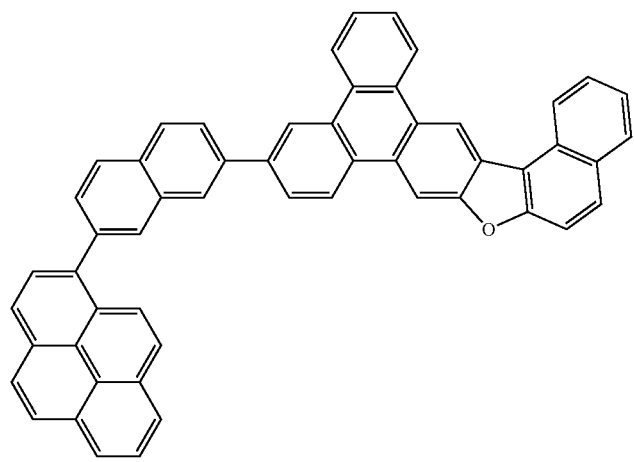
Compound 192
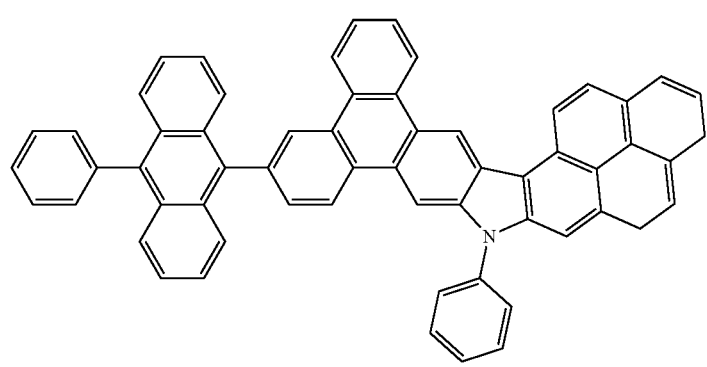
Compound 193
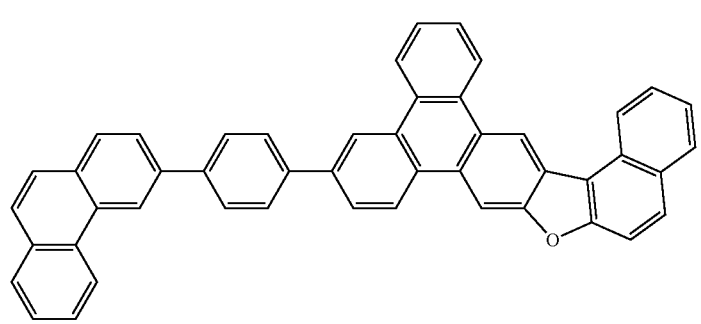
Compound 194
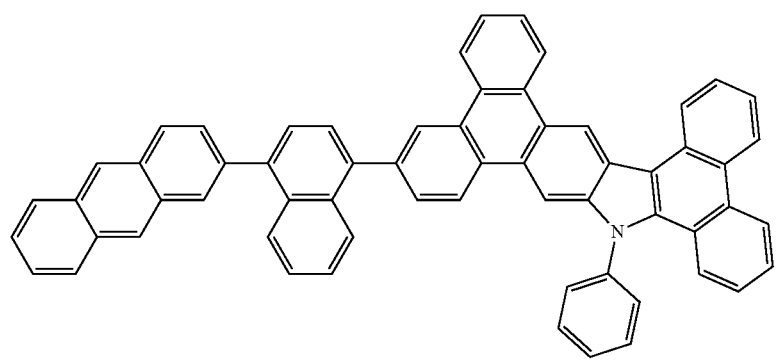

Compound 195
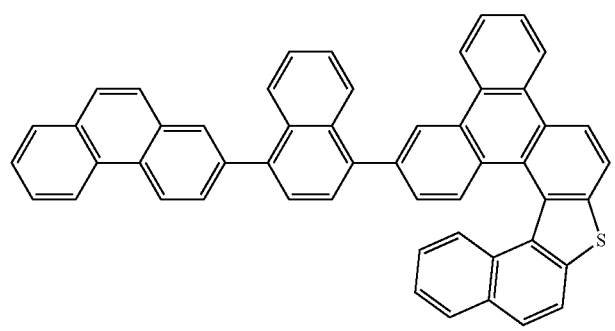
Compound 196
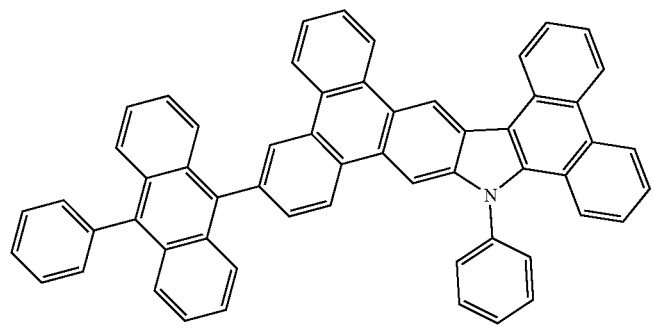
Compound 197
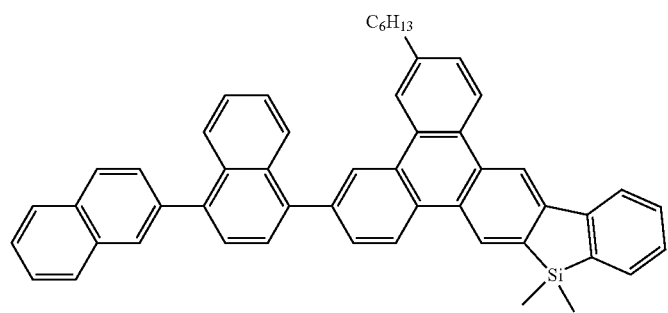
Compound 198
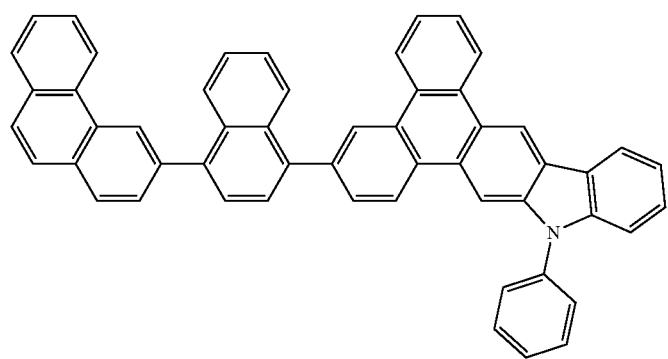

Compound 199
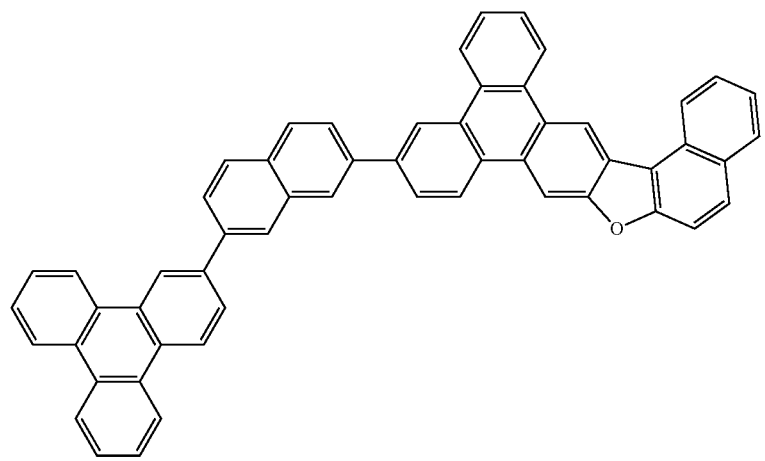
Compound 200
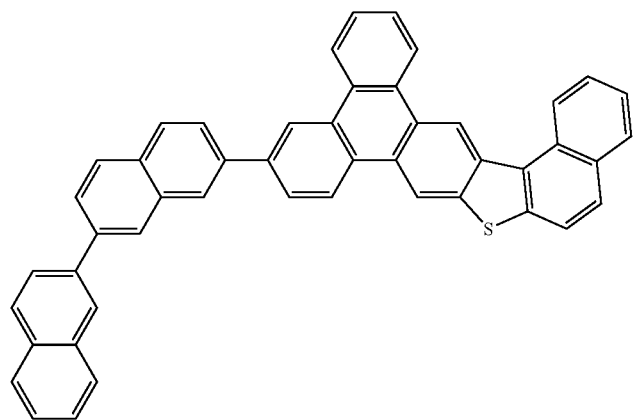
Compound 201
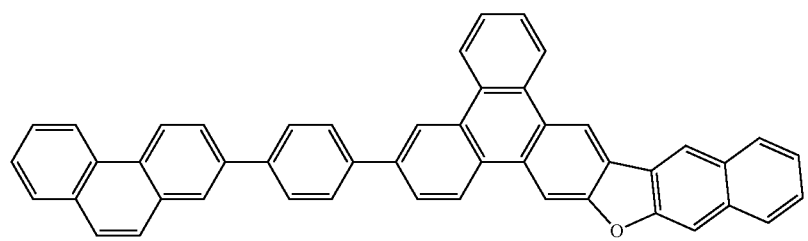
Compound 202
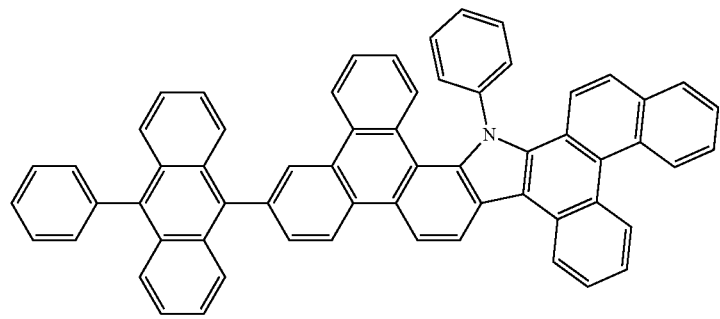

-continued
Compound 203
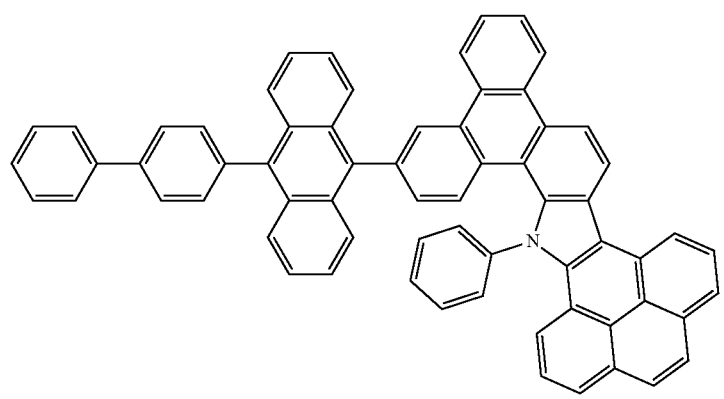
Compound 204
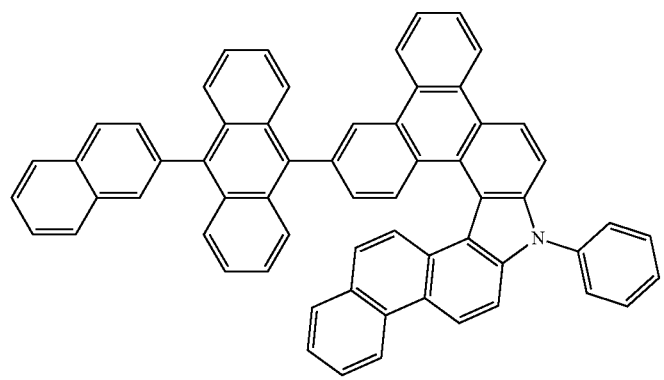
Compound 205
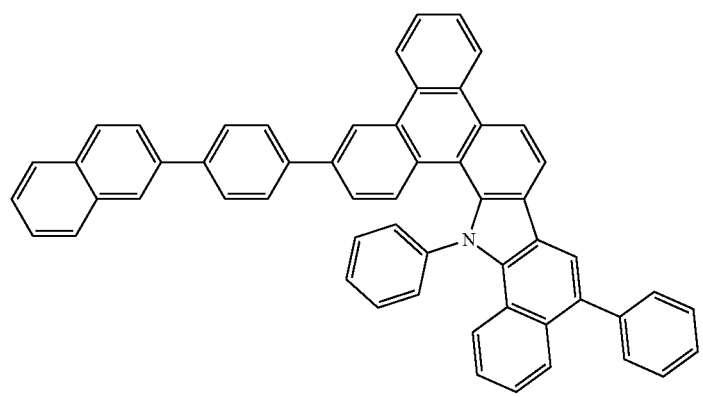
Compound 206
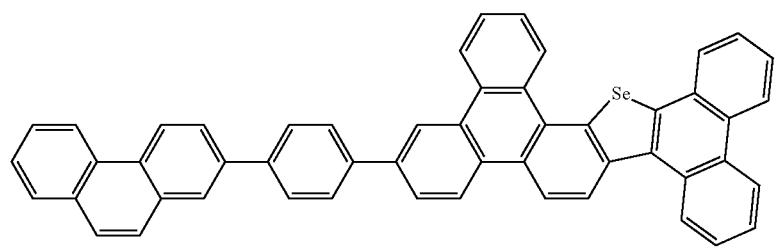

Compound 207
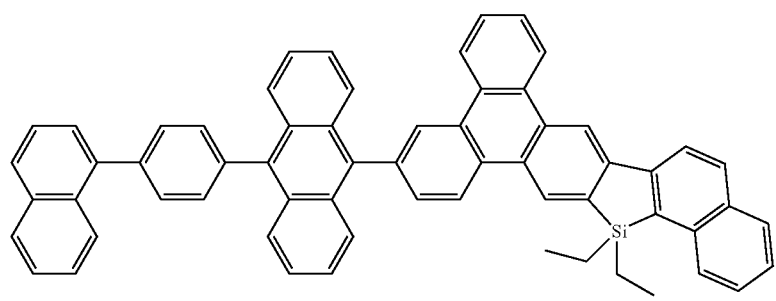
Compound 208
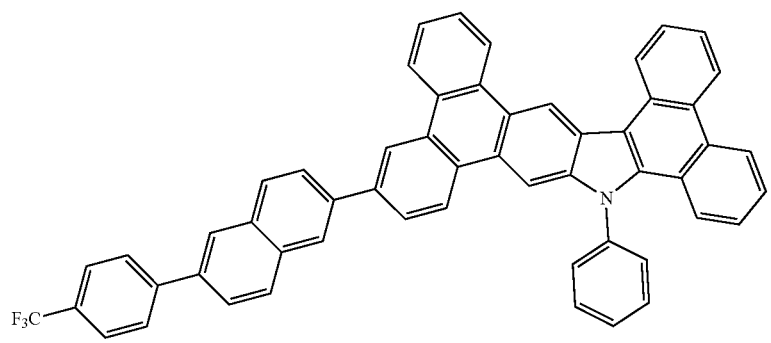
Compound 209
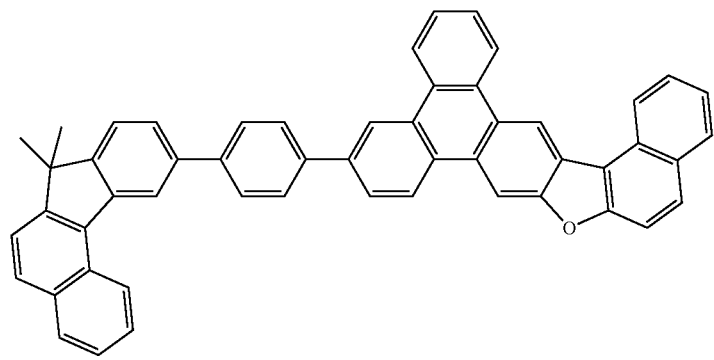
Compound 210
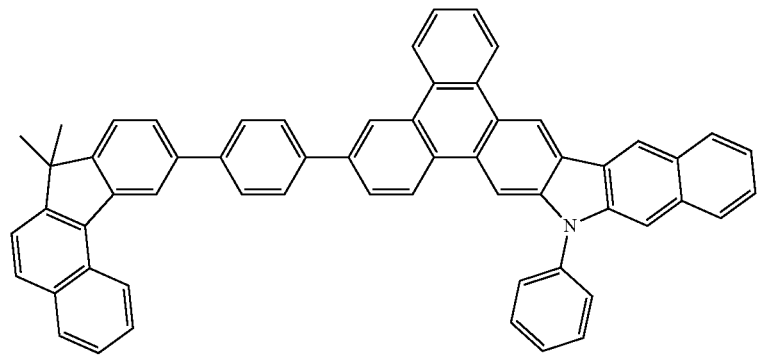

Compound 211
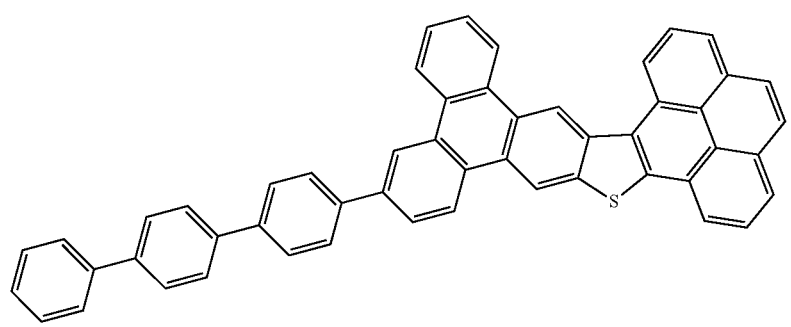
Compound 212
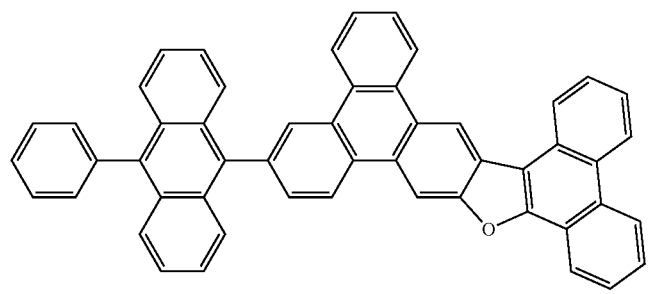
Compound 213
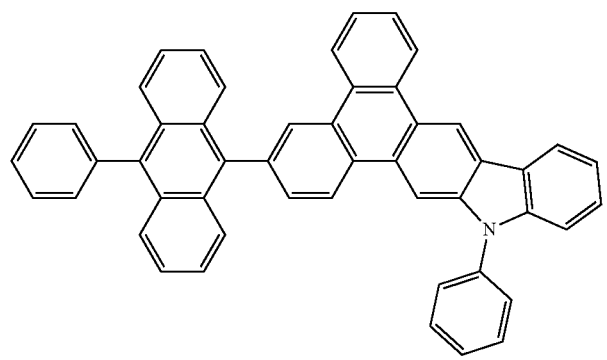
Compound 214
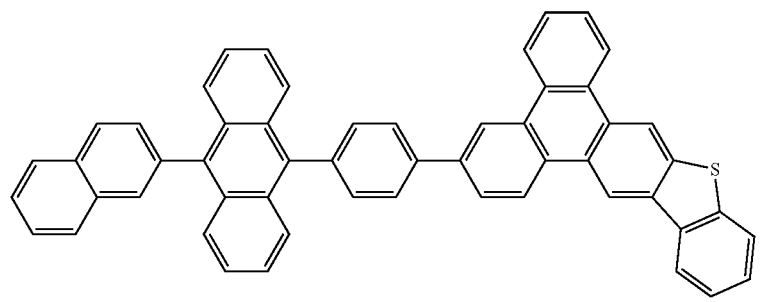
Compound 215
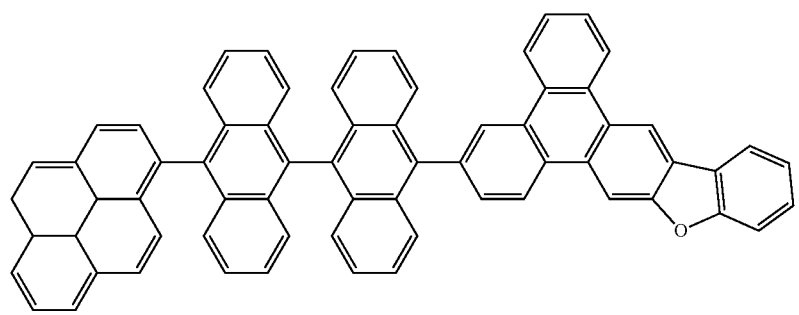

Compound 216
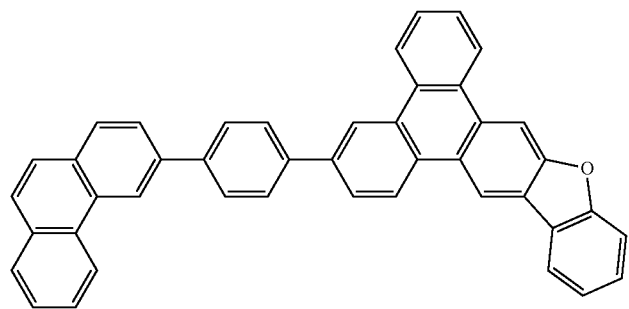
Compound 217
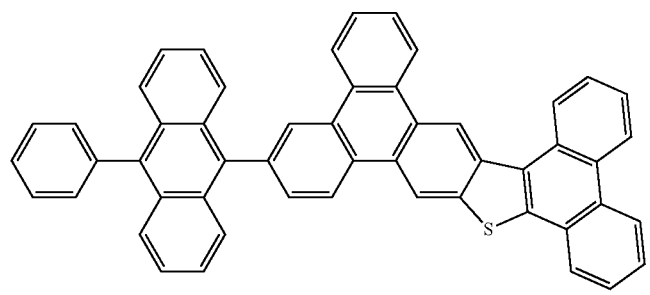
Compound 218
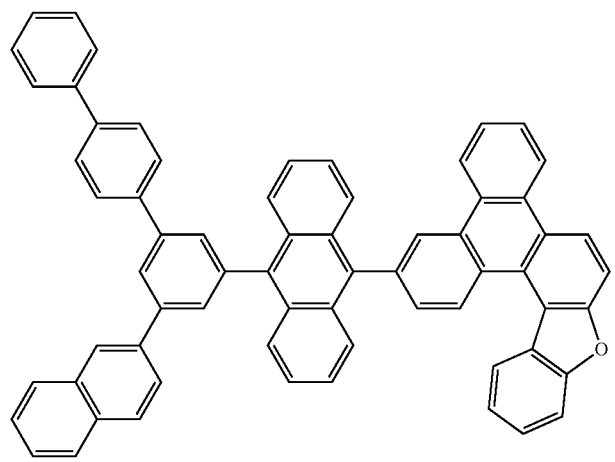
Compound 219
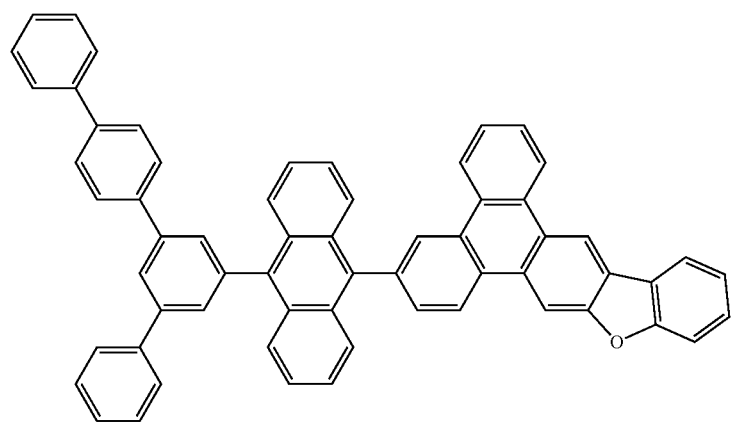

-continued
Compound 220
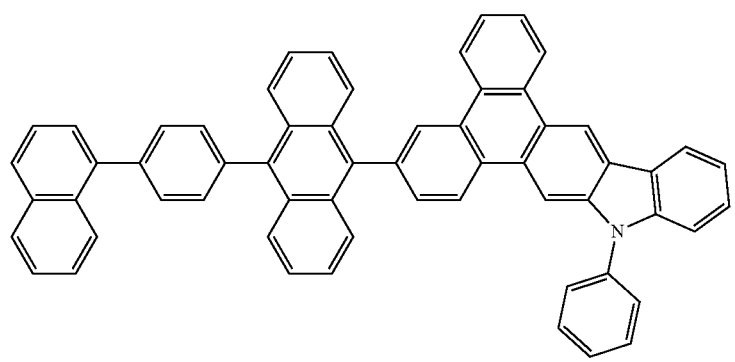
Compound 221
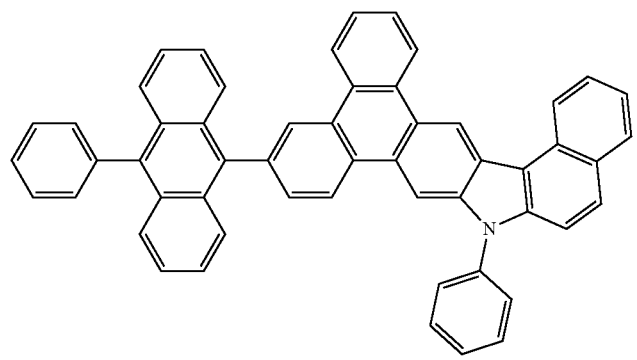
Compound 222
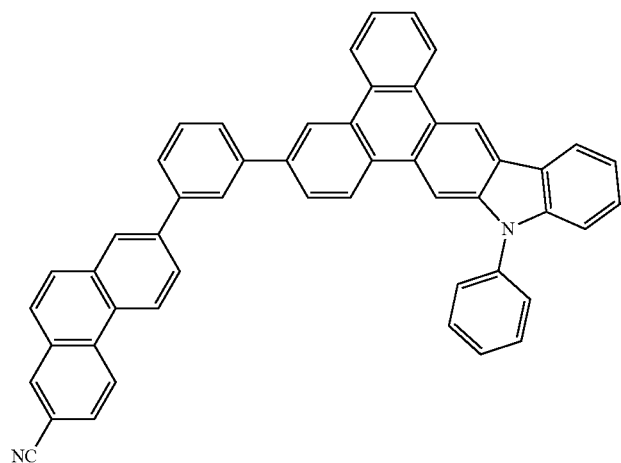
Compound 223
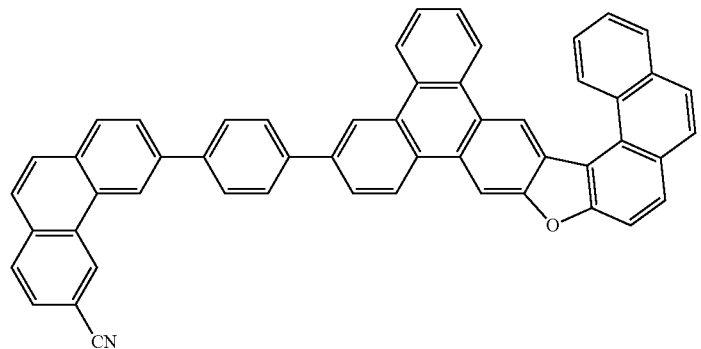

Compound 224
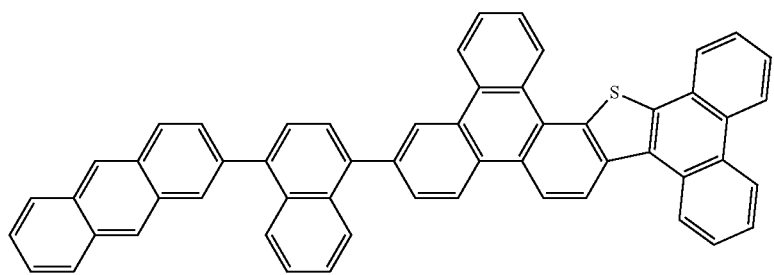
Compound 225
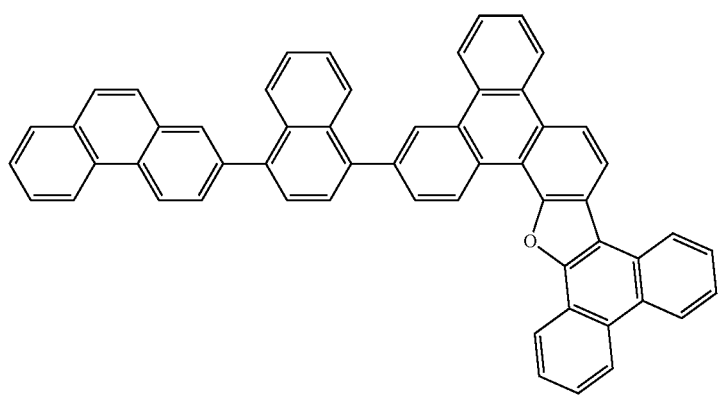
Compound 226
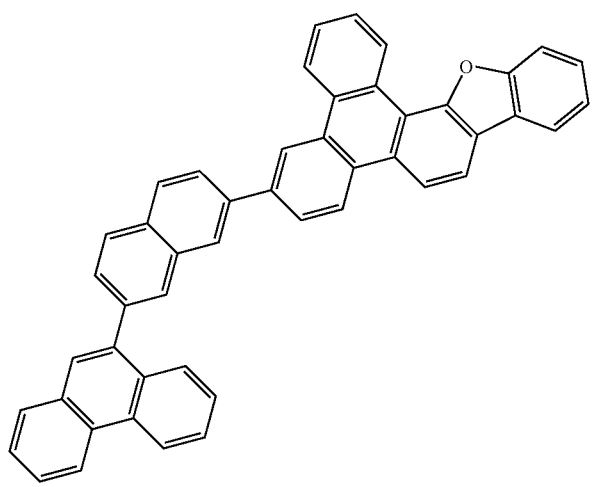
Compound 227
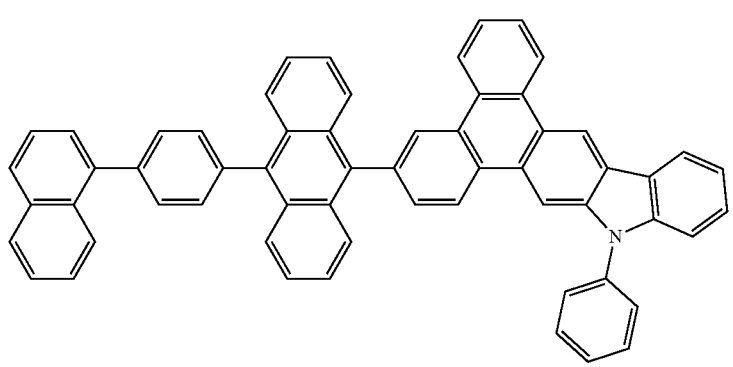

Compound 228
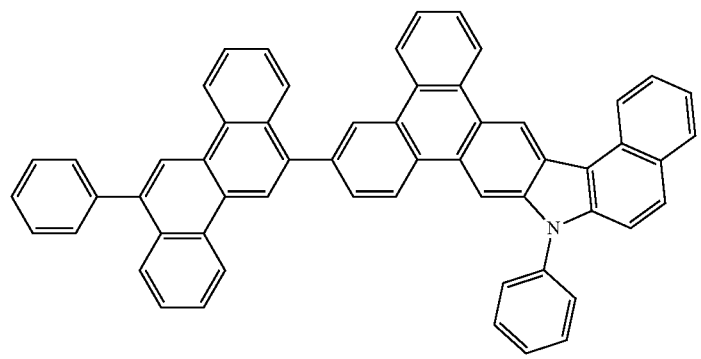
Compound 229
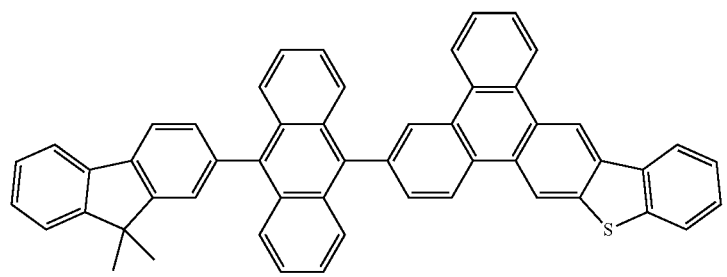
Compound 230
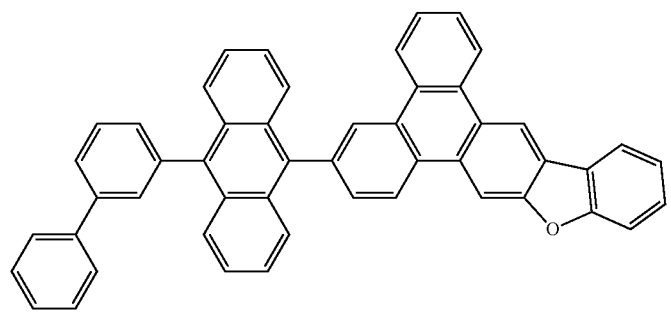
Compound 231
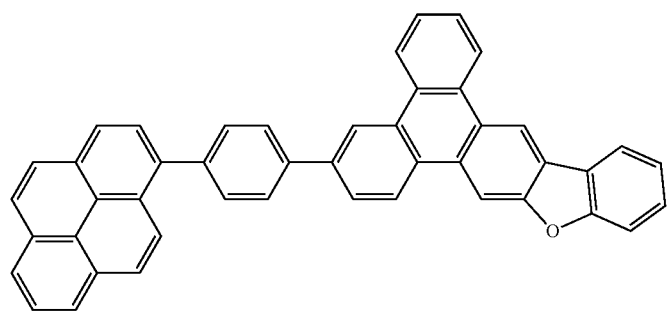
Compound 232
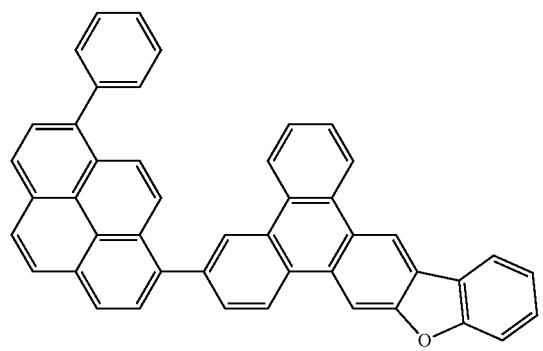

-continued
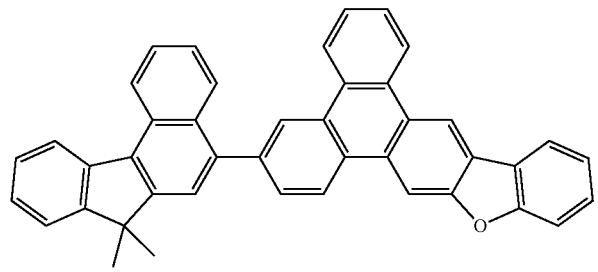
Compound 233
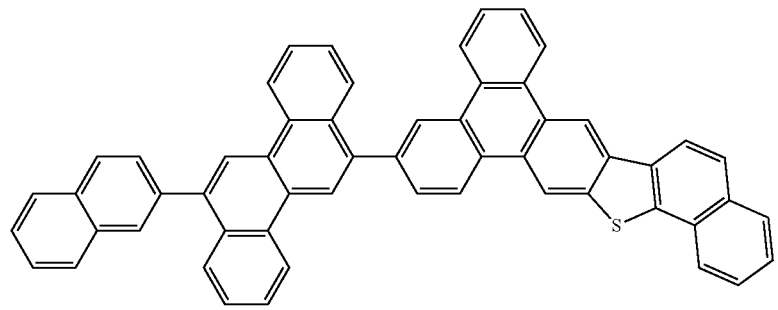
Compound 234
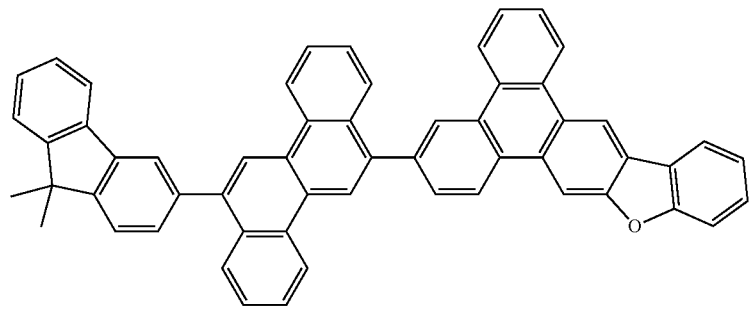
Compound 235
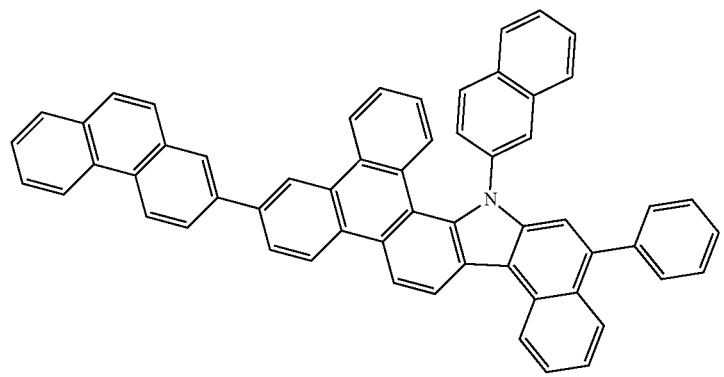
Compound 236
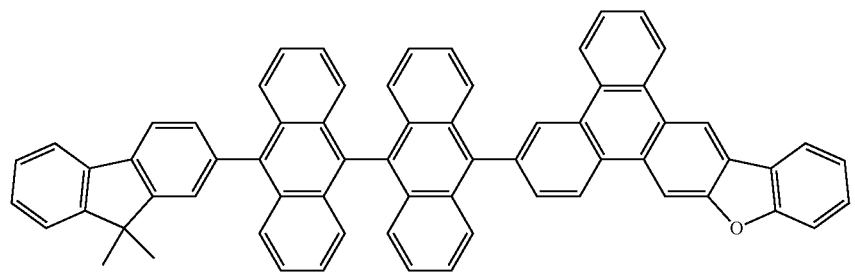
Compound 237

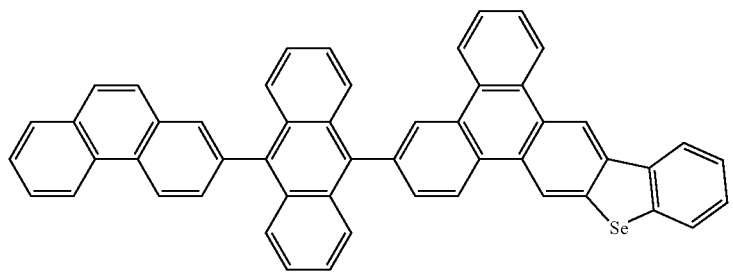
Compound 238
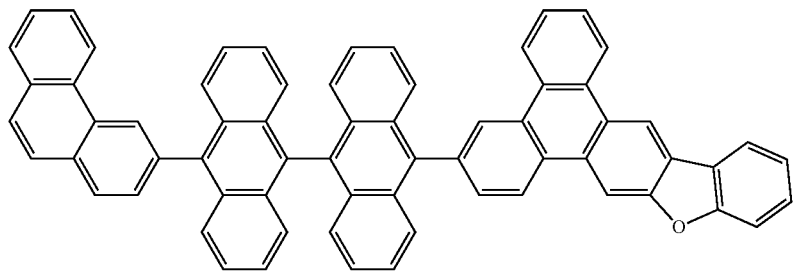
Compound 239
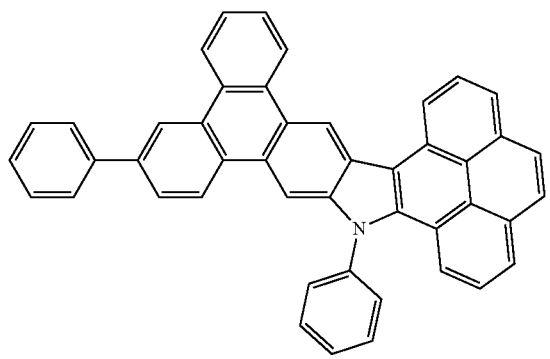
Compound 240
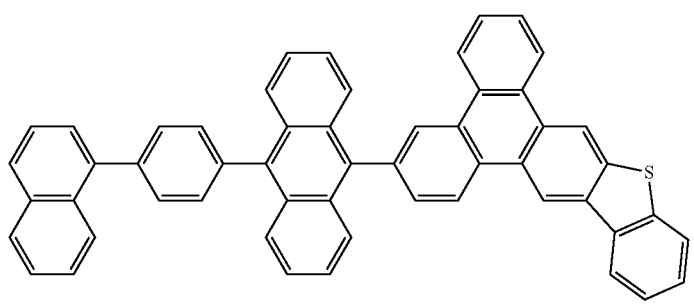
Compound 241
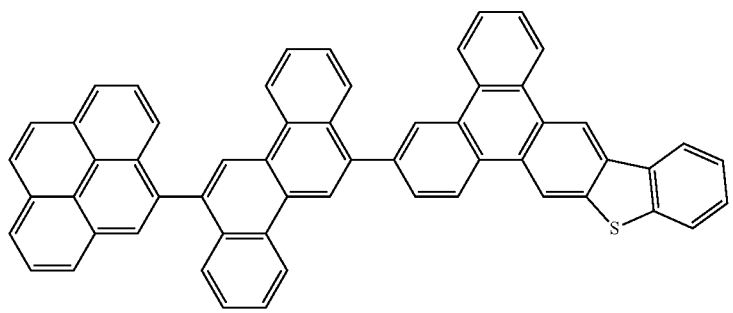
Compound 242

Compound 243
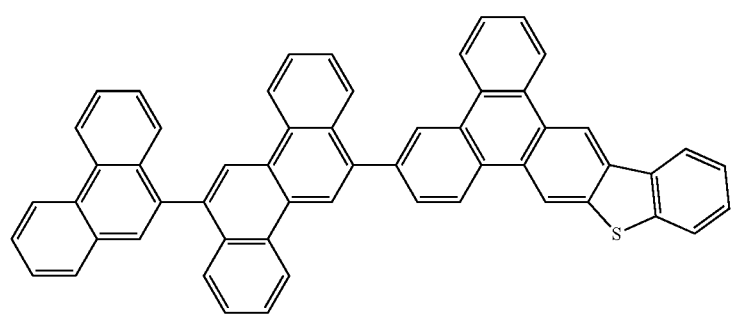
Compound 244
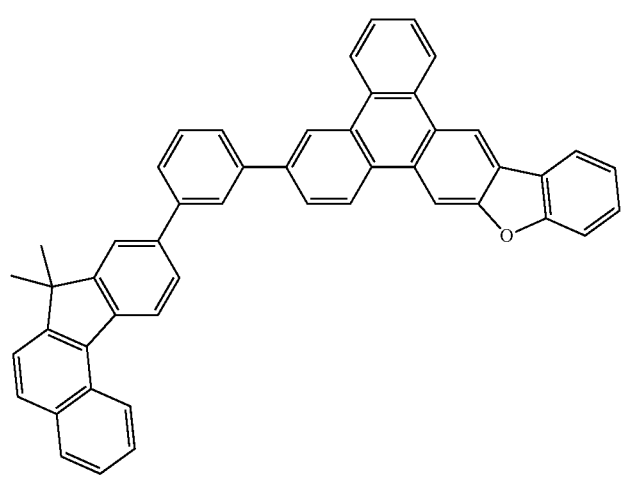
Compound 245
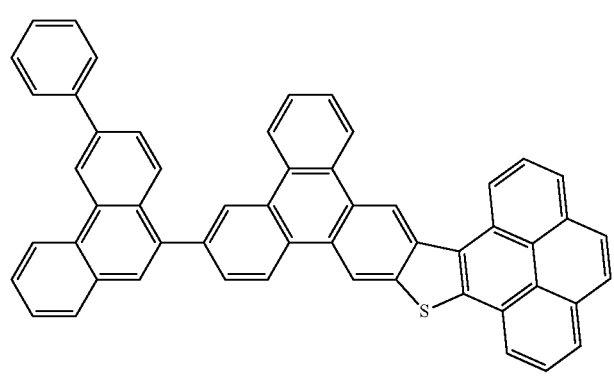
Compound 246
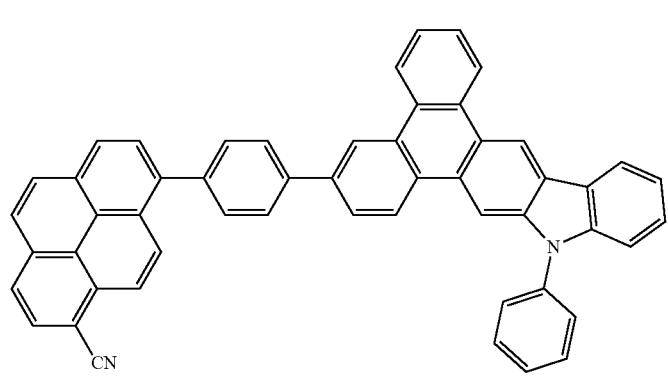

Compound 247
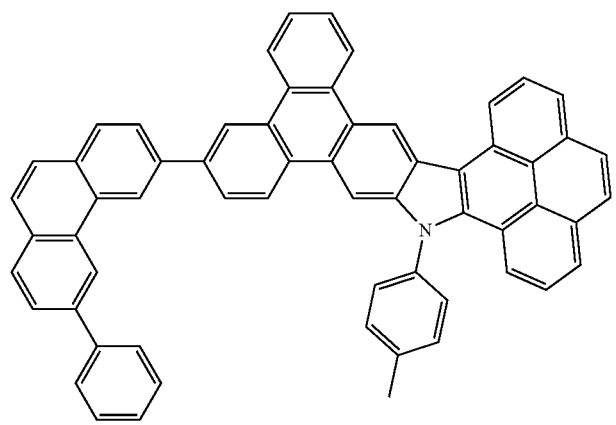
Compound 248
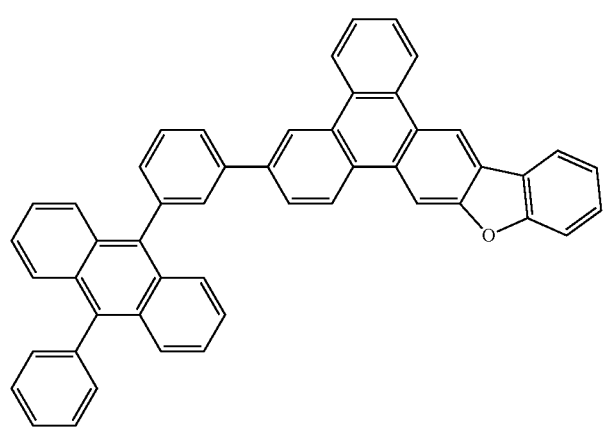
Compound 249
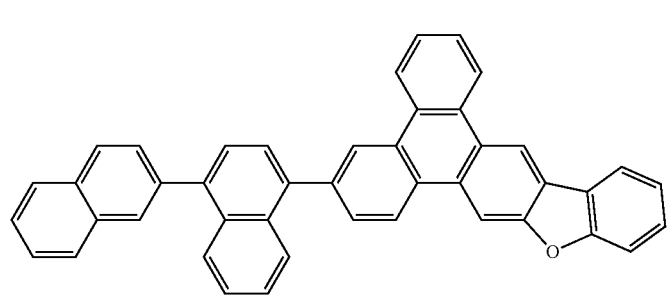
Compound 250
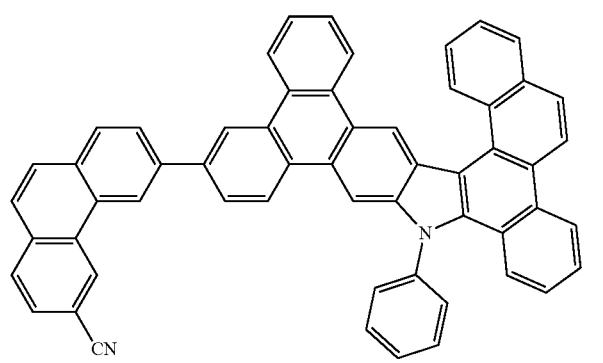

-continued
Compound 251
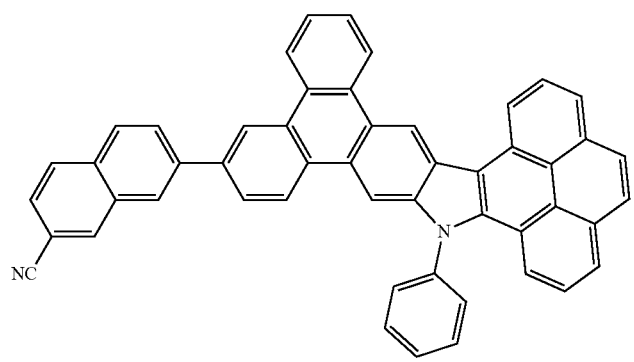
Compound 252
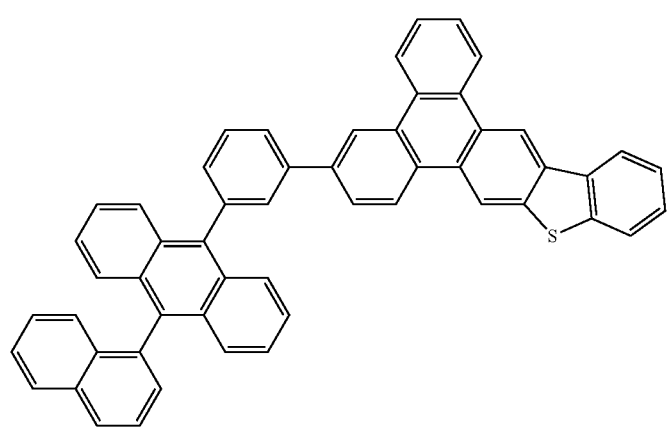
Compound 253
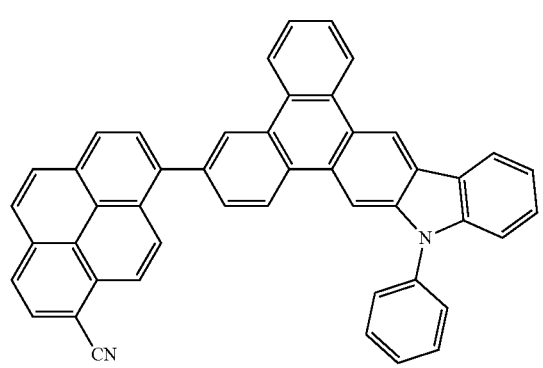
Compound 254
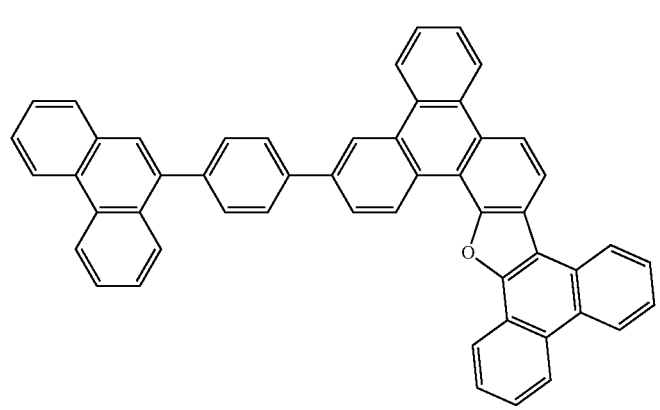

-continued
Compound 255
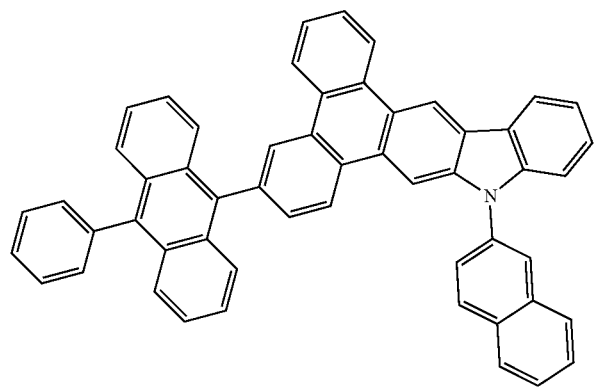
Compound 256
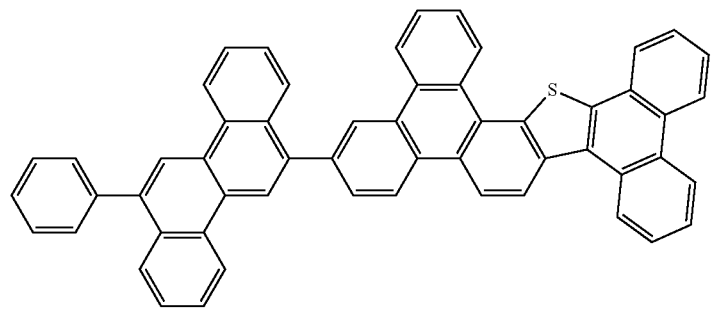
Compound 257
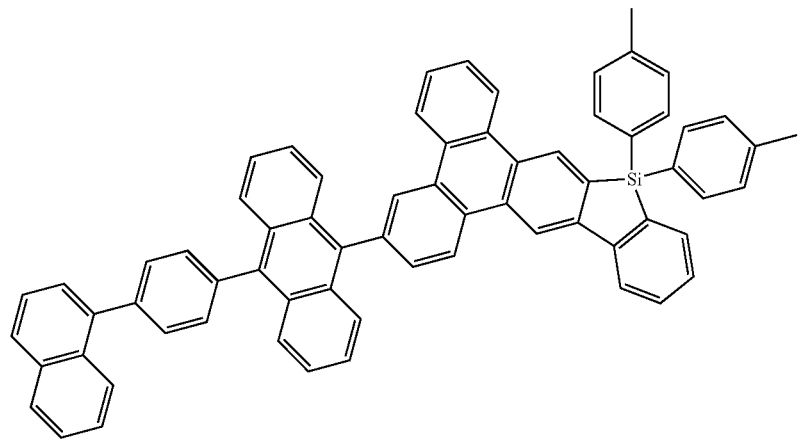
Compound 258
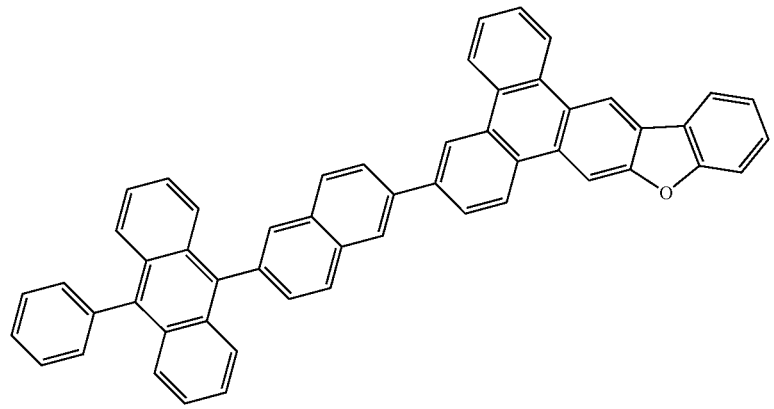

-continued
Compound 259
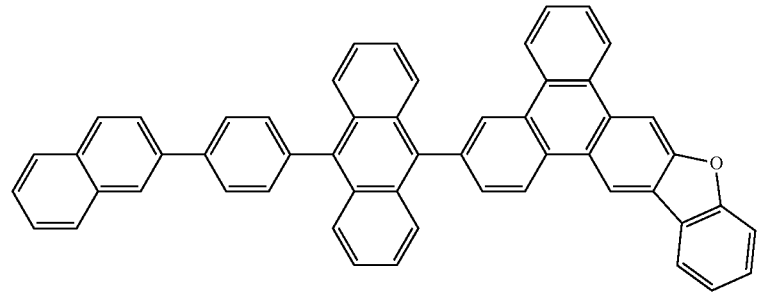
Compound 260
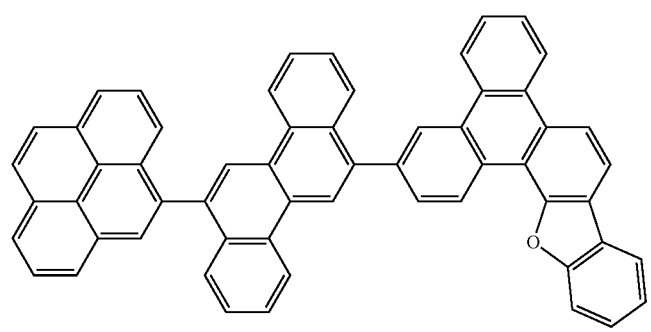
Compound 261
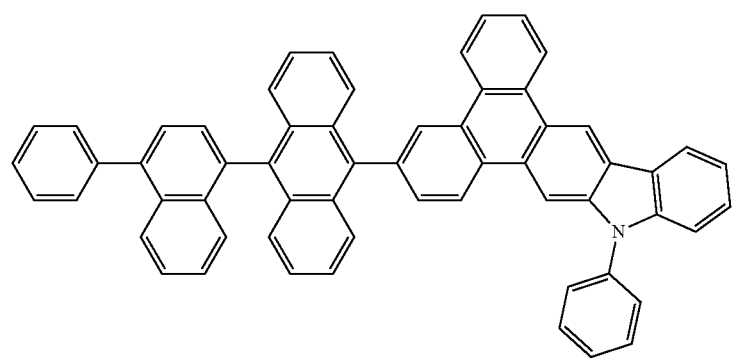
Compound 262
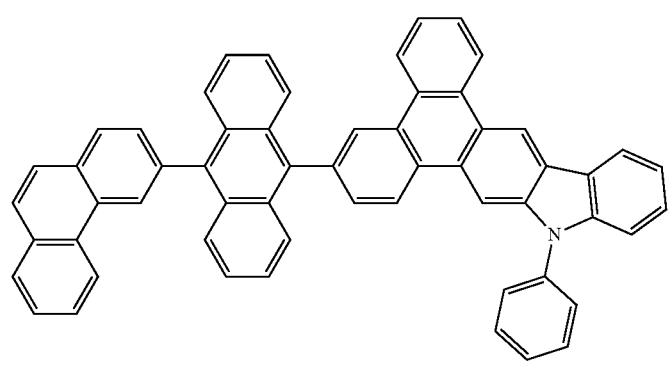

-continued
Compound 263
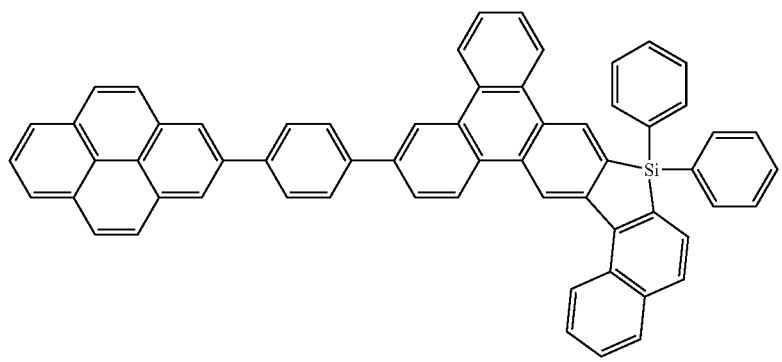
Compound 264
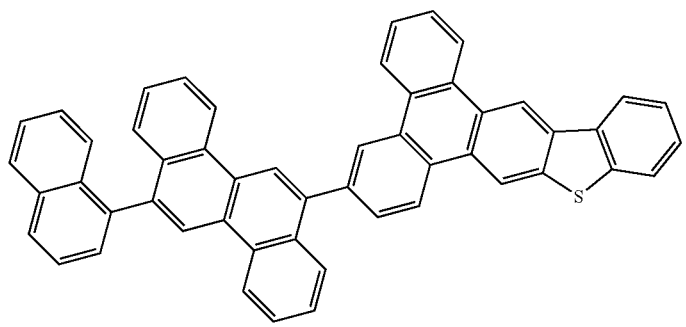
Compound 265
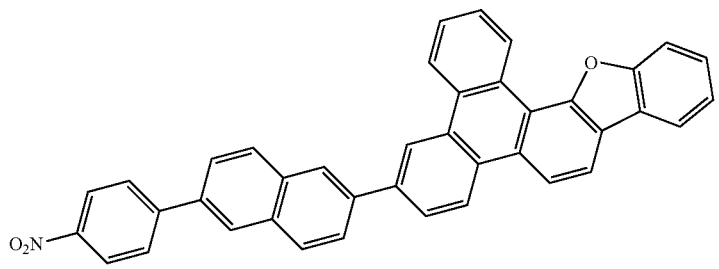
Compound 266
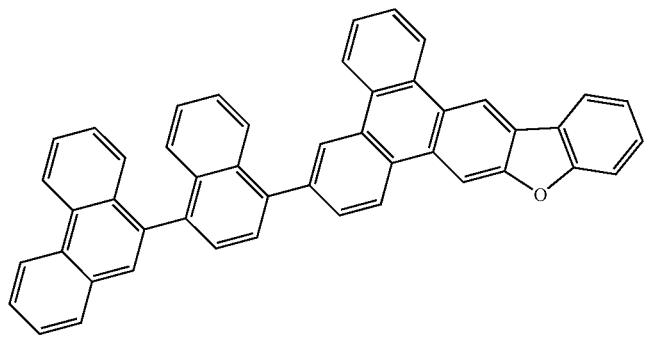

-continued
Compound 267
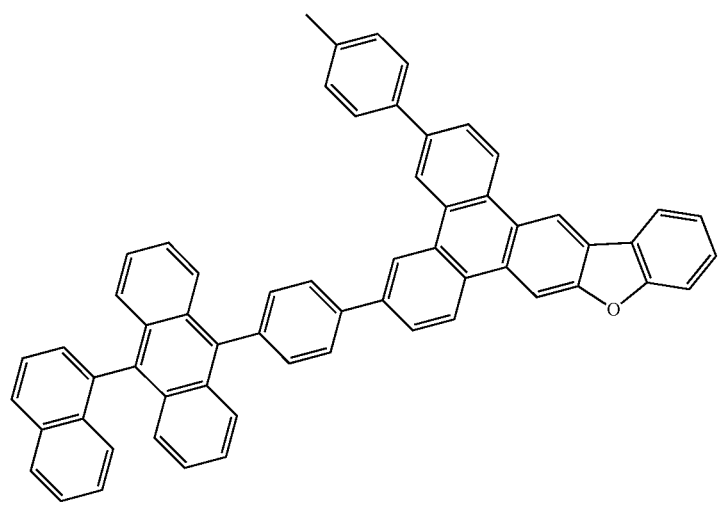
Compound 268
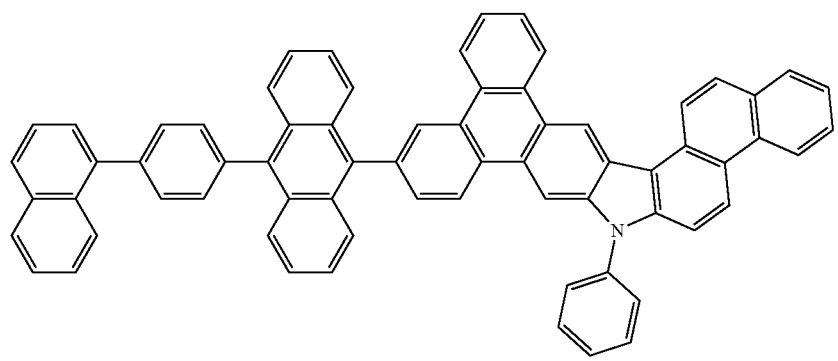
Compound 269
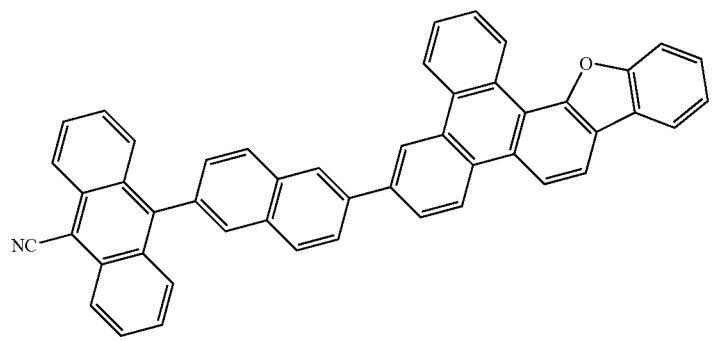
Compound 270
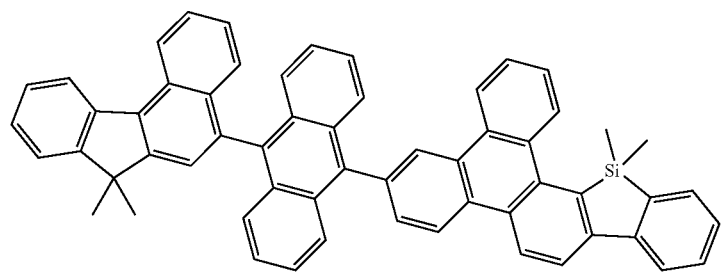

-continued
Compound 271
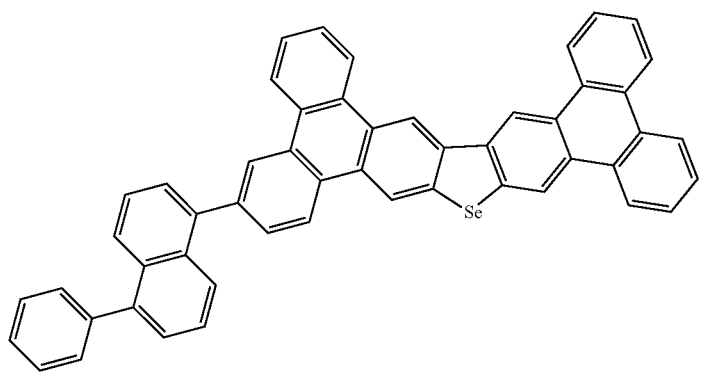
Compound 272
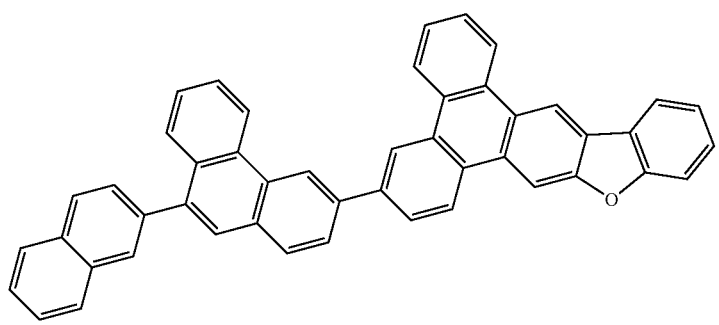
Compound 273
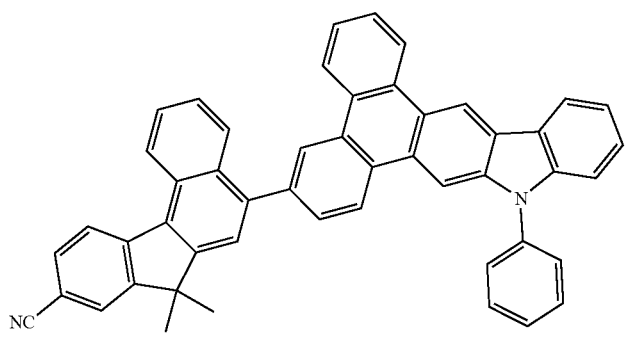
Compound 274
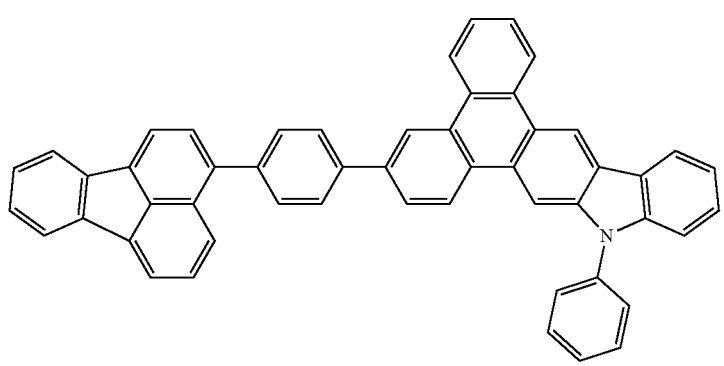

-continued
Compound 275
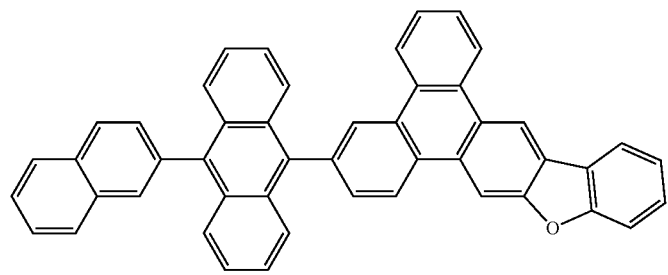
Compound 276
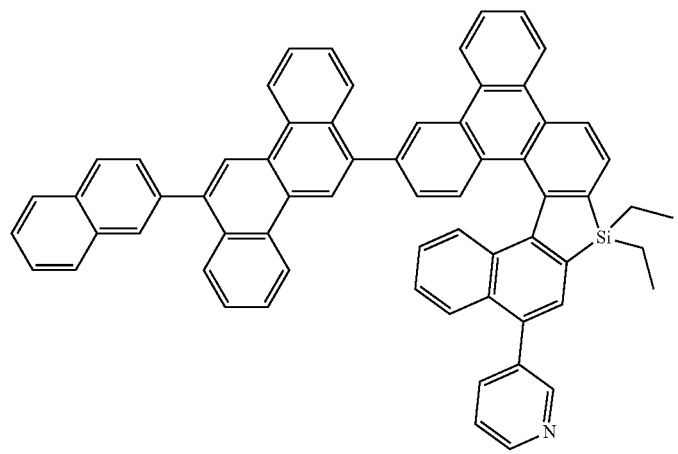
Compound 277
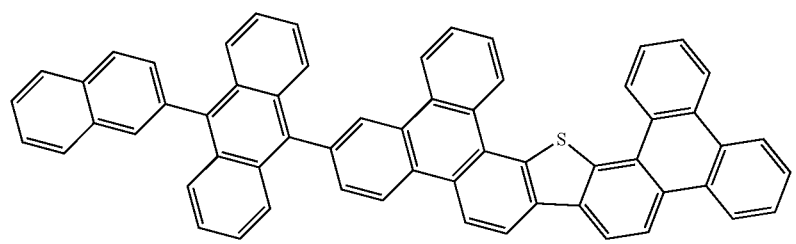
Compound 278
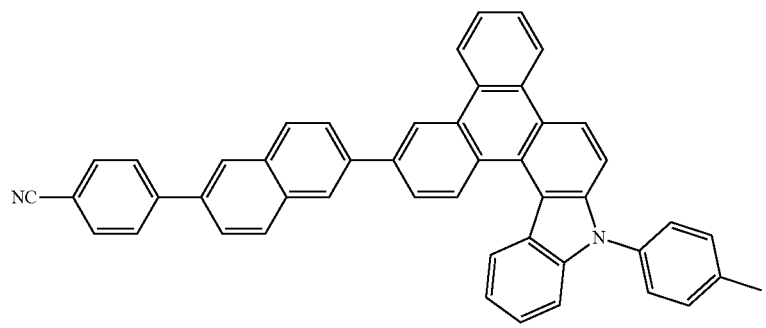
Compound 279
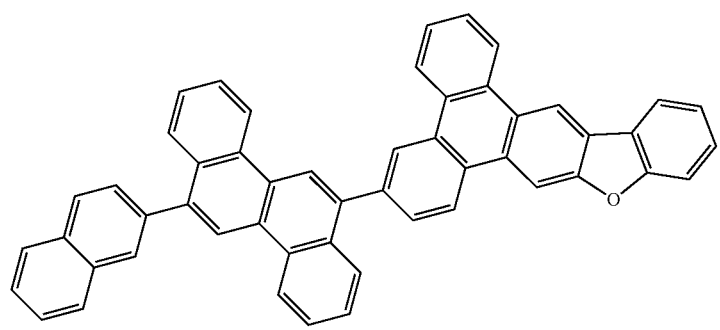

Compound 280
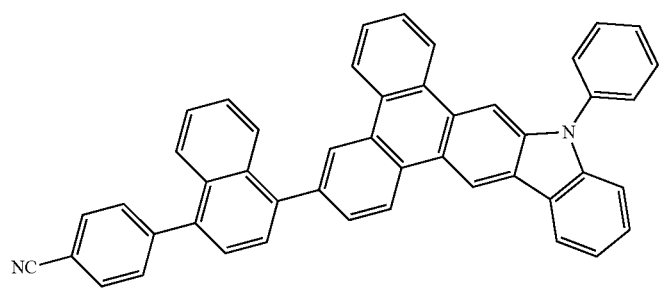
Compound 281
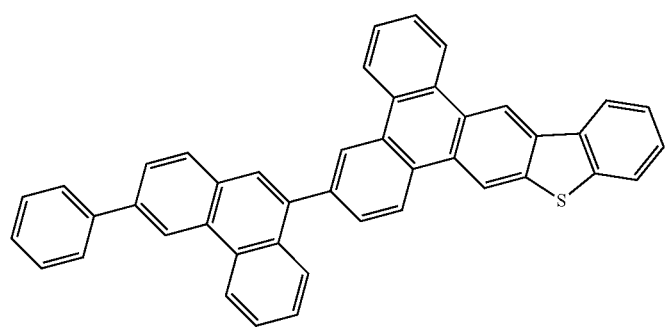
Compound 282
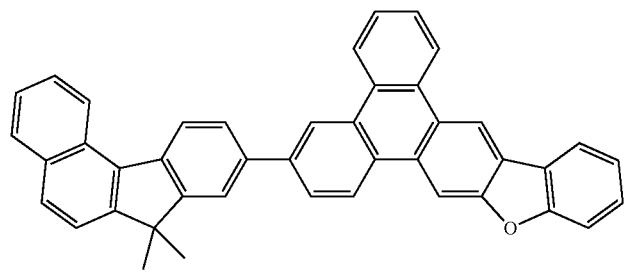
Compound 283
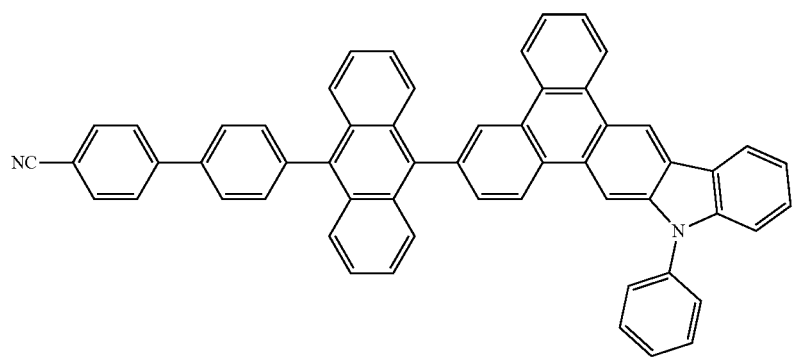

Compound 284
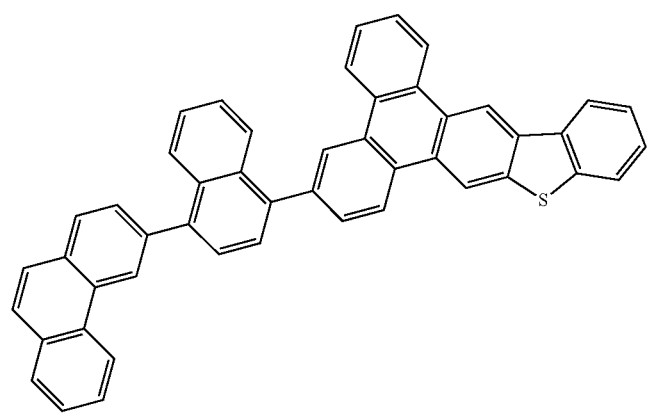
Compound 285
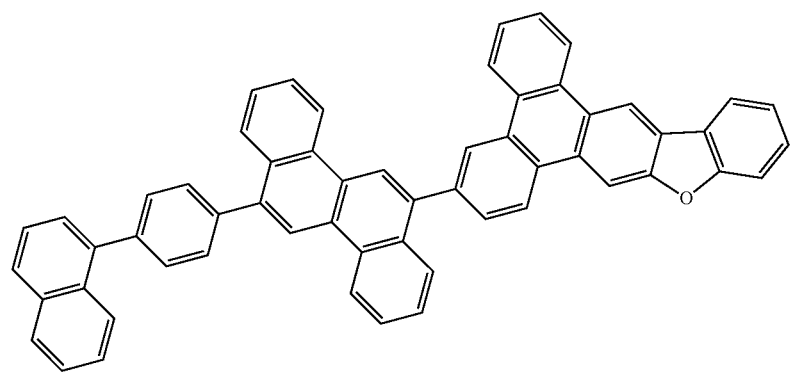
Compound 286
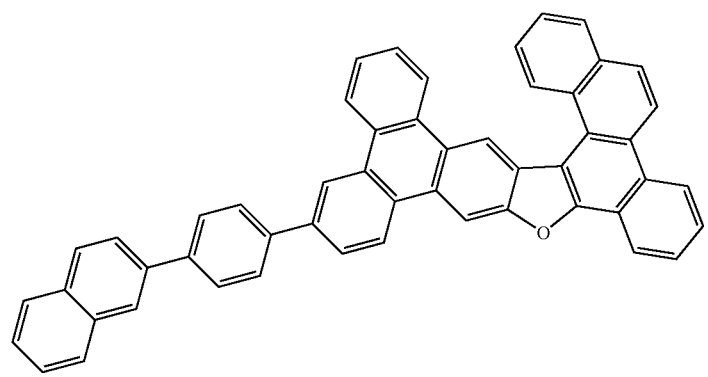
Compound 287
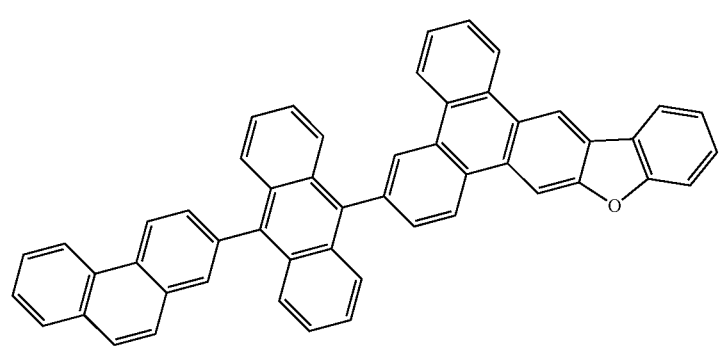

Compound 288
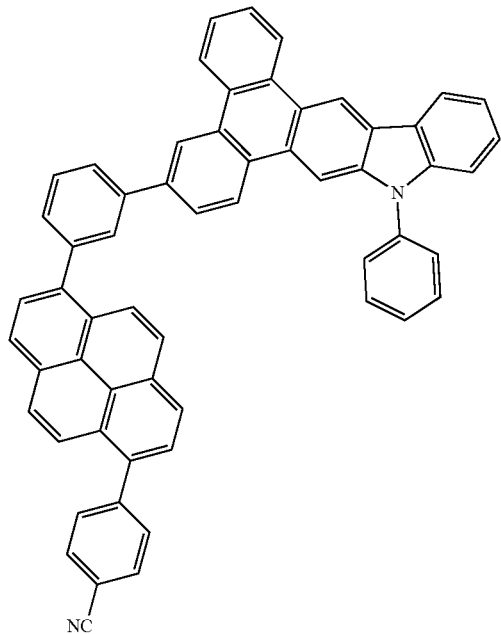
Compound 289
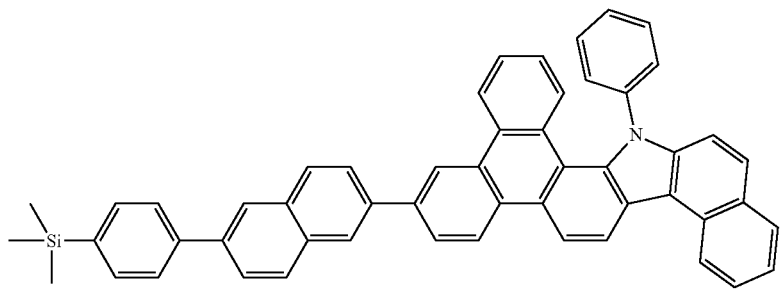
Compound 290
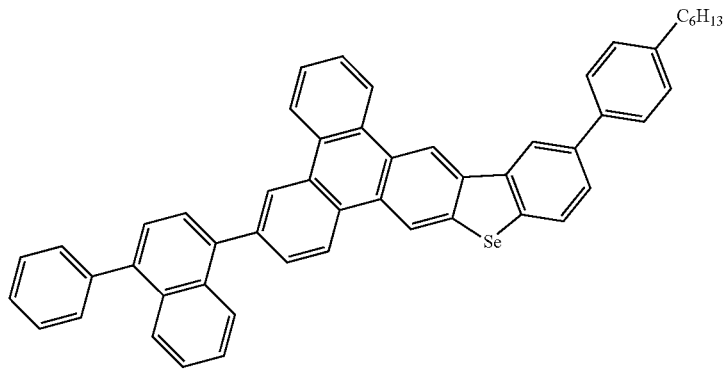
Compound 291
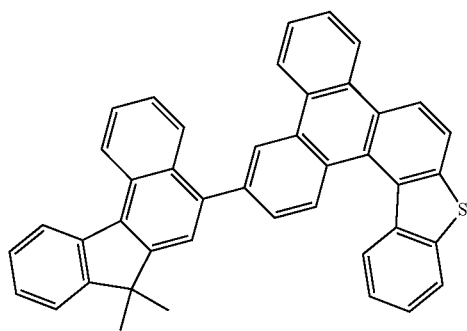

Compound 292
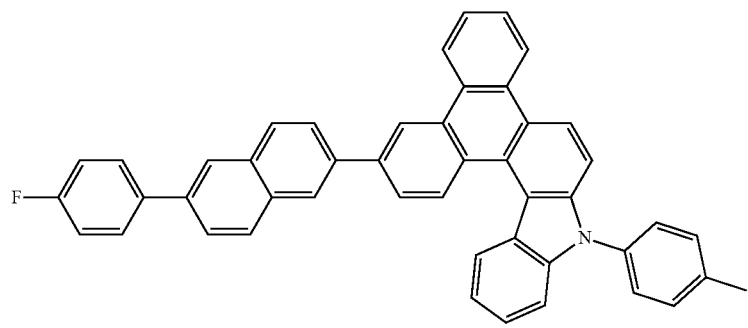
Compound 293
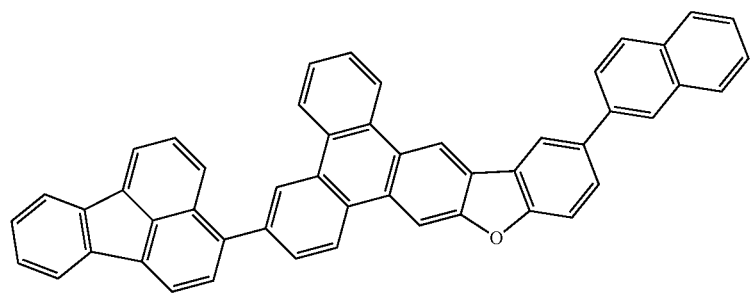
Compound 294
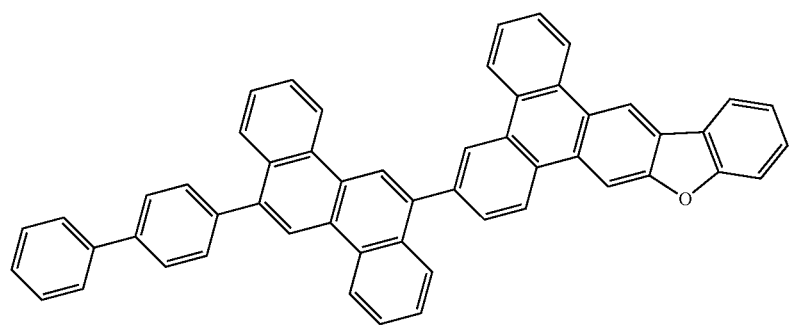
Compound 295
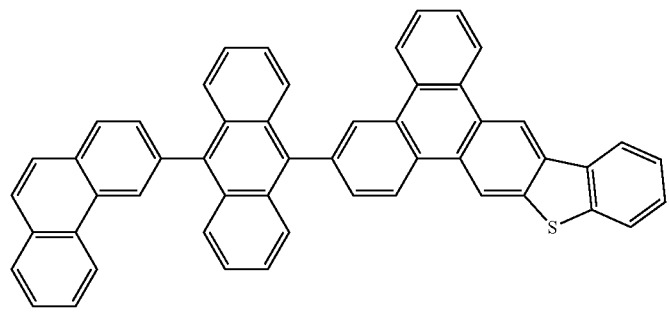
Compound 296
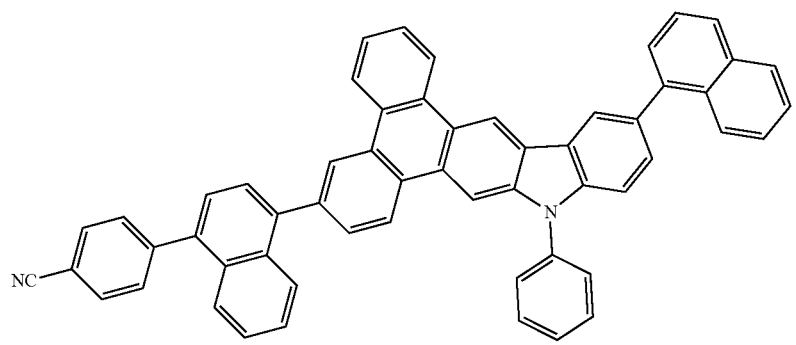

Compound 297
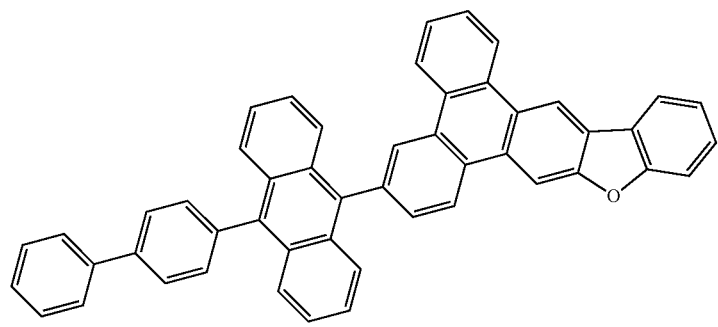
Compound 298
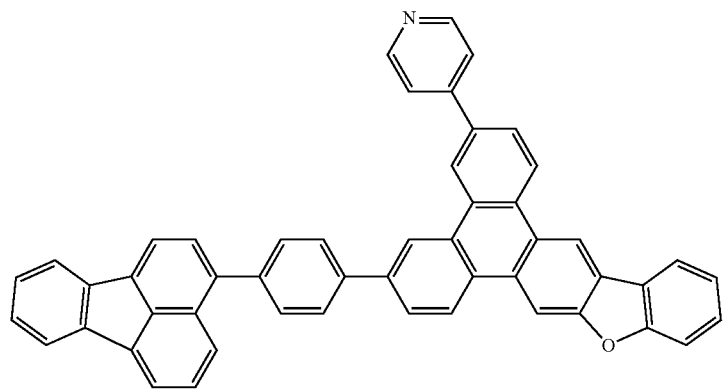
Compound 299
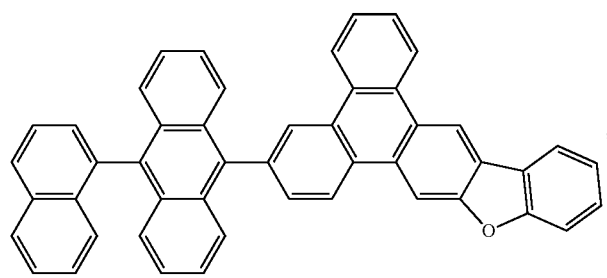
and
Compound 300
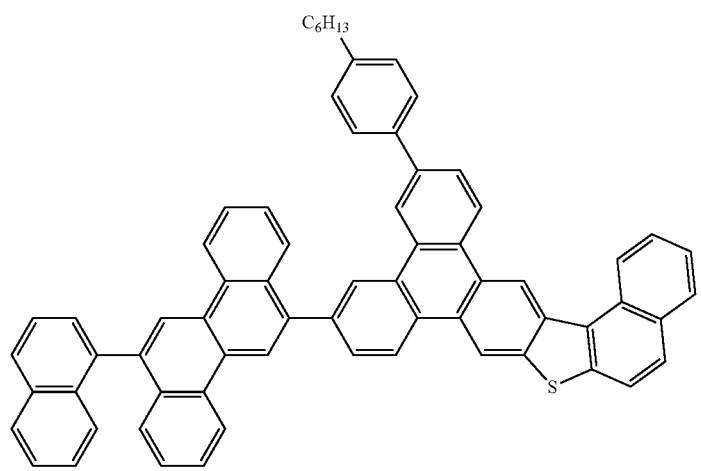

An organic electroluminescence device comprising an anode, a cathode and one or more organic layers formed between the anode and the cathode. At least one of the organic layers comprises the organic compound of the present invention.

The organic layers may comprise an emissive layer having a dopant. The organic compound of formula (1) is comprised as the dopant.

The organic layers may comprise an emissive layer having a host. The organic compound of formula (1) is comprised as the host.

The light emitting layer may comprise the compound of formula (1) as an electron transporting material.

The organic electroluminescence device may be a lighting panel.

The organic electroluminescence device may be a backlight panel.

Referring to FIG. 1, the first organic EL device 510 may comprise an anode 310, a cathode 380 and one or more organic layers 320, 330, 340E, 350, 360, 370 formed between the anode 310 and the cathode 380. From the bottom to the top, the one or more organic layers may comprise a hole injection layer 320, a hole transport layer 330, an emissive layer 340E, a hole blocking layer 350, an electron transport layer 360 and an electron injection layer 370.

FIG. 1, the emissive layer 340E may contain about 5% of dopant 340C and about 95% of host H1 doped with the organic compound of formula (1) 340C. The dopant 340C may be a blue guest material for tuning the wavelength at which the emissive layer 340E emits light, so that the color of the emitted light may be blue. The organic compound of formula (1) may be the dopant 340C of the emissive layer 340E.

Referring to FIG. 2 is a cross-sectional view of an organic EL device without the organic compound of formula (1). FIG. 2, the organic EL device 400 may comprise an anode 310, a cathode 380 and one or more organic layers 320, 330, 340, 350, 360, 370 formed between the anode 310 and the cathode 380. From the bottom to the top, the one or more organic layers may comprise a hole injection layer 320, a hole transport layer 330, an emissive layer 340, a hole blocking layer 350, an electron transport layer 360 and an electron injection layer 370. The emissive layer 340 may contain about 5% of dopant D1 and about 95% of host H1 doped with the dopant D1. The dopant D1 may be a blue guest material.

Referring to FIG. 3, the second organic EL device 520 may comprise an anode 310, a cathode 380 and one or more organic layers 320, 330, 340E, 350, 360, 370 formed between the anode 310 and the cathode 380. From the bottom to the top, the one or more organic layers may comprise a hole injection layer 320, a hole transport layer 330, an emissive layer 340E, a hole blocking layer 350, an electron transport layer 360 and an electron injection layer 370.

FIG. 3, the emissive layer 340E may contain from 95% of host 340H and 5% of dopant D1. The dopant D1 may be a blue guest material for tuning the wavelength at which the emissive layer 340E emits light, so that the color of the emitted light may be blue. The organic compound of formula (1) may be the host 340H of the emissive layer 340E.

Referring to FIG. 4, the third organic EL device 530 may comprise an anode 310, a cathode 380 and one or more organic layers 320, 330, 340, 350, 360ET, 370 formed between the anode 310 and the cathode 380. From the bottom to the top, the one or more organic layers may comprise a hole injection layer 320, a hole transport layer 330, an emissive layer 340, a hole blocking layer 350, an electron transport layer 360ET and an electron injection layer 370.

FIG. 4, the electron transport layer 360ET may contain about 50% of organic compound of formula (1) 360C and about 50% of Liq.

A method of producing the first organic EL device 510 of FIG. 1, the second organic EL device 520 of FIG. 3, the third organic EL device 530 of FIG. 4 and the organic EL device 400 of FIG. 2 is described. ITO-coated glasses with 9~12 ohm/square in resistance and 120~160 nm in thickness are provided (hereinafter ITO substrate) and cleaned in a number of cleaning steps in an ultrasonic bath (e.g., detergent, deionized water).

Before vapor deposition of the organic layers, cleaned ITO substrates may be further treated by UV and ozone. All pre-treatment processes for ITO substrate are under clean room (class 100), so that an anode 310 may be formed.

One or more organic layers 320, 330, 340 (FIG. 2), 340E (FIG. 1 and FIG. 3), 350, 360ET (FIG. 4), 370 are applied onto the anode 310 in order by vapor deposition in a high-vacuum unit ($10^{-7}$ Torr), such as resistively heated quartz boats. The thickness of the respective layer and the vapor deposition rate (0.1~0.3 nm/sec) are precisely monitored or set with the aid of a quartz-crystal monitor. It is also possible, as described above, each of the organic layers may comprise more than one organic compound. For example, an emissive layer 340E or 340 may be formed of a dopant and a host doped with the dopant. An emissive layer 340E or 340 may also be formed of a co-host and a host co-deposited with the co-host. This may be successfully achieved by co-vaporization from two or more sources. Accordingly, the compounds for the organic layers of the present invention are thermally stable.

Referring to FIG. 1 (the organic EL device 510), FIG. 2 (the organic EL device 400), FIG. 3 (the organic EL device 520) and FIG. 4 (the organic EL device 530), onto the anode 310, Dipyrazino[2,3-f:2,3-]quinoxaline-2,3,6,7,10,11-hexacarbonitrile (HAT-CN) may be applied to form a hole injection layer (HIL) 320 having a thickness of about 20 nm. Onto the HIL 320, N,N-Bis(naphthalene-1-yl)-N,N-bis(phenyl)-benzidine (NPB) may be applied to form a hole transporting layer (HTL) 330 having a thickness of about 110 nm.

Referring to FIG. 1 to FIG. 4, onto the HTL 330, an emissive layer (EML) 340E or an emissive layer (EML) 340 may be formed to have a thickness of about 30 nm. 14,14-dimethyl-11-(3-(pyren-1-yl)phenyl)-14H-indeno[1,2-b]triphenylene (H1) may be applied to form a host H1 of an emissive layer 340E of FIG. 1, an emissive layer 340 of FIG. 4 and an emissive layer 340 of FIG. 2. Referring to FIG. 1, the emissive layer 340E may further comprise the organic compound 340C as a dopant, also a blue guest of the emissive layer 340E. Referring to FIG. 2, the emissive layer 340 may further comprise N1,N1,N6,N6-tetra-m-tolylpyrene-1,6-diamine as a dopant, also a blue guest of the emissive layer 340E.

Referring to FIG. 1 to FIG. 4, onto the EML 340E or EML 340, 2,4-di([1,1':3',1''-terphenyl]-5'-yl)-6-(14,14-dimethyl-14H-indeno[1,2-b]triphe nylen-12-yl)-1,3,5-triazine (HB1) may be applied to form a hole blocking layer (HBL) 350 having a thickness of about 10 nm.

Referring to FIG. 1 to FIG. 3, onto the HBL 350, 8-hydroxyquinolato-lithium (Liq) may be applied to co-deposit with 2-(naphthalen-1-yl)-9-(4-(1-(4-(10-(naphthalen-2-yl)anthracen-9-yl)phenyl)-1H-benzo[d]imidazol-2-yl) phenyl)-1,10-phenanthroline (ET1) at a ratio of 1:1 as the electron transporting layer 360ET, which having a thickness of about 30 nm. The organic compound 360C may be applied to co-deposit with 8-hydroxyquinolato-lithium (Liq) at a ratio of 1:1 as an electron transporting material, thereby forming an electron transporting layer 360ET of the organic EL device 530 (FIG. 4).

Referring to FIG. 1 to FIG. 4, the organic EL device 510, 520, 530 or 400 may further comprise a low work function metal, such as Al, Mg, Ca, Li or K, as a cathode 380 by thermal evaporation. The cathode 380 having a thickness of about 120 nm may help electrons injecting the electron transporting layer 360 or 360ET from cathode 380. Between the cathode 380 (e.g., Al in Table 1, 3 or 5) and the electron transporting layer 360 or 360ET, a thin electron injecting layer (EIL) 370 of Liq is introduced. The electron injecting layer (EIL) 370 has a thickness of about 1 nm is to reduce the electron injection barrier and to improve the performance of the organic EL device 510, 520, 530 or 400. The material of the electron injecting layer 370 may alternatively be metal halide or metal oxide with low work function, such as LiF, MgO, or $Li_2O$.

Table 1 shows the layer thickness and materials of the organic EL device 510 (FIG. 1) or 400 (FIG. 2).

TABLE 1

| Device layer thickness | | |
| --- | --- | --- |
| Layer | Material | Thickness (nm) |
| Cathode | Al | 160 |
| EIL | Liq | 1 |
| ETL | ET1:Liq (50%) | 30 |
| HBL | HB1 | 10 |
| EML | H1:340C or D1(5%) | 30 |
| HTL | NPB | 110 |
| HIL | HAT-CN | 20 |
| Anode | ITO substrate | 120~160 |

The organic compounds Liq, ET1, HB1, H1, D1, NPB and HAT-CN for producing the organic EL device 400 or 510 in this invention may have the formulas as follows:

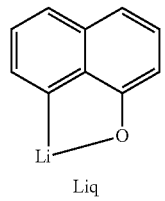

Liq

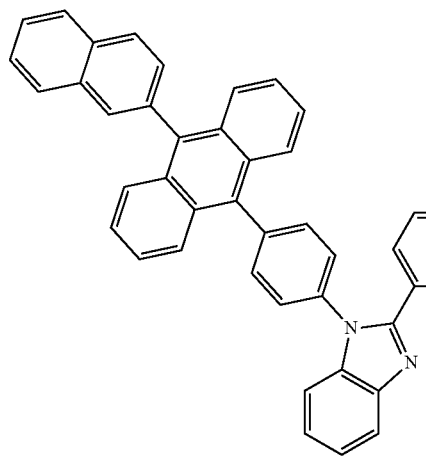

ET1

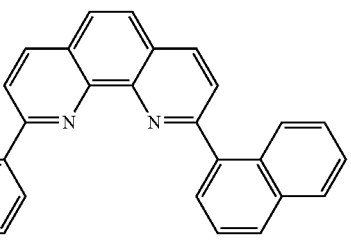

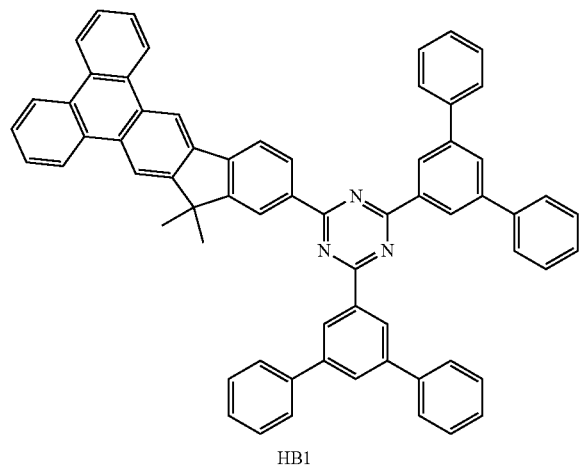

HB1

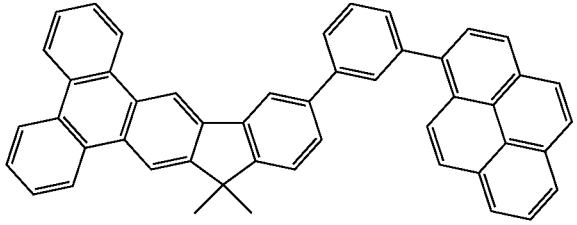

H1

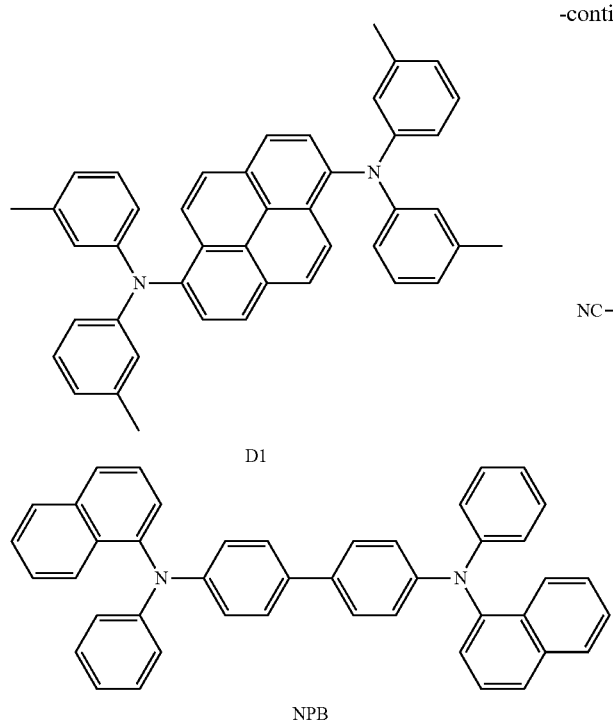

D1

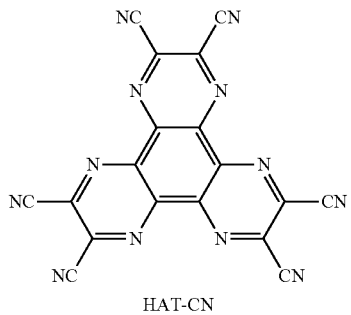

HAT-CN

NPB

To those organic EL devices of FIG. 1 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 1 and FIG. 2 may be summarized in Table 2 below. The half-life time is defined as the time that the initial luminance of 1000 cd/m² has dropped to half.

TABLE 2

(The "Comp." is short for "Compound")

| Host | Dopant (D1 or 340C) | Driving Voltage (V) | Current Efficiency (cd/A) | Half-life (hours) |
|------|---------------------|---------------------|---------------------------|-------------------|
| H1 | D1 | 4.0 | 5.2 | 170 |
| H1 | Comp. 25 | 3.7 | 6.0 | 230 |
| H1 | Comp. 35 | 3.9 | 5.5 | 190 |
| H1 | Comp. 38 | 3.6 | 5.8 | 220 |
| H1 | Comp. 47 | 3.6 | 6.3 | 250 |
| H1 | Comp. 52 | 3.5 | 6.1 | 280 |
| H1 | Comp. 55 | 3.8 | 5.7 | 210 |
| H1 | Comp. 63 | 4.1 | 5.2 | 270 |
| H1 | Comp. 14 | 3.3 | 6.9 | 330 |
| H1 | Comp. 27 | 3.7 | 5.8 | 240 |
| H1 | Comp. 40 | 3.6 | 6.2 | 280 |
| H1 | Comp. 76 | 4.1 | 5.1 | 170 |
| H1 | Comp. 84 | 3.8 | 5.8 | 270 |
| H1 | Comp. 106 | 3.8 | 5.8 | 240 |
| H1 | Comp. 118 | 3.5 | 6.3 | 180 |
| H1 | Comp. 138 | 3.4 | 6.6 | 290 |

According to Table 1, in the first organic EL device 510, the organic compound of formula (1) comprised as a dopant 340C of FIG. 1, which the most of organic compound 340C exhibit performance better than a prior art organic EL material (D1).

In a second embodiment of the present invention, a second organic EL device using the organic compound of formula (1) is disclosed. The method of producing the second organic EL device 520 of FIG. 3 is substantially the same as the method of producing the organic EL device 400 of FIG. 2. The difference is that the host 340C of FIG. 3 is made by using the organic compound of formula (1) rather than H1.

Table 3 shows the layer thickness and materials of the organic EL device 520 (FIG. 3) or 400 (FIG. 2).

TABLE 3

| Layer | Material | Thickness (nm) |
|-------|----------|----------------|
| Cathode | Al | 160 |
| EIL | Liq | 1 |
| ETL | ET1:Liq (50%) | 30 |
| HBL | HB1 | 10 |
| EML | H1 or 340H:D1(5%) | 30 |
| HTL | NPB | 110 |
| HIL | HAT-CN | 20 |
| Anode | ITO substrate | 120~160 |

To those organic EL devices of FIG. 3 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 3 and FIG. 2 may be summarized in Table 4 below. The half-life time is defined as the time that the initial luminance of 1000 cd/m² has dropped to half.

TABLE 4

(The "Comp." is short for "Compound")

| Host (H1 or 340C) | Dopant | Driving Voltage (V) | Current Efficiency (cd/A) | Half-life (hours) |
|---|---|---|---|---|
| H1 | D1 | 4.0 | 5.2 | 170 |
| Comp. 73 | D1 | 3.9 | 5.3 | 200 |
| Comp. 97 | D1 | 3.9 | 5.3 | 210 |
| Comp. 162 | D1 | 3.8 | 5.7 | 230 |
| Comp. 140 | D1 | 3.7 | 6.2 | 250 |
| Comp. 71 | D1 | 3.4 | 6.8 | 300 |
| Comp. 102 | D1 | 3.5 | 6.2 | 280 |
| Comp. 107 | D1 | 3.8 | 5.5 | 200 |
| Comp. 131 | D1 | 3.5 | 6.3 | 270 |
| Comp. 167 | D1 | 3.2 | 7.2 | 340 |
| Comp. 175 | D1 | 3.9 | 5.3 | 190 |
| Comp. 129 | D1 | 3.8 | 5.7 | 180 |
| Comp. 141 | D1 | 3.6 | 5.9 | 260 |
| Comp. 191 | D1 | 3.7 | 5.8 | 220 |
| Comp. 171 | D1 | 3.4 | 6.4 | 320 |
| Comp. 181 | D1 | 3.3 | 6.8 | 310 |
| Comp. 193 | D1 | 3.5 | 6.3 | 250 |
| Comp. 209 | D1 | 3.6 | 6.0 | 240 |

According to Table 4, in the second organic EL device 520, the organic compound of formula (1) comprised as a host 340C of FIG. 3 exhibits performance better than a prior art organic EL material (H1).

In a second embodiment of the present invention, a third organic EL device using the organic compound of formula (1) is disclosed. The method of producing the third organic EL device 530 of FIG. 4 is substantially the same as the method of producing the organic EL device 400 of FIG. 2. The difference is that an electron transport material 360C of FIG. 4 is made by using the organic compound of formula (1) rather than ET1.

Table 5 shows the layer thickness and materials of the organic EL device 530 (FIG. 4) or 400 (FIG. 2).

TABLE 5

Device layer thickness

| Layer | Material | Thickness (nm) |
|---|---|---|
| Cathode | Al | 160 |
| EIL | Liq | 1 |
| ETL | ET1 or 360C:Liq (50%) | 30 |
| HBL | HB1 | 10 |
| EML | H1:D1(5%) | 30 |
| HTL | NPB | 110 |
| HIL | HAT-CN | 20 |
| Anode | ITO substrate | 120~160 |

To those organic EL devices of FIG. 4 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 4 and FIG. 2 may be summarized in Table 6 below. The half-life time is defined as the time that the initial luminance of 1000 cd/m² has dropped to half.

TABLE 6

(The "Comp." is short for "Compound")

| Host | ETM for ETL 360 | Driving Voltage (V) | Current Efficiency (cd/A) | Half-life (hours) |
|---|---|---|---|---|
| H1 | ET1 | 4.0 | 5.2 | 170 |
| H1 | Comp. 73 | 3.9 | 5.4 | 210 |
| H1 | Comp. 89 | 3.7 | 5.7 | 220 |
| H1 | Comp. 97 | 3.8 | 5.7 | 230 |
| H1 | Comp. 174 | 3.7 | 5.9 | 190 |
| H1 | Comp. 68 | 3.4 | 6.8 | 300 |
| H1 | Comp. 160 | 3.5 | 6.5 | 250 |
| H1 | Comp. 162 | 3.2 | 7.1 | 360 |
| H1 | Comp. 176 | 3.7 | 5.6 | 220 |
| H1 | Comp. 183 | 3.5 | 6.6 | 280 |
| H1 | Comp. 185 | 3.4 | 6.9 | 270 |
| H1 | Comp. 196 | 3.7 | 5.8 | 240 |
| H1 | Comp. 212 | 3.4 | 5.9 | 220 |
| H1 | Comp. 217 | 3.3 | 6.7 | 310 |
| H1 | Comp. 221 | 3.8 | 5.8 | 200 |

According to Table 6, in the third organic EL device 530, the organic compound of formula (1) comprised as an electron transport material 360C of FIG. 4 exhibit performance better than a prior art organic EL material (ET1).

Detailed preparation of the organic compounds of the present invention will be clarified by exemplary embodiments below, but the present invention is not limited thereto. EXAMPLES 1 to 42 show the preparation of the organic compounds of the present invention.

Example 1

Synthesis of 1-bromo-2-methoxynaphthalene

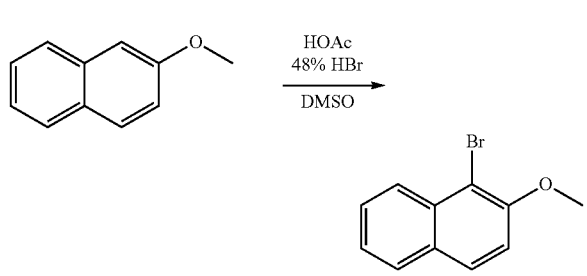

Under nitrogen condition, 2-methoxynaphthalene (40 g, 25.3 mmol) was dissolved in HOAc (400 ml) at room temperature. A mixture of 48% $HBr_{(aq)}$ (200 mL) and DMSO (200 mL) was added and stirred for 6 hours. After the reaction was finished, 1800 ml of water was added and the mixture was filtered to give a solid. The solid was washed with water and small amount of methanol, and then the crude product was purified by column chromatography on silica to obtain 1-bromo-2-methoxynaphthalene (53.1 g, 89%).

Synthesis of 1-(5-chloro-2-fluorophenyl)-2-methoxynaphthalene

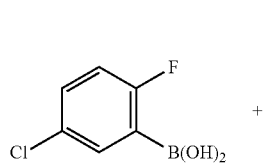

219

-continued

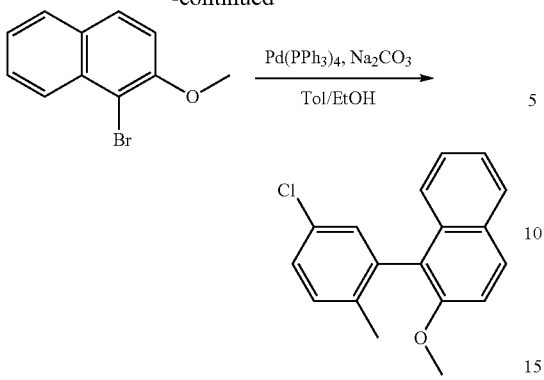

A mixture of (5-chloro-2-fluorophenyl)boronic acid (22.1 g, 127.1 mmol), 1-bromo-2-methoxynaphthalene (30 g, 127.1 mmol), 190 ml of 2M Na$_2$CO$_{3(aq)}$, 190 ml of ethanol, 380 ml of toluene, and Pd(PPh$_3$)$_4$ (1.5 g, 1.27 mmol) was added under nitrogen condition, and then heated at 100° C. for 16 hours. After the reaction was finished, the mixture was cooled to room temperature. The organic layer was extracted with ethyl acetate and water, and then dried with anhydrous MgSO$_4$. The solvent was removed, and the residue was purified by column chromatography on silica to obtain 1-(5-chloro-2-fluorophenyl)-2-methoxynaphthalene (30.2 g, 83%) as a yellow solid.

Synthesis of 1-(5-chloro-2-fluorophenyl)naphthalen-2-ol

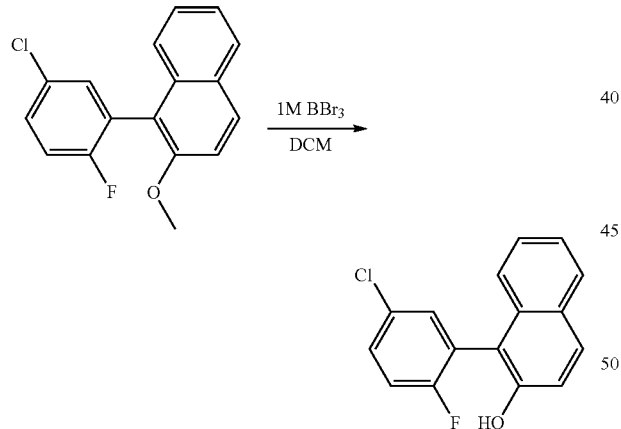

Under nitrogen condition, 1-(5-chloro-2-fluorophenyl)-2-methoxynaphthalene (20 g, 69.9 mmol) was dissolved in anhydrous dichloromethane (600 ml) at 0° C., 1 M BBr$_3$ (76.9 ml, 76.9 mmol) solution was added, and then stirred for 3 hours. After the reaction was finished, 60 ml of methanol was added to the mixture, and then neutralized with 10% NaNCO$_{3(aq)}$. The mixture was extracted with dichloromethane and water. The organic layer was separated and dried with anhydrous MgSO$_4$, and then the solvent was evaporated under reduced pressure. The residue was purified by column chromatography on silica to afford 1-(5-chloro-2-fluorophenyl)naphthalen-2-ol (14.8 g, 78%) as a white solid.

220

Synthesis of 10-chloronaphtho[2,1-b]benzofuran

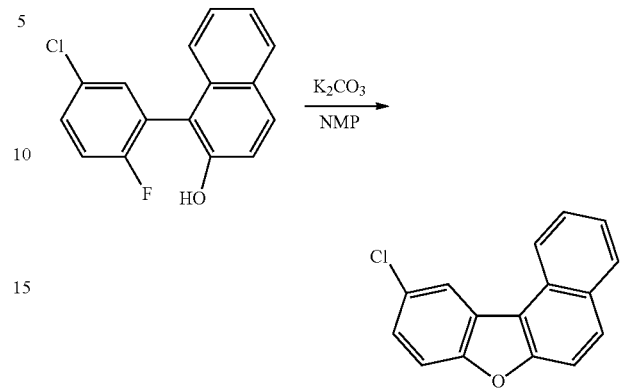

Under nitrogen condition, a mixture of 1-(5-chloro-2-fluorophenyl)naphthalen-2-ol (20 g, 73.5 mmol), K$_2$CO$_3$ (11.2 g, 80.9 mmol), and 180 ml of 1-methyl-2-pyrrolidone was added and heated at 150° C. for 16 hours. After the reaction was finished, the solvent was distilled under reduced pressure. The residue was extracted with ethyl acetate and water. The organic layer was separated, and the solvent was evaporated under reduced pressure. The residue was purified by column chromatography on silica to give 10-chloronaphtho[2,1-b]benzofuran (12.8 g, 69%) as a white solid.

Synthesis of 10-(3'-methoxy-[1,1'-biphenyl]-2-yl)naphtho[2,1-b]benzofuran

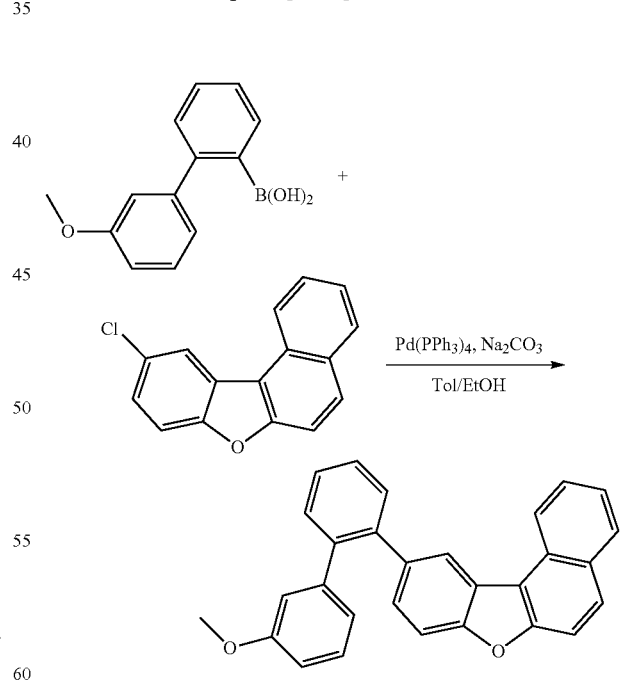

A mixture of (3'-methoxy-[1,1'-biphenyl]-2-yl)boronic acid (20 g, 87.7 mmol), 10-chloronaphtho[2,1-b]benzofuran (22.2 g, 87.7 mmol), 88 ml of 2M Na$_2$CO$_{3(aq)}$, 88 ml of ethanol, 176 ml of toluene, and Pd(PPh$_3$)$_4$ (1 g, 0.88 mmol) was added under nitrogen condition, and then heated at 100° C. for 17 hours. After the reaction was finished, the mixture was cooled to room temperature. The organic layer was extracted with ethyl acetate and water, and then dried with anhydrous MgSO$_4$. The solvent was removed, and the residue was purified by column chromatography on silica to obtain 10-(3'-methoxy-[1,1'-biphenyl]-2-yl)naphtho[2,1-b]benzofuran (28.8 g, 82%) as a white solid.

Synthesis of 11-methoxynaphtho[2,1-b]triphenyleno[2,3-d]furan

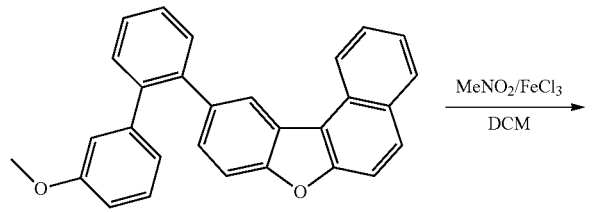

Under nitrogen condition, 10-(3'-methoxy-[1,1'-biphenyl]-2-yl)naphtho[2,1-b]benzofuran (18.8 g, 47 mmol) was dissolved in anhydrous dichloromethane (940 ml) at 0° C., and then the mixture of iron(III) chloride (38.1 g, 235 mmol) and 47 ml of nitromethane were added. The mixture was stirred for 1 hour, and then 300 ml of methanol was added to the mixture. The mixture was filtered to give a solid. The solid was washed with water and methanol, and then the crude product was purified by column chromatography on silica to obtain 11-methoxynaphtho[2,1-b]triphenyleno[2,3-d]furan (15.3 g, 82%) as a yellow solid.

Synthesis of naphtho[2,1-b]triphenyleno[2,3-d]furan-11-ol

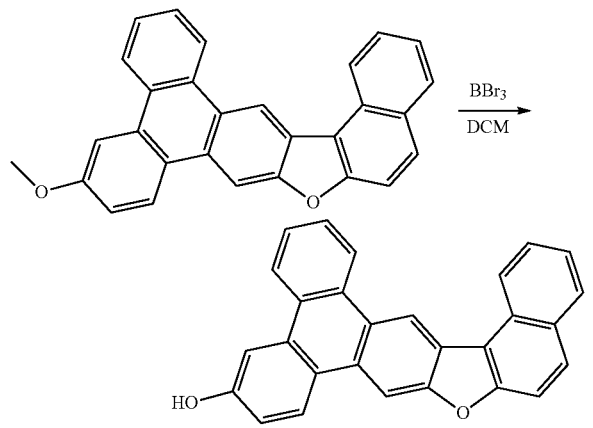

Under nitrogen condition, 11-methoxynaphtho[2,1-b]triphenyleno[2,3-d]furan 1 (18.8 g, 47.2 mmol) was dissolved in anhydrous dichloromethane (600 ml) at 0° C., 1 M BBr$_3$ (51.9 ml, 51.9 mmol) solution was added, and then stirred for 2 hours. After the reaction was finished, 100 ml of methanol was added to the mixture, and then neutralized with 10% NaNCO$_{3(aq)}$. The mixture was extracted with dichloromethane and water. The organic layer was separated and dried with anhydrous MgSO$_4$, and then the solvent was evaporated under reduced pressure. The crude product was purified by column chromatography on silica to obtain naphtho[2,1-b]triphenyleno[2,3-d]furan-11-ol (16.1 g, 89%) as a white solid.

Synthesis of naphtho[2,1-b]triphenyleno[2,3-d]furan-11-yl trifluoromethanesulfonate

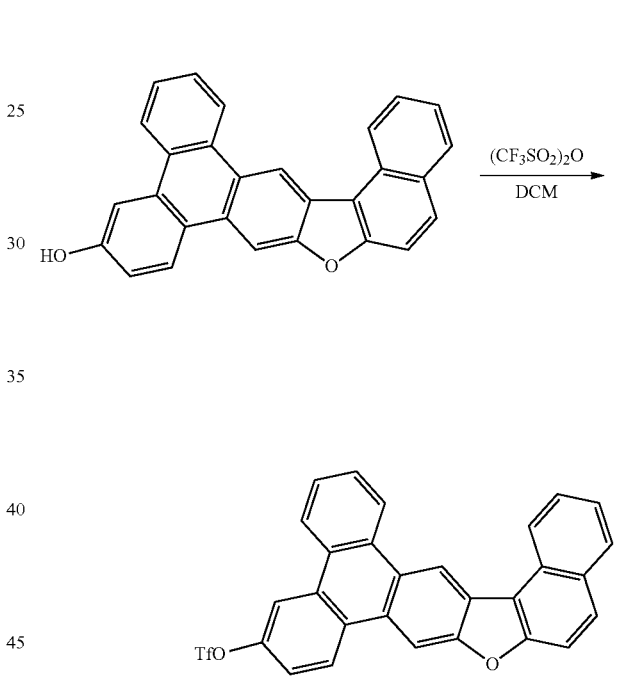

Under nitrogen condition, naphtho[2,1-b]triphenyleno[2,3-d]furan-11-ol (28.2 g, 73.3 mmol) was mixed with 900 ml of dichloromethane. Triethylamine (141.7 g, 102.6 mmol) was added and the mixture was stirred for 1 hour. Trifluoromethanesulfonic anhydride (35.1 g, 124.5 mmol) was added and the mixture was stirred for 17 hours. After the reaction was finished, the solvent was removed under reduced pressure, and the crude product was purified by column chromatography to obtain naphtho[2,1-b]triphenyleno[2,3-d]furan-11-yl trifluoromethanesulfonate (24.2 g, 64%) as yellow solid.

Synthesis of 4,4,5,5-tetramethyl-2-(naphtho[2,1-b]triphenyleno[2,3-d]furan-11-yl)-1,3,2-d ioxaborolane

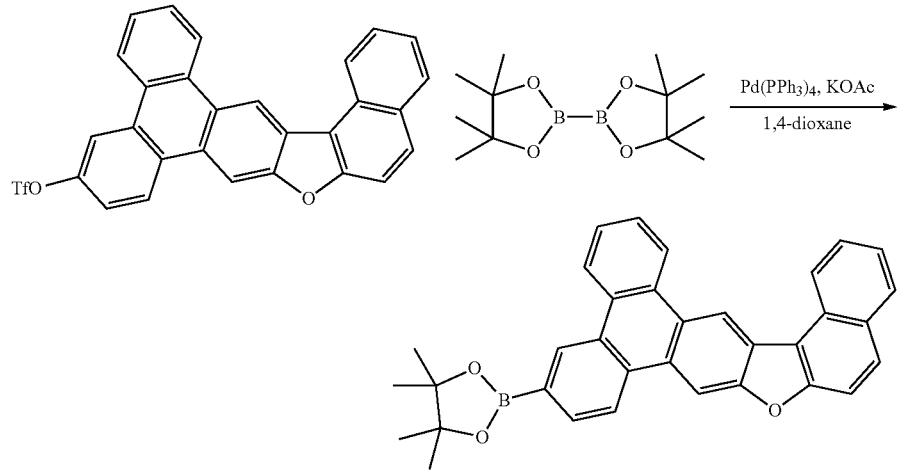

A mixture of naphtho[2,1-b]triphenyleno[2,3-d]furan-11-yl trifluoromethanesulfonate (19 g, 36.9 mmol), bis(pinacolato)diboron (11.3 g, 44.3 mmol), potassium acetate (7.2 g, 73.9 mmol), 200 ml of 1,4-dioxane and Pd(PPh$_3$)$_4$ (0.43 g, 0.4 mmol) was added, and then heated at 100° C. for 6 hours under nitrogen condition. After the mixture was cooled to room temperature, and then filtered to give the filtrate. The filtrate was evaporated under reduced pressure. The crude product was purified by column chromatography on silica to obtain 4,4,5,5-tetramethyl-2-(naphtho[2,1-b]triphenyleno[2,3-d]furan-11-yl)-1,3,2-d ioxaborolane (12 g, 66%) as a white solid.

Synthesis of 2-(4-chlorophenyl)-4,4,5,5-tetramethyl-1,3,2-dioxaborolane 3a

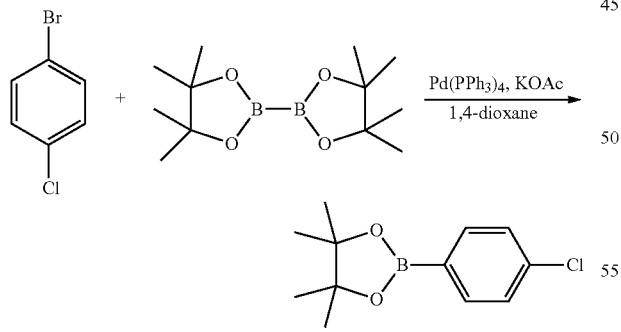

A mixture of 1-bromo-4-chlorobenzene (20.9 g, 109.9 mmol), bis(pinacolato)diboron (33.5 g, 131.9 mmol), potassium acetate (21.6 g, 219.8 mmol), 200 ml of 1,4-dioxane, and Pd(PPh$_3$)$_4$ (1.3 g, 1.1 mmol) was added, and then heated at 100° C. for 6 hours under nitrogen condition. After the mixture was cooled to room temperature, and then filtered to give the filtrate. The filtrate was evaporated under reduced pressure. The crude product was purified by column chromatography on silica to obtain 2-(4-chlorophenyl)-4,4,5,5-tetramethyl-1,3,2-dioxaborolane (16.5 g, 63%) as a white solid.

Synthesis of 4-(6-chloronaphthalen-2-yl)benzonitrile 6a

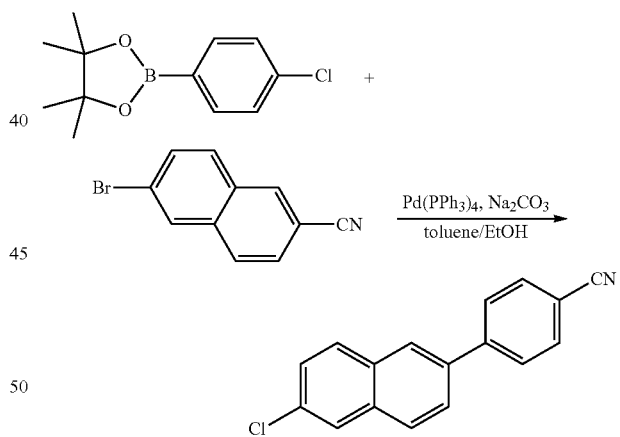

Under nitrogen condition, a mixture of 2-(4-chlorophenyl)-4,4,5,5-tetramethyl-1,3,2-dioxaborolane (10.4 g, 43.6 mmol), 6-bromo-2-naphthonitrile (10.1 g, 43.6 mmol), 33 ml of 2M Na$_2$CO$_{3(aq)}$, 33 ml of ethanol, 99 ml of toluene, and Pd(PPh$_3$)$_4$ (0.5 g, 0.44 mmol) was added and then heated at 100° C. for 16 hours. After the reaction was finished, the mixture was cooled to room temperature. The organic layer was extracted with ethyl acetate and water, and then dried with anhydrous MgSO$_4$. The solvent was removed, and the crude product was purified by column chromatography on silica to obtain 4-(6-chloronaphthalen-2-yl)benzonitrile (5.2 g, 45%) as a white solid.

Synthesis of 6-(4-(naphtho[2,1-b]triphenyleno[2,3-d]furan-11-yl)phenyl)-2-naphthonitrile (Compound 25)

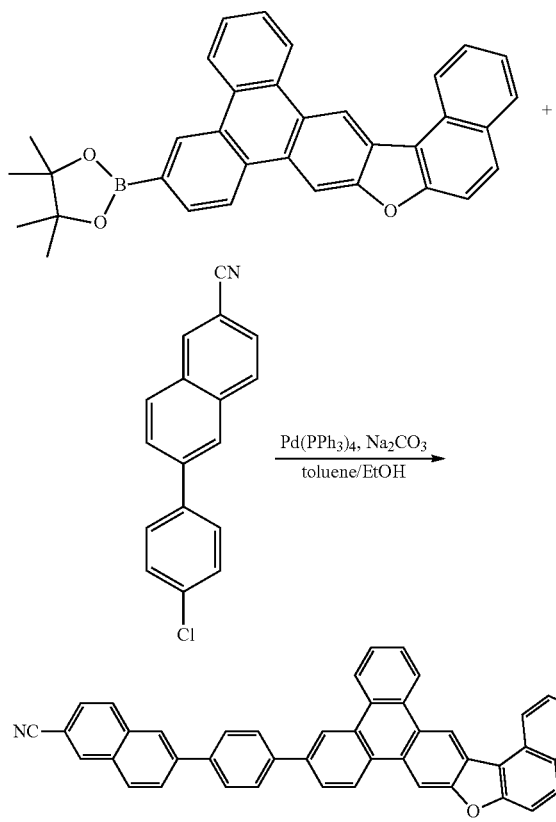

Under nitrogen condition, a mixture of 4,4,5,5-tetramethyl-2-(naphtho[2,1-b]triphenyleno[2,3-d]furan-11-yl)-1,3,2-dioxaborolane (2.9 g, 5.8 mmol), 4-(6-chloronaphthalen-2-yl)benzonitrile (1.5 g, 5.8 mmol), 3.9 ml of 2M Na$_2$CO$_3$ (aq), 3.9 ml of ethanol, 7.8 ml of toluene, and Pd(PPh$_3$)$_4$ (0.04 g, 0.039 mmol) was added and then heated at 100° C. for 17 hours. After the reaction was finished and cooled to room temperature. The mixture was filtered to give a solid. The solid was washed with water and methanol, and then filtered to give 6-(4-(naphtho[2,1-b]triphenyleno[2,3-d]furan-11-yl)phenyl)-2-naphthonitrile (2.4 g, 69%) as an off-white solid. MS (m/z, EI$^+$)::595.23

Examples 2 to 42

Synthesis of 2-bromo-3-methoxynaphthalene

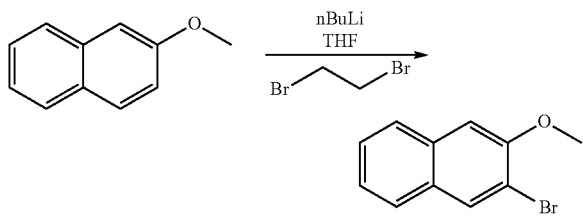

Under nitrogen condition, 2-methoxynaphthalene (20 g, 126.5 mmol) was dissolved in anhydrous tetrahydrofuran (170 ml) at room temperature. 2.5M n-BuLi (55.7 ml, 139.2 mmol) was slowly dripped, and then stirred for 3 hours. Cooled to −68° C. and then 1,2-dibromoethane (35.3 mL, 189.8 mmol) was slowly dripped, and then warmed to room temperature for 18 hours. Afterwards, 1M NaOH$_{(aq)}$(139.2 ml, 139.2 mmol) was added to the mixture, and then refluxed for 1 hour. The mixture was extracted with ethyl acetate, water and sat. NaCl$_{(aq)}$ and then dried with anhydrous MgSO4. The crude product was recrystallized from hexane to obtain 2-bromo-3-methoxynaphthalene (30.2 g, 83%) as a white solid.

Synthesis of 9-(5-chloro-2-nitrophenyl)phenanthrene 1a

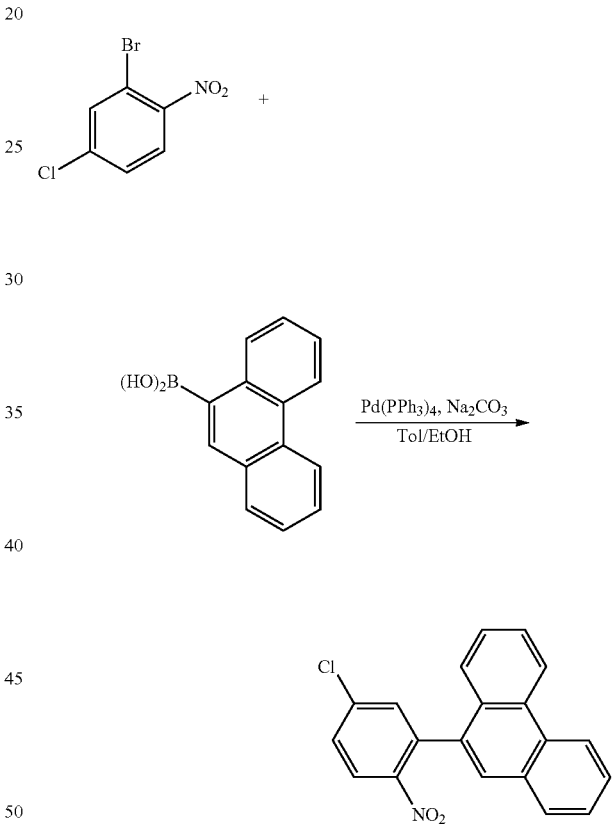

A mixture of 2-bromo-4-chloro-1-nitrobenzene (20 g, 84.6 mmol), phenanthren-9-ylboronic acid (18.8 g, 84.6 mmol), 63 ml of 2M Na$_2$CO$_{3(aq)}$, 63 ml of ethanol, 189 ml of toluene, and Pd(PPh$_3$)$_4$ (1 g, 0.8 mmol) was added under nitrogen condition, and then heated at 100° C. for 16 hours. After the reaction was finished, the mixture was cooled to room temperature. The organic layer was extracted with ethyl acetate and water, and then dried with anhydrous MgSO$_4$. The solvent was removed, and the residue was purified by column chromatography on silica to obtain 9-(5-chloro-2-nitrophenyl)phenanthrene (1a, 21.7 g, 82%) as a yellow solid.

Synthesis of Intermediate 1b to 1h were according to the synthesis method of Intermediate 1a.

| Reactant structure | Product structure (Weight, Yield) |
|---|---|
| 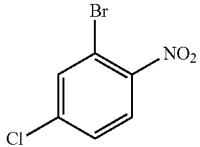 (20 g, 85.1 mmol)    (21 g, 85.1 mmol) | 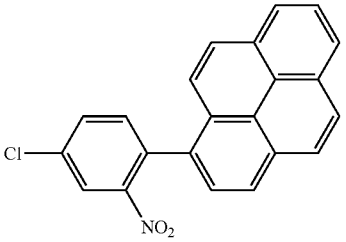 1b (23.7 g, 78%) |
| 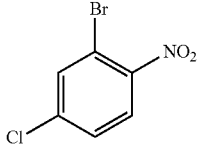 (20 g, 85.1 mmol)    (23.2 g, 85.1 mmol) | 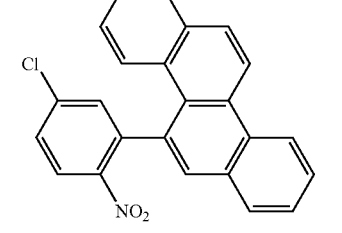 1c (23.2 g, 71%) |
| 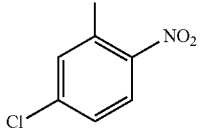 (20 g, 85.1 mmol)    (18.9 g, 85.1 mmol) | 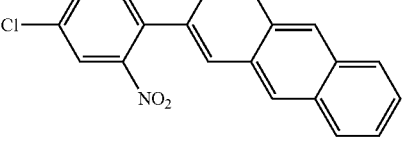 1d (21.6 g, 76%) |
| 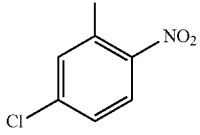 (20 g, 85.1 mmol)    (14.7 g, 85.1 mmol) | 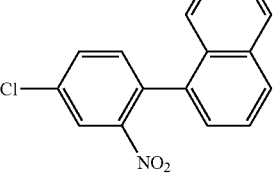 1e (18.8 g, 78%) |
| 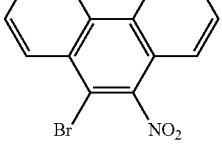 (15 g, 49.8 mmol)    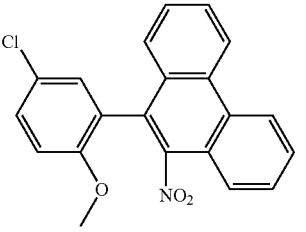 (9.3 g, 49.8 mmol) | 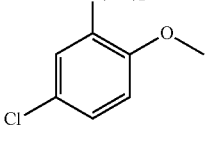 1f (12.1 g, 67%) |

-continued

| Reactant structure | | Product structure (Weight, Yield) |
|---|---|---|
| 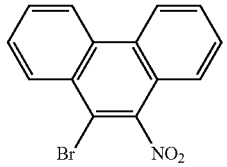 (15 g, 49.8 mmol) | 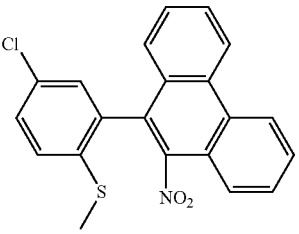 (10.1 g, 49.8 mmol) | 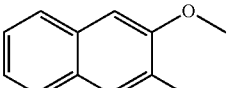 1g (11.7 g, 62%) |
| 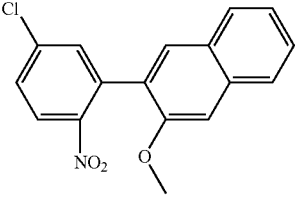 (30 g, 127.1 mmol) | 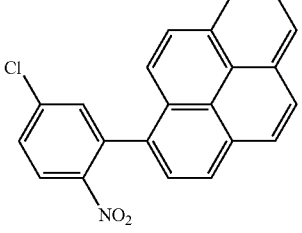 (25.5 g, 127.1 mmol) | 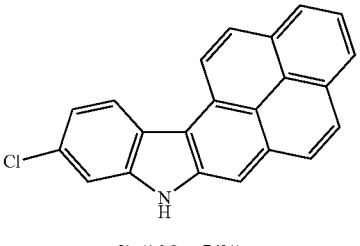 1h (31.4 g, 79%) |

Synthesis of 11-chloro-9H-dibenzo[a,c]carbazole 2a

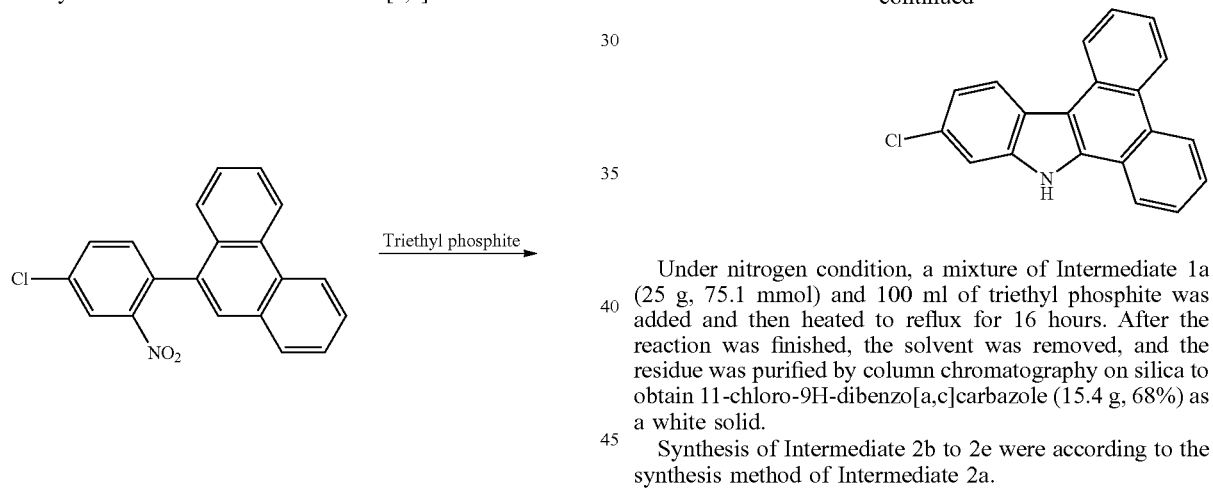

Under nitrogen condition, a mixture of Intermediate 1a (25 g, 75.1 mmol) and 100 ml of triethyl phosphite was added and then heated to reflux for 16 hours. After the reaction was finished, the solvent was removed, and the residue was purified by column chromatography on silica to obtain 11-chloro-9H-dibenzo[a,c]carbazole (15.4 g, 68%) as a white solid.

Synthesis of Intermediate 2b to 2e were according to the synthesis method of Intermediate 2a.

-continued

| Reactant structure | Product structure (Weight, Yield) |
|---|---|
| 1c (25 g, 65.3 mmol) | 2c (16.3 g, 71%) |
| 1d (25 g, 75.1 mmol) | 2d (8.8 g, 39%) |
| 1e (25 g, 88.3 mmol) | 2e (17.5 g, 79%) |

Synthesis of 11-chloro-9-phenyl-9H-dibenzo[a,c]carbazole 3a

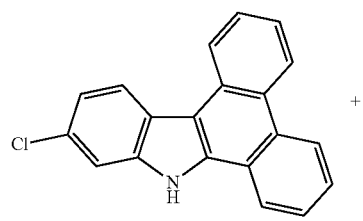

+

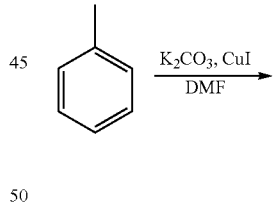

$\xrightarrow{K_2CO_3, CuI}{DMF}$

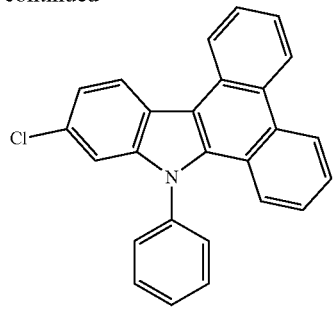

Under nitrogen condition, a mixture of 11-chloro-9H-dibenzo[a,c]carbazole (20 g, 66.4 mmol), iodobenzene (16.3 g, 79.7 mmol), K$_2$CO$_3$ (13.8 g, 99.6 mmol), CuI (6.3 g, 33.2 mmol0) and 400 ml of N,N-dimethylformamide was added and then heated to reflux for 16 hours. After the reaction was finished, the mixture was cooled to room temperature. The organic layer was extracted with ethyl acetate and water, and then dried with anhydrous MgSO$_4$. The solvent was removed, and the residue was purified by column chromatography on silica to obtain 11-chloro-9-phenyl-9H-dibenzo[a,c]carbazole (21.8 g, 87%) as a yellow solid.

Synthesis of Intermediate 3b to 3e were according to the synthesis method of Intermediate 3a.

| Reactant structure | Product structure (Weight, Yield) |
|---|---|
| 2b (30 g, 92.3 mmol) | 3b (31.8 g, 86%) |
| 2c (30 g, 85.5 mmol) | 3c (29.6 g, 81%) |
| 2d (30 g, 99.6 mmol) | 3d (30.8 g, 82%) |
| 2e (30 g, 118.5 mmol) | 3e (32.1 g, 82%) |

Synthesis of 10-(5-chloro-2-methoxyphenyl)phenanthren-9-amine 4a

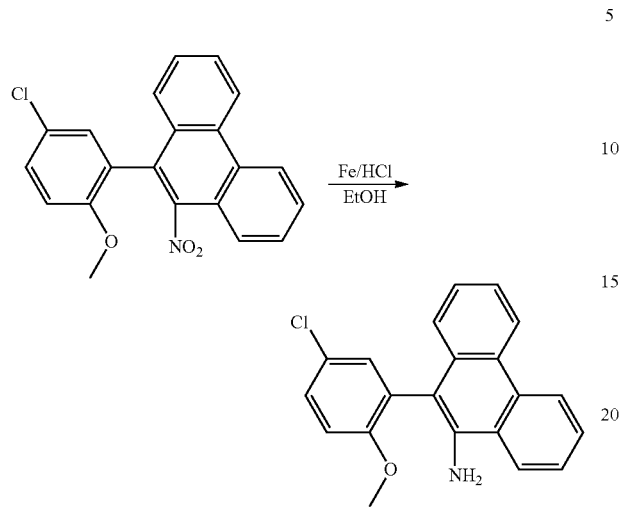

A mixture of 9-(5-chloro-2-methoxyphenyl)-10-nitrophenanthrene (20 g, 55.1 mmol), iron powder (18.5 g, 330.5 mmol), 20 ml of conc. HCl and 280 ml of an aqueous ethanol (EtOH:$H_2O$=3:1) was added and then heated at 85° C. for 3 hours. After the reaction was finished, the mixture was cooled to room temperature. The mixture was filtered, the filtrate was neutralized with NaOH$_{(aq)}$ and extracted with ethyl acetate and water. The organic layer was dried with anhydrous $MgSO_4$ and the solvent was evaporated under reduced pressure. The residue was purified by column chromatography on silica to give 10-(5-chloro-2-methoxyphenyl)phenanthren-9-amine (13.9 g, 76%) as a yellow solid.

Synthesis of Intermediate 4b and 4c were according to the synthesis method of Intermediate 4a.

Synthesis of 12-chlorophenanthro[9,10-b]benzofuran

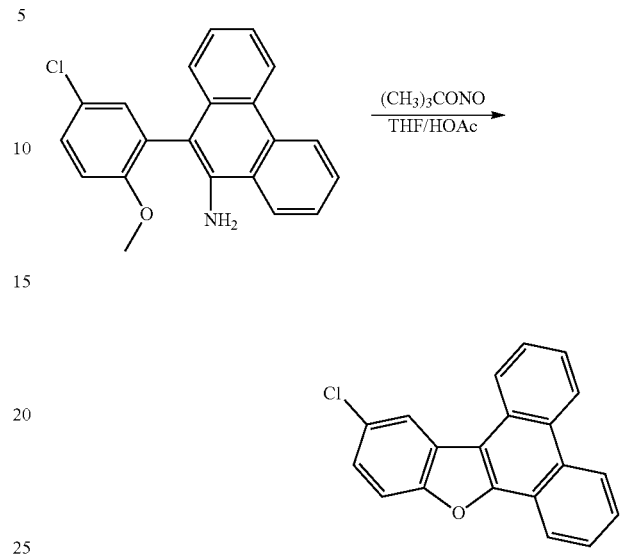

A mixture of 10-(5-chloro-2-methoxyphenyl)phenanthren-9-amine (25 g, 75.1 mmol), 125 ml of tetrahydrofuran and 250 ml of glacial acetic acid was stirred at −10° C., and then tert-butyl nitrite (23.2 g, 29.8 ml, 90%, 225.2 mmol) was added over a period of 10 minutes. The reaction mixture was stirred at −10° C. for 2 hours, and then warmed to room temperature for 5 hours. The reaction was finished, and then diluted with 700 mL of water. The crude precipitate was purified by column chromatography on silica to afford 12-chlorophenanthro[9,10-b]benzofuran (15.6 g, 69%) as a white solid.

| Reactant structure | Product structure (Weight, Yield) |
|---|---|
| ![](chlorophenyl-thiomethyl-nitrophenanthrene) 1g (25 g, 75.1 mmol) | ![](chlorophenyl-thiomethyl-aminophenanthrene) 4b (9.3 g, 41%) |
| ![](chlorophenyl-methoxynaphthyl-nitro) 2h (30 g, 118.5 mmol) | ![](chlorophenyl-methoxynaphthyl-amino) 4c (32.1 g, 82%) |

Synthesis of 2-chloronaphtho[2,3-b]benzofuran

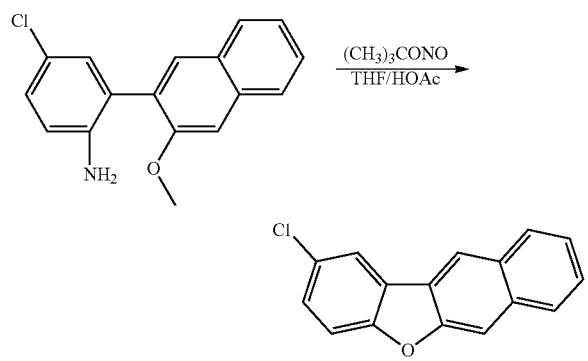

Synthesis of 4-chloro-2-(3-methoxynaphthalen-2-yl)aniline (16 g, 72%) was prepared according to the synthesis method of 12-chlorophenanthro[9,10-b]benzofuran Synthesis of (4-chloro-2-(10-iodophenanthren-9-yl)phenyl)(methyl)sulfane

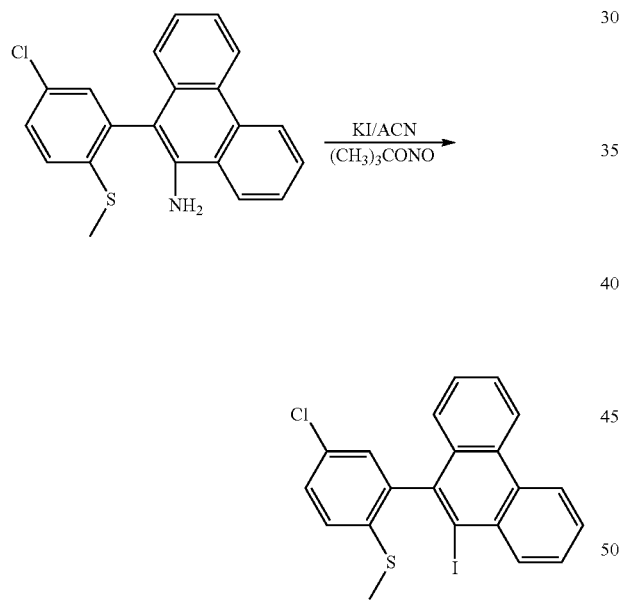

Under nitrogen condition, a mixture of tert-butyl nitrite (7.9 g, 9.1 ml, 90%, 68.8 mmol), anhydrous potassium iodide (9.5 g, 57.3 mmol) and 860 mL of anhydrous acetonitrile was heated at 80° C., and then 10-(5-chloro-2-(methylthio)phenyl)phenanthren-9-amine (20 g, 57.3 mmol) was added slowly over a period of 1 hour, giving rise to a reaction with vigorous foaming and evolution of nitrogen gas. After the reaction was finished, the mixture was cooled to room temperature and poured into 600 ml of 10% $HCl_{(aq)}$. The crude precipitate was purified by column chromatography on silica to give (4-chloro-2-(10-iodophenanthren-9-yl)phenyl)(methyl)sulfane (7.6 g, 29%) as a white solid.

Synthesis of 12-chlorobenzo[b]phenanthro[9,10-d]thiophene

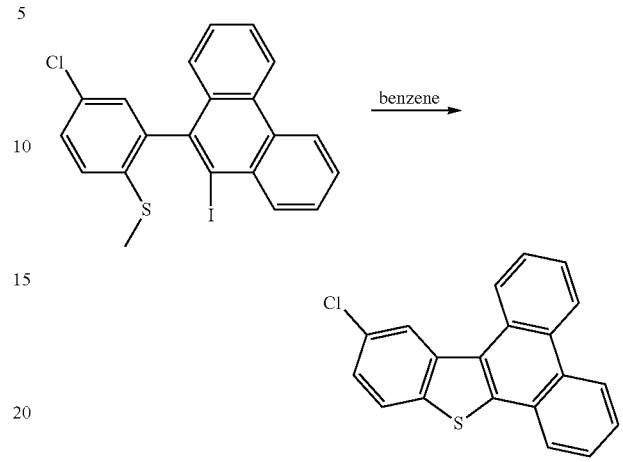

Under nitrogen condition, (4-chloro-2-(10-iodophenanthren-9-yl)phenyl)(methyl)sulfane (20 g, 43.5 mmol) was dissolved in benzene (200 ml) and refluxed for 16 hours. After the reaction was finished, the solvent was distilled under reduced pressure. The residue was extracted with ethyl acetate and water, and then dried with anhydrous $MgSO_4$. The crude precipitate was purified by column chromatography on silica to give 12-chlorobenzo[b]phenanthro[9,10-d]thiophene (10.9 g, 79%) as a white solid.

Synthesis of 5-(4,4,5,5-tetramethyl-1,3,2-dioxaborolan-2-yl)isophthalonitrile 5a

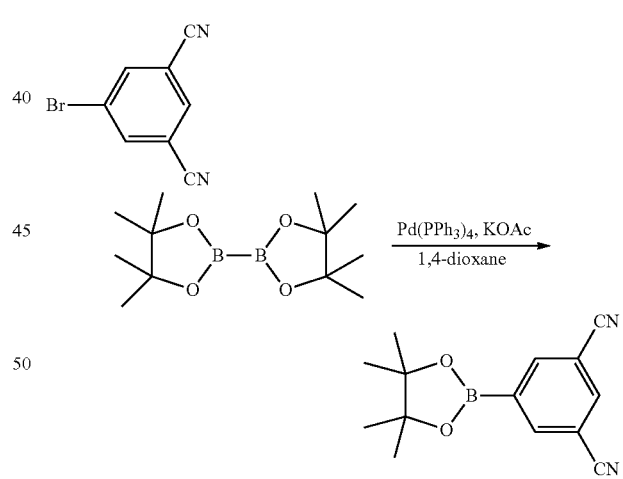

A mixture of 5-bromoisophthalonitrile (20 g, 96.6 mmol), bis(pinacolato)diboron (29.4 g, 115.9 mmol), potassium acetate (19 g, 193.2 mmol), 200 ml of 1,4-dioxane, and $Pd(PPh_3)_4$ (1.1 g, 0.93 mmol) was added, and then heated at 100° C. for 6 hours under nitrogen condition. After the mixture was cooled to room temperature, and then filtered to give the filtrate. The filtrate was evaporated under reduced pressure. The crude product was purified by column chromatography on silica to obtain 5-(4,4,5,5-tetramethyl-1,3,2-dioxaborolan-2-yl)isophthalonitrile (11.8 g, 51%) as a white solid.

Synthesis of Intermediate 5b to 5e were according to the synthesis method of Intermediate 5.

| Reactant structure | Product structure (Weight, Yield) |
|---|---|
| 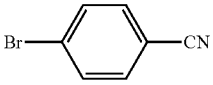<br>3b (20 g, 109.9 mmol) | 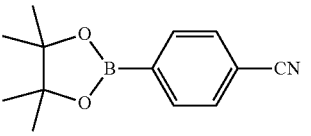<br>5b (16.4 g, 65%) |
| 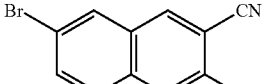<br>3c (20 g, 109.9 mmol) | 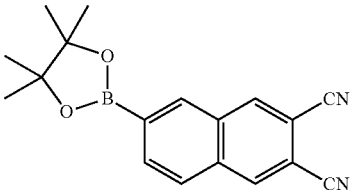<br>5c (15.9 g, 63%) |

Synthesis of 5-(6-bromonaphthalen-2-yl)isophthalonitrile 7a

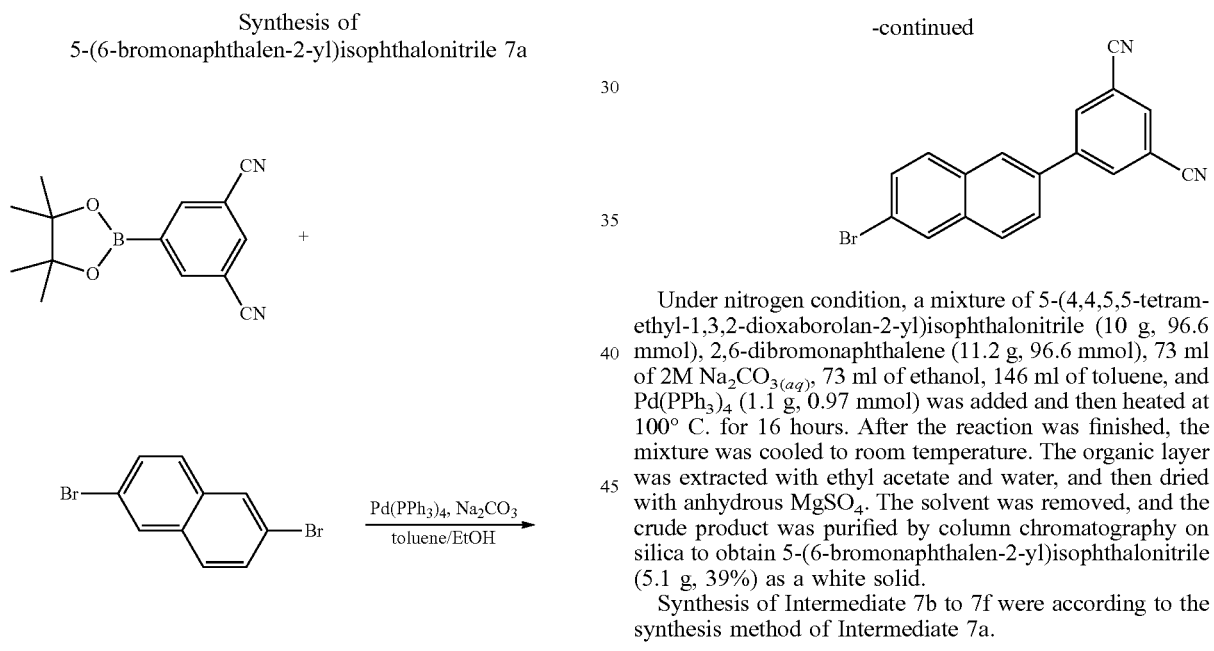

Under nitrogen condition, a mixture of 5-(4,4,5,5-tetramethyl-1,3,2-dioxaborolan-2-yl)isophthalonitrile (10 g, 96.6 mmol), 2,6-dibromonaphthalene (11.2 g, 96.6 mmol), 73 ml of 2M $Na_2CO_{3(aq)}$, 73 ml of ethanol, 146 ml of toluene, and $Pd(PPh_3)_4$ (1.1 g, 0.97 mmol) was added and then heated at 100° C. for 16 hours. After the reaction was finished, the mixture was cooled to room temperature. The organic layer was extracted with ethyl acetate and water, and then dried with anhydrous $MgSO_4$. The solvent was removed, and the crude product was purified by column chromatography on silica to obtain 5-(6-bromonaphthalen-2-yl)isophthalonitrile (5.1 g, 39%) as a white solid.

Synthesis of Intermediate 7b to 7f were according to the synthesis method of Intermediate 7a.

| Reactant structure | | Product structure (Weight, Yield) |
|---|---|---|
| 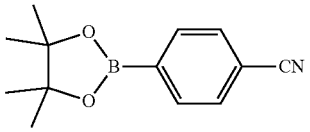<br>3b (10 g, 43.6 mmol) | 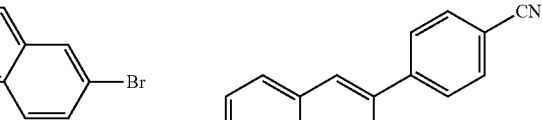<br>(12.4 g, 43.6 mmol) | <br>7b (4.8 g, 45%) |

-continued
| Reactant structure | Product structure (Weight, Yield) |
|---|---|
| 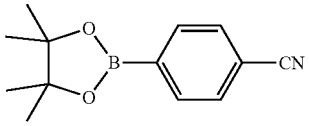 3c (10 g, 43.6 mmol)    (11.2 g, 43.6 mmol) | 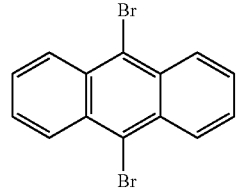 7c (5.4 g, 37%) |
| 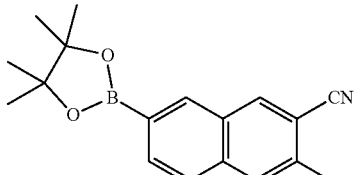 3d (10 g, 32.9 mmol)    (9.3 g, 32.9 mmol) | 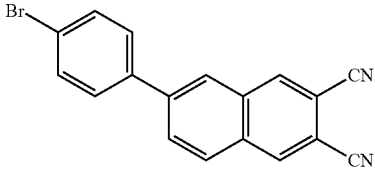 7d (7.1 g, 65%) |
| 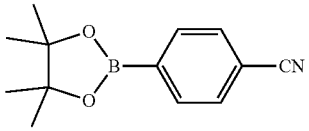 3c (10 g, 43.6 mmol)    (14.6 g, 43.6 mmol) | 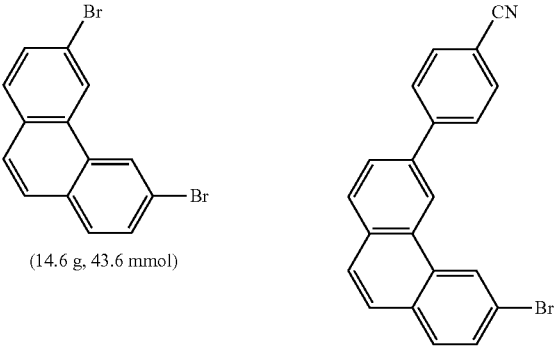 7e (7.6 g, 49%) |
| 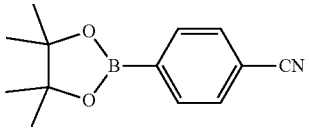 3c (10 g, 43.6 mmol)    (16.7 g, 43.6 mmol) | 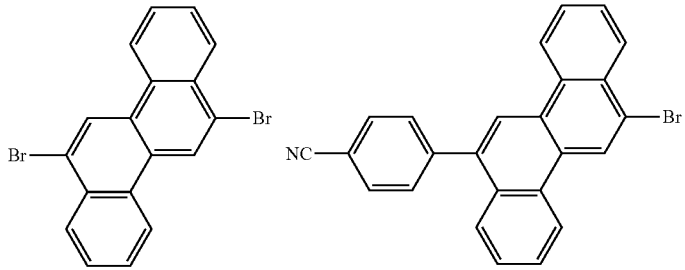 7f (7.6 g, 43%) |

We have used the same synthesis methods to get a series of intermediates and the following compounds are synthesized analogously.
| Ex. | Reactant structure | |
|---|---|---|
| 2 | 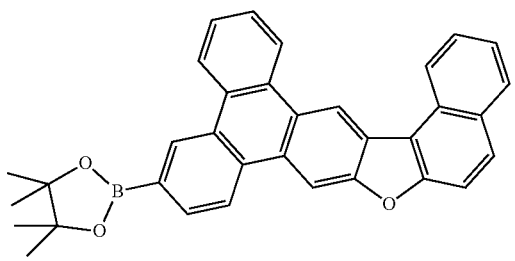 (4.9 g, 10 mmol) | 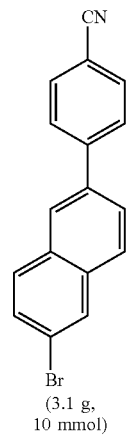 (3.1 g, 10 mmol) |
| 3 | 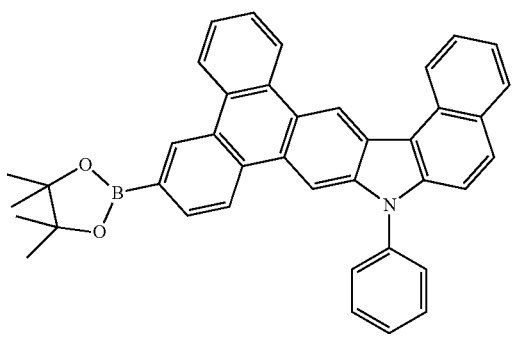 (5.7 g, 10 mmol) | 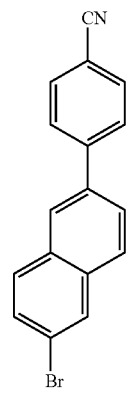 (3.1 g, 10 mmol) |
| 4 | 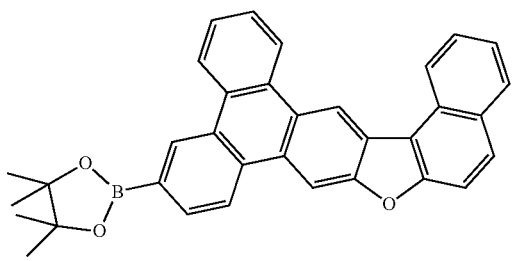 (4.9 g, 10 mmol) | 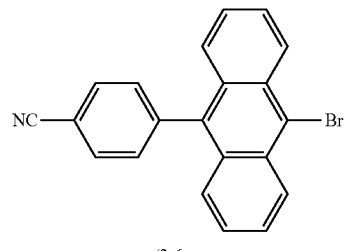 (3.6 g, 10 mmol) |

| | | |
|---|---|---|
| 5 | 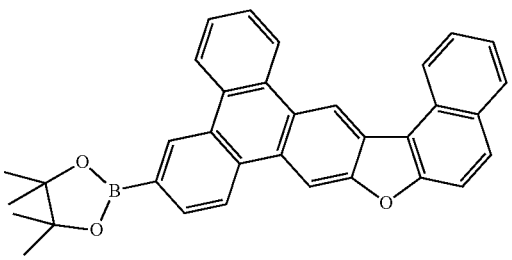<br>(4.9 g, 10 mmol) | 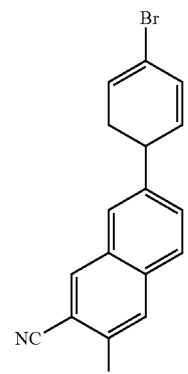<br>(3.3 g, 10 mmol) |
| 6 | 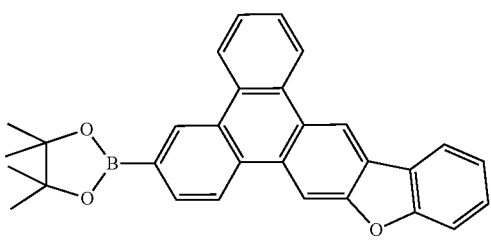<br>(4.4 g, 10 mmol) | 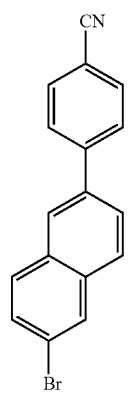<br>(3.1 g, 10 mmol) |
| 7 | 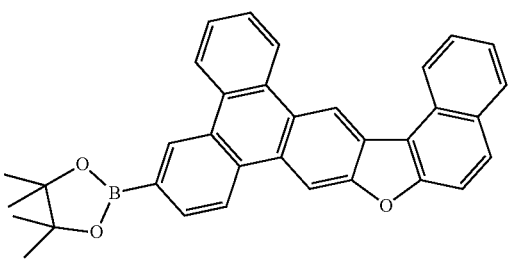<br>(4.9 g, 10 mmol) | 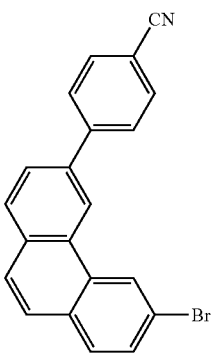<br>(3.6 g, 10 mmol) |

| | | |
|---|---|---|
| 8 | 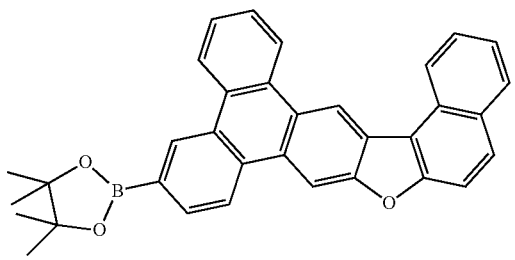(4.9 g, 10 mmol) | 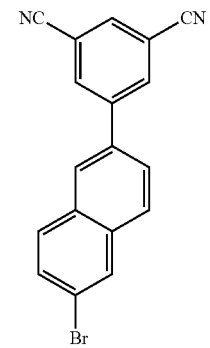(3.3 g, 10 mmol) |
| 9 | 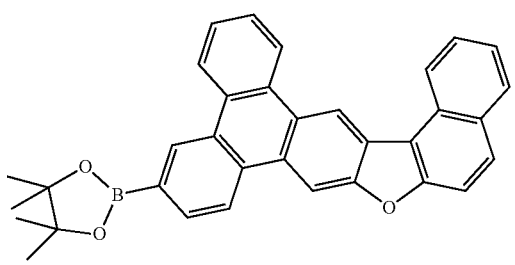(4.9 g, 10 mmol) | 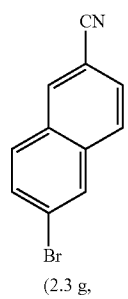(2.3 g, 10 mmol) |
| 10 | 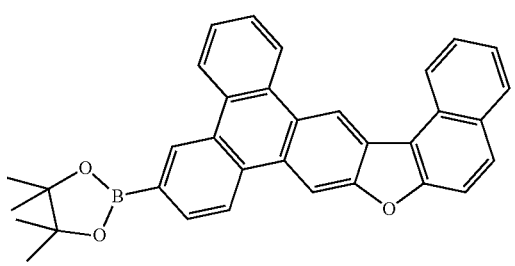(4.9 g, 10 mmol) | 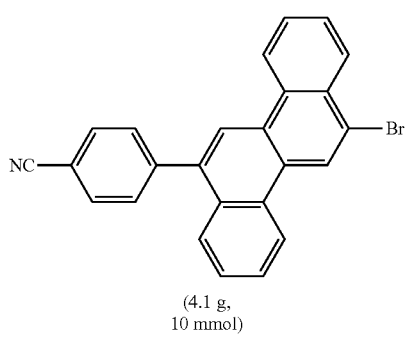 [SMILES: N#Cc1ccc(-c2cc3c4ccccc4c(Br)cc3c3ccccc23)cc1](4.1 g, 10 mmol) |
| 11 | 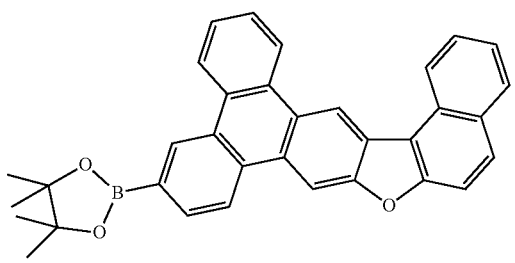(4.9 g, 10 mmol) | 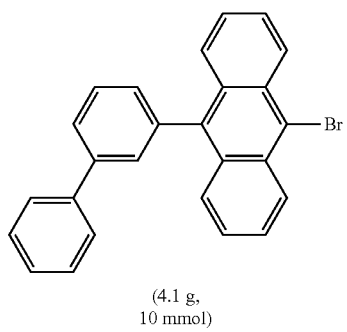 [SMILES: Brc1c2ccccc2c(-c2cccc(-c3ccccc3)c2)c2ccccc12](4.1 g, 10 mmol) |

| 12 | 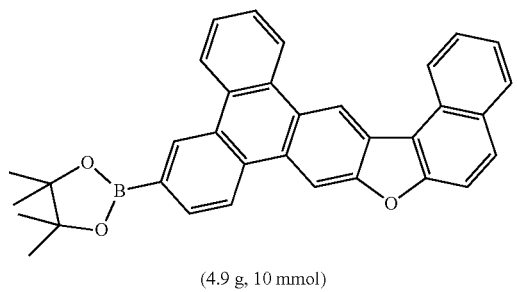 [SMILES: CC1(C)OB(c2ccc3c(c2)c2ccccc2c2cc4c(cc32)oc2ccc3ccccc3c24)OC1(C)C] (4.9 g, 10 mmol) | 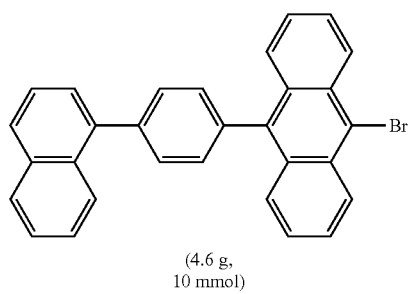 [SMILES: Brc1c2ccccc2c(-c2ccc(-c3cccc4ccccc34)cc2)c2ccccc12] (4.6 g, 10 mmol) |
|---|---|---|
| 13 | 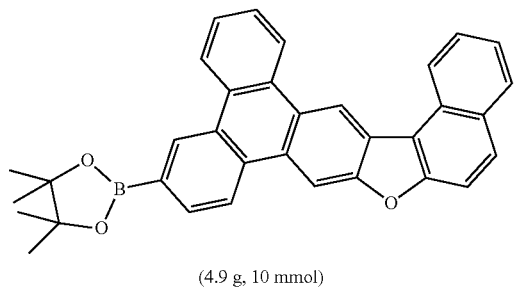 [SMILES: CC1(C)OB(c2ccc3c(c2)c2ccccc2c2cc4c(cc32)oc2ccc3ccccc3c24)OC1(C)C] (4.9 g, 10 mmol) | 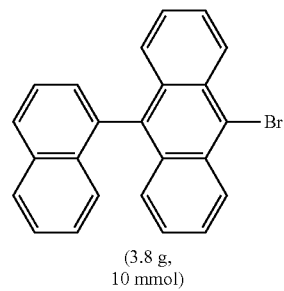 [SMILES: Brc1c2ccccc2c(-c2cccc3ccccc23)c2ccccc12] (3.8 g, 10 mmol) |
| 14 | 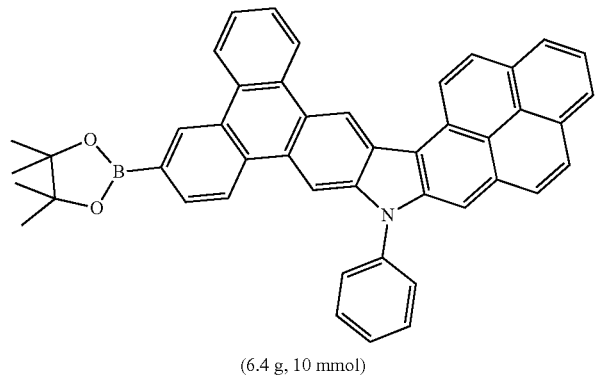 [SMILES: CC1(C)OB(c2ccc3c(c2)c2ccccc2c2cc4c5c6ccc7cccc8ccc(cc5n(-c5ccccc5)c4cc32)c6c87)OC1(C)C] (6.4 g, 10 mmol) | 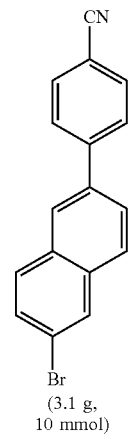 (3.1 g, 10 mmol) |
| 15 | 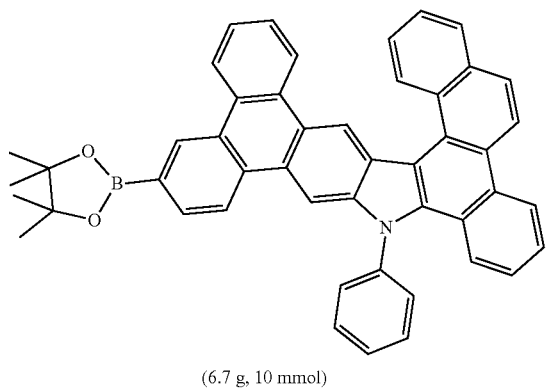 [SMILES: CC1(C)OB(c2ccc3c(c2)c2ccccc2c2cc4c5c6c7ccccc7ccc6c6ccccc6c5n(-c5ccccc5)c4cc32)OC1(C)C] (6.7 g, 10 mmol) | 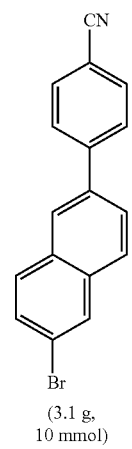 (3.1 g, 10 mmol) |

| | | |
|---|---|---|
| 16 | 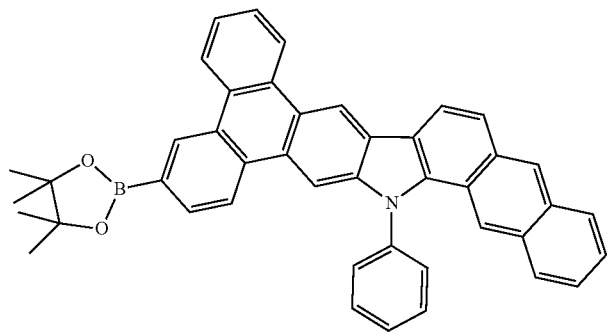<br>(6.2 g, 10 mmol) | 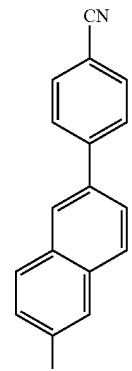<br>(3.1 g, 10 mmol) |
| 17 | 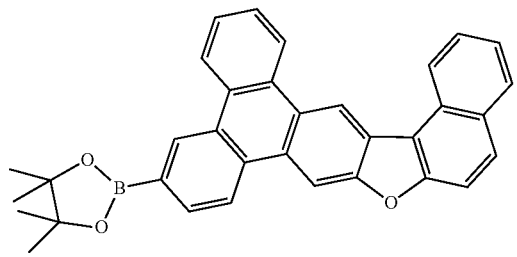<br>(4.9 g, 10 mmol) | 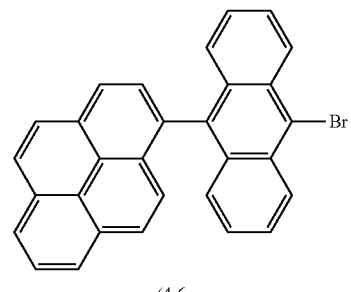<br>(4.6 g, 10 mmol) |
| 18 | 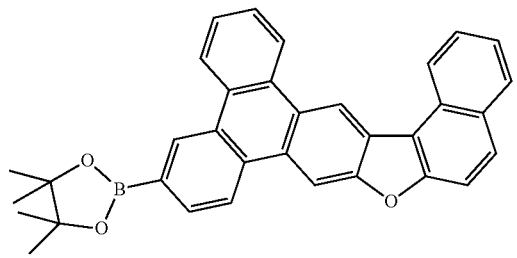<br>(4.9 g, 10 mmol) | 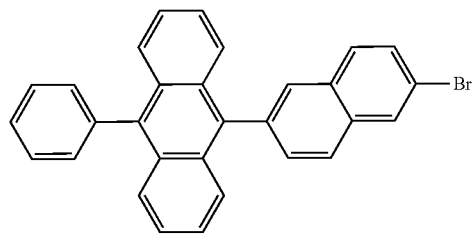<br>(4.6 g, 10 mmol) |
| 19 | 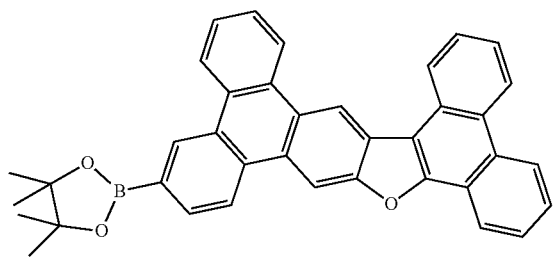<br>(5.4 g, 10 mmol) | 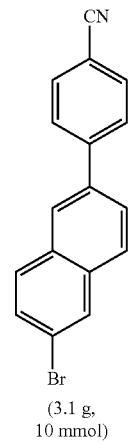<br>(3.1 g, 10 mmol) |

| 20 | 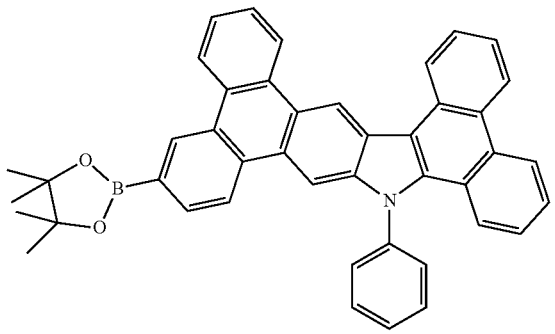 (6.2 g, 10 mmol) | 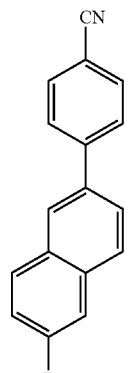 (3.1 g, 10 mmol) |
| --- | --- | --- |
| 21 | 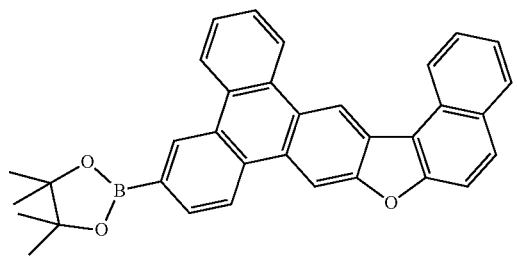 (4.9 g, 10 mmol) | 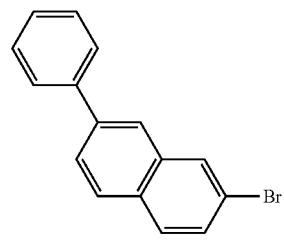 (2.8 g, 10 mmol) |
| 22 | 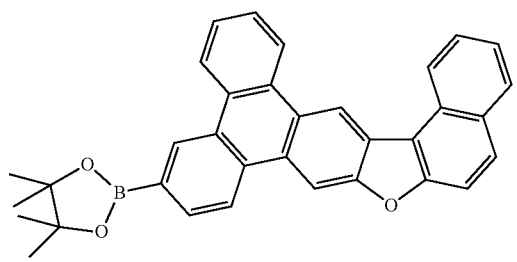 (4.9 g, 10 mmol) | 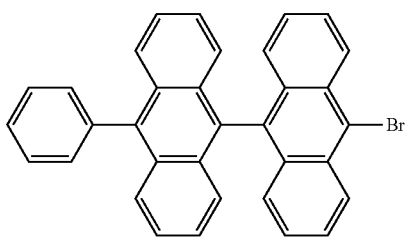 (5.1 g, 10 mmol) |
| 23 | 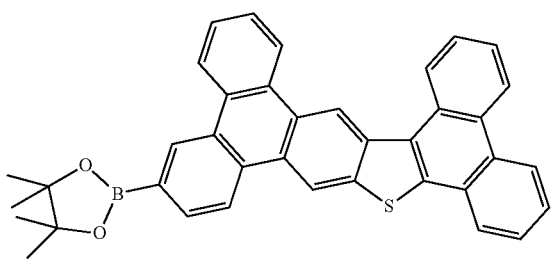 (5.6 g, 10 mmol) | 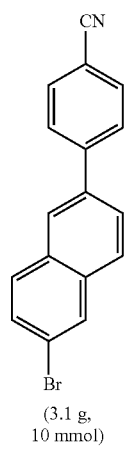 (3.1 g, 10 mmol) |

| | | |
|---|---|---|
| 24 | 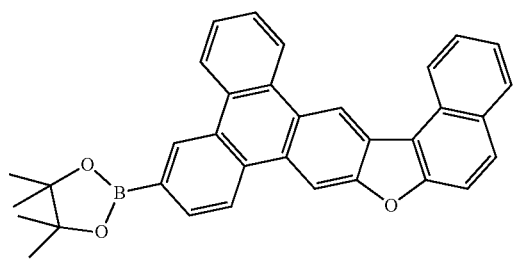<br>(4.9 g, 10 mmol) | 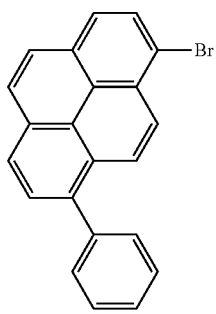<br>(3.6 g, 10 mmol) |
| 25 | 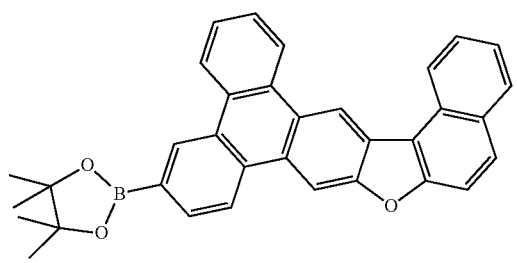<br>(4.9 g, 10 mmol) | 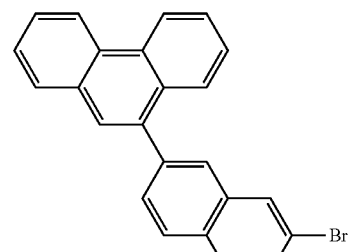<br>(3.8 g, 10 mmol) |
| 26 | 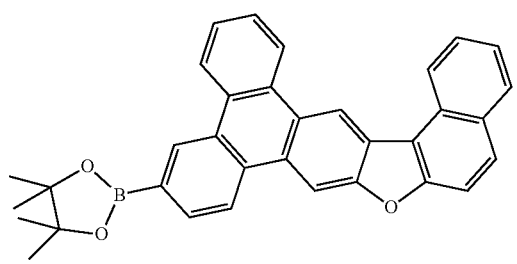<br>(4.9 g, 10 mmol) | 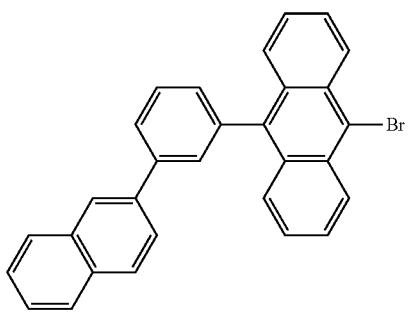<br>(4.6 g, 10 mmol) |
| 27 | 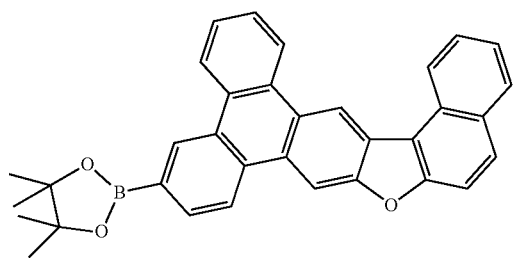<br>(4.9 g, 10 mmol) | 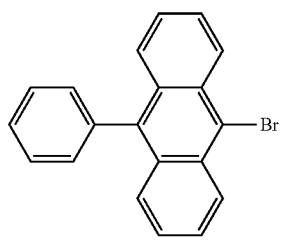<br>(3.3 g, 10 mmol) |

| | | |
|---|---|---|
| 28 | 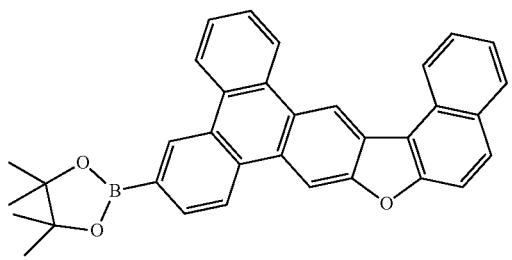<br>(4.9 g, 10 mmol) | 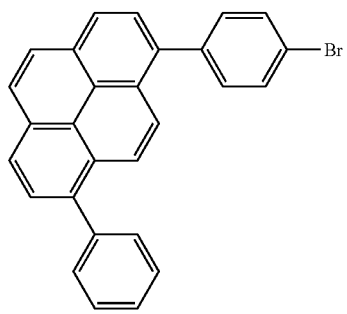<br>(4.3 g, 10 mmol) |
| 29 | 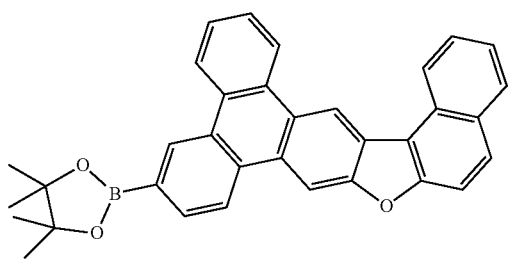<br>(4.9 g, 10 mmol) | 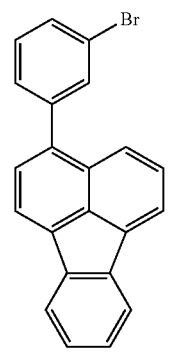<br>(3.6 g, 10 mmol) |
| 30 | 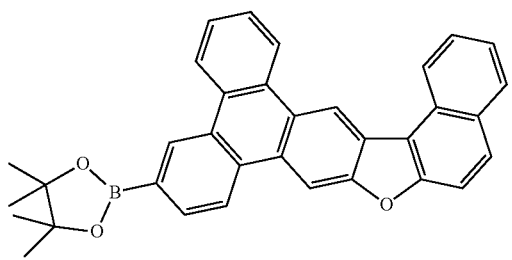<br>(4.9 g, 10 mmol) | 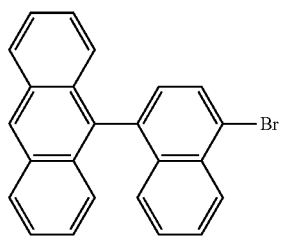<br>(3.8 g, 10 mmol) |
| 31 | 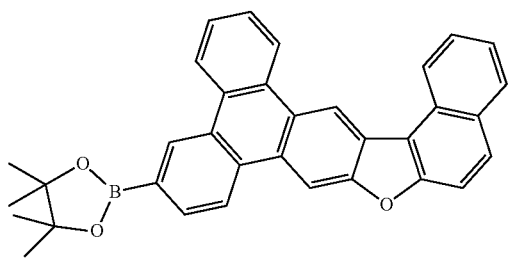<br>(4.9 g, 10 mmol) | 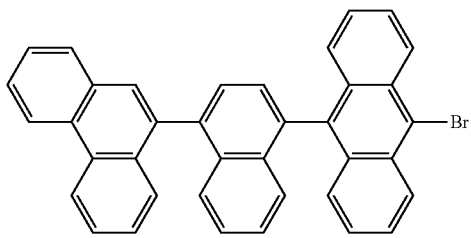<br>(5.6 g, 10 mmol) |

| 32 | 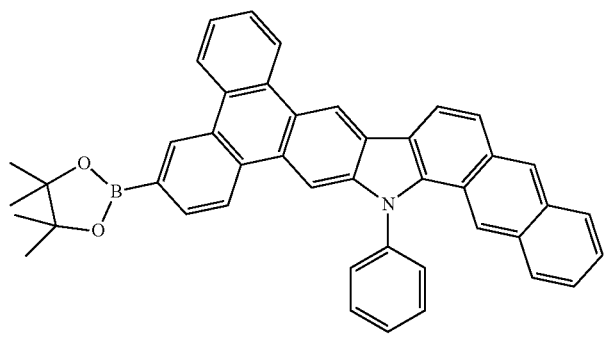 (6.2 g, 10 mmol) | 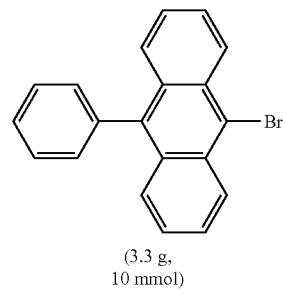 [SMILES: Brc1c2ccccc2c(-c2ccccc2)c2ccccc12] (3.3 g, 10 mmol) |
|---|---|---|
| 33 | 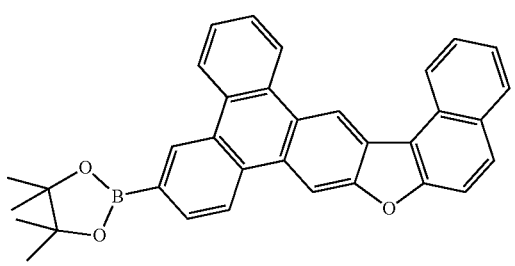 (4.9 g, 10 mmol) | 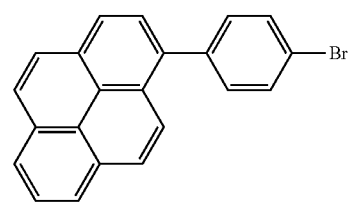 (3.6 g, 10 mmol) |
| 34 | 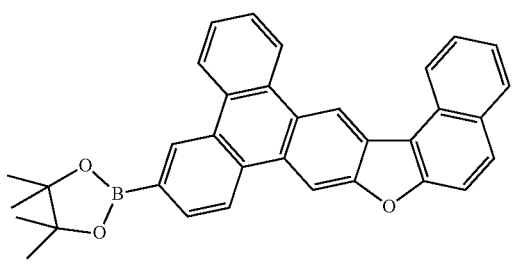 (4.9 g, 10 mmol) | 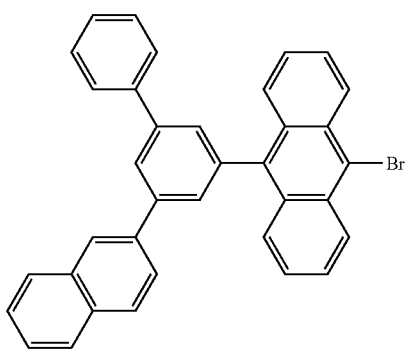 (5.4 g, 10 mmol) |
| 35 | 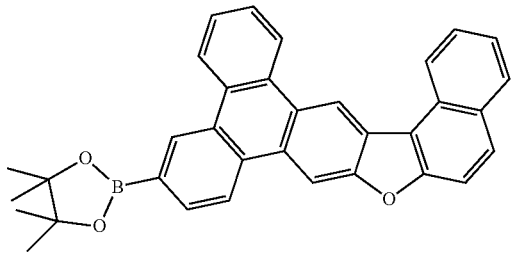 (4.9 g, 10 mmol) | 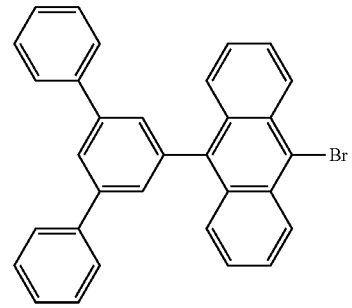 (4.9 g, 10 mmol) |

-continued
| 36 | 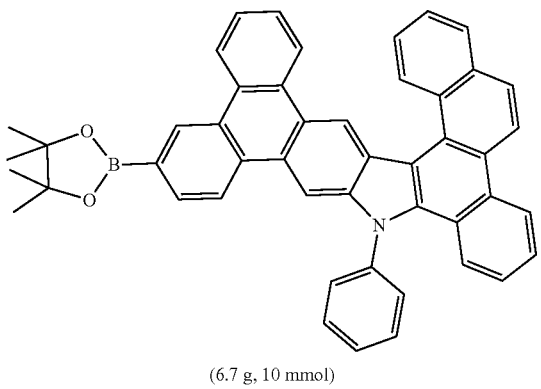 [SMILES: CC1(C)OB(c2ccc3c(c2)c2ccccc2c2cc4c5c6c7ccccc7ccc6c6ccccc6c5n(-c5ccccc5)c4cc32)OC1(C)C] (6.7 g, 10 mmol) | 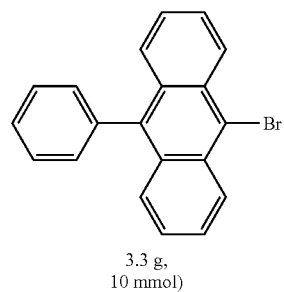 [SMILES: Brc1c2ccccc2c(-c2ccccc2)c2ccccc12] 3.3 g, 10 mmol) |
| --- | --- | --- |
| 37 | 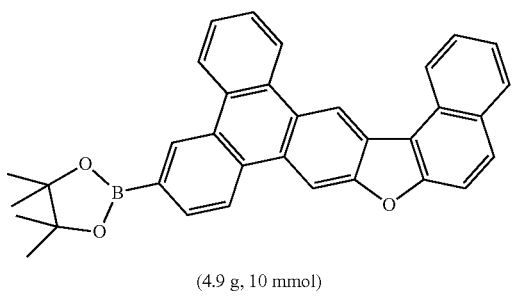 [SMILES: CC1(C)OB(c2ccc3c(c2)c2ccccc2c2cc4c(cc32)oc2ccc3ccccc3c24)OC1(C)C] (4.9 g, 10 mmol) | 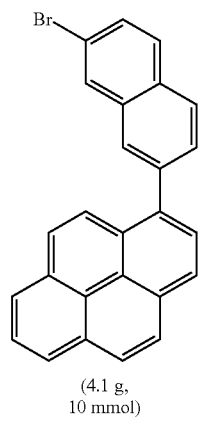 [SMILES: Brc1ccc2ccc(-c3ccc4ccc5cccc6ccc3c4c56)cc2c1] (4.1 g, 10 mmol) |
| 38 | 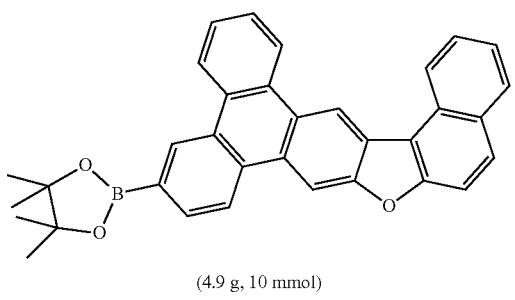 [SMILES: CC1(C)OB(c2ccc3c(c2)c2ccccc2c2cc4c(cc32)oc2ccc3ccccc3c24)OC1(C)C] (4.9 g, 10 mmol) | 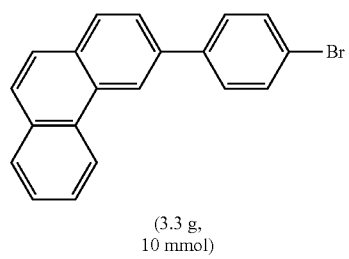 (3.3 g, 10 mmol) |
| 39 | 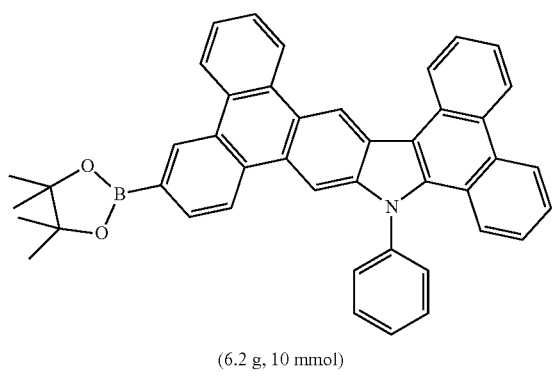 [SMILES: CC1(C)OB(c2ccc3c(c2)c2ccccc2c2cc4c5c6ccccc6c6ccccc6c5n(-c5ccccc5)c4cc32)OC1(C)C] (6.2 g, 10 mmol) | 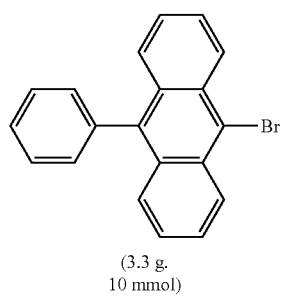 [SMILES: Brc1c2ccccc2c(-c2ccccc2)c2ccccc12] (3.3 g. 10 mmol) |

-continued
| | | | |
|---|---|---|---|
| 40 | 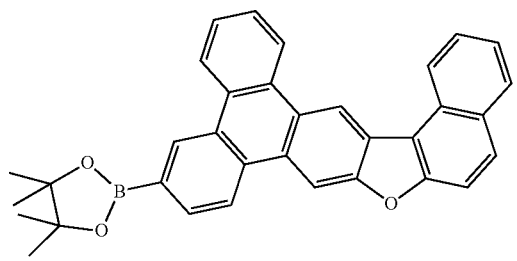<br>(4.9 g, 10 mmol) | 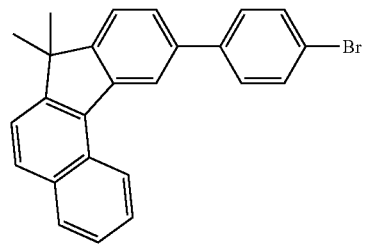<br>(4.0 g, 10 mmol) | |
| 41 | 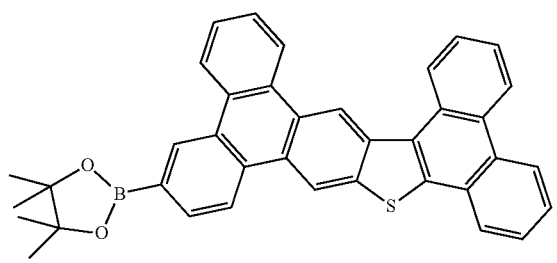<br>(5.6 g, 10 mmol) | 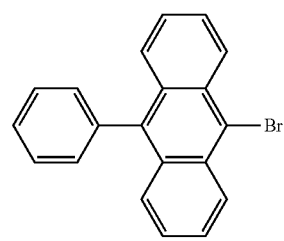<br>(3.3 g, 10 mmol) | |
| 42 | 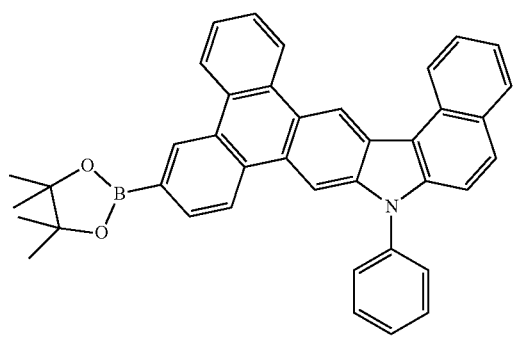<br>(5.7 g, 10 mmol) | 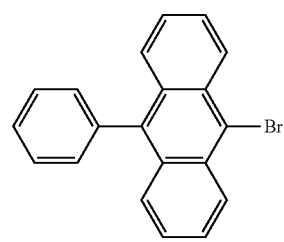<br>(3.3 g, 10 mmol) | |
| Ex. | Product structure | Weight Yield |
|---|---|---|
| 2 | 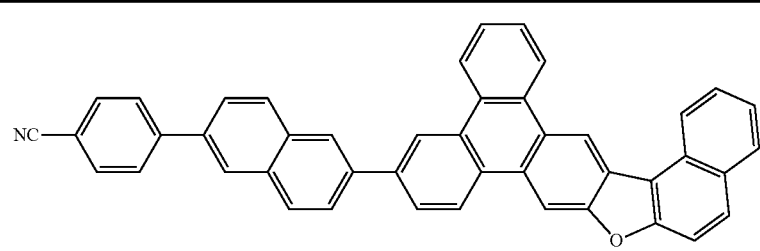<br>Comp. 14<br>MS (m/z, EI⁺): 595.68 | 3.9 g<br>66% |

| | | |
|---|---|---|
| 3 | 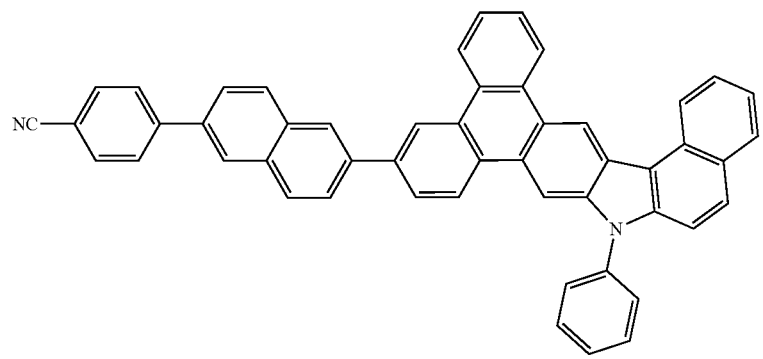
Comp. 27
MS (m/z, EI⁺): 670.81 | 3.9 g
58% |
| 4 | 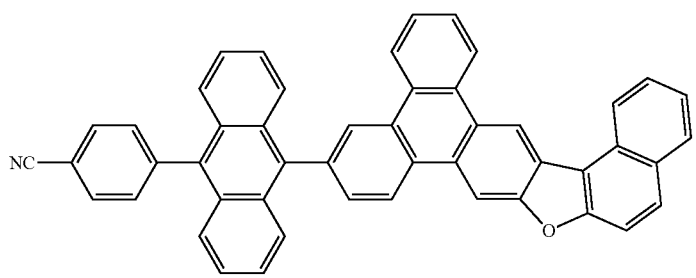
Comp. 35
MS (m/z, EI⁺): 645.72 | 4.3 g
67% |
| 5 | 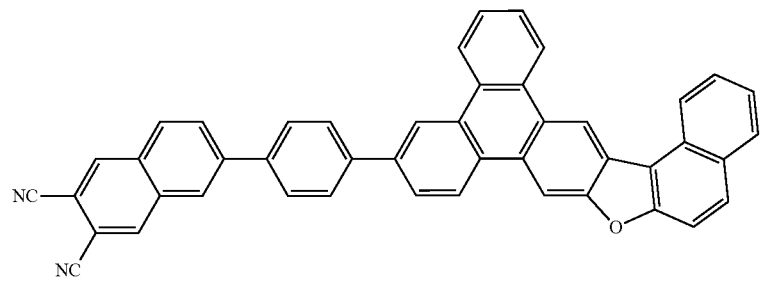
Comp. 38
MS (m/z, EI⁺): 620.69 | 2.4 g
62% |
| 6 | 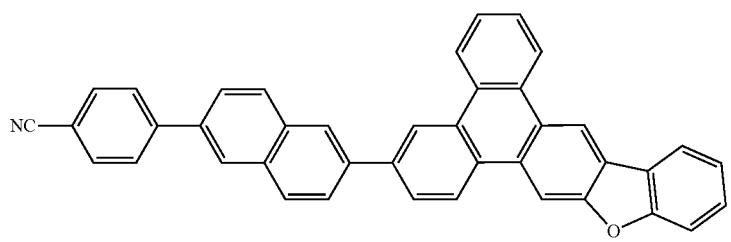
Comp. 40
MS (m/z, EI⁺): 545.63 | 3.3 g
61% |

| | | |
|---|---|---|
| 7 | 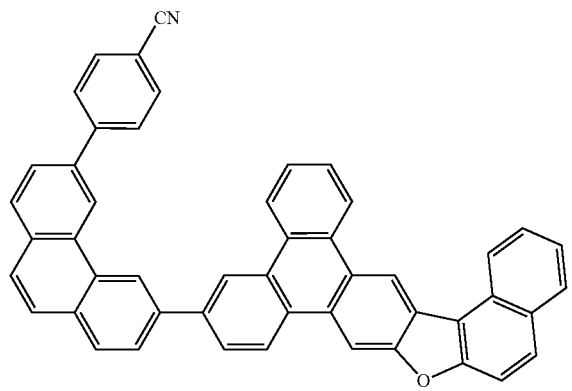
Comp. 47
MS (m/z, EI+): 645.76 | 6.5 g
55% |
| 8 | 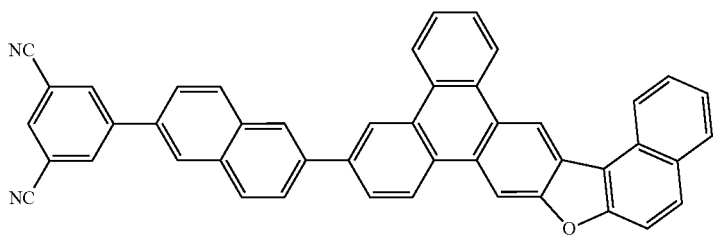
Comp. 52
MS (m/z, EI+): 620.69 | 3.4 g
54% |
| 9 | 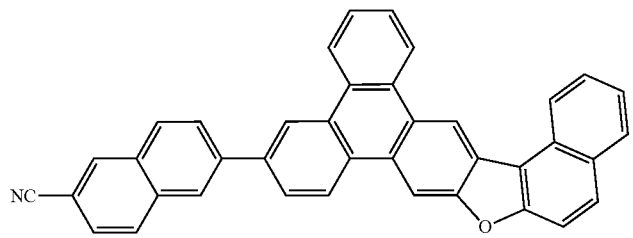
Comp. 55
MS (m/z, EI+): 519.57 | 3.3 g
64% |
| 10 | 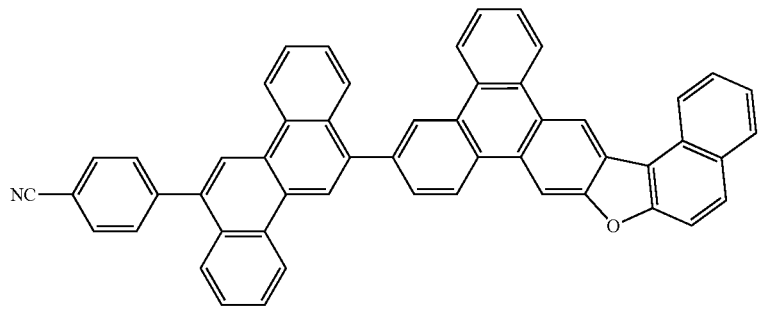
Comp. 63
MS (m/z, EI+): 695.82 | 3.8 g
54% |

-continued
| | | |
|---|---|---|
| 11 | 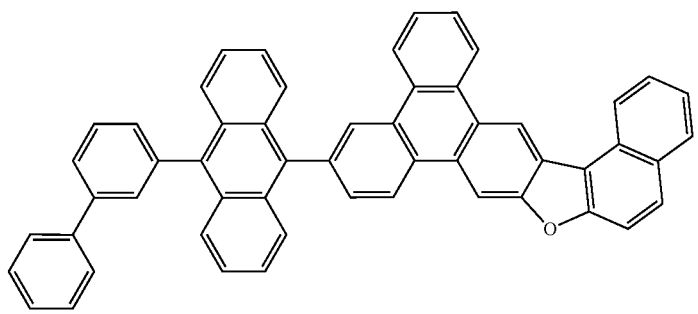
Comp. 68
MS (m/z, EI⁺): 696.83 | 4.0 g
57% |
| 12 | 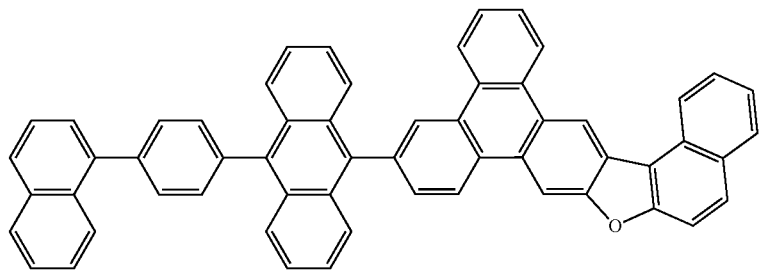
Comp. 71
MS (m/z, EI⁺): 746.89 | 4.7 g
63% |
| 13 | 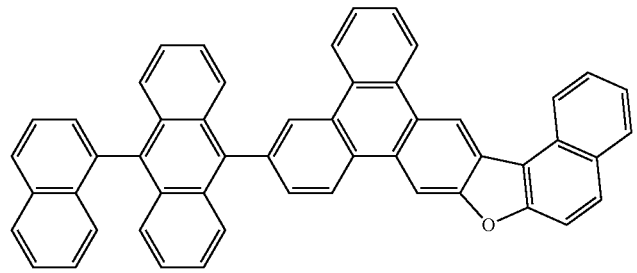
Comp. 73
MS (m/z, EI⁺): 670.77 | 6.0 g
59% |
| 14 | 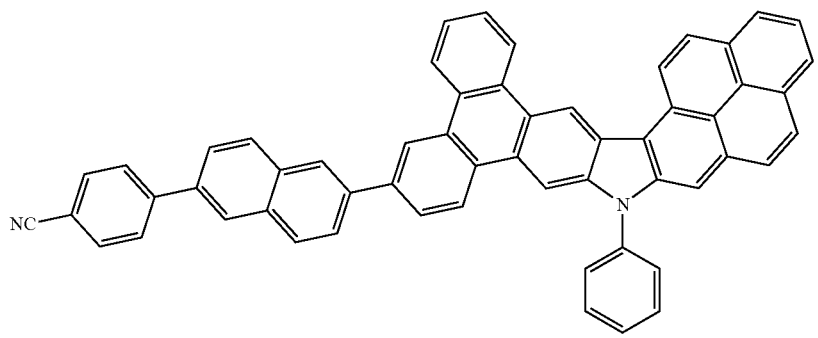
Comp. 76
MS (m/z, EI⁺): 744.86 | 4.2 g
57% |

-continued
| 15 | 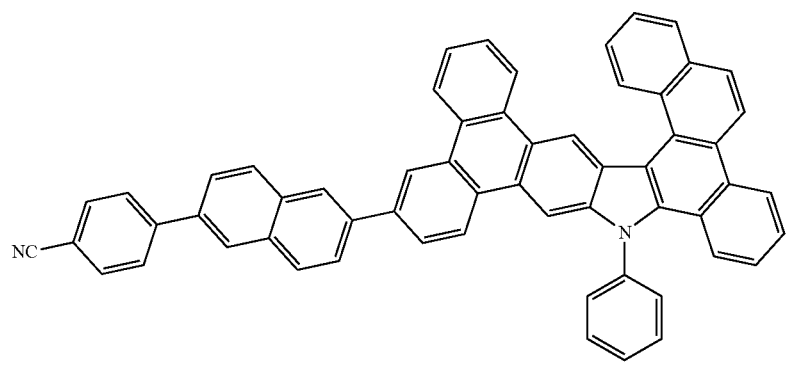<br>Comp. 84<br>MS (m/z, EI$^+$): 770.89 | 4.8 g<br>62% |
| 16 | 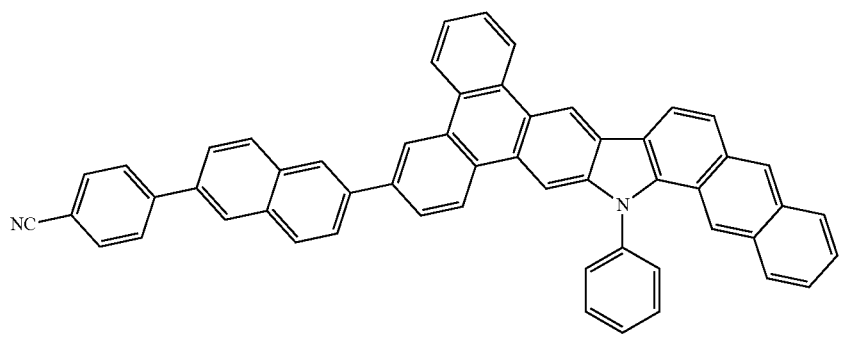<br>Comp. 91<br>MS (m/z, EI$^+$): 720.88 | 4.3 g<br>63% |
| 17 | 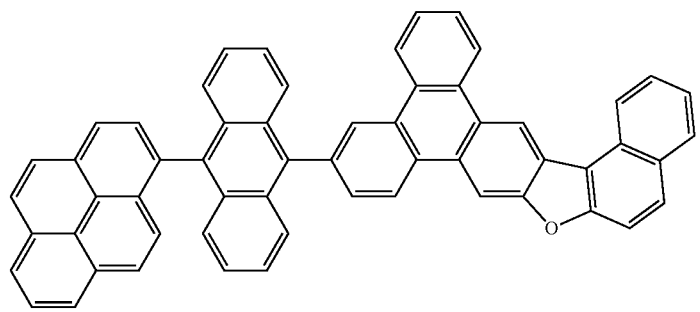<br>Comp. 97<br>MS (m/z, EI$^+$): 744.86 | 4.8 g<br>64% |
| 18 | 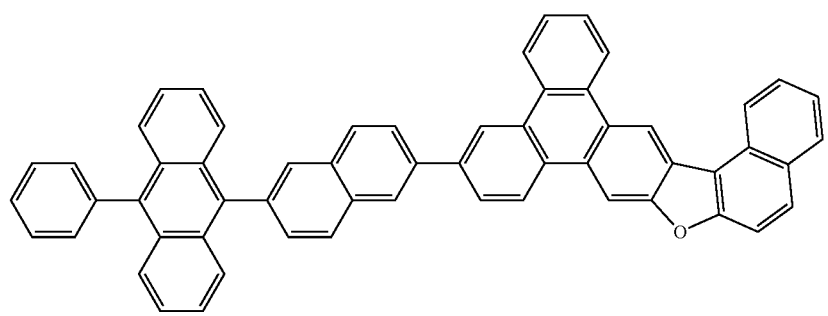<br>Comp. 102<br>MS (m/z, EI$^+$): 746.87 | 4.4 g<br>59% |

| | | |
|---|---|---|
| 19 | 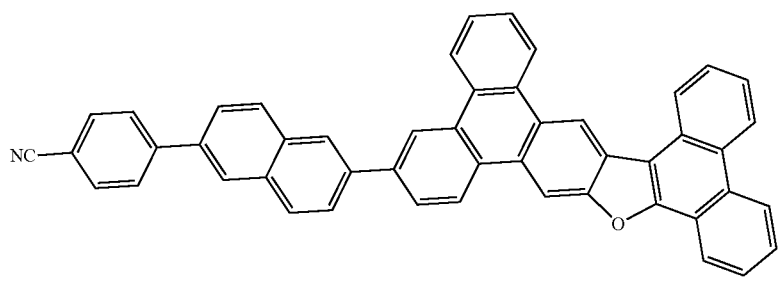
Comp. 106
MS (m/z, EI⁺): 645.72 | 3.9 g
60% |
| 20 | 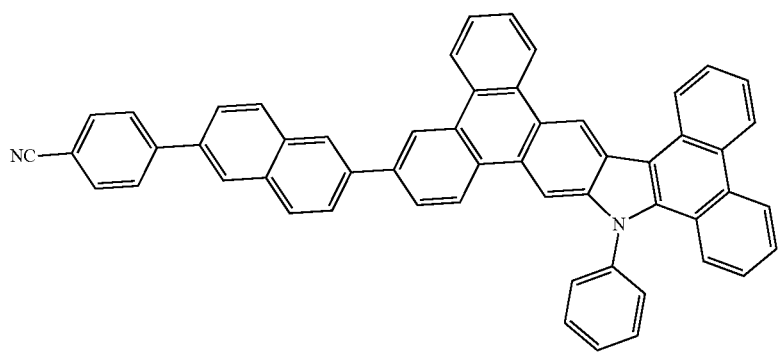
Comp. 118
MS (m/z, EI⁺): 720.86 | 4.0 g
56% |
| 21 | 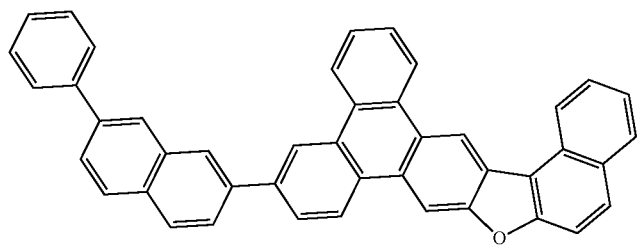
Comp. 129
MS (m/z, EI⁺): 570.71 | 3.1 g
54% |
| 22 | 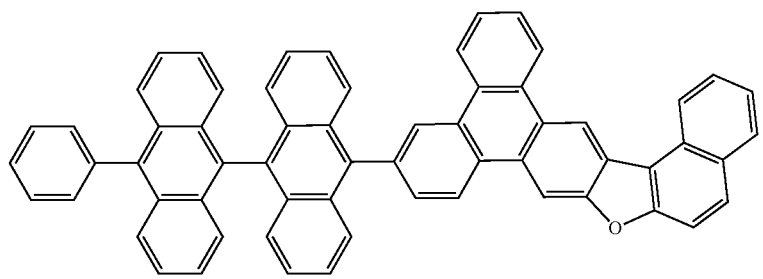
Comp. 131
MS (m/z, EI⁺): 796.95 | 5.7 g
72% |

-continued
| 23 | 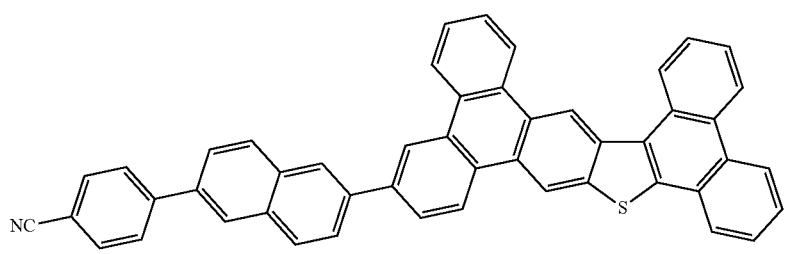
Comp. 138
MS (m/z, EI+): 661.83 | 67% |
| 24 | 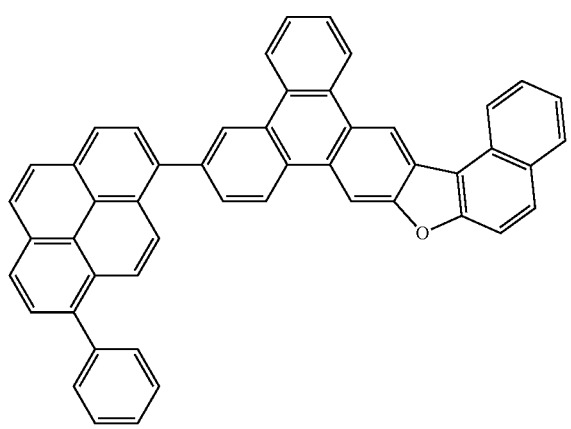
Comp. 140
MS (m/z, EI+): 644.76 | 4.7 g
73% |
| 25 | 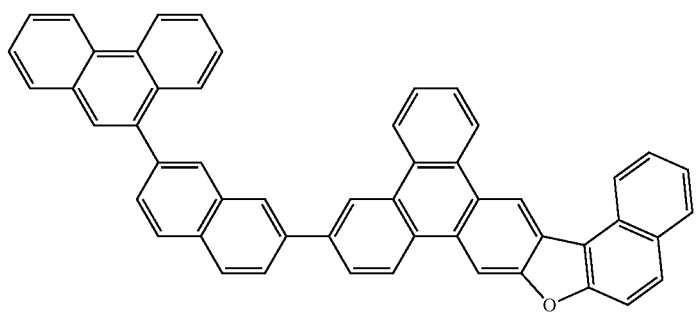
Comp. 141
MS (m/z, EI+): 670.89 | 4.7 g
70% |
| 26 | 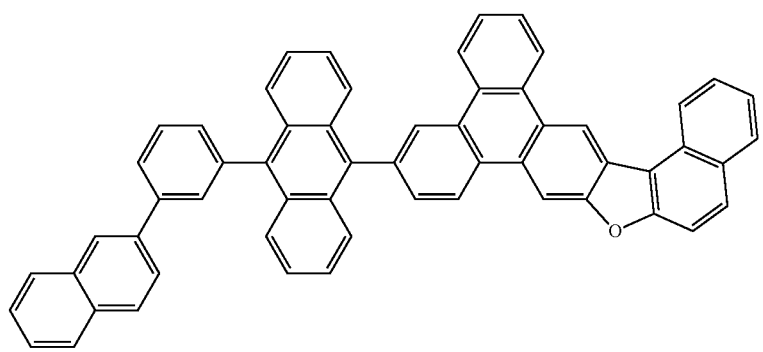
Comp. 160
MS (m/z, EI+): 746.89 | 5.0 g
67% |

| | | |
|---|---|---|
| 27 | 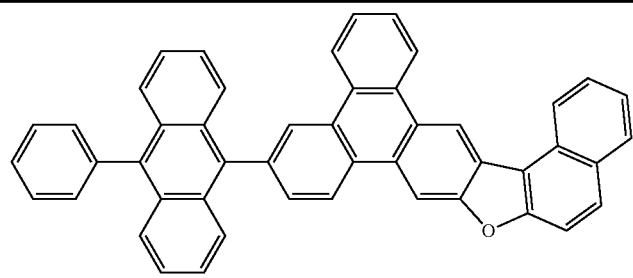
Comp. 162
MS (m/z, EI+): 620.77 | 3.5 g
56% |
| 28 | 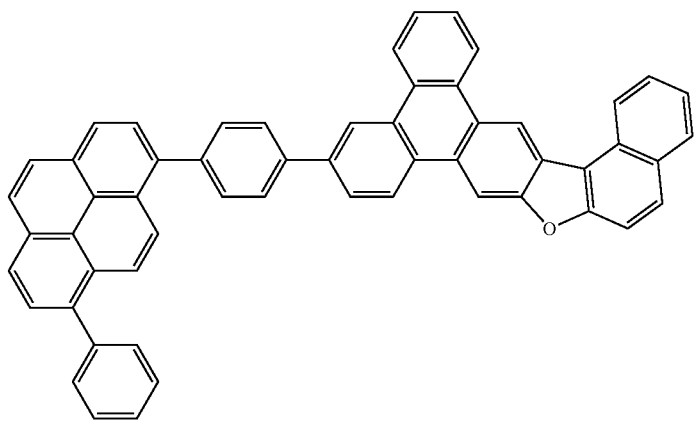
Comp. 167
MS (m/z, EI+): 720.83 | 5.0 g
69% |
| 29 | 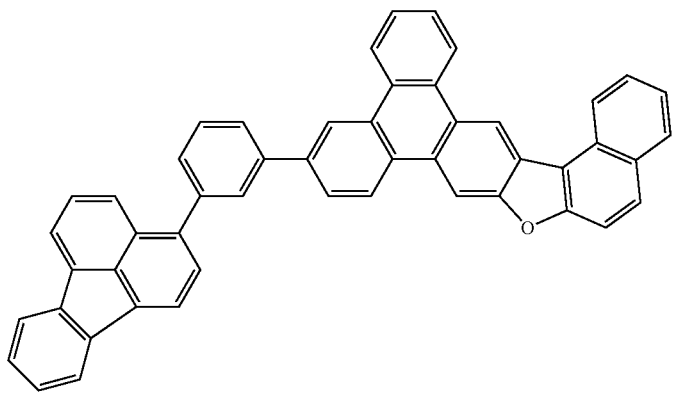
Comp. 171
MS (m/z, EI+): 644.74 | 4.3 g
67% |
| 30 | 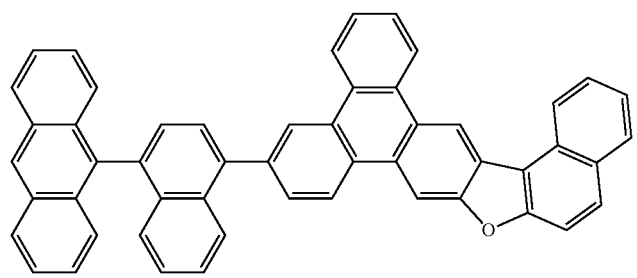
Comp. 174
MS (m/z, EI+): 670.81 | 4.0 g
60% |

| | | |
|---|---|---|
| 31 | 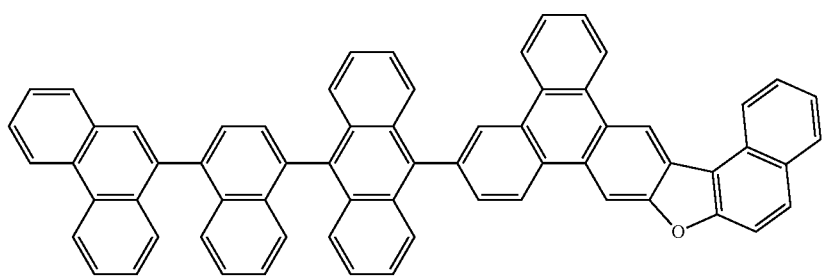<br>Comp. 175<br>MS (m/z, EI+): 847.0 | 64% |
| 32 | 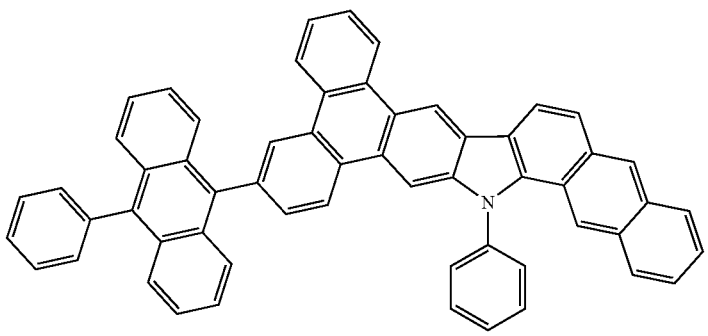<br>Comp. 176<br>MS (m/z, EI+): 745.89 | 4.6 g<br>62% |
| 33 | 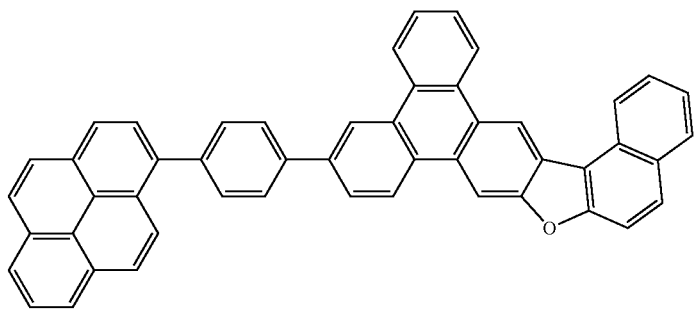<br>Comp. 181<br>MS (m/z, EI+): 644.73 | 4.2 g<br>65% |
| 34 | 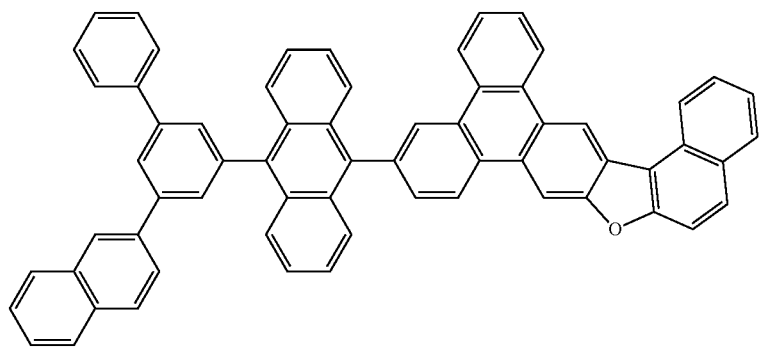<br>Comp. 183<br>MS (m/z, EI+): 822.99 | 5.3 g<br>54% |

| | | |
|---|---|---|
| 35 | 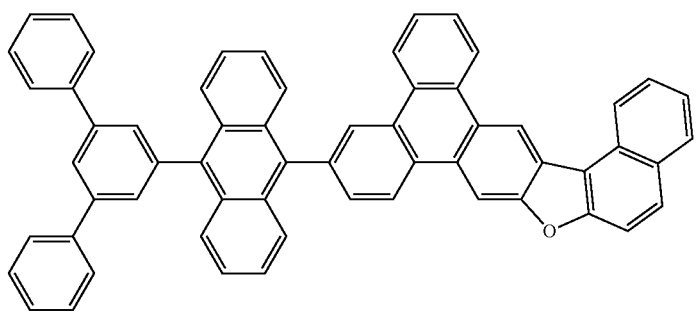
Comp. 185
MS (m/z, EI+): 772.95 | 4.9 g<br>63% |
| 36 | 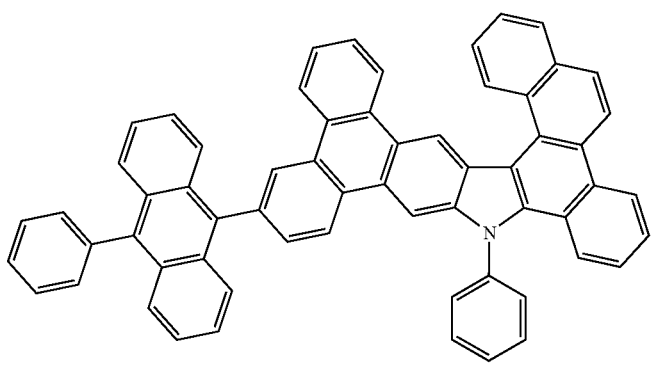
Comp. 187
MS (m/z, EI+): 795.94 | 4.1 g<br>51% |
| 37 | 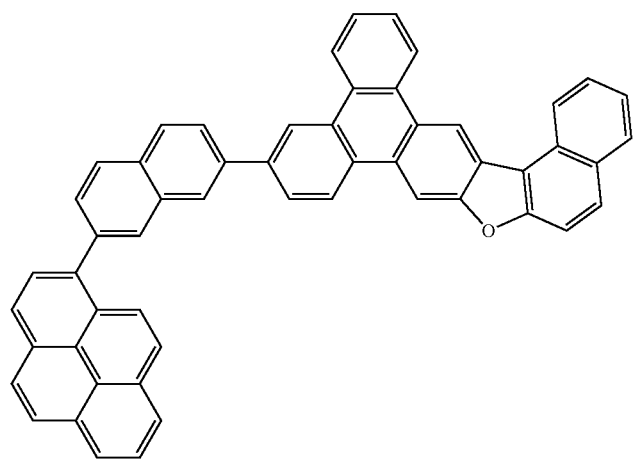
Comp. 191
MS (m/z, EI+): 694.84 | 4.3 g<br>62% |

-continued
| 38 | 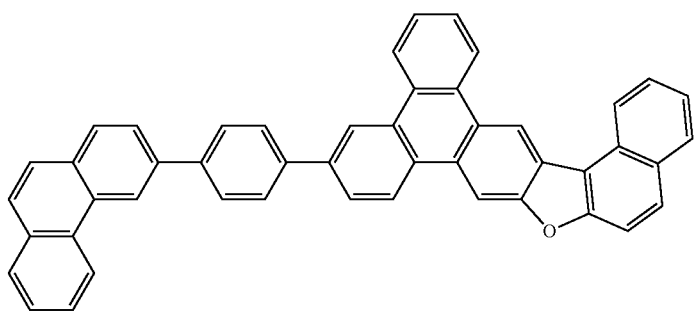<br>Comp. 193<br>MS (m/z, EI⁺): 620.71 | 4.0 g<br>64% |
|---|---|---|
| 39 | 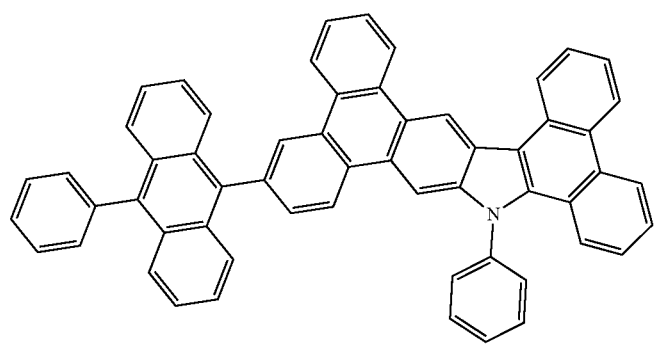<br>Comp. 196<br>MS (m/z EI⁺): 745.9 | 5.1 g<br>69% |
| 40 | 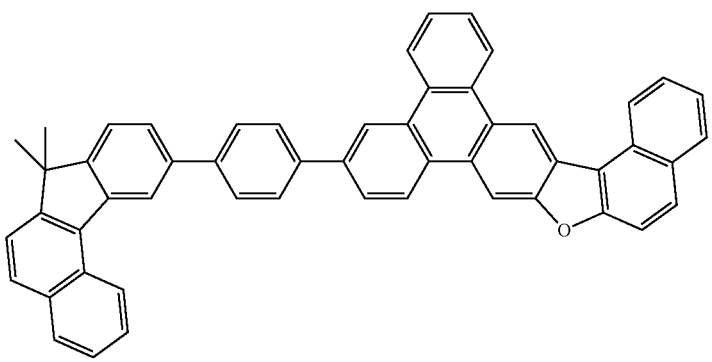<br>Comp. 209<br>MS (m/z, EI⁺): 686.85 | 4.0 g<br>58% |
| 41 | 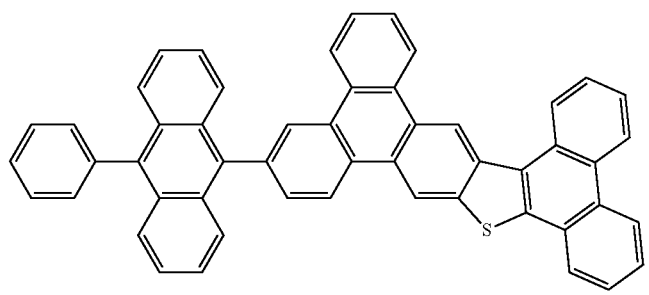<br>Comp. 217<br>MS (m/z, EI⁺): 686.88 | 4.1 g<br>59% |

| 42 | 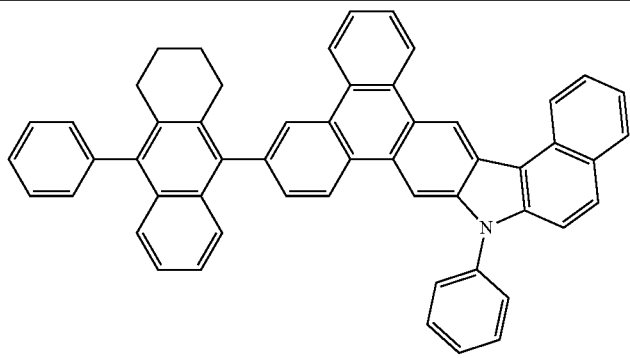<br>Comp. 221<br>MS (m/z, EI⁺): 695.82 | 4.7 g<br>67% |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. An organic compound selected from the group consisting of:

formula (2-1)

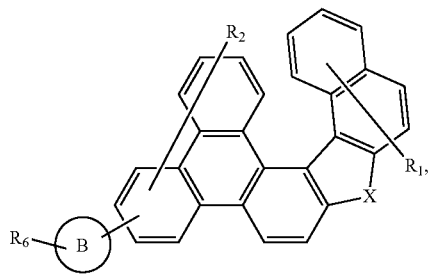

formula (2-2)

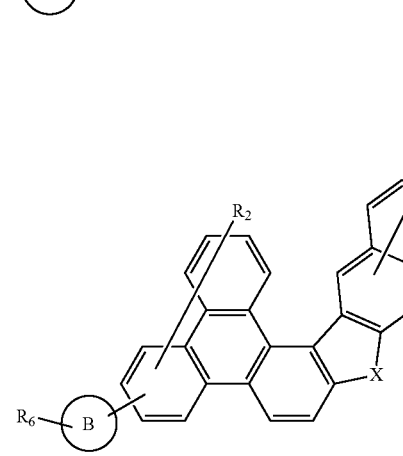

formula (2-3)

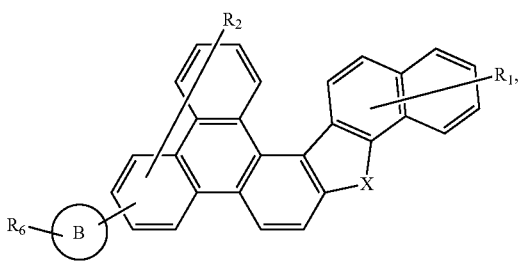

formula (2-4)

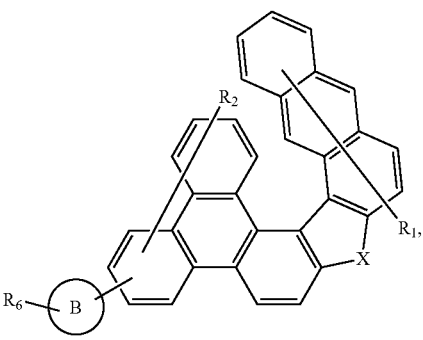

formula (2-5)

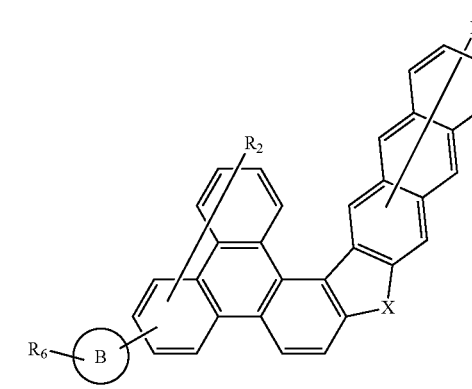

formula (2-6)
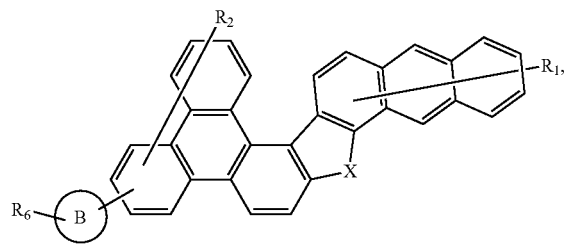
formula (2-7)
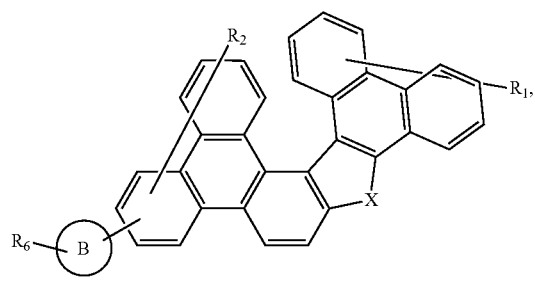
formula (2-8)
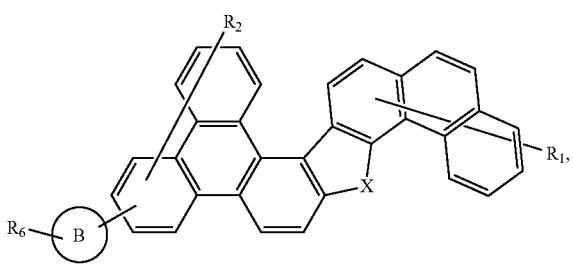
formula (2-9)
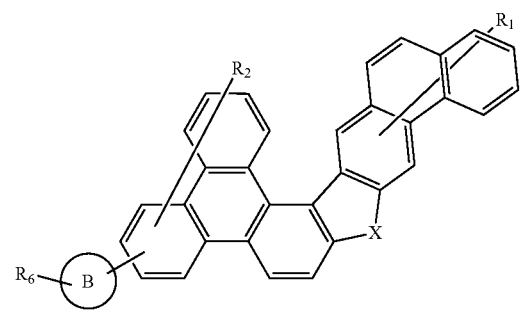
,
formula (2-10)
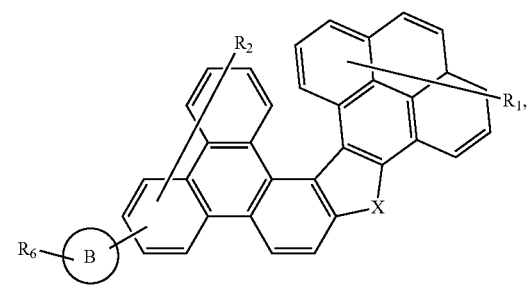
formula (2-11)
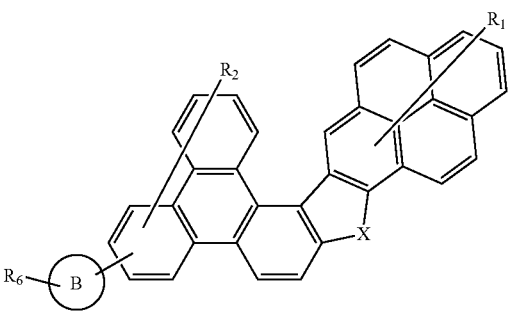
,
formula (2-12)
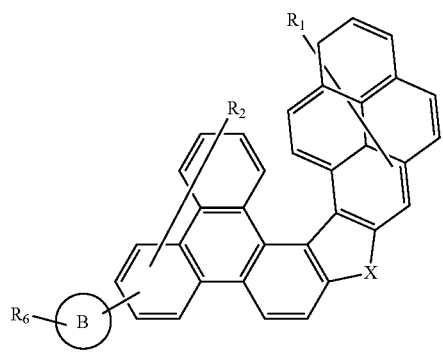
,
formula (2-13)
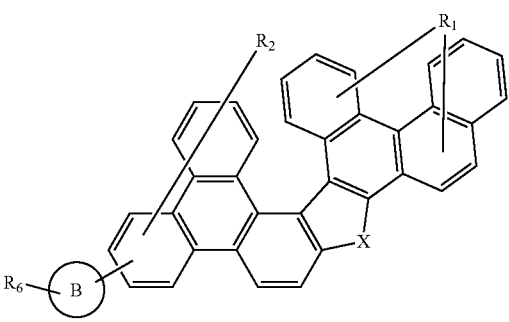
,
formula (2-14)
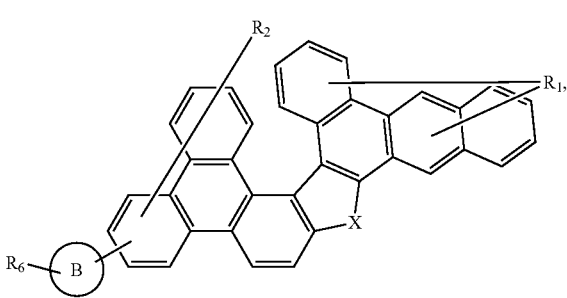
, formula (2-15)
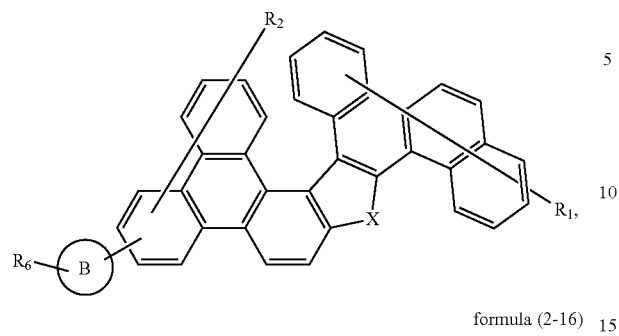
formula (2-16)
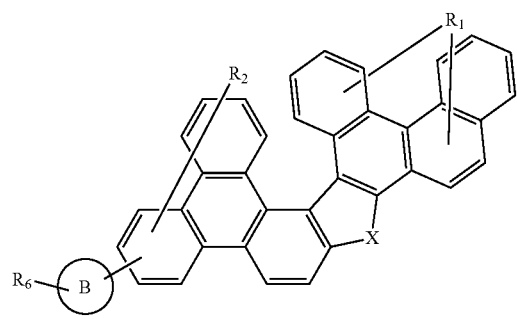
formula (2-17)
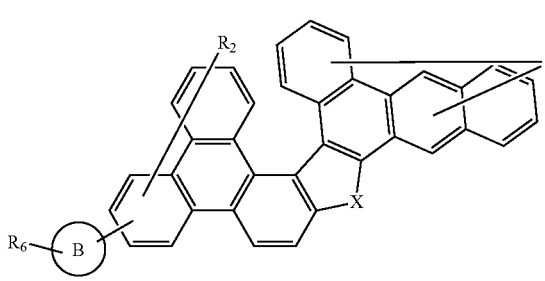
formula (2-18)
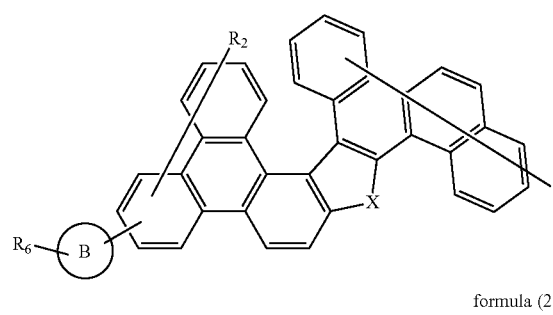
formula (2-19)
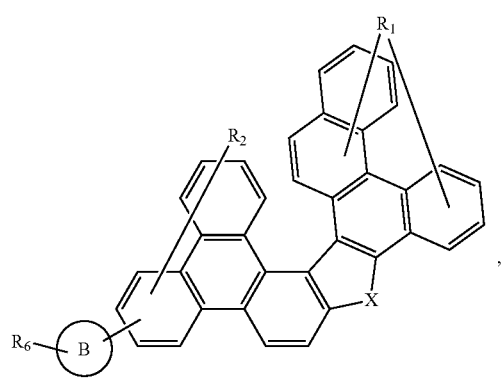
formula (2-20)
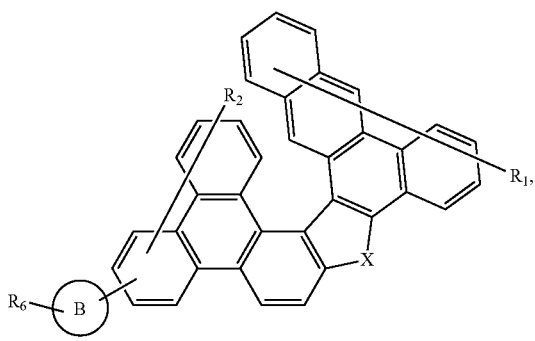
formula (2-21)
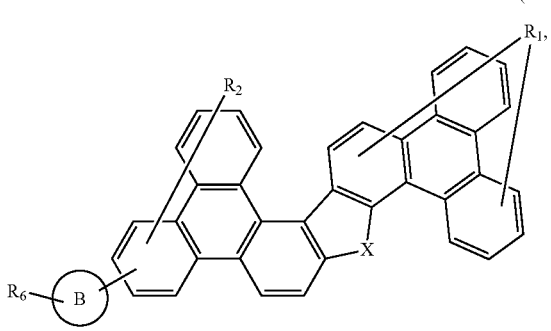
formula (2-22)
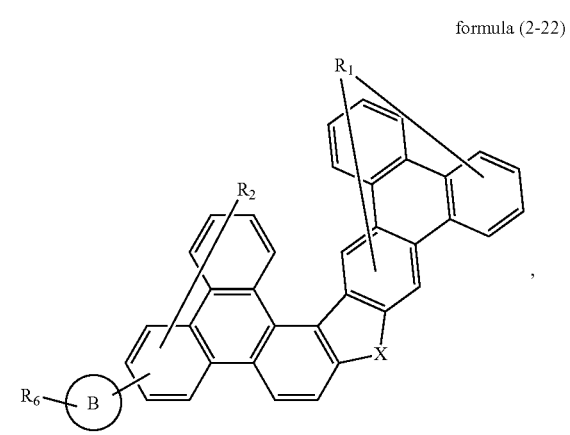
and
formula (2-23)

formula (4-1)
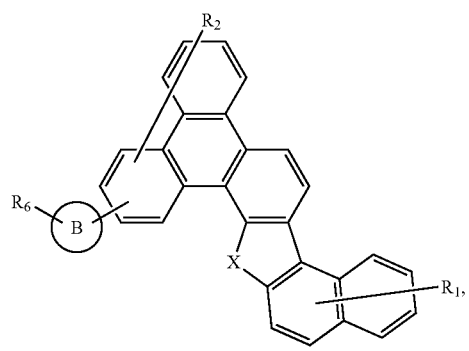
formula (4-2)
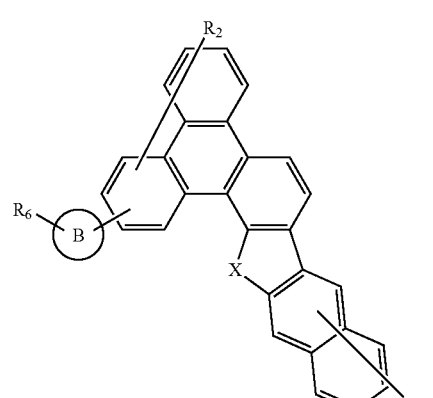
formula (4-3)
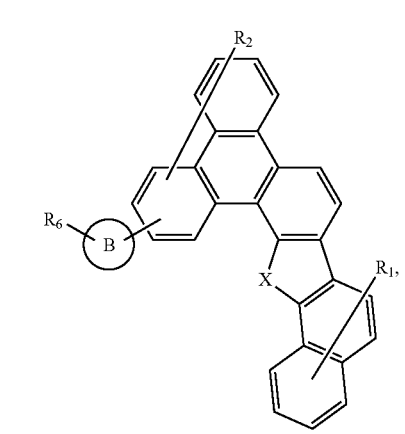
formula (4-4)
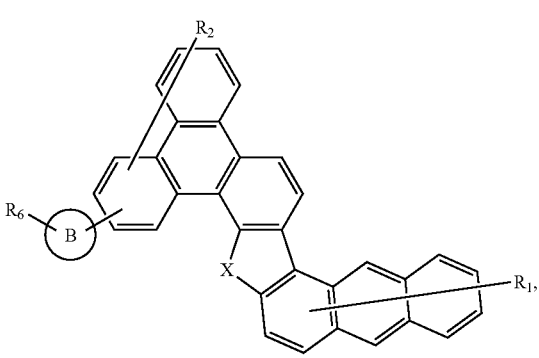
formula (4-5)
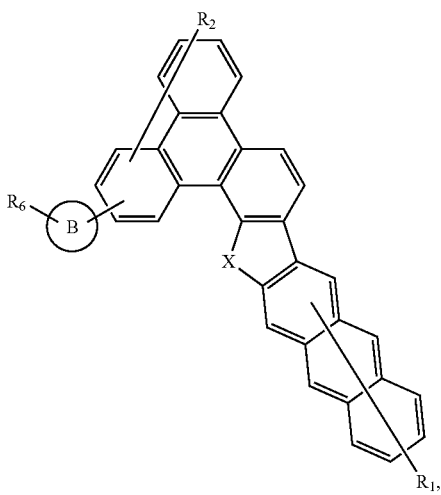
formula (4-6)
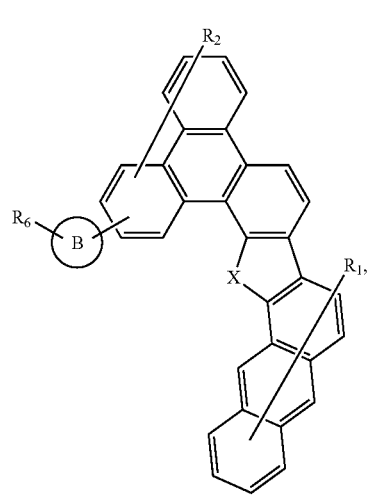
formula (4-7)
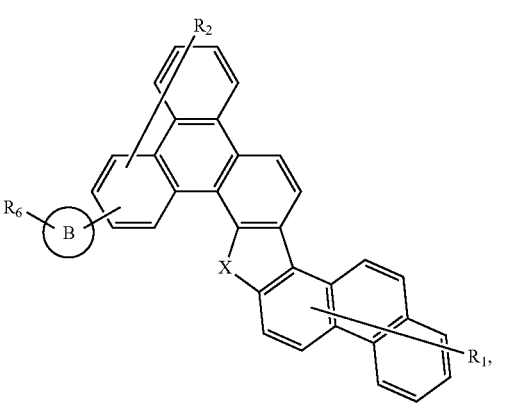

formula (4-8)
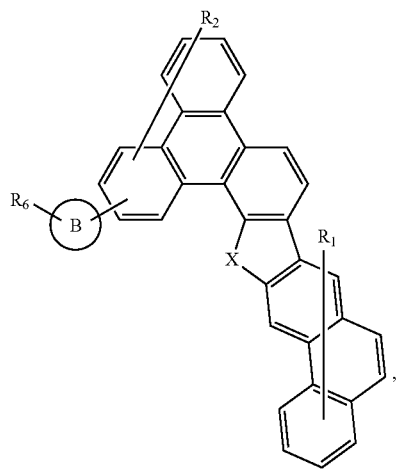
formula (4-9)
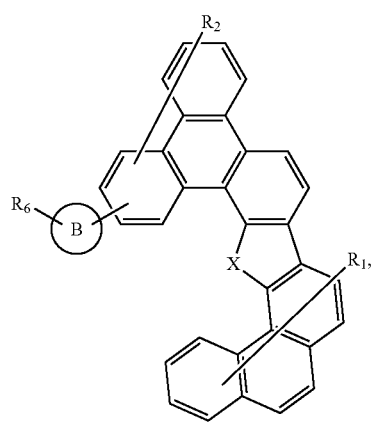
formula (4-10)
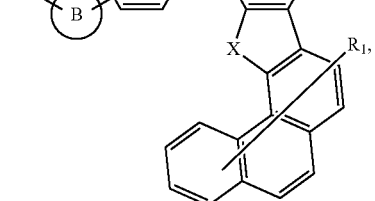
formula (4-11)
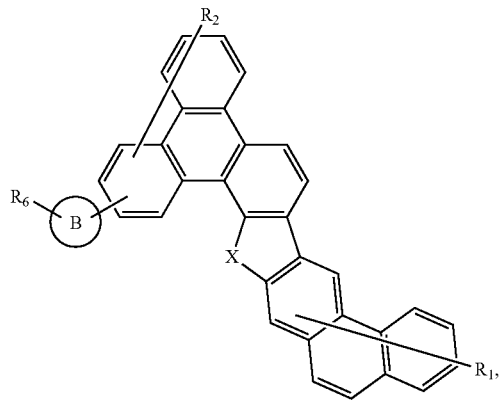
formula (4-12)
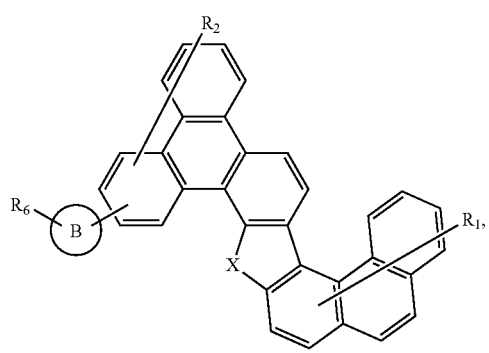
formula (4-13)

-continued
formula (4-14)
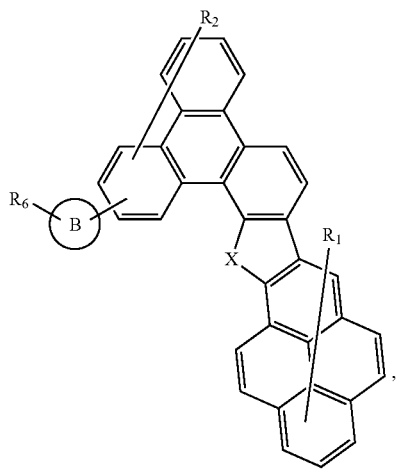
formula (4-15)
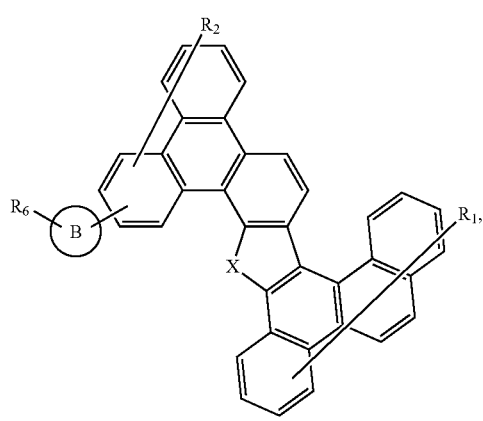
formula (4-16)
formula (4-17)
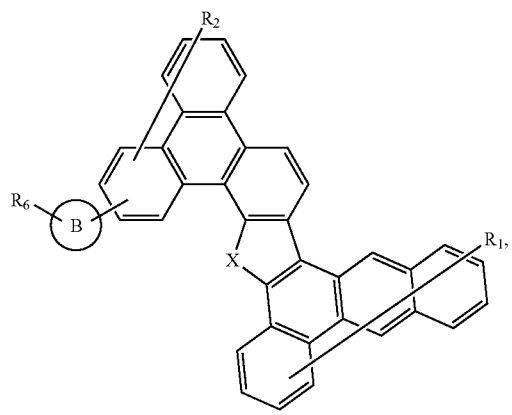
formula (4-18)
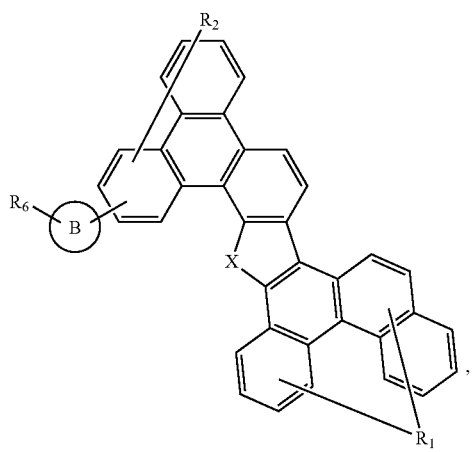
formula (4-19)
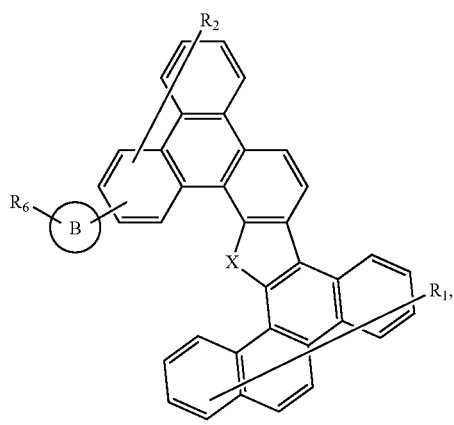

-continued
formula (4-20)
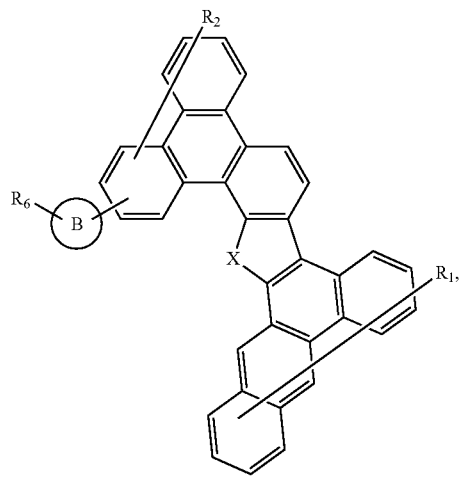
formula (4-21)
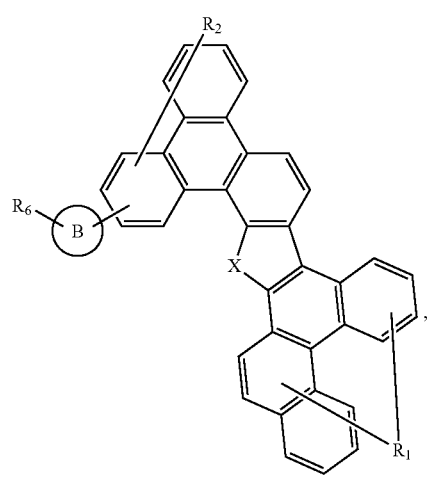
formula (4-22)
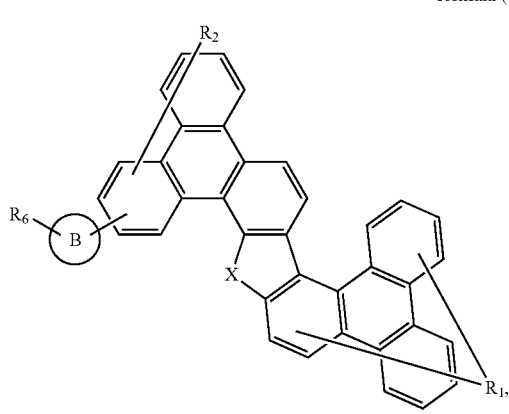
formula (4-23)
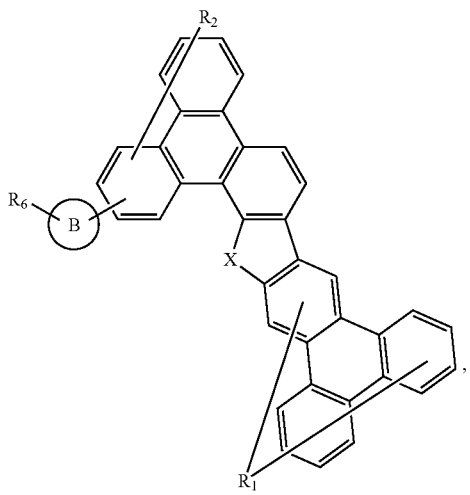
formula (4-24)
formula (4-25)
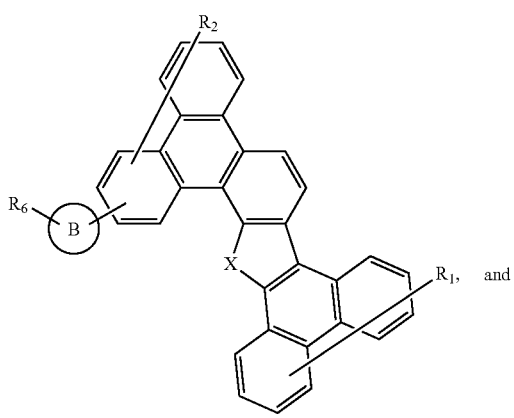 and formula (4-26)
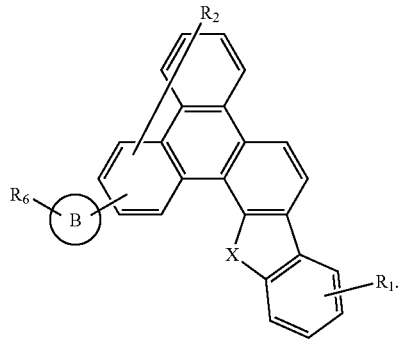
formula (5-1)
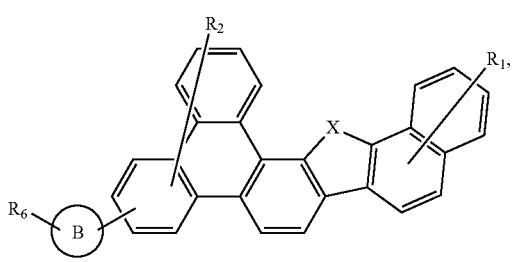
formula (5-2)
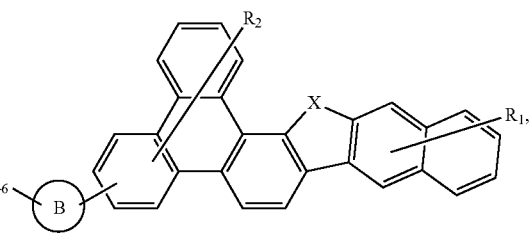
formula (5-3)
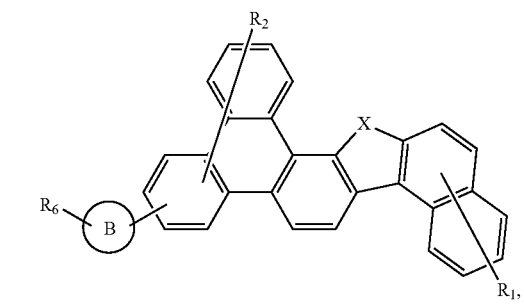
formula (5-4)
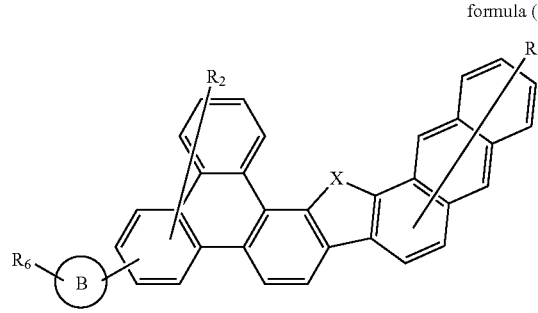
formula (5-5)
formula (5-6)
formula (5-7)
formula (5-8)
formula (5-9)
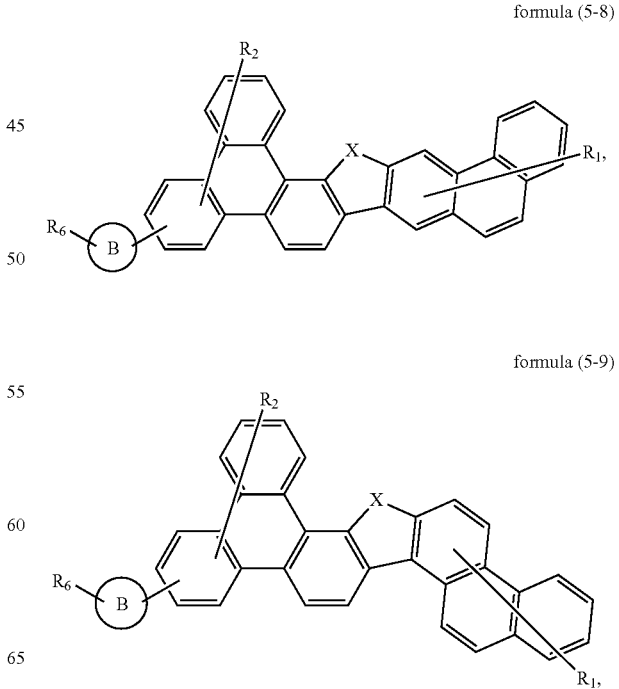

formula (5-10)
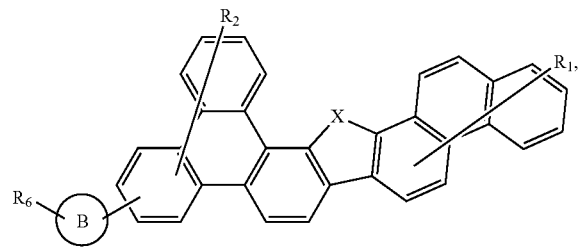
formula (5-11)
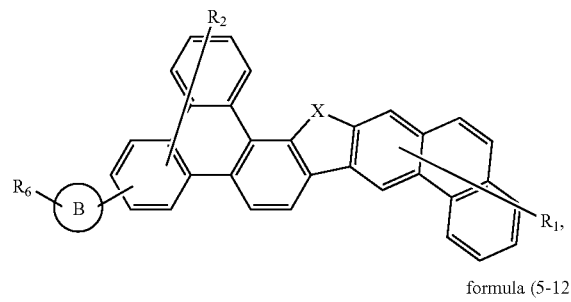
formula (5-12)
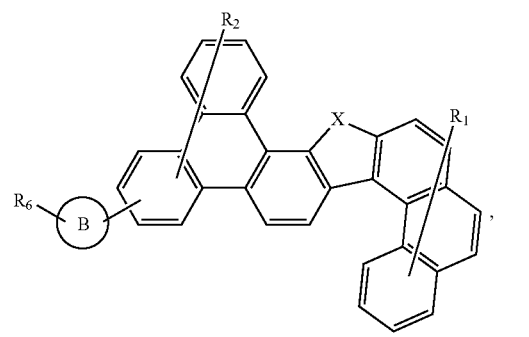
formula (5-13)
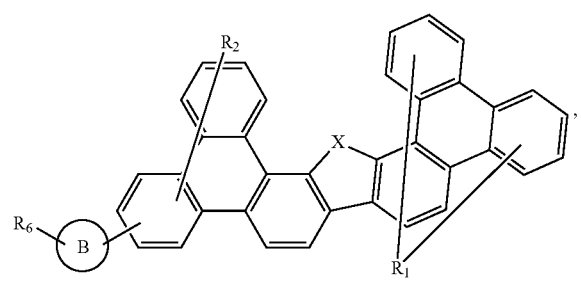
formula (5-14)
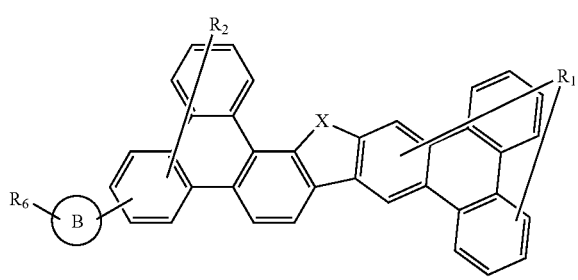
formula (5-15)
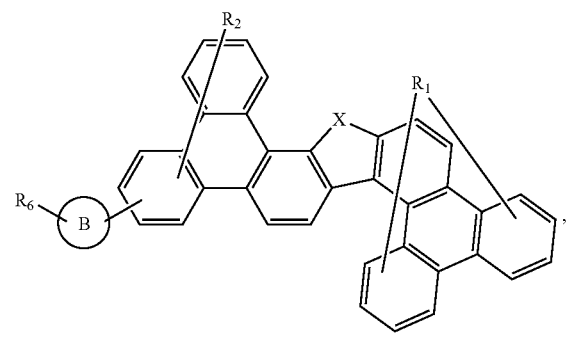
formula (5-16)
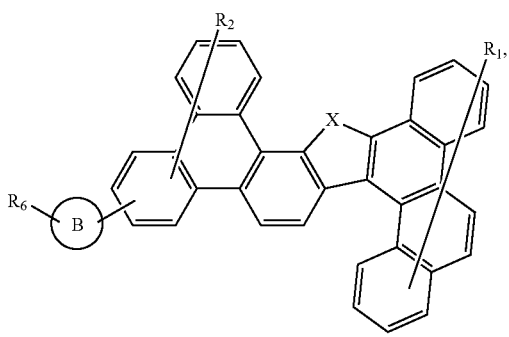
formula (5-17)
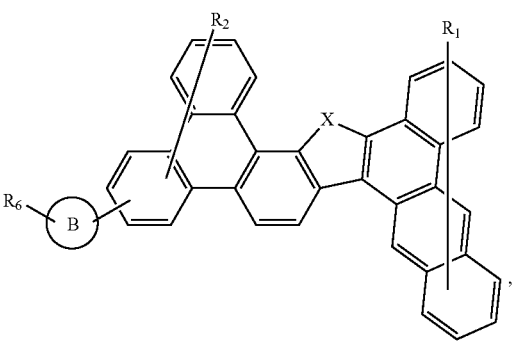
formula (5-18)
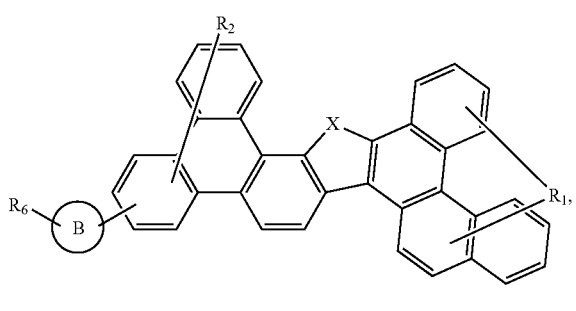

formula (5-19)
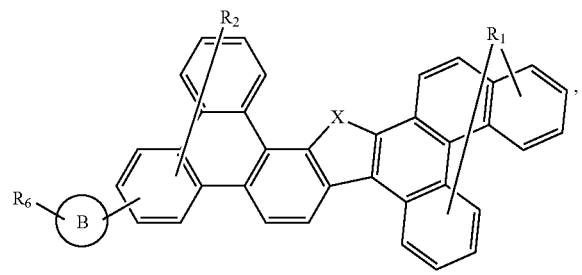
formula (5-20)
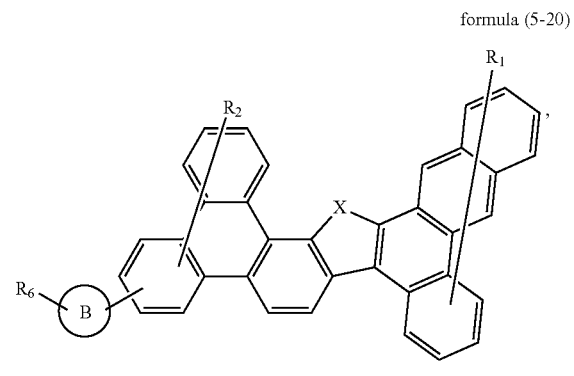
formula (5-21)
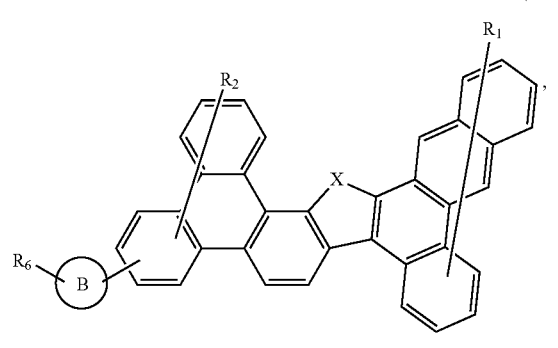
formula (5-22)
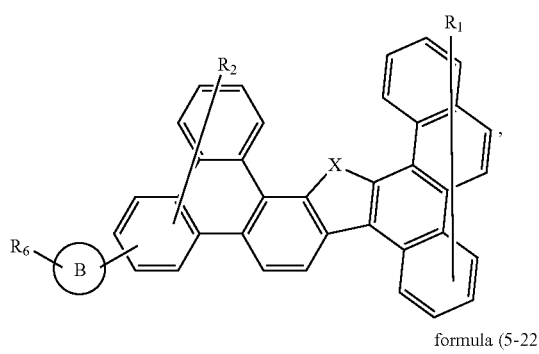
and
formula (5-23)
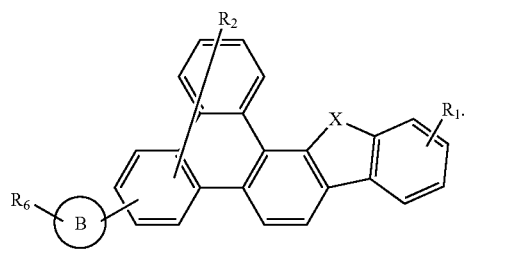
formula (7-1)
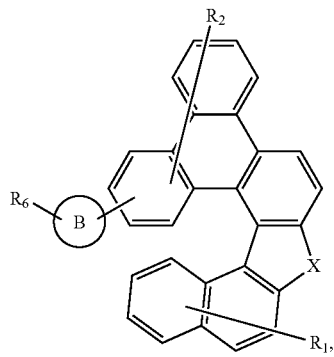
formula (7-2)
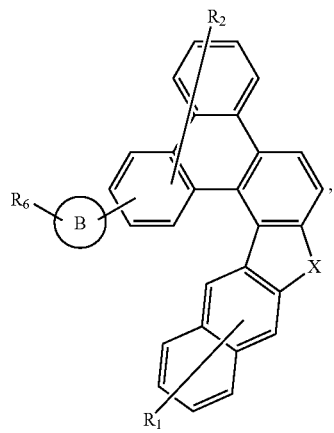
formula (7-3)
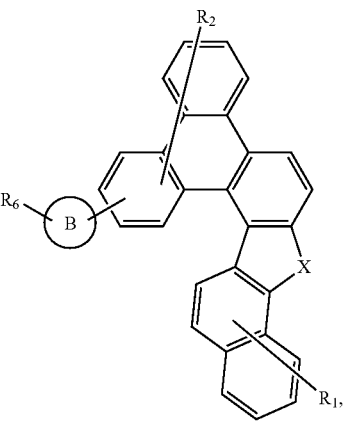
formula (7-4)
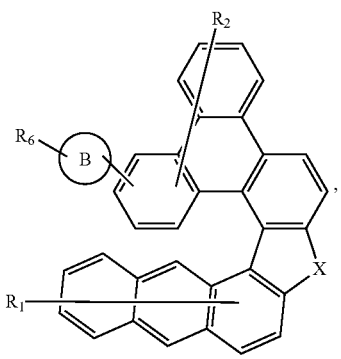

formula (7-5)
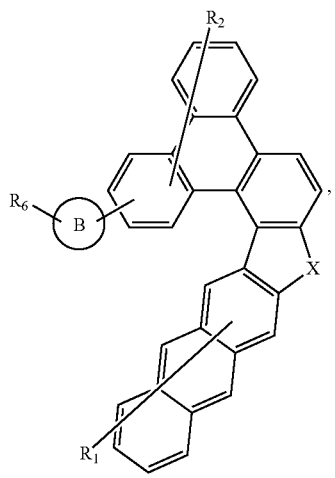
formula (7-6)
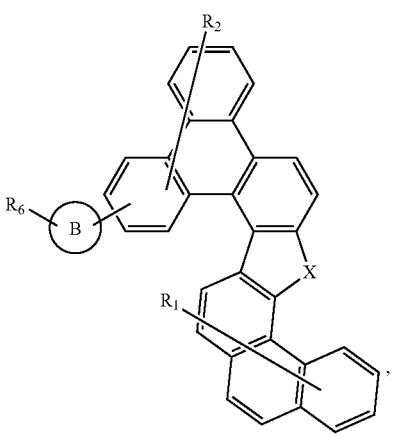
formula (7-7)
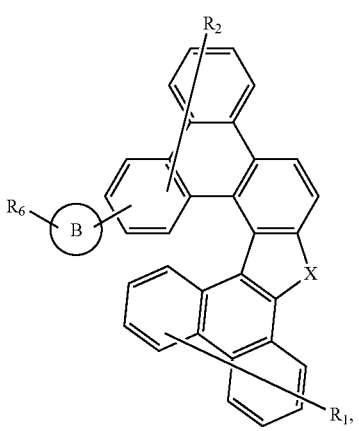
formula (7-8)
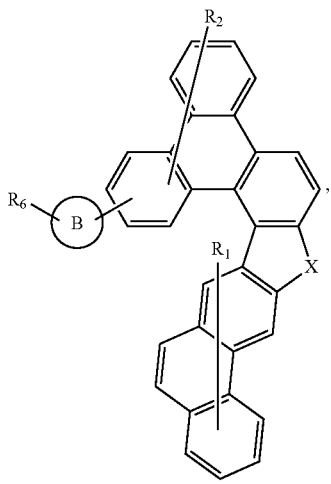
formula (7-9)
formula (7-10)

-continued
formula (7-11)
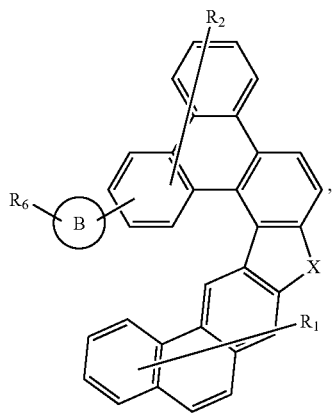
formula (7-12)
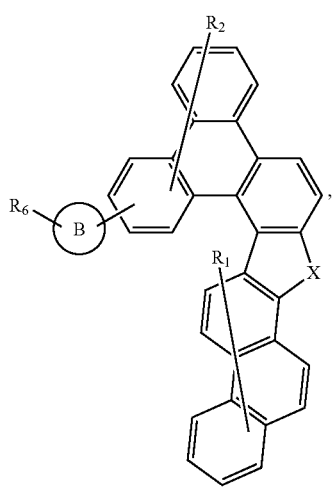
formula (7-13)
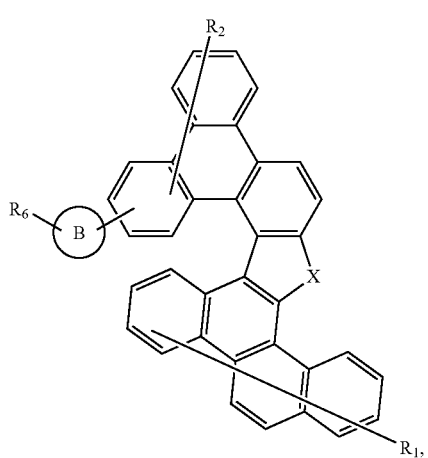
-continued
formula (7-14)
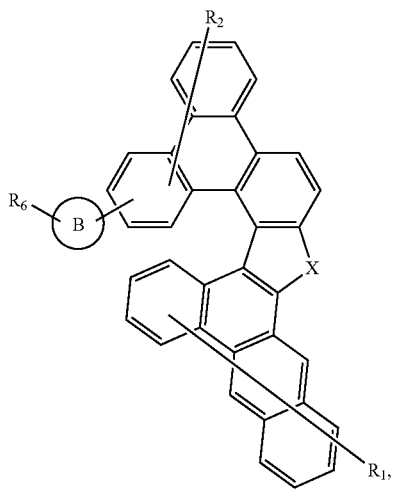
formula (7-15)
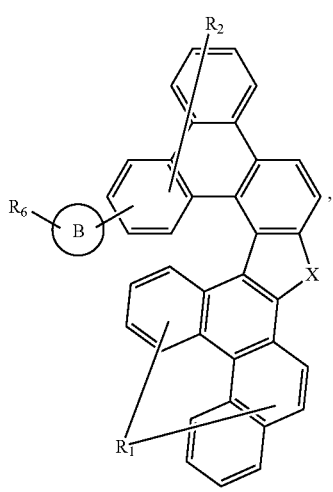
formula (7-16)
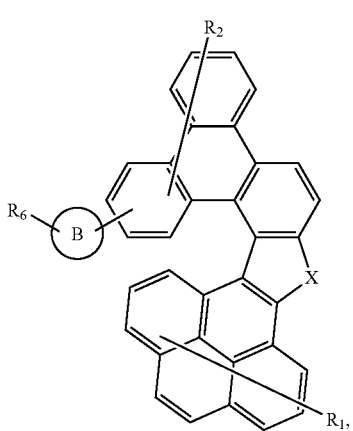

formula (7-17)
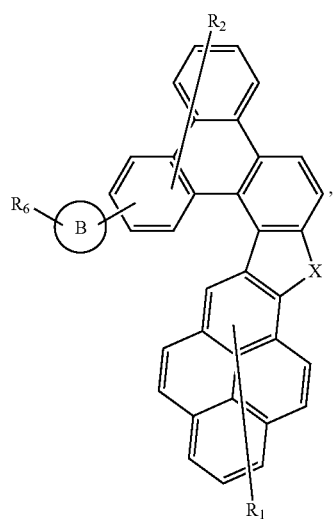
formula (7-18)
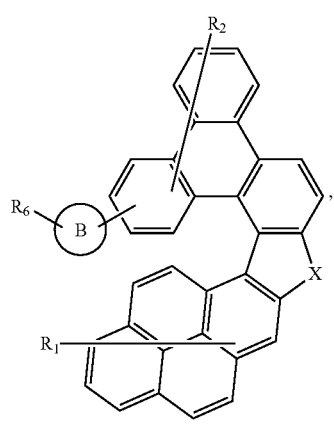
formula (7-19)
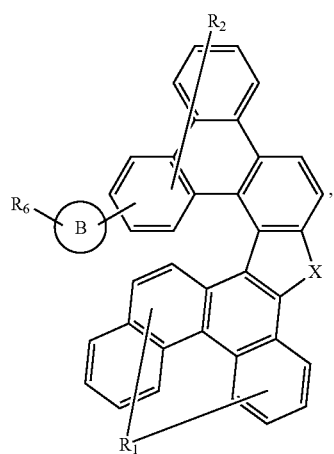
formula (7-20)
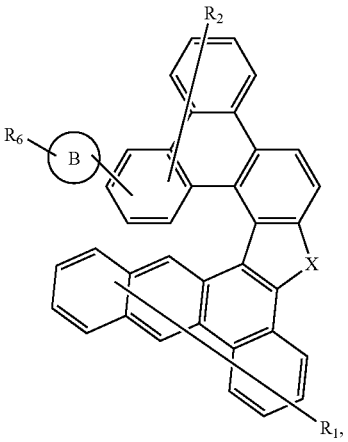
formula (7-21)
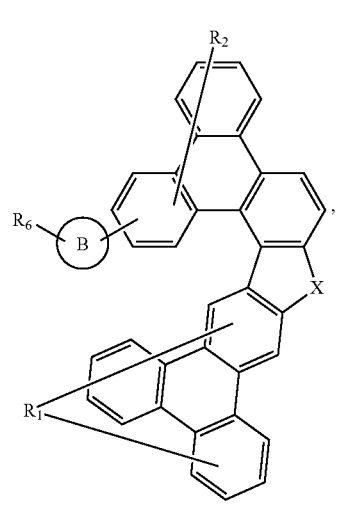
formula (7-22)
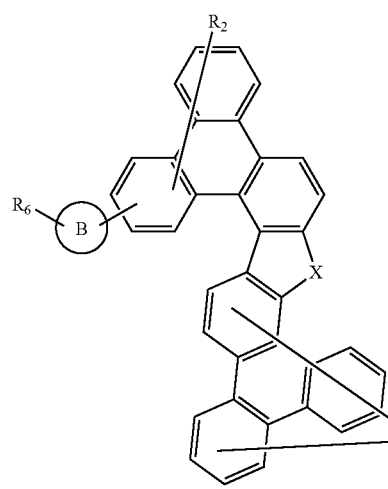, and formula (7-23)

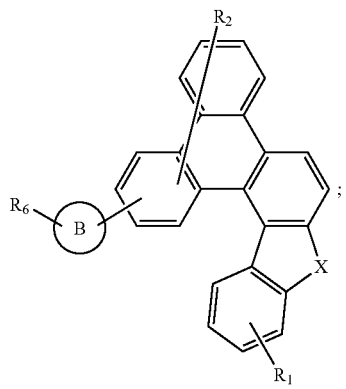

wherein X represents a divalent bridge selected from the group consisting of O, S, Se, $NR_3$ and $SiR_4R_5$;

wherein $R_6$ represents no substitution, mono substitution or di substitutions, and each of the substitutions is selected from the group consisting of halogen, trifluoromethyl, cyano, nitro, silyl, and combinations thereof;

wherein $R_2$ represents mono to the maximum allowable substitution, or no substitution;

wherein ring A represents a monocyclic aromatic hydrocarbyl or a polycyclic aromatic hydrocarbyl having 2, 3 or 4 fused rings;

wherein ring B is one of the following:

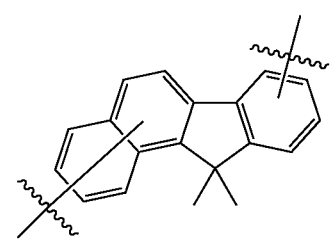

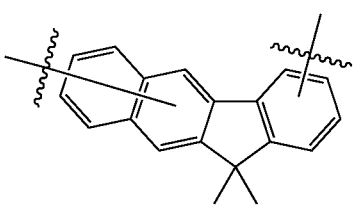

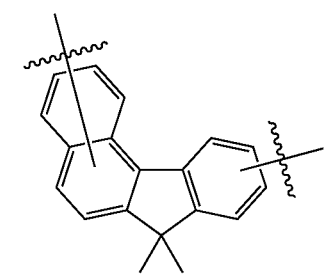

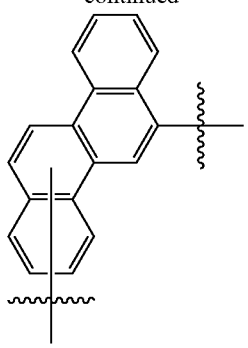

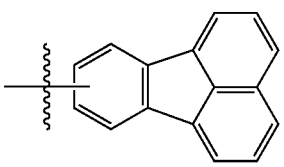

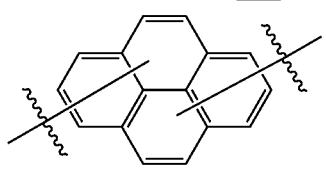

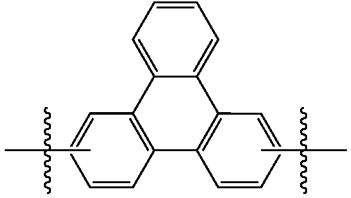

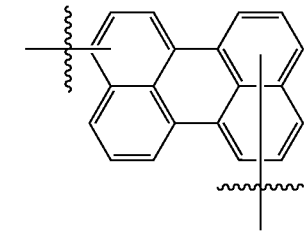

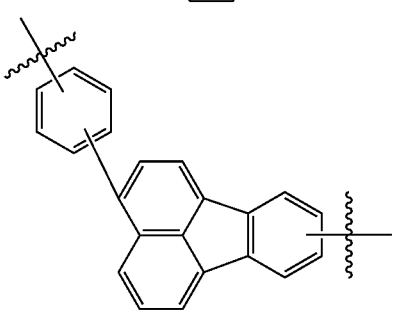

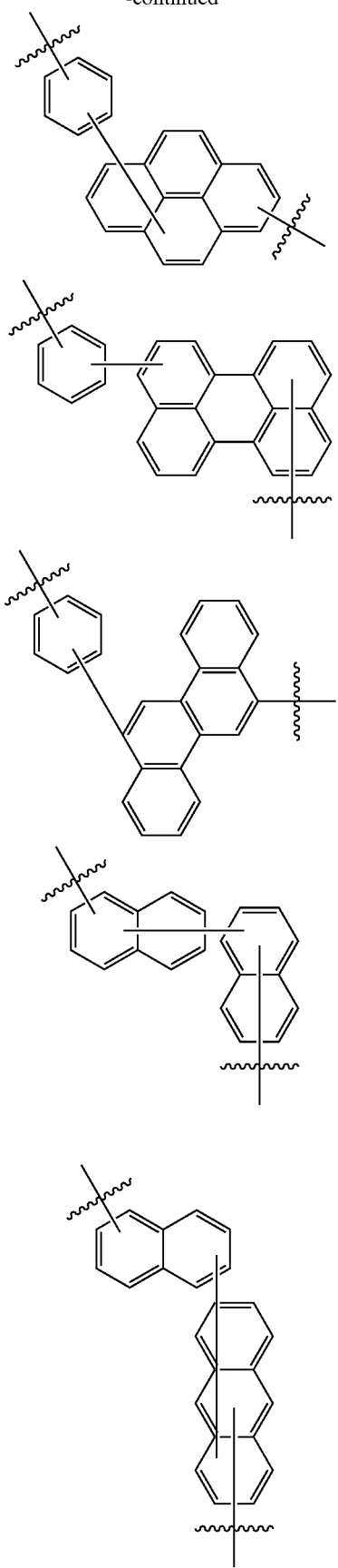
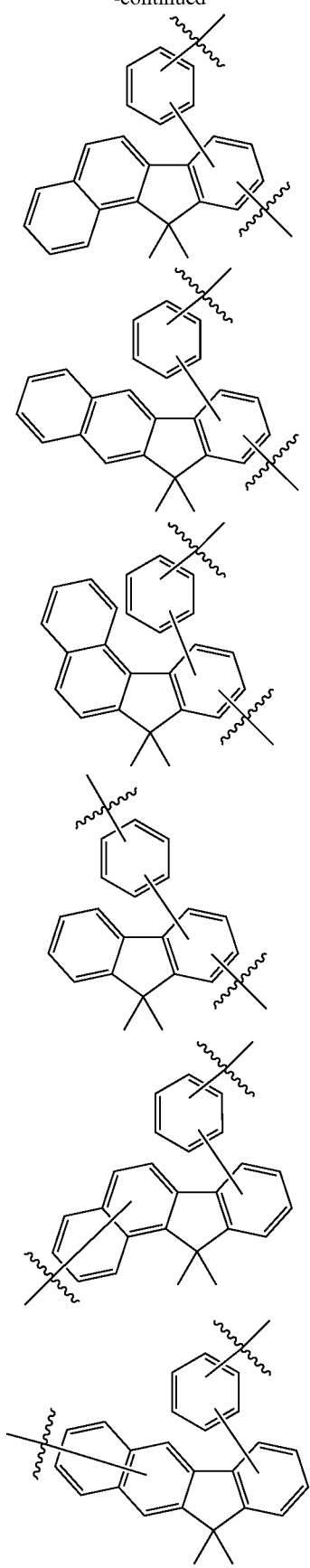

315
-continued
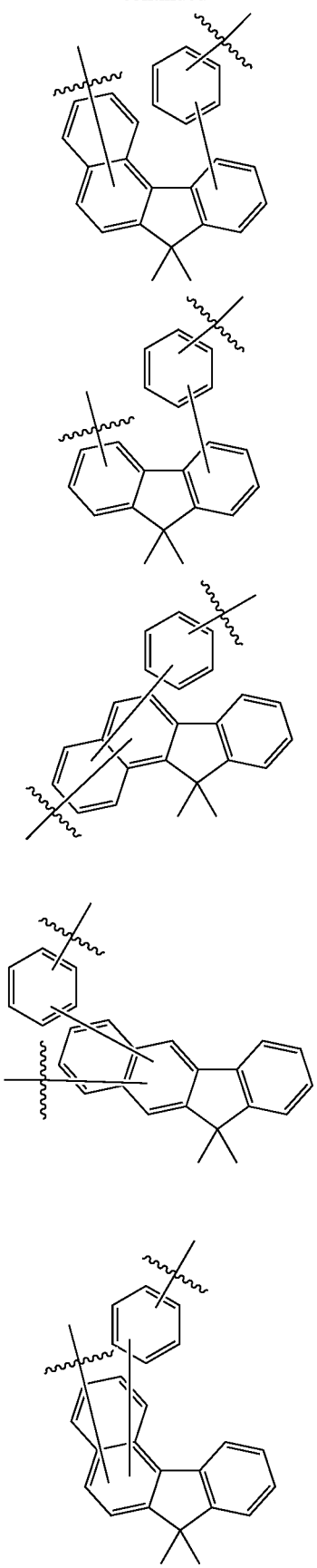
316
-continued
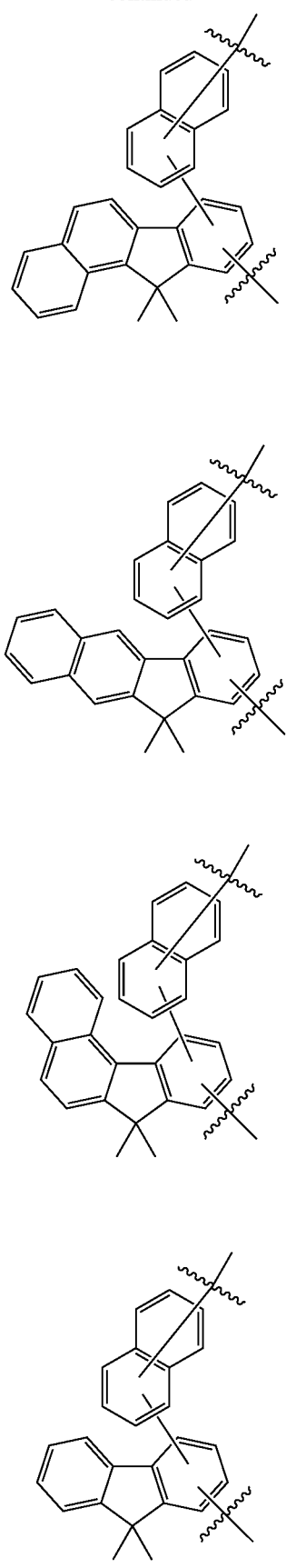

317
-continued
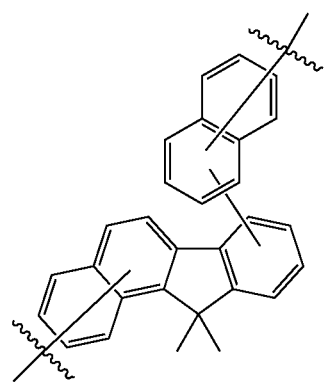
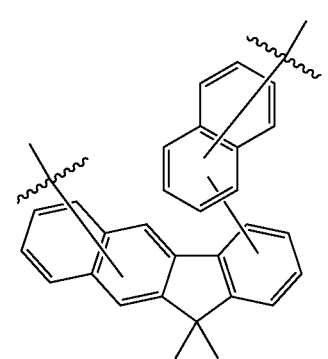
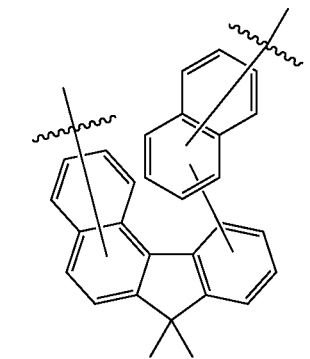
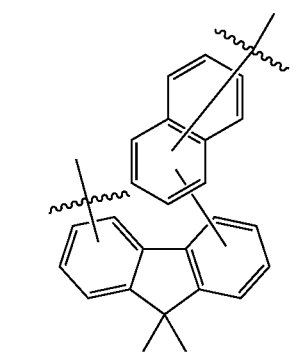
318
-continued
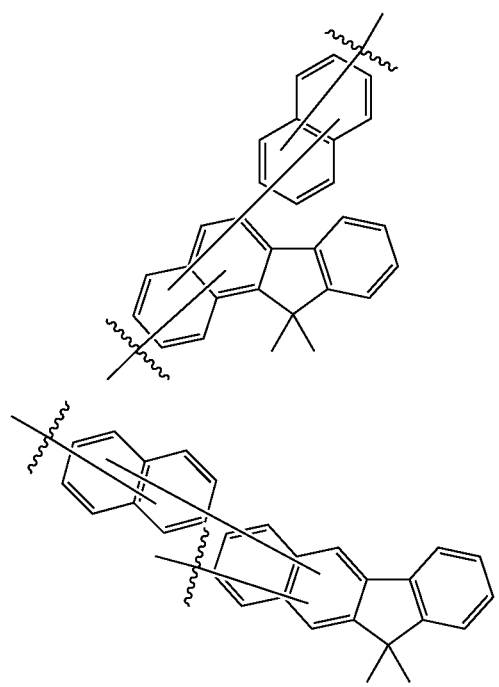
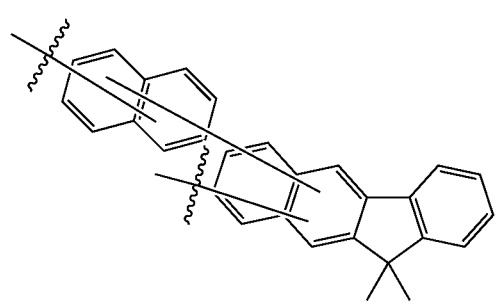
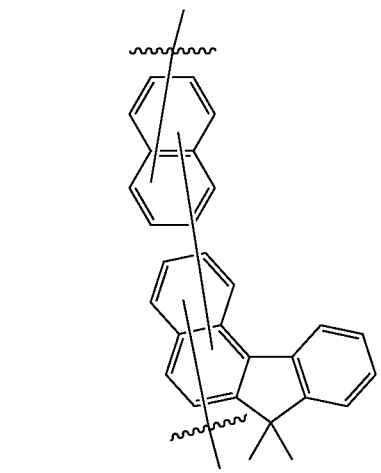
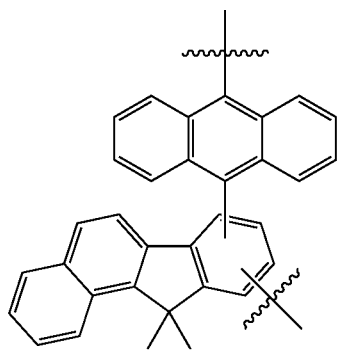

319
-continued
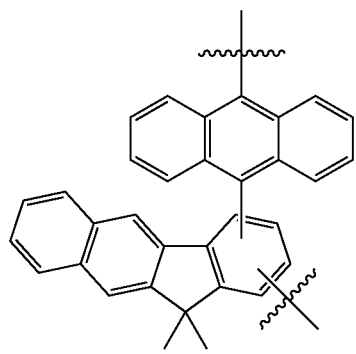
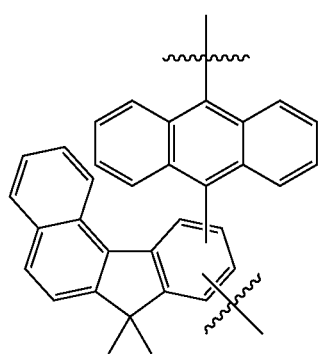
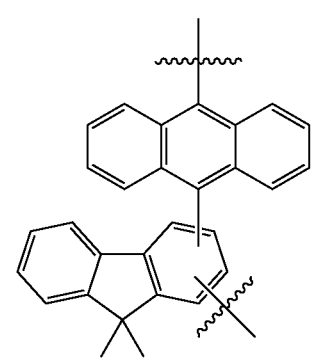
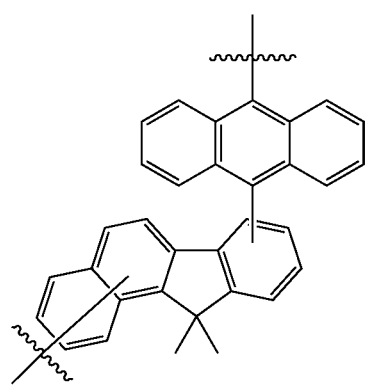
320
-continued
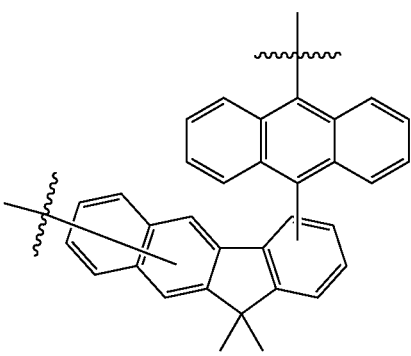
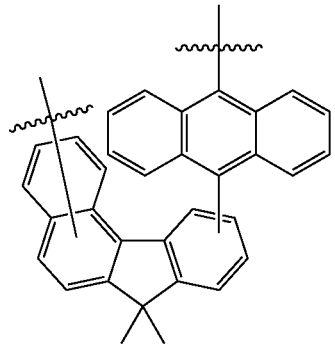
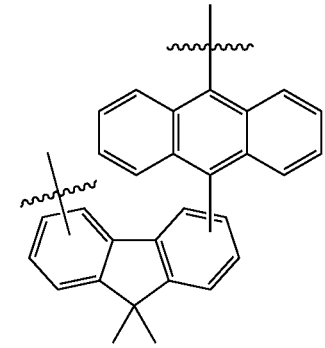
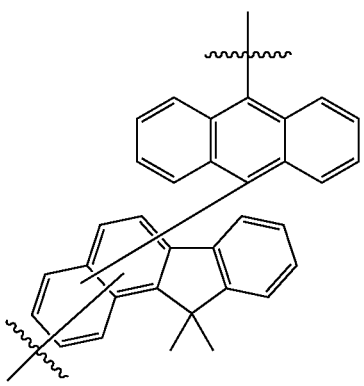

321
-continued
322
-continued
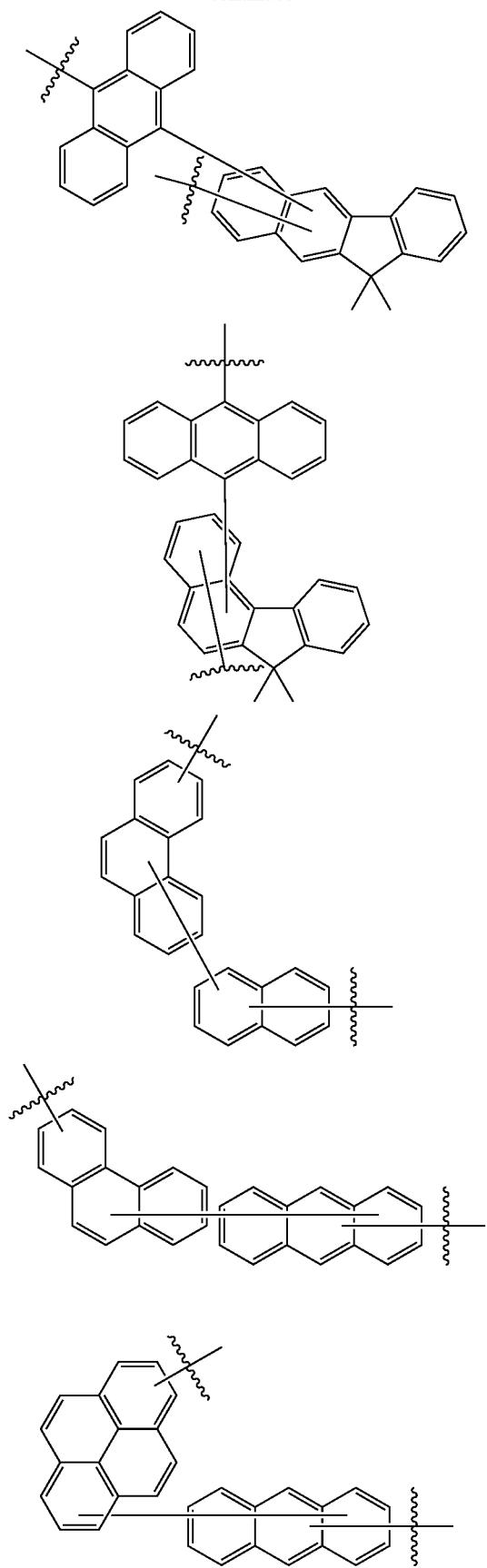

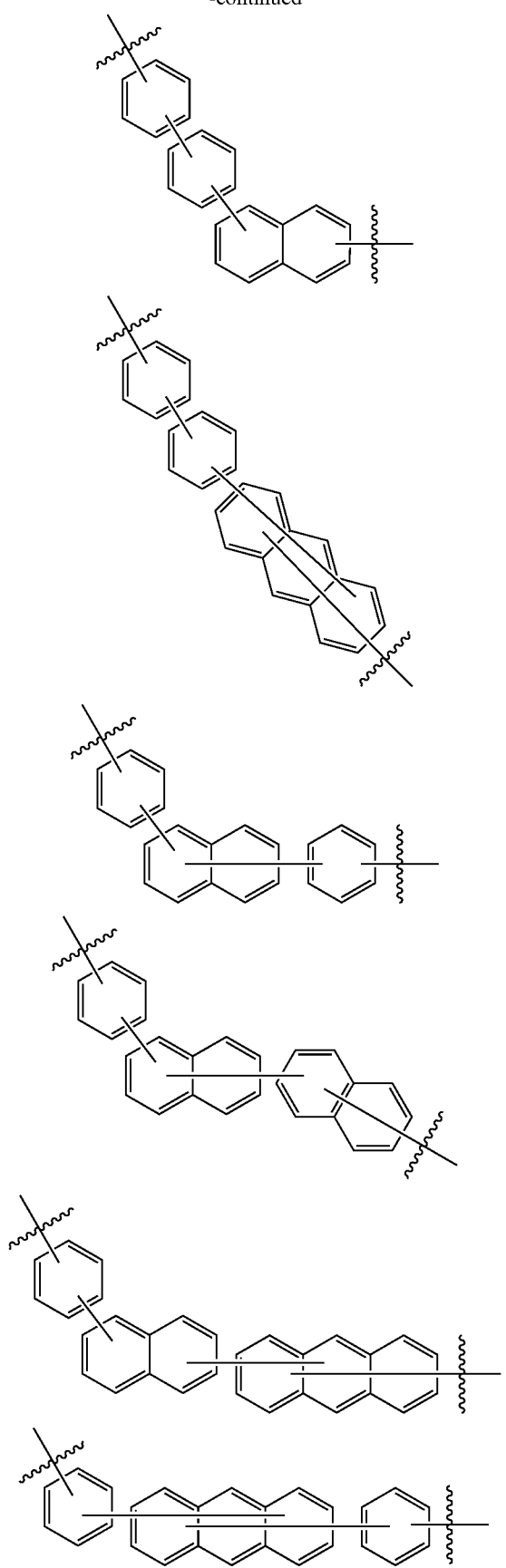
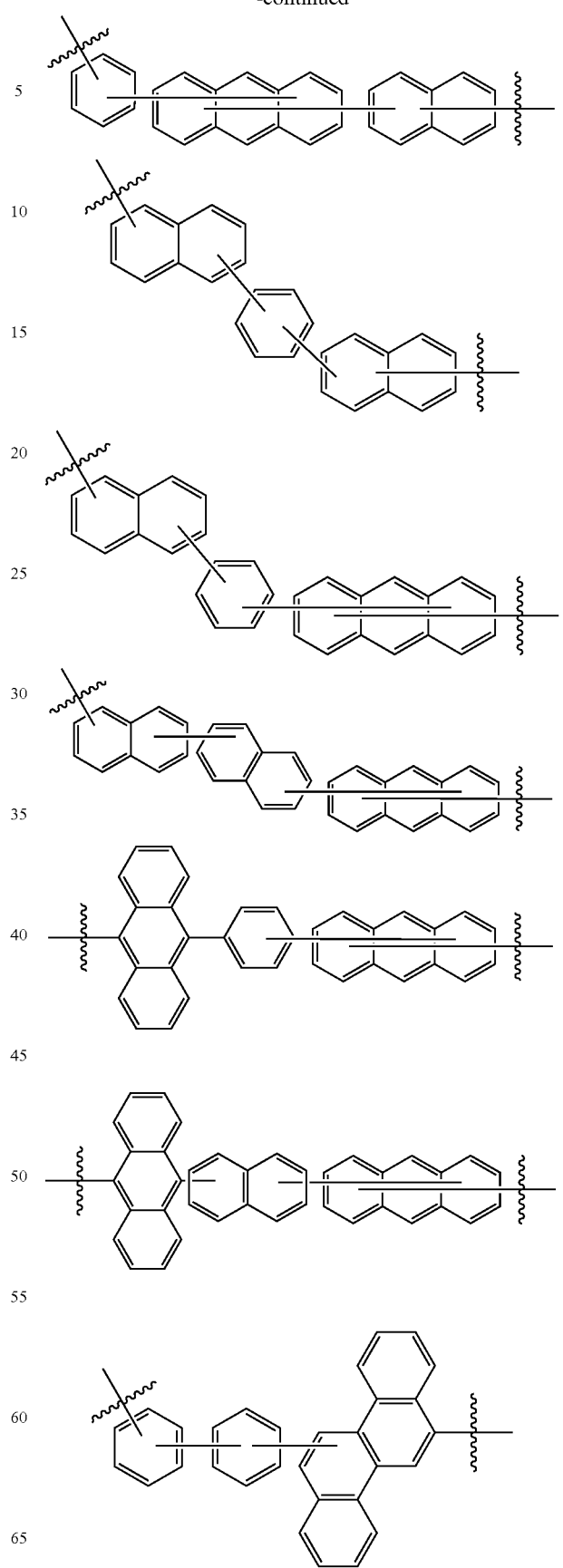

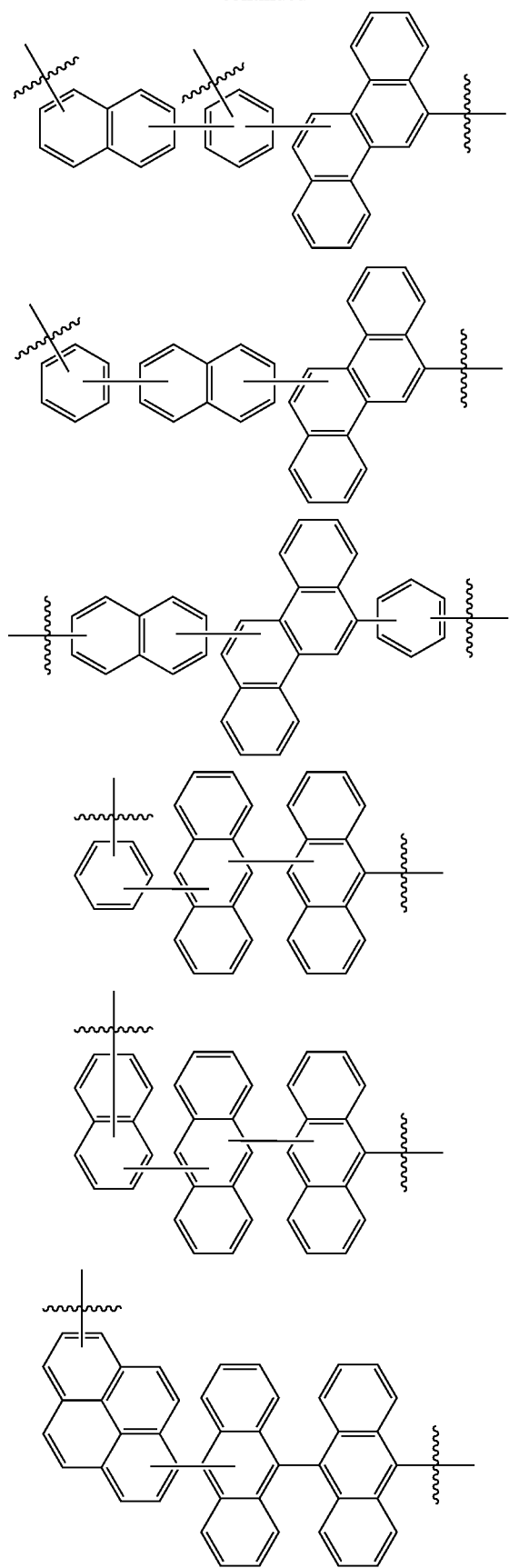
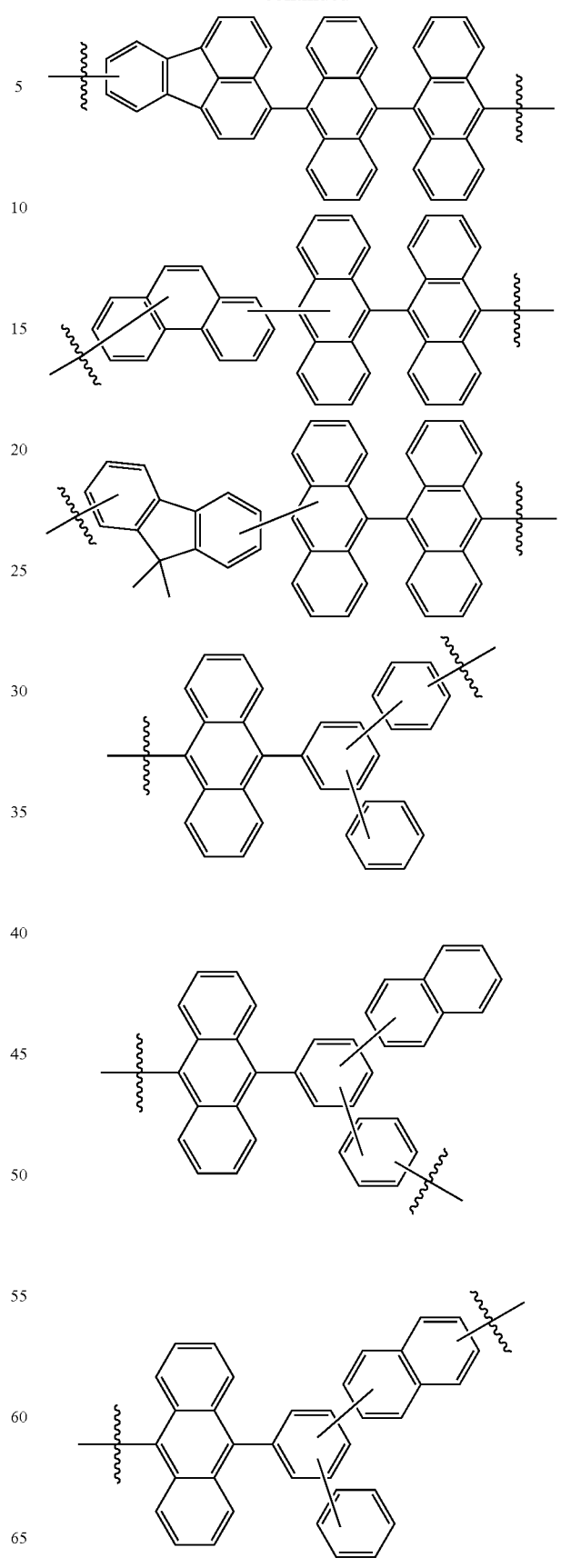

327
-continued
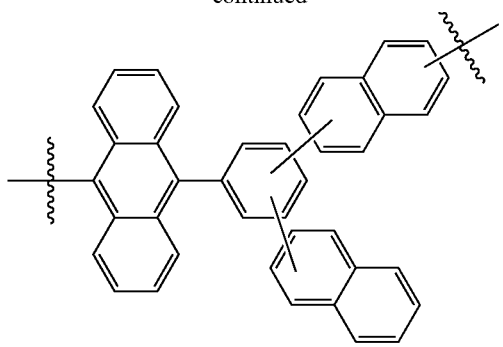
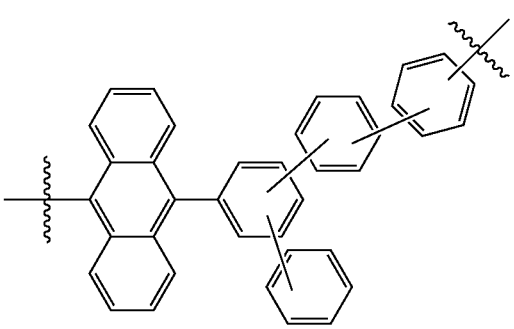
328
-continued
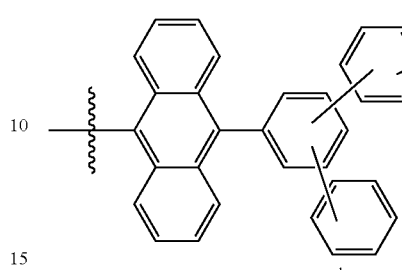
and
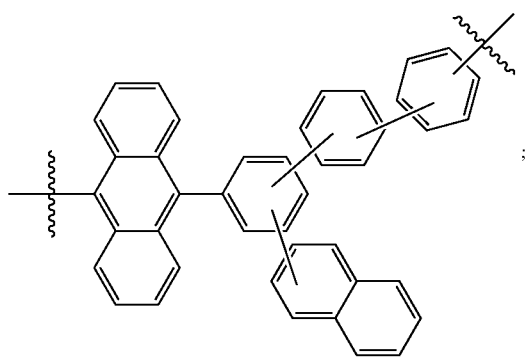
and
wherein each of $R_1$ to $R_5$ is hydrogen or a substituent selected from the group consisting of alkyl, aryl, aralkyl, heteroaryl, and combinations thereof.
2. An organic compound selected from the group consisting of:
Compound 1
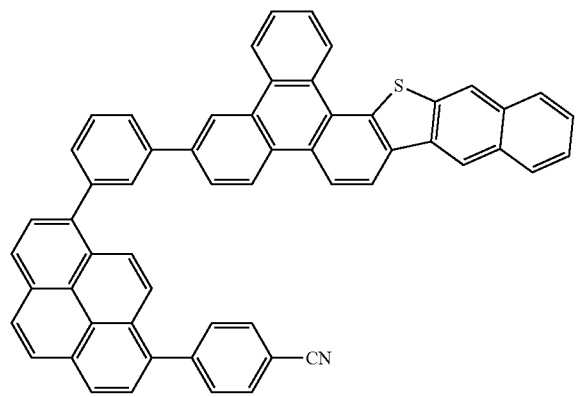
Compound 2
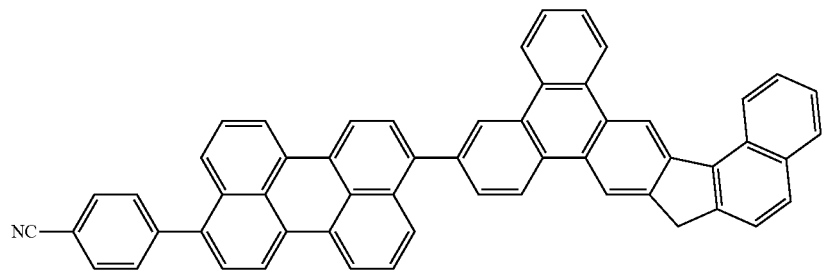

-continued
Compound 3
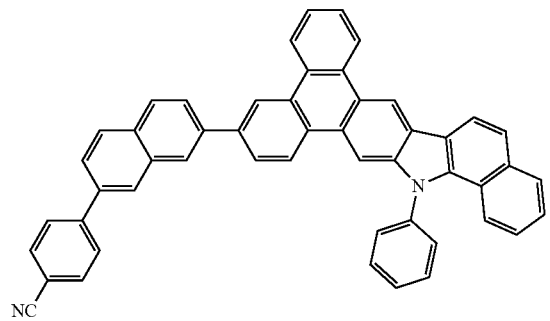
Compound 4
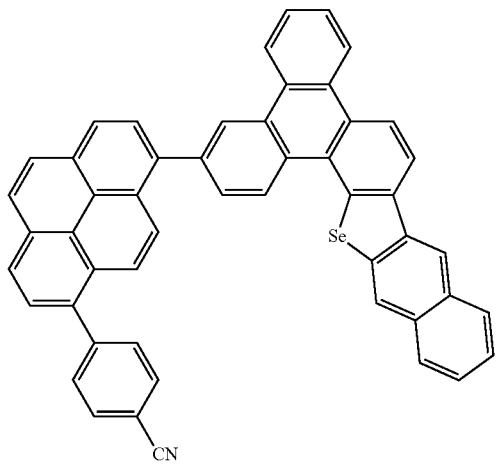
Compound 5
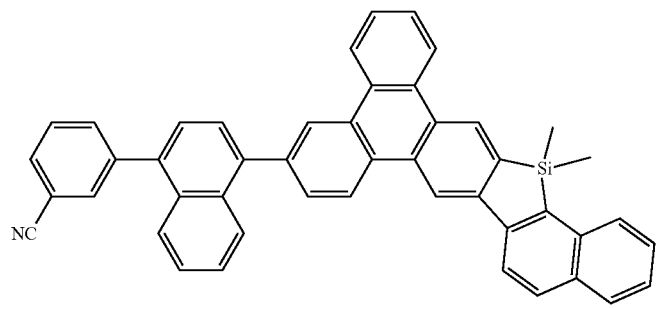
Compound 6
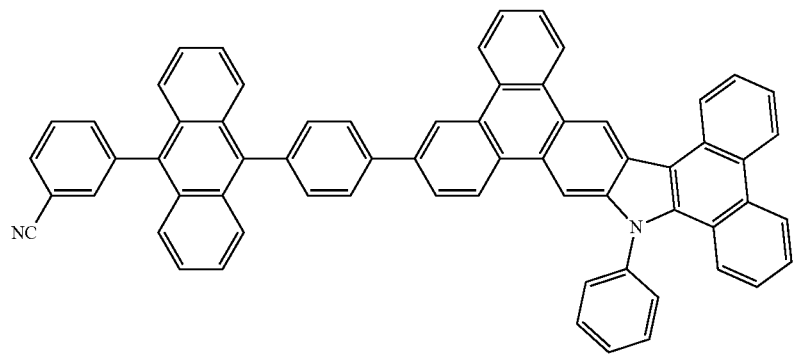
Compound 7
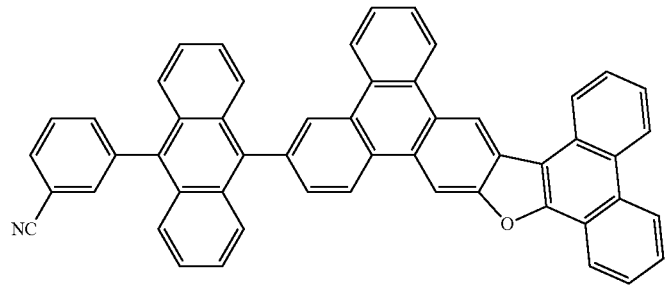

-continued
Compound 8
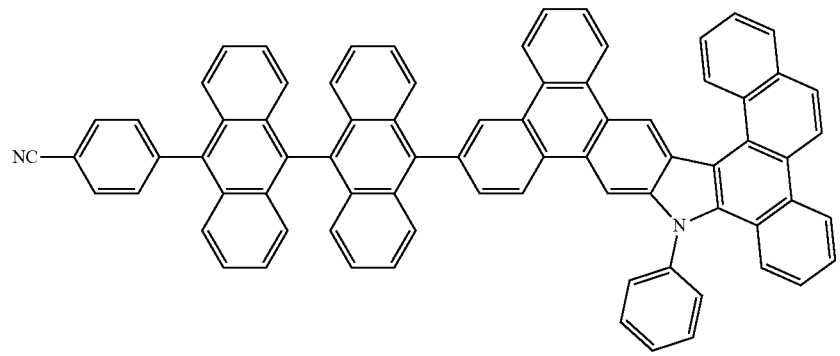
Compound 9
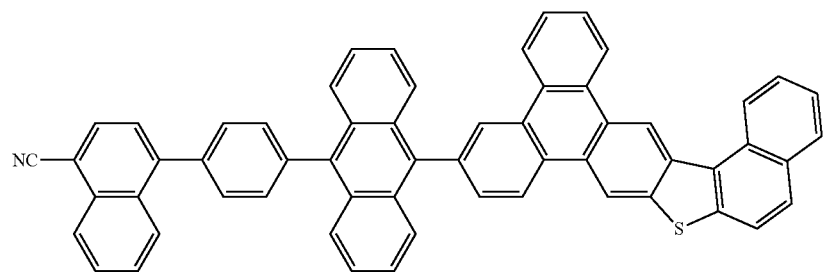
Compound 10
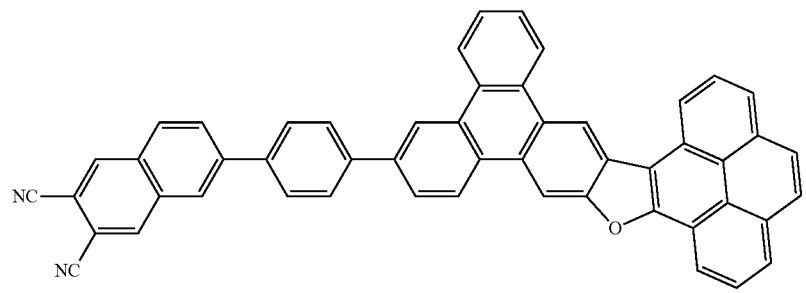
Compound 11
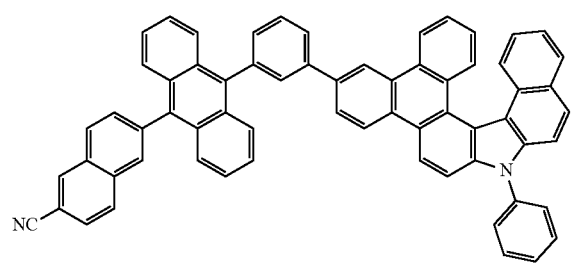
Compound 12
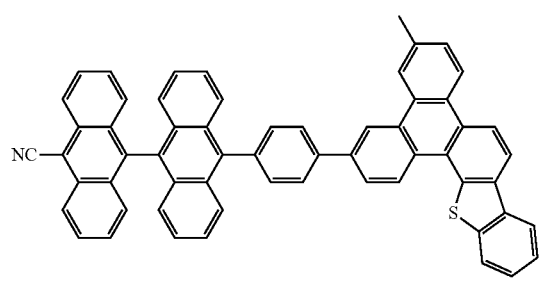
Compound 13
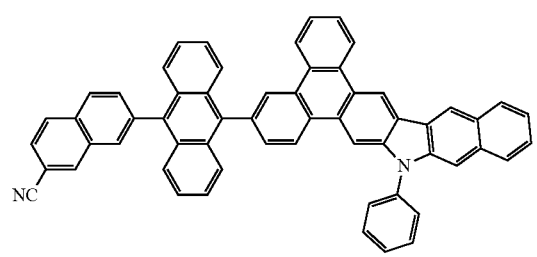
Compound 14
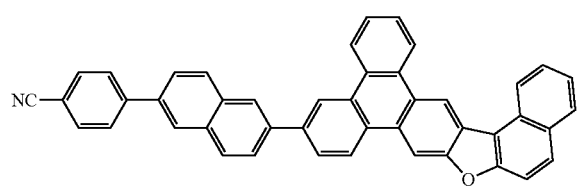

Compound 15
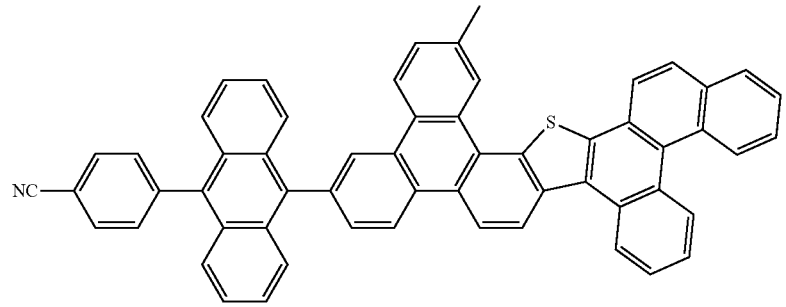
Compound 16
Compound 17
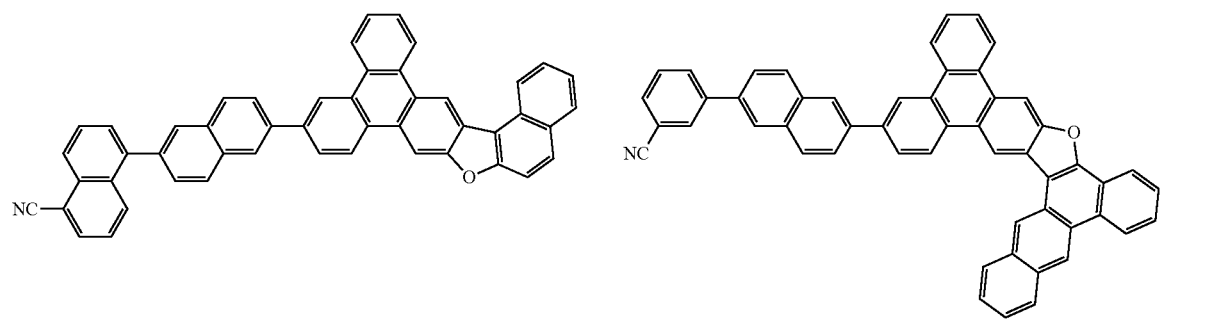
Compound 18
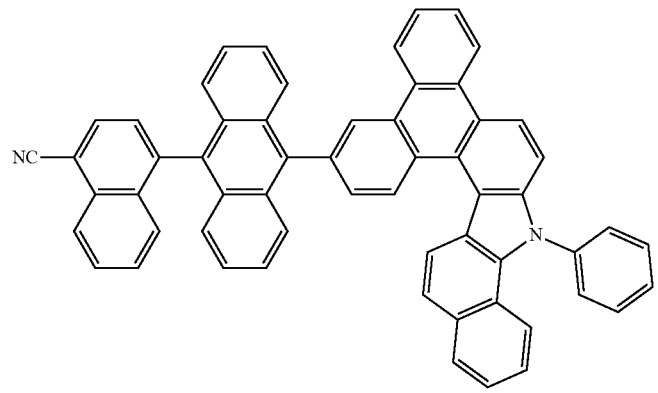
Compound 19
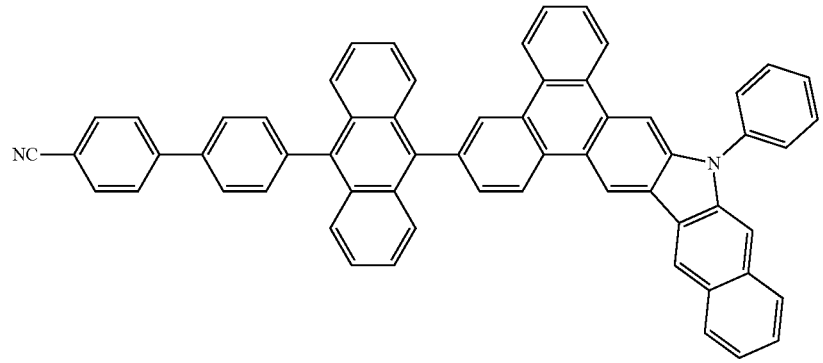

-continued
Compound 20
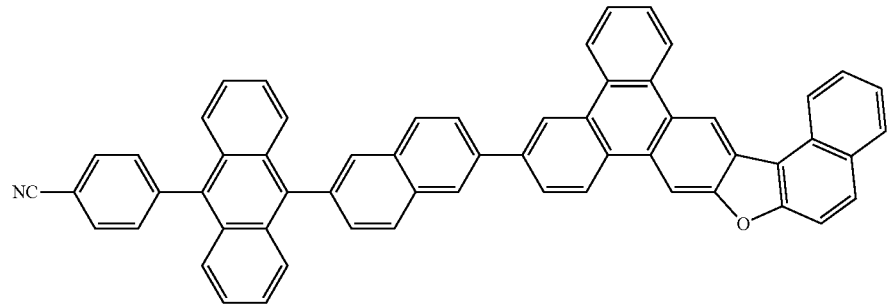
Compound 21
Compound 22
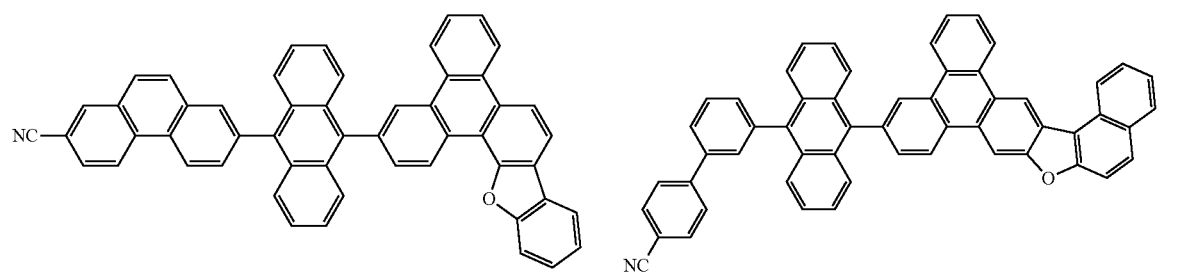
Compound 23
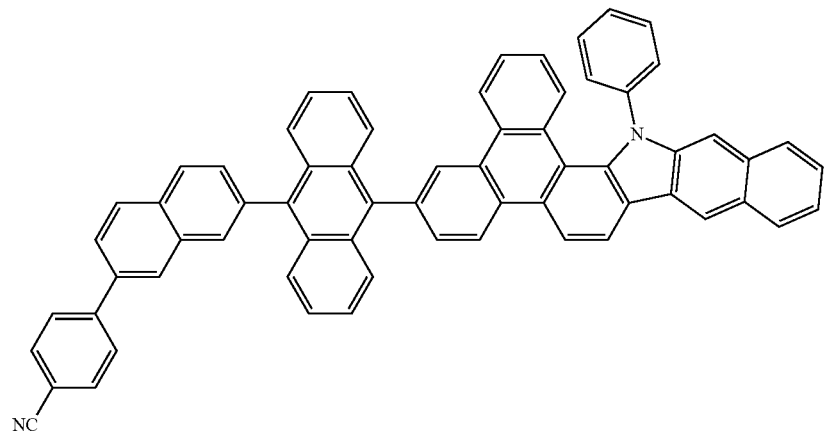
Compound 24
Compound 25
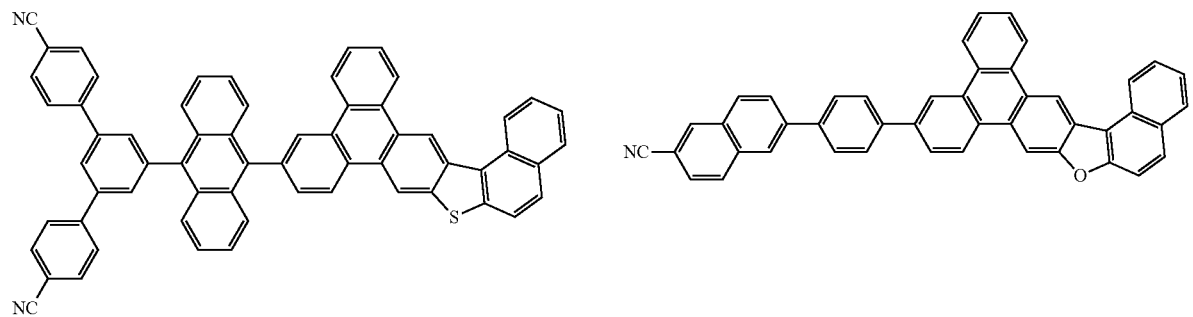

-continued
Compound 26
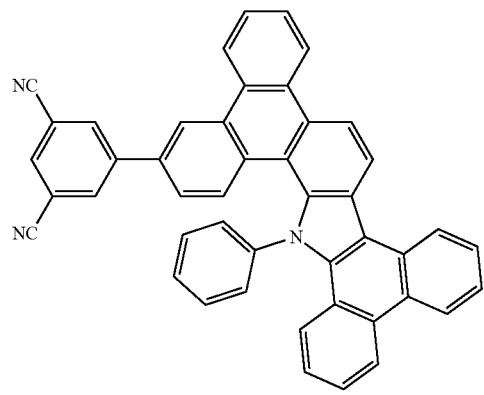
Compound 27
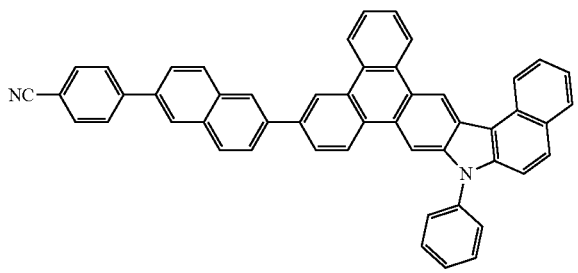
Compound 28
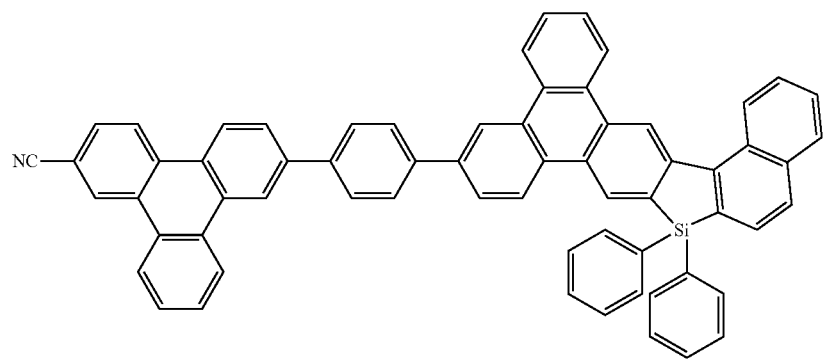
Compound 29
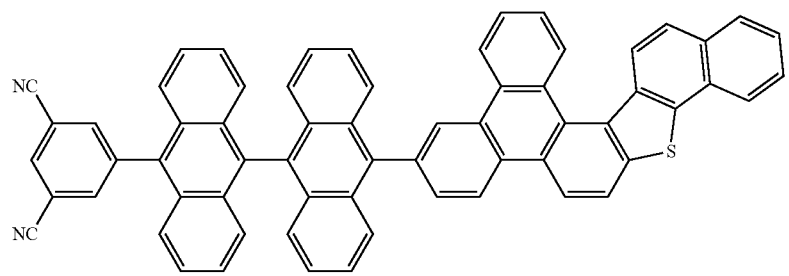
Compound 30
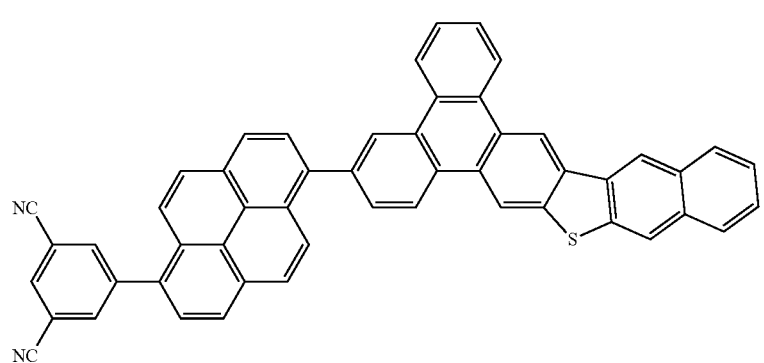

Compound 31
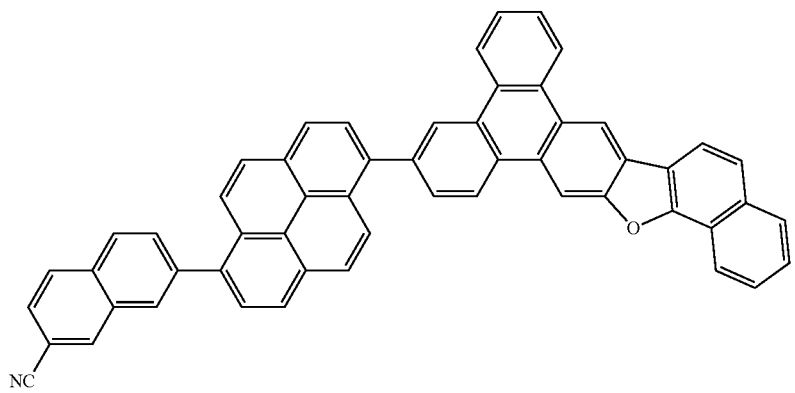
Compound 32
Compound 33
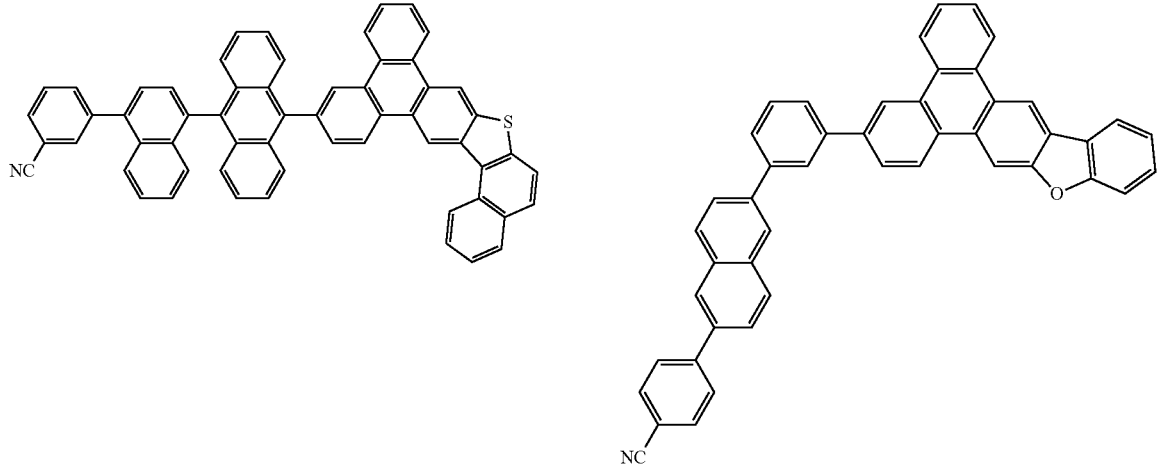
Compound 34
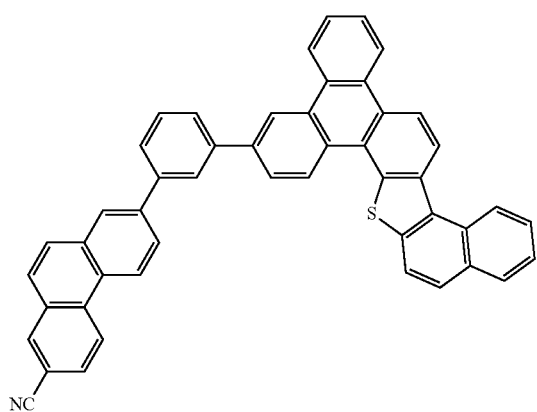
Compound 35
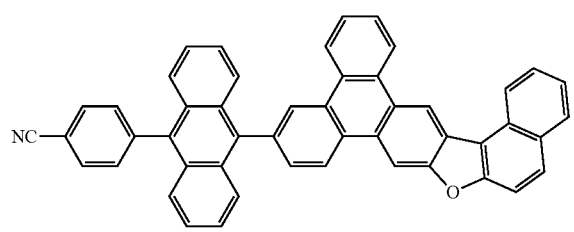
Compound 36
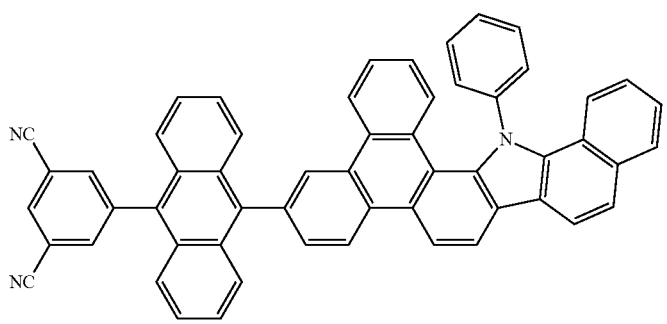

-continued
Compound 37
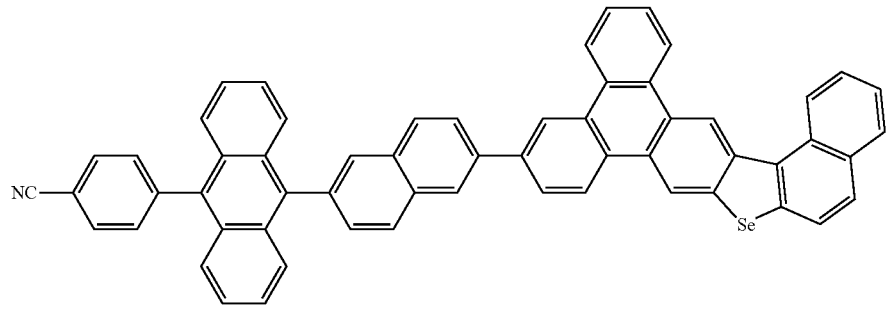
Compound 38
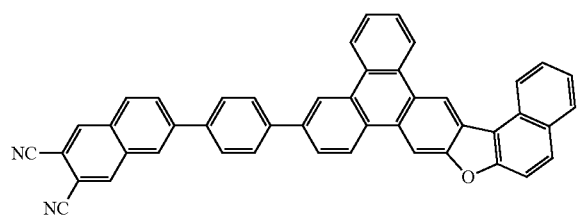
Compound 39
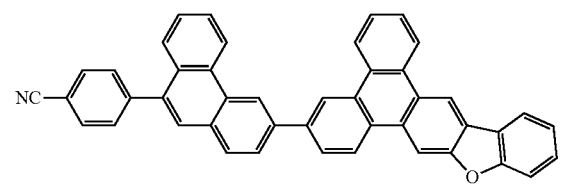
Compound 40
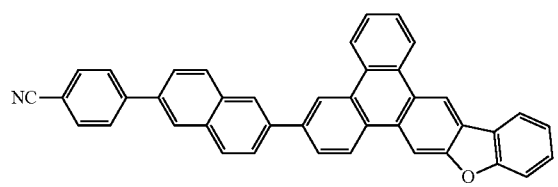
Compound 41
Compound 42
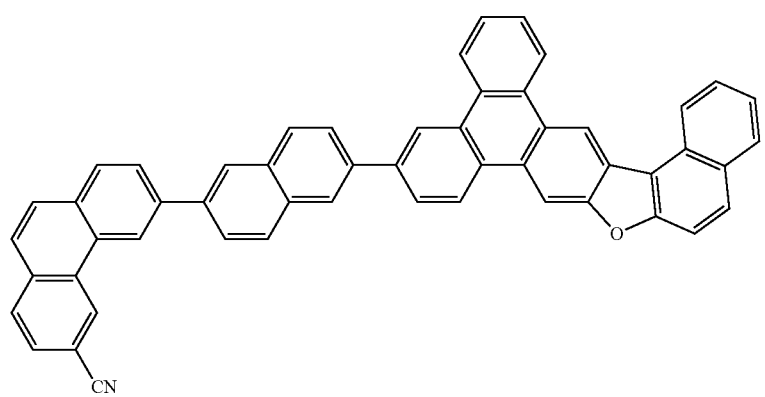
Compound 43
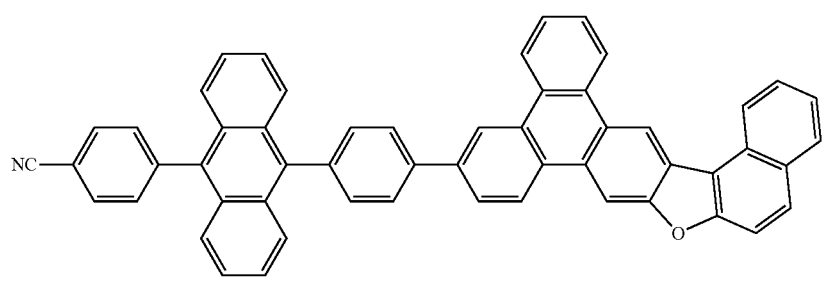

-continued
Compound 44
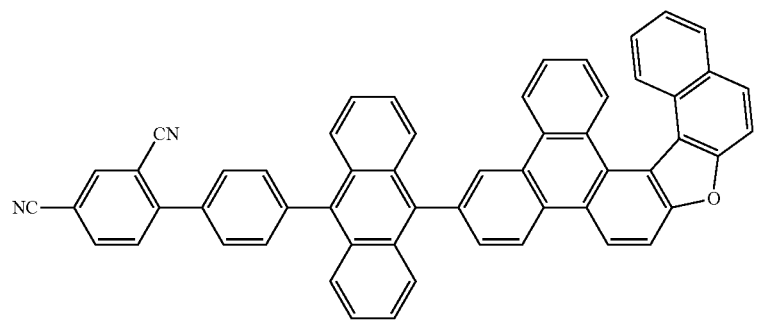
Compound 45
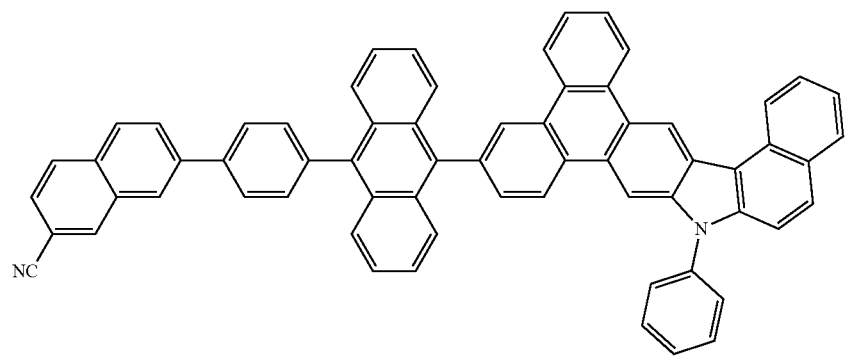
Compound 46
Compound 47
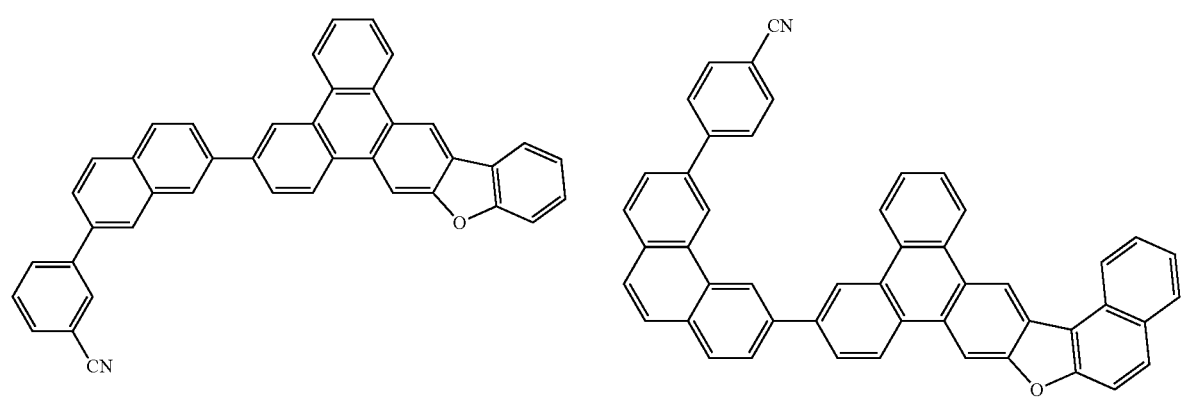
Compound 48
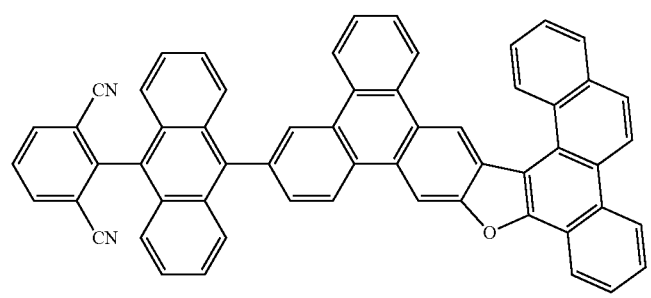

-continued
Compound 49
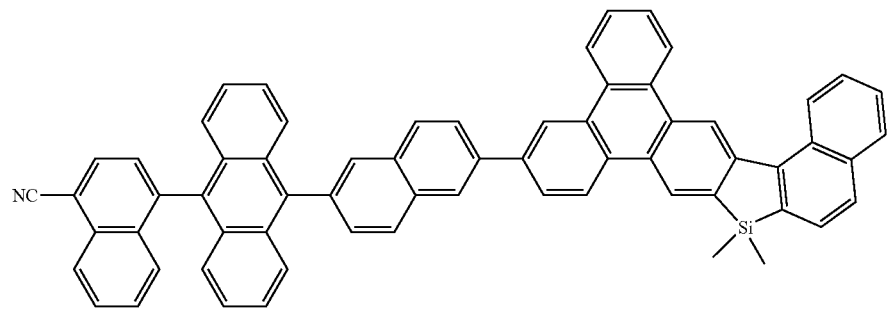
Compound 50
Compound 51
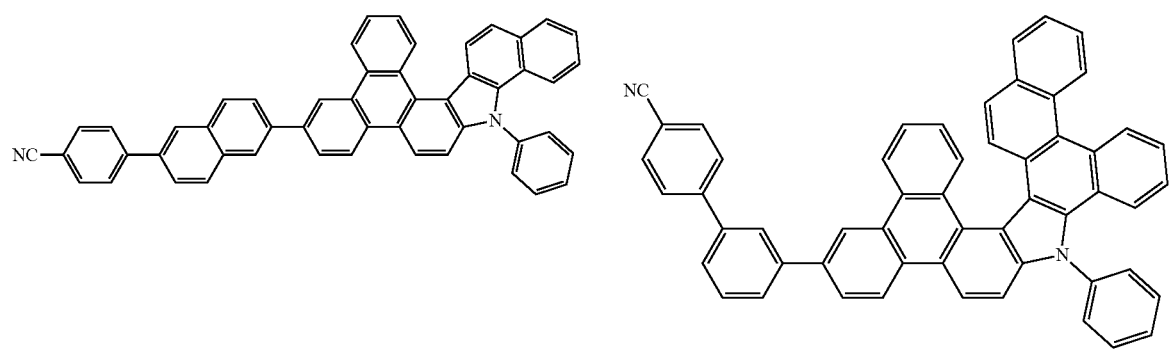
Compound 52
Compound 53
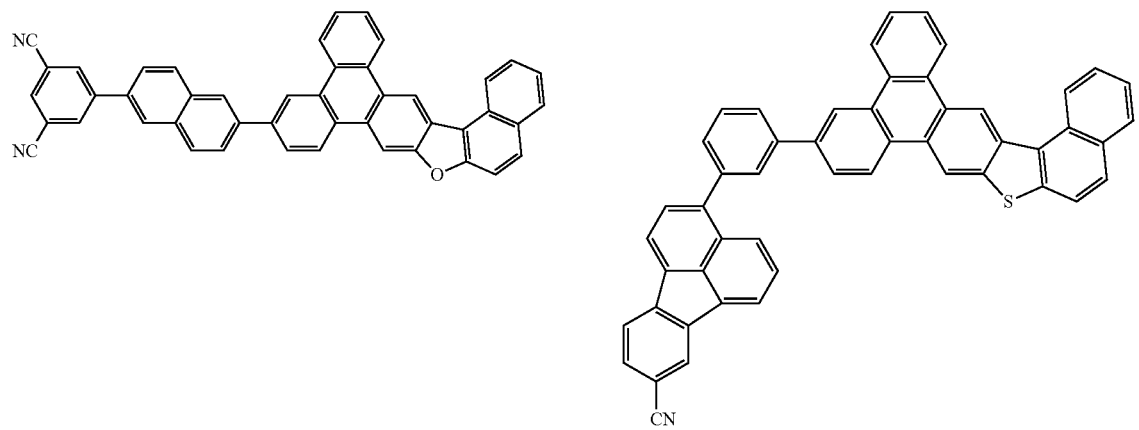
Compound 54
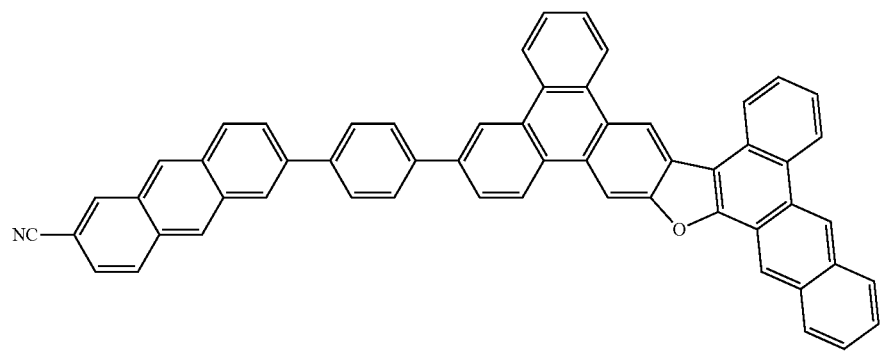

-continued
Compound 55
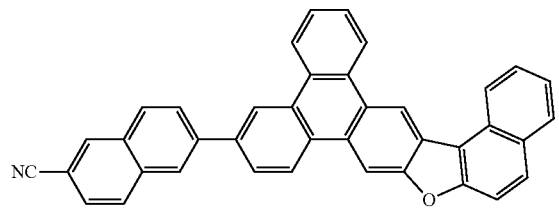
Compound 56
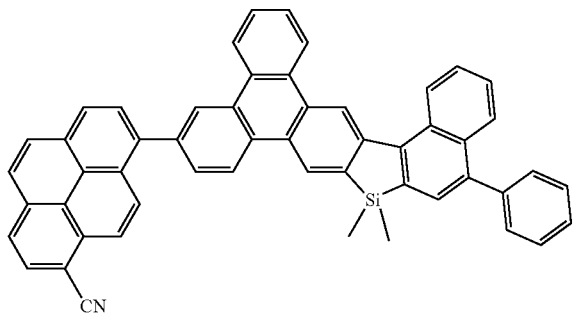
Compound 57
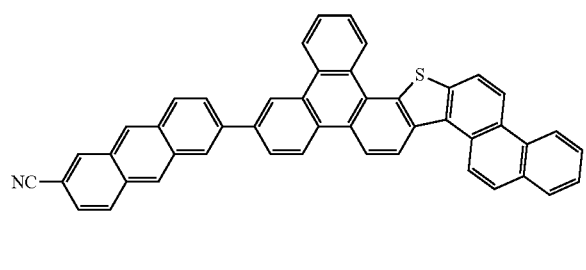
Compound 58
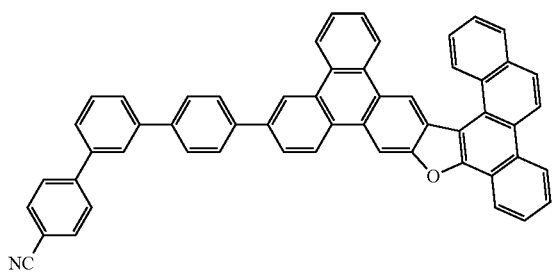
Compound 59
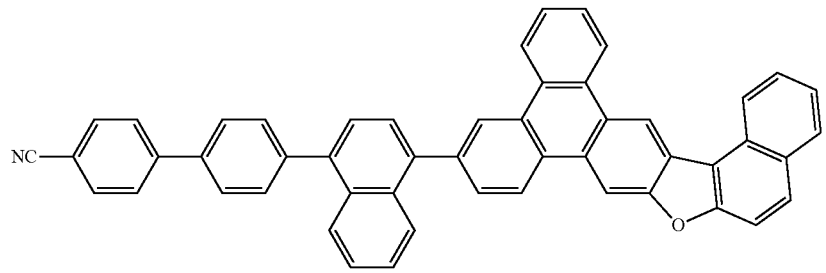
Compound 60
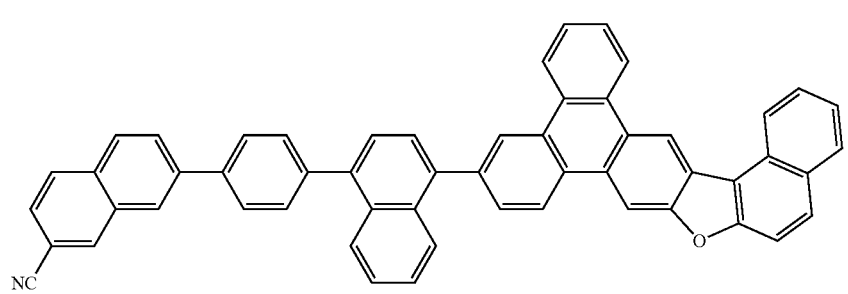
Compound 61
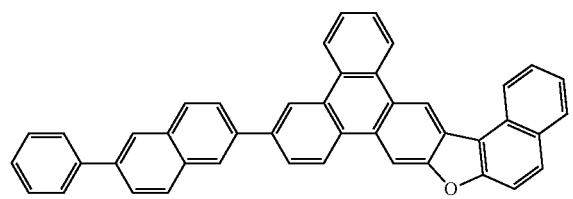
Compound 62
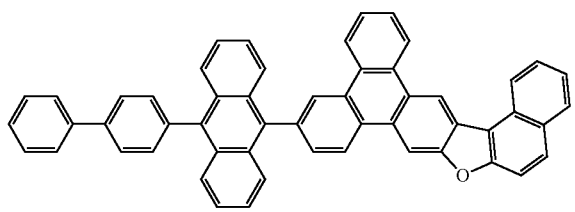

-continued
Compound 63
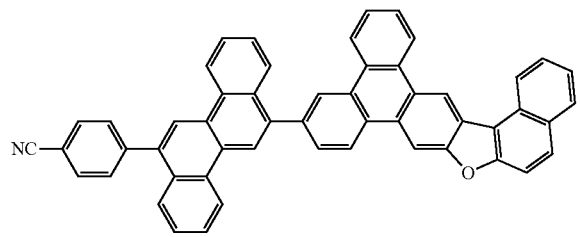
Compound 64
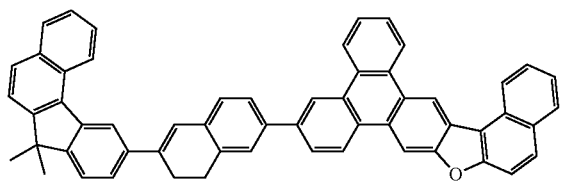
Compound 65
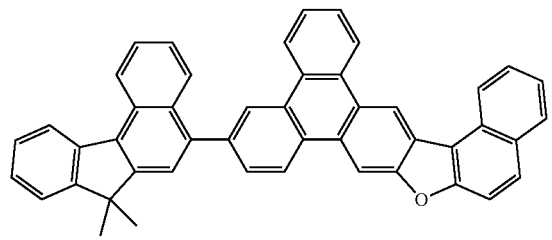
Compound 66
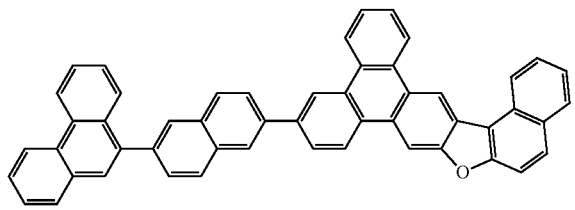
Compound 67
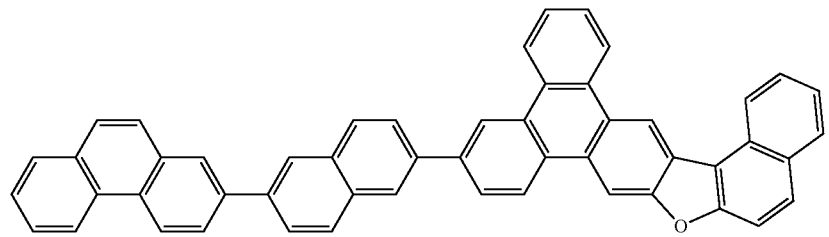
Compound 68
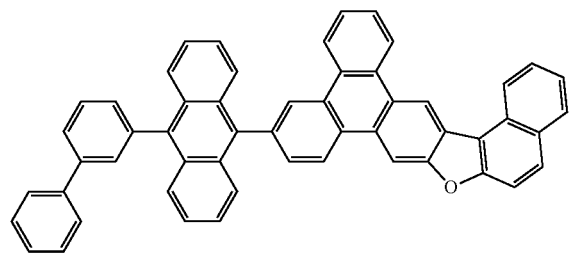
Compound 69
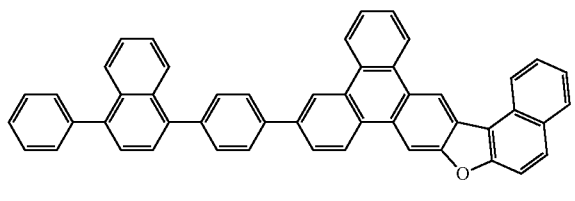
Compound 70
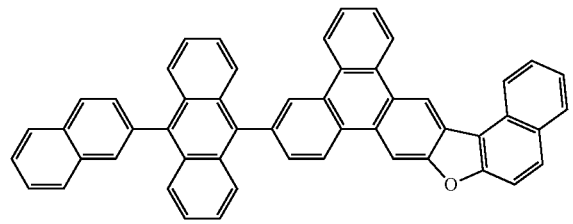
Compound 71
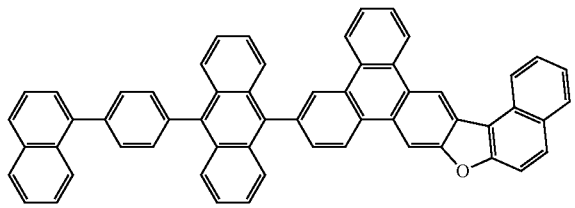
Compound 72
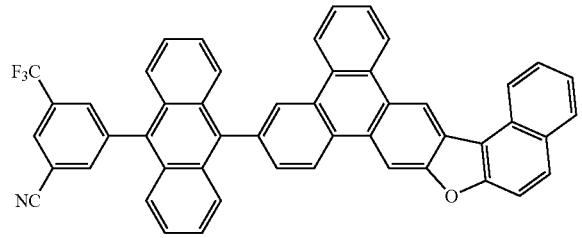
Compound 73
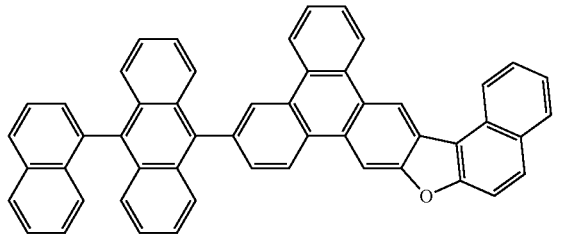

Compound 74
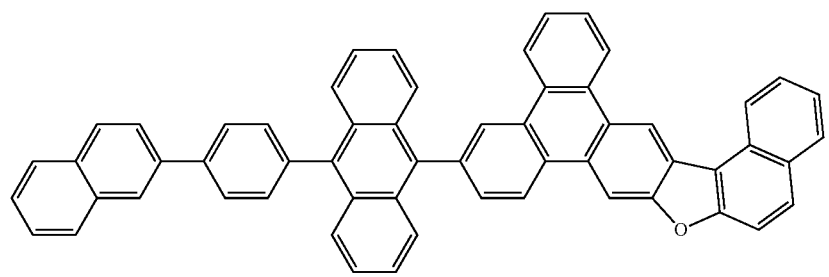
Compound 75
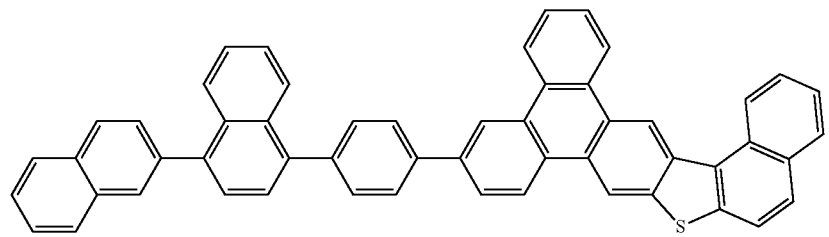
Compound 76
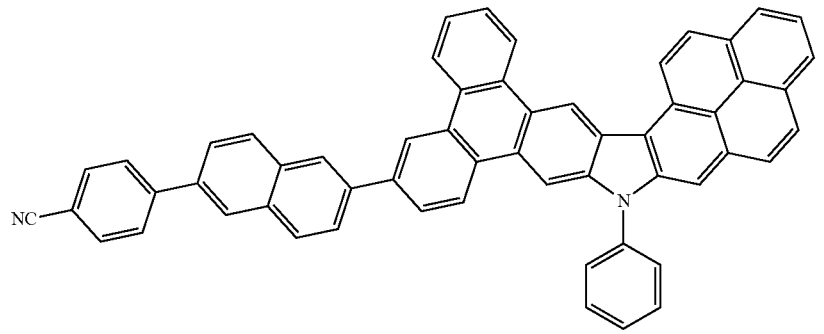
Compound 77
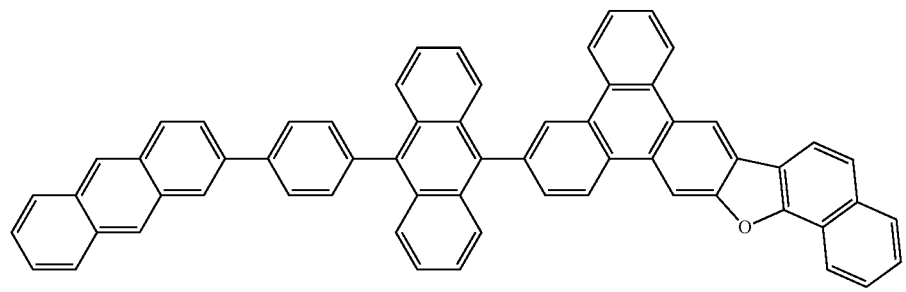
Compound 78
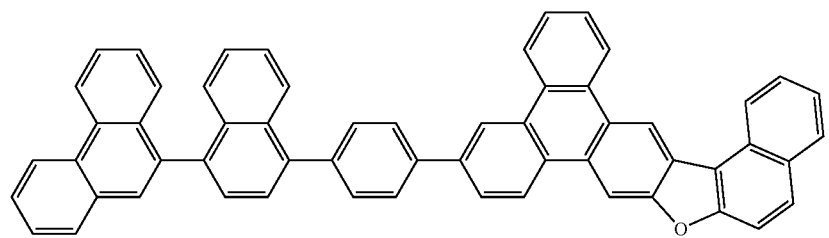
Compound 79
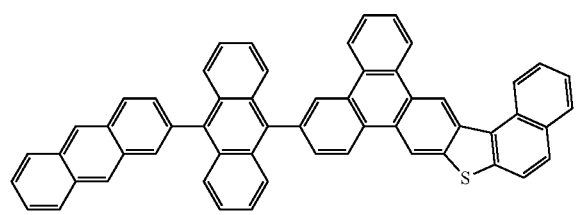
Compound 80
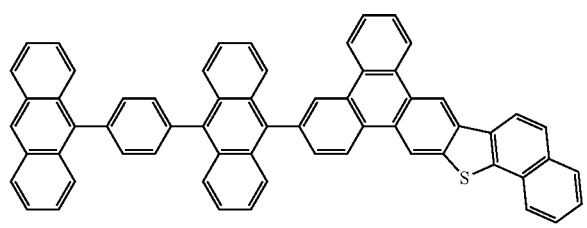

Compound 81
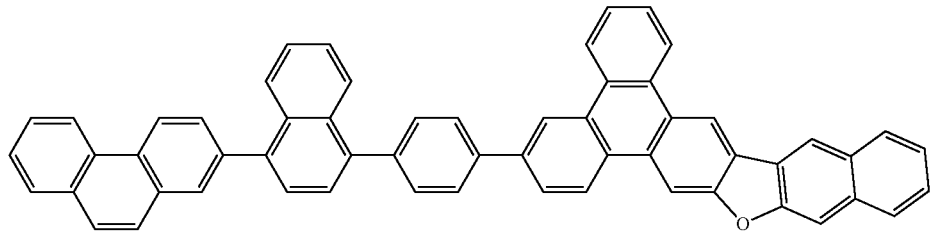
Compound 82
Compound 83
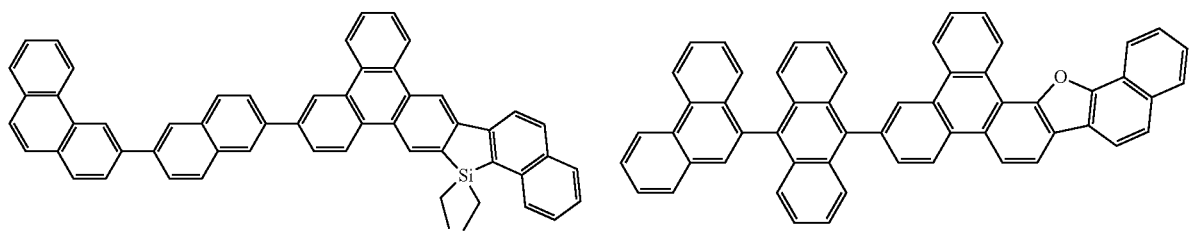
Compound 84
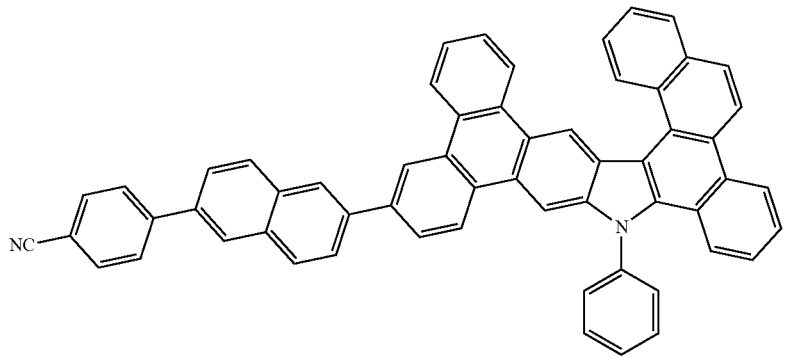
Compound 85
Compound 86
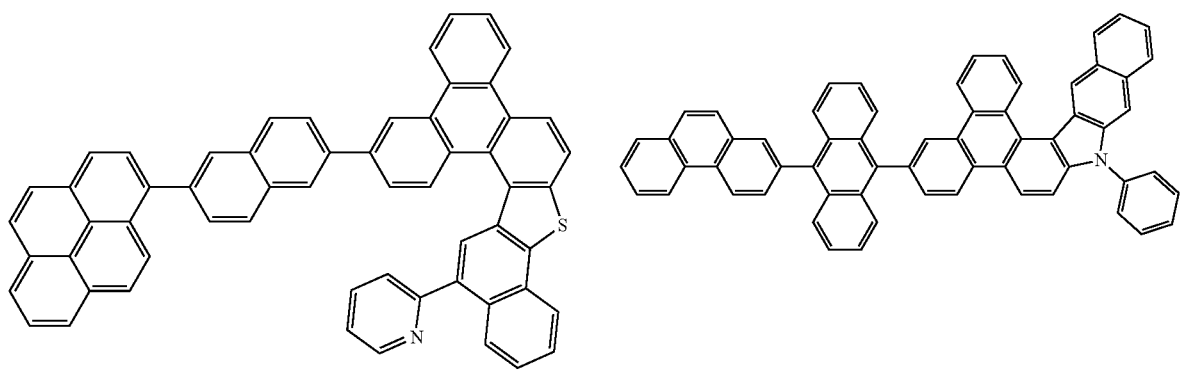
Compound 87
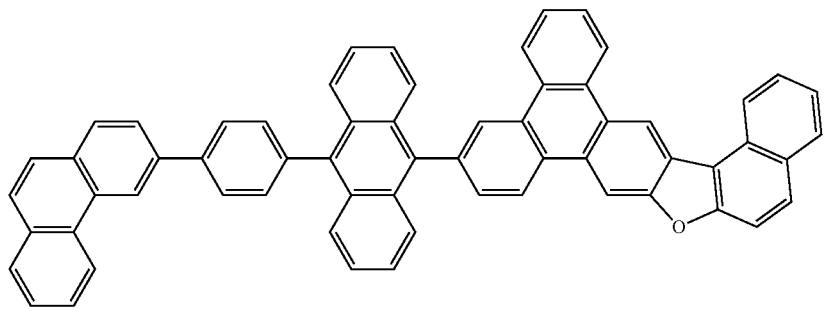

-continued
Compound 88
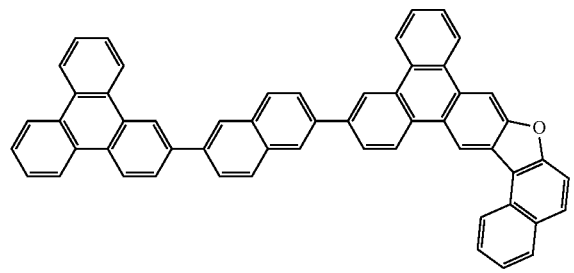
Compound 89
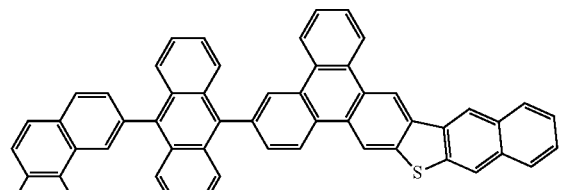
Compound 90
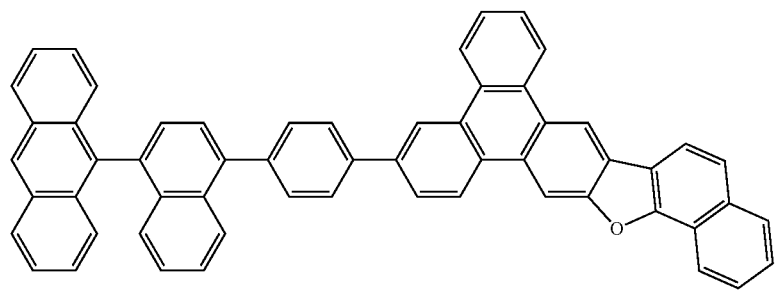
Compound 91
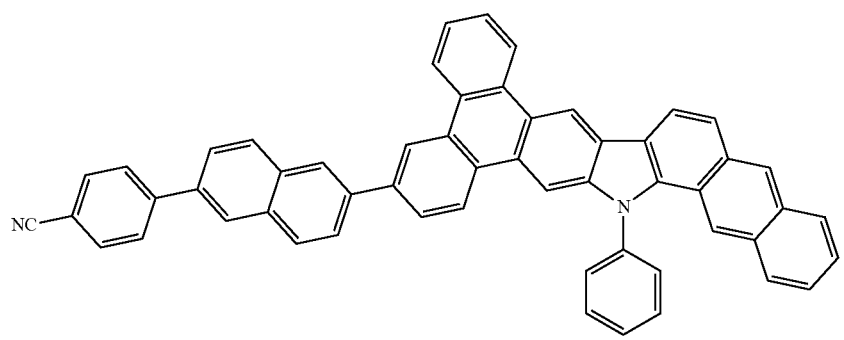
Compound 92
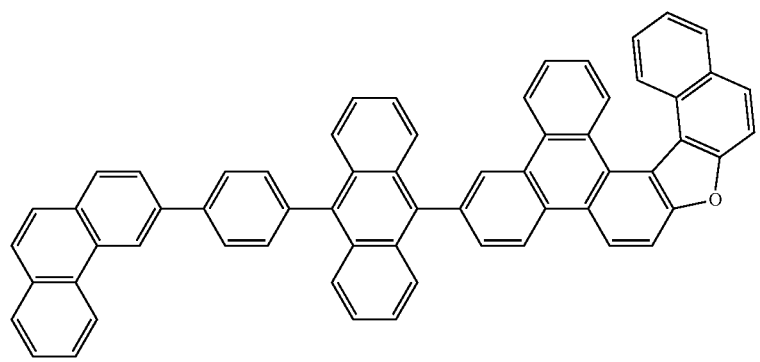

-continued
Compound 93
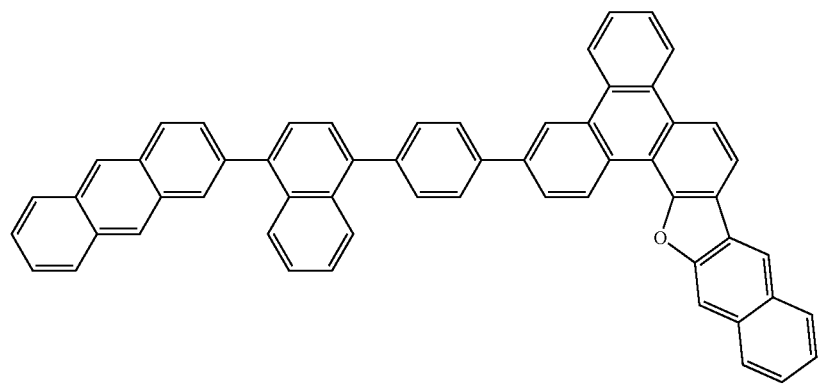
Compound 94
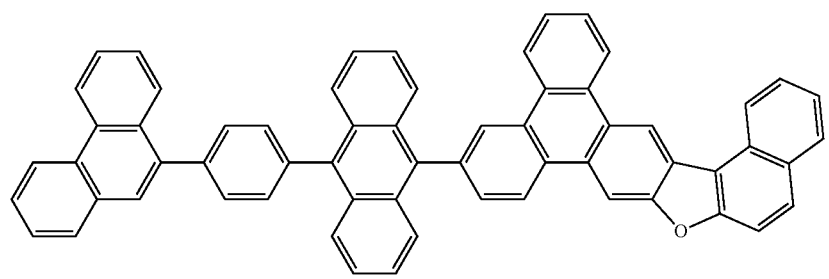
Compound 95
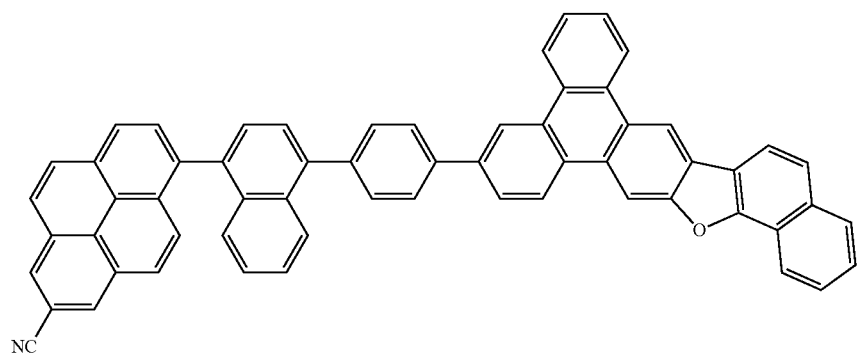
Compound 96
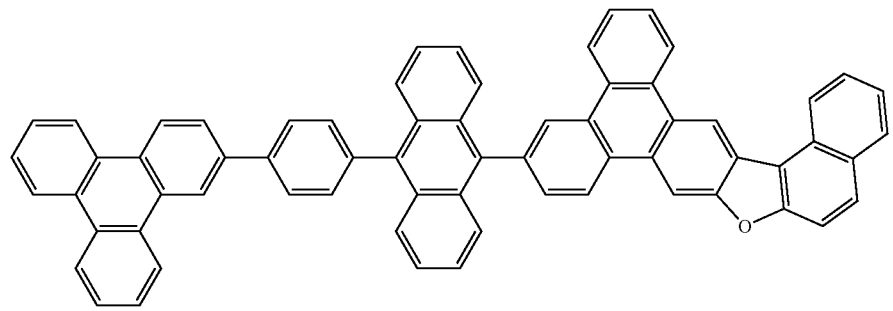
Compound 97
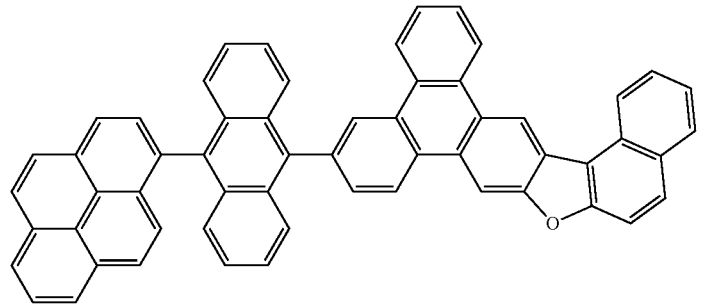

-continued
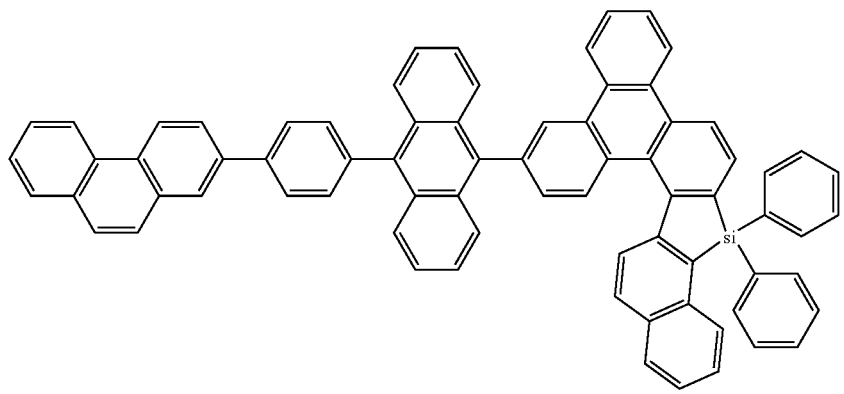
Compound 98
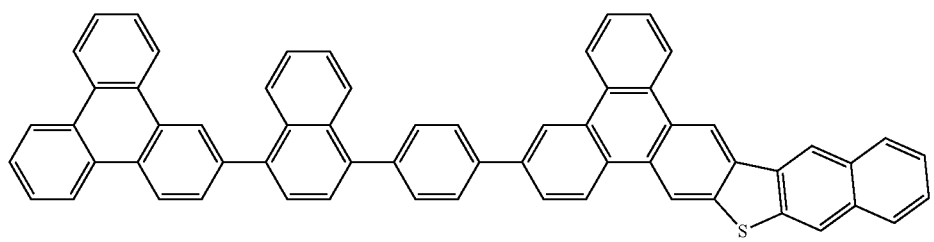
Compound 99
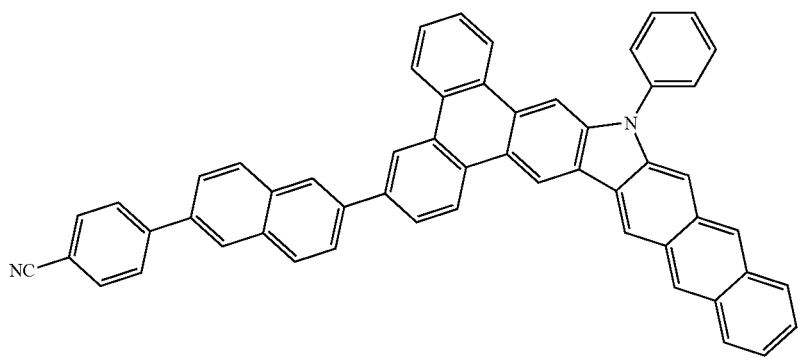
Compound 100
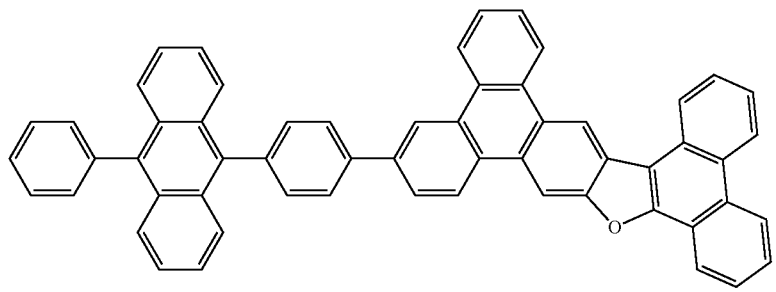
Compound 101
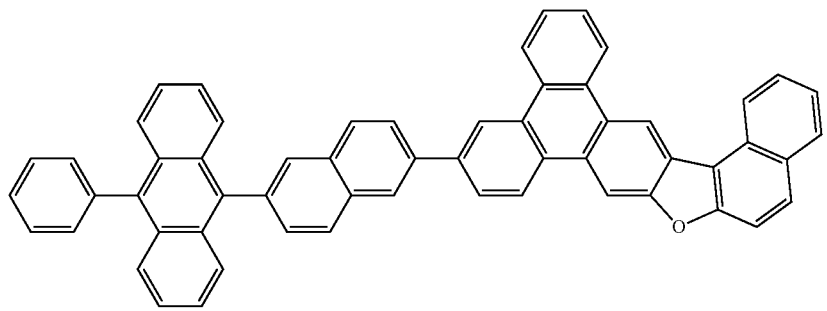
Compound 102

-continued
Compound 103
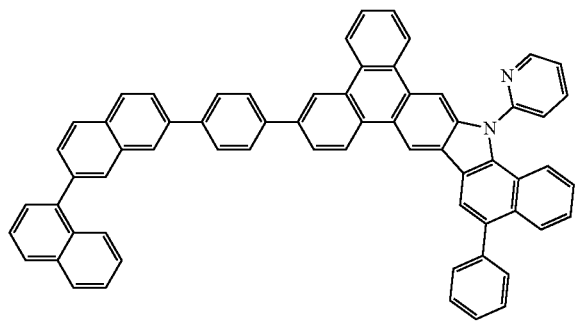
Compound 104
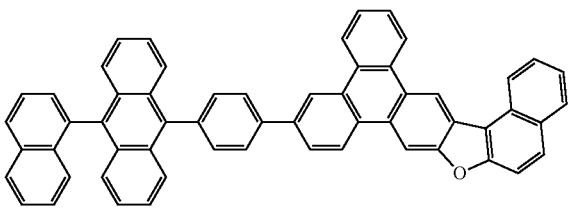
Compound 105
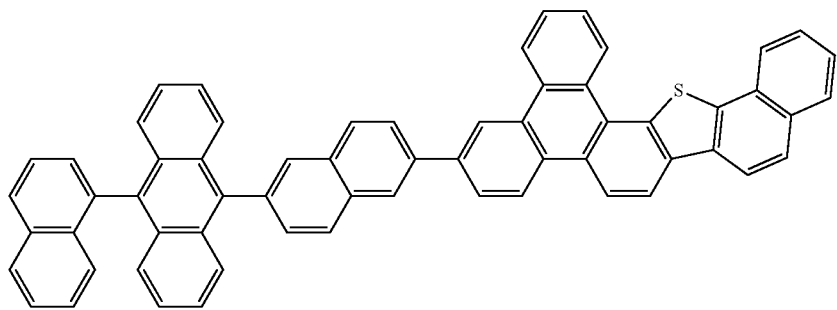
Compound 106
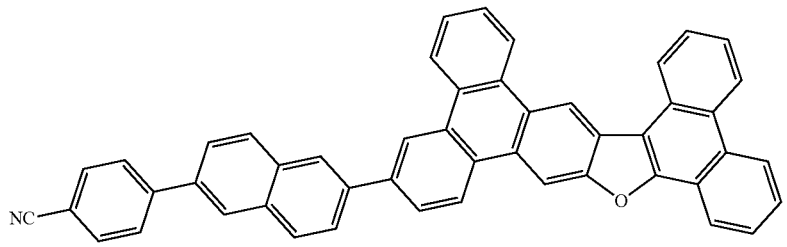
Compound 107
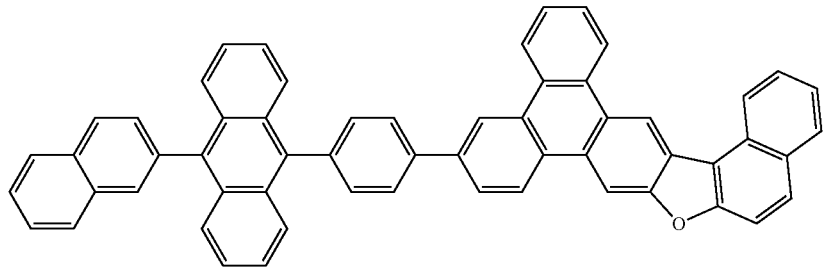
Compound 108
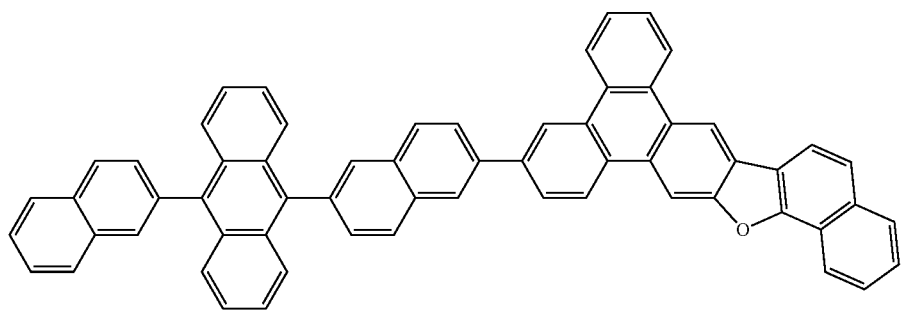

Compound 109
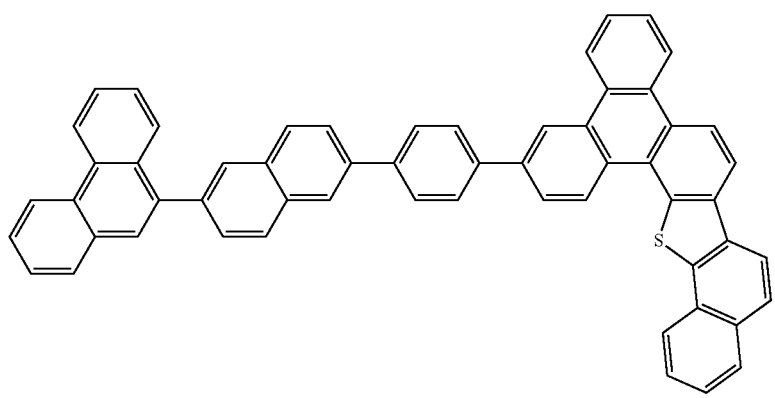
Compound 110
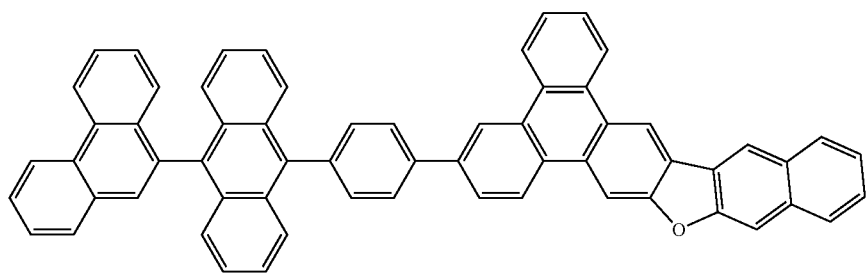
Compound 111
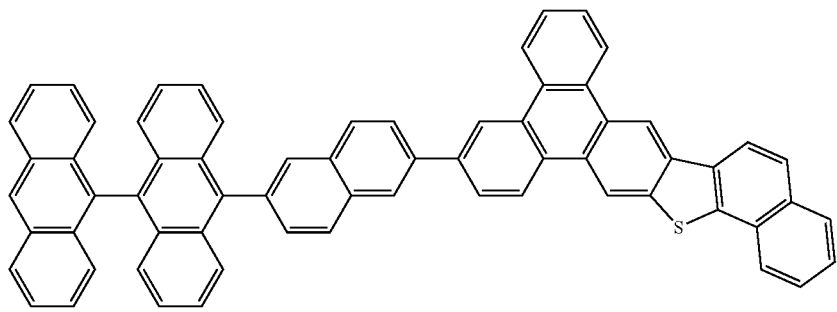
Compound 112
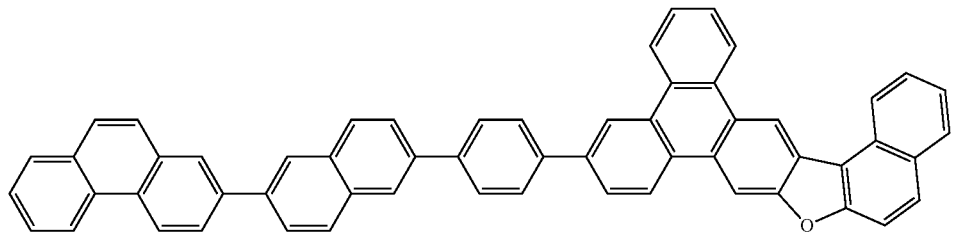
Compound 113
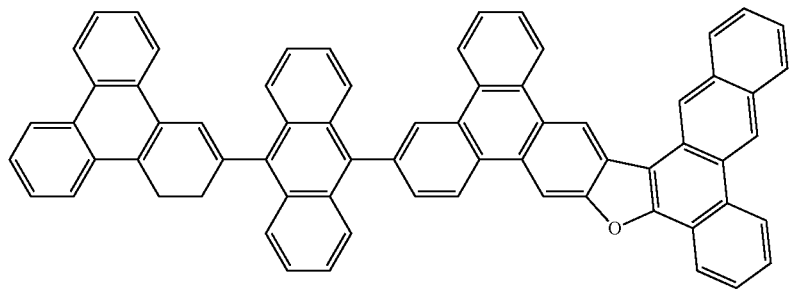

Compound 114
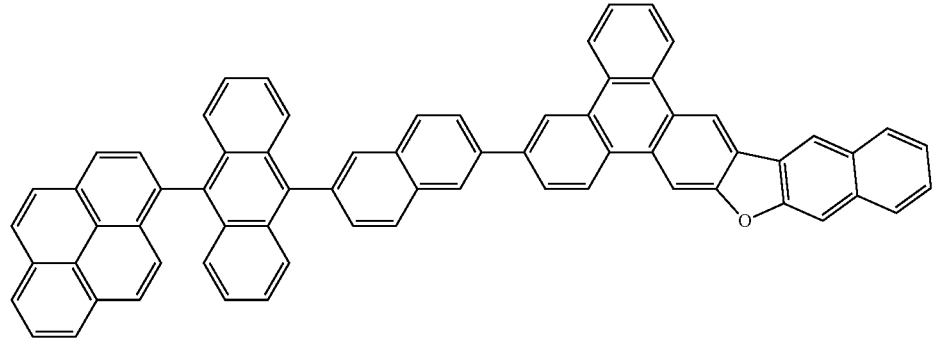
Compound 115
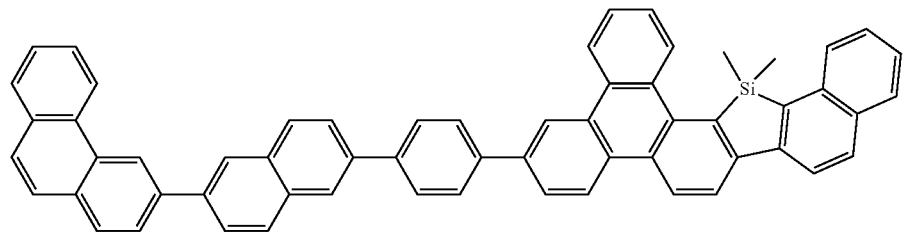
Compound 116
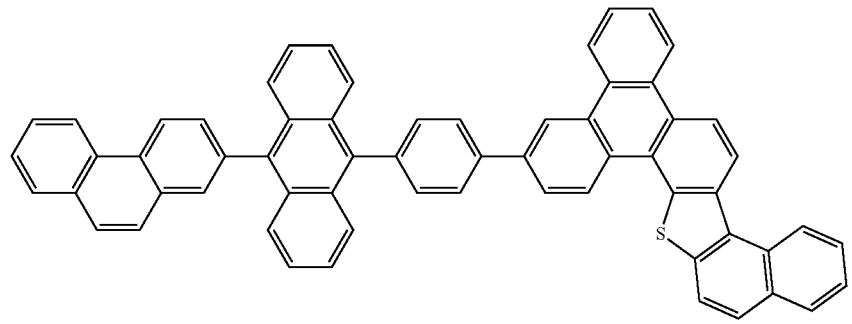
Compound 117
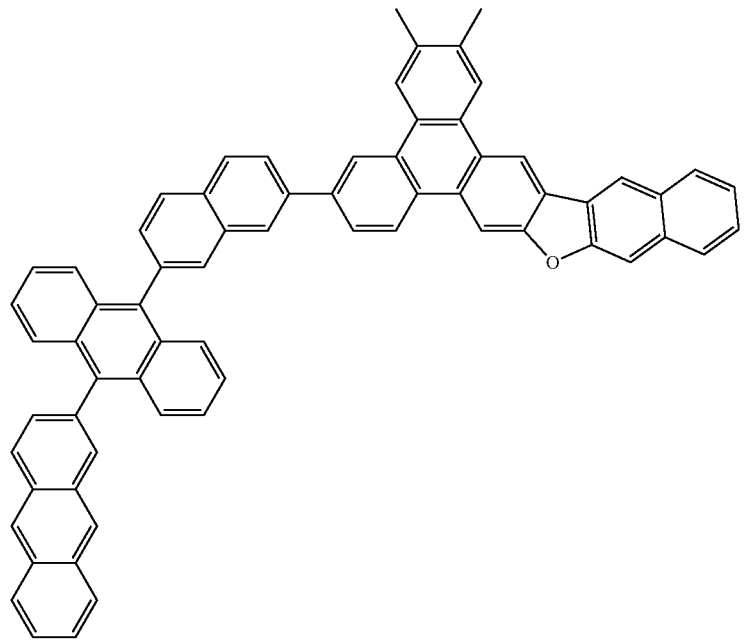

-continued
Compound 118
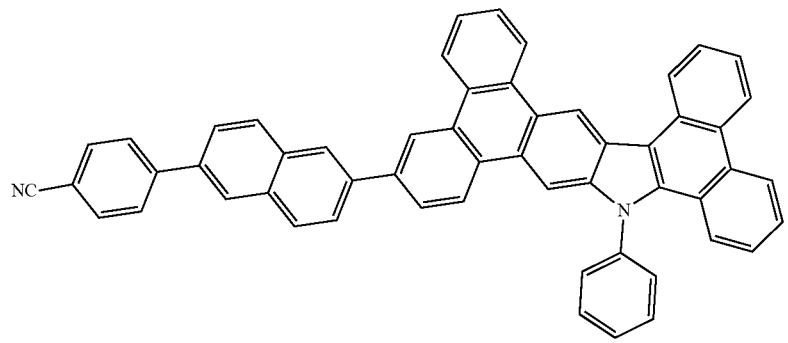
Compound 119
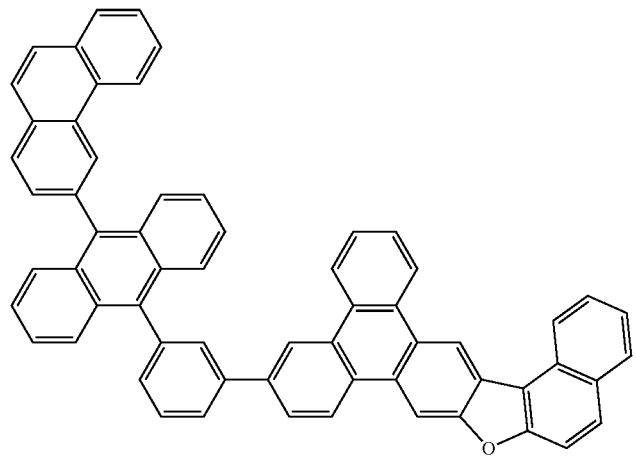
Compound 120
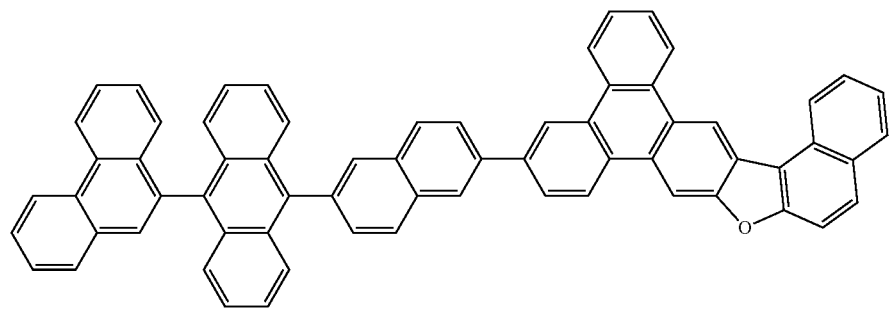
Compound 121
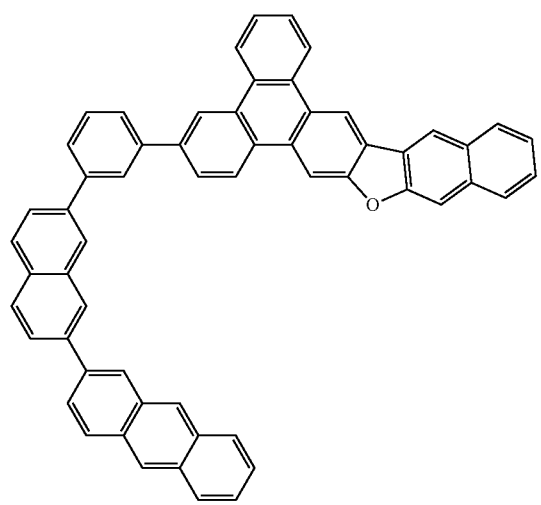
Compound 122
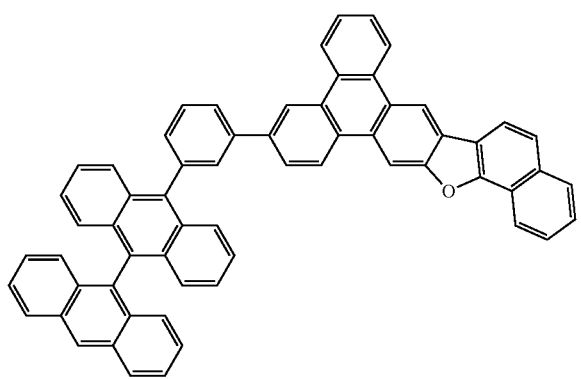

Compound 123
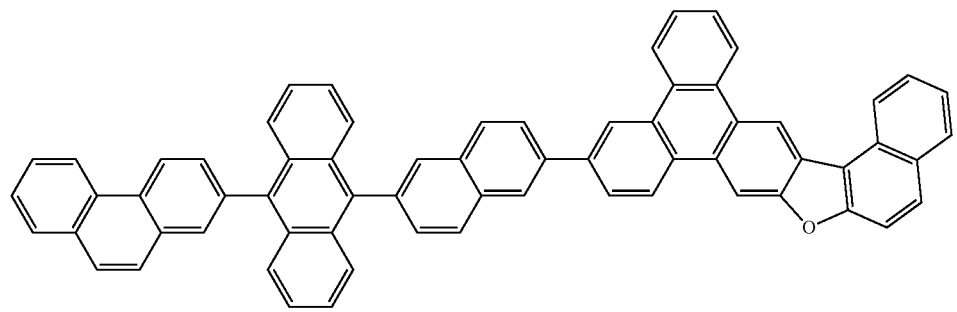
Compound 124
Compound 125
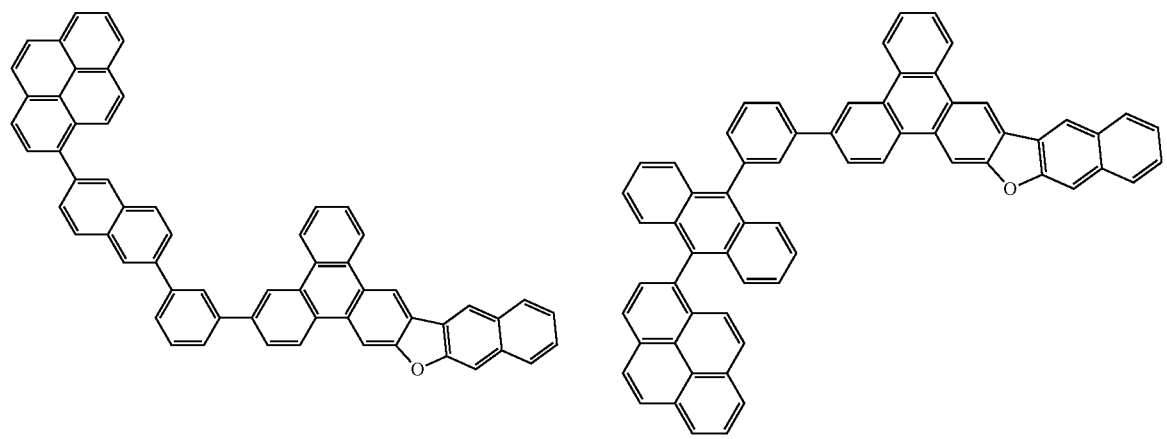
Compound 126
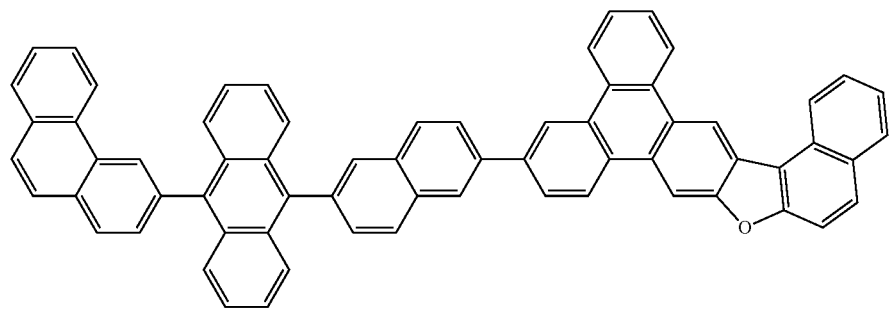
Compound 127
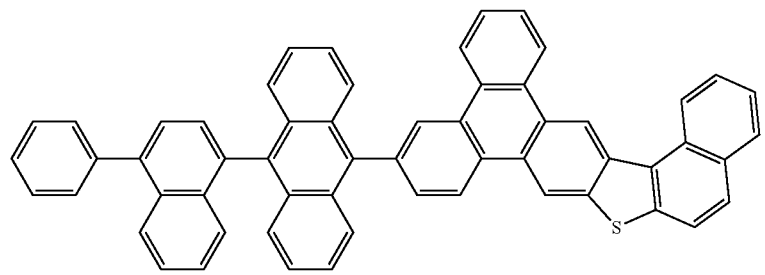

-continued
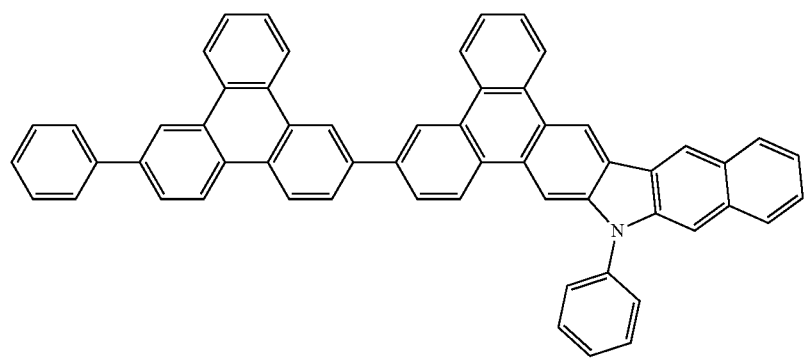
Compound 128
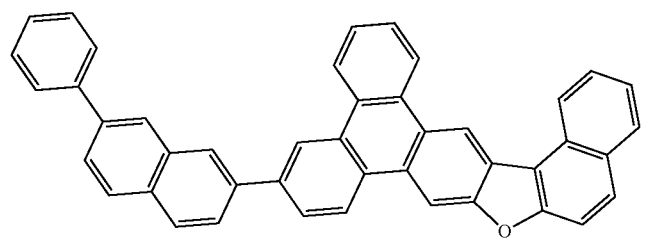
Compound 129
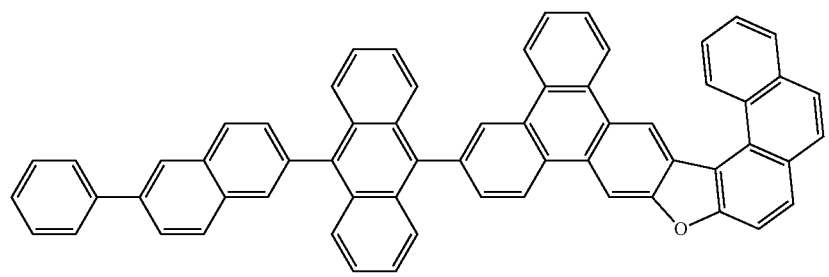
Compound 130
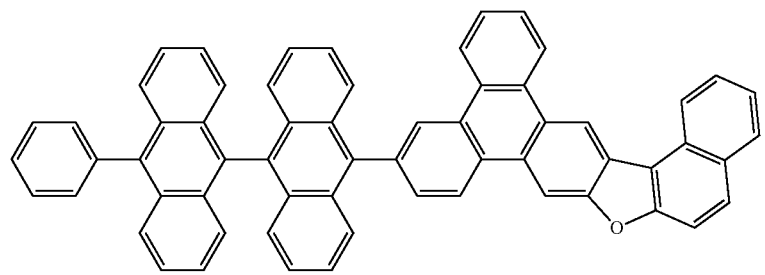
Compound 131
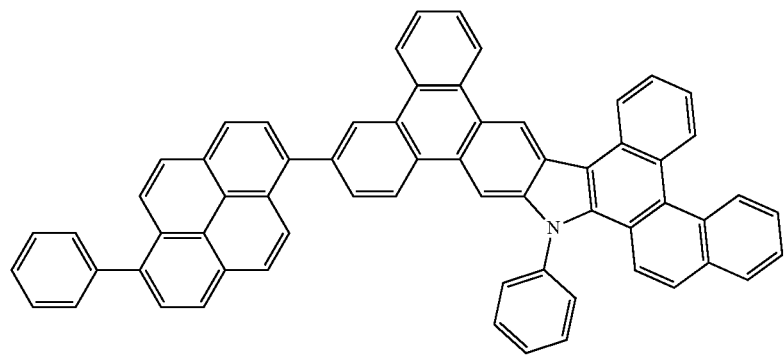
Compound 132

-continued
Compound 133
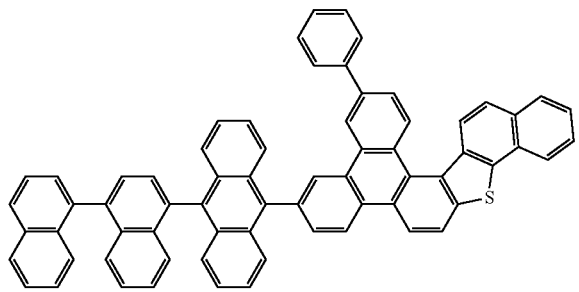
Compound 134
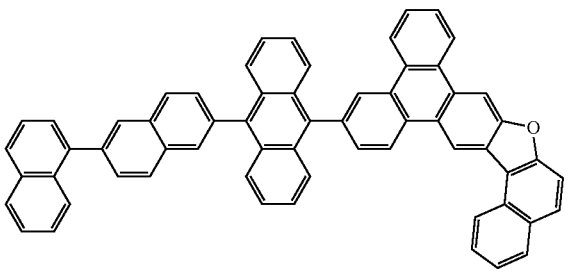
Compound 135
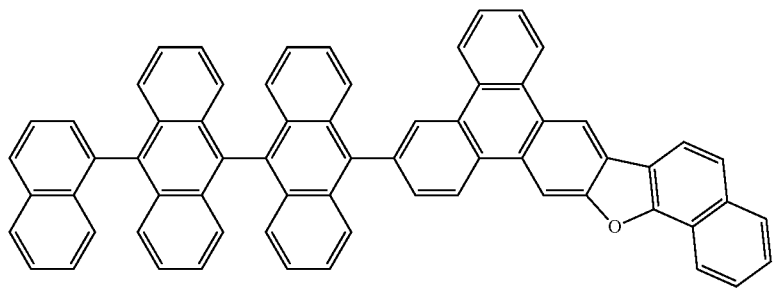
Compound 136
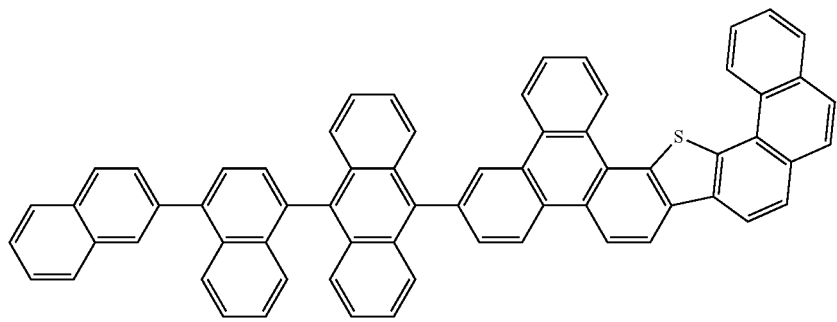
Compound 137
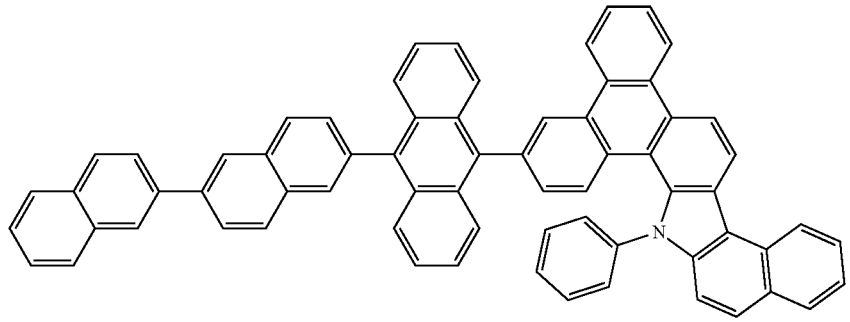
Compound 138
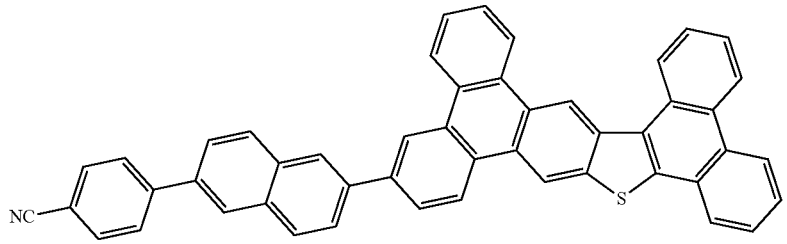

-continued
Compound 139
Compound 140
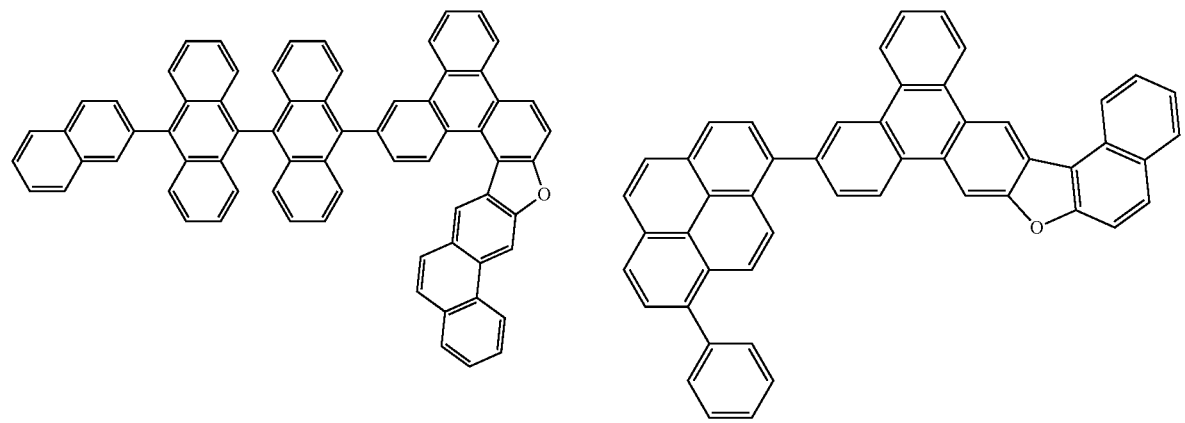
Compound 141
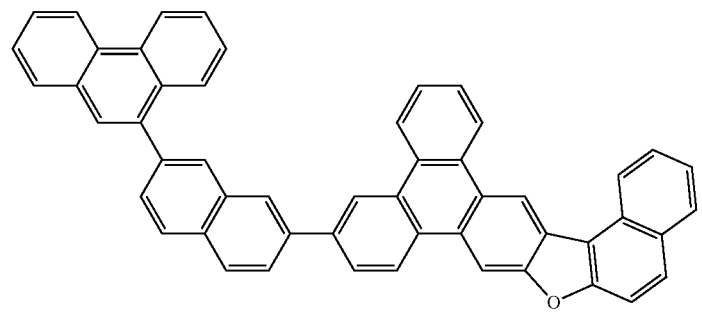
Compound 142
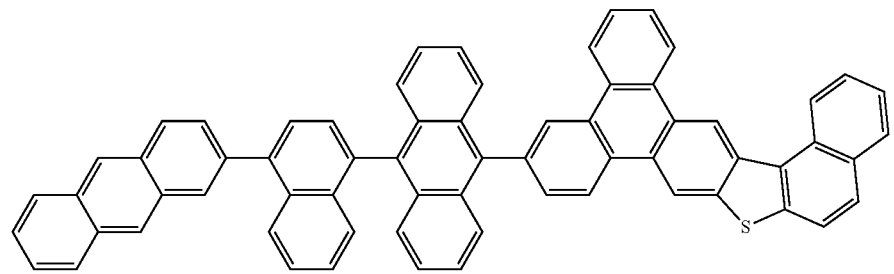
Compound 143
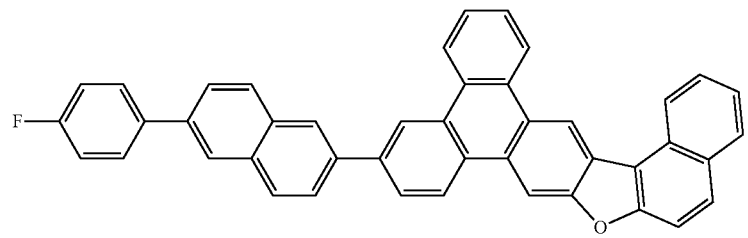
Compound 144
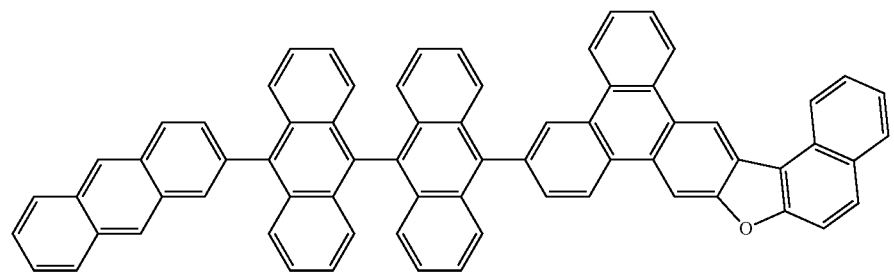

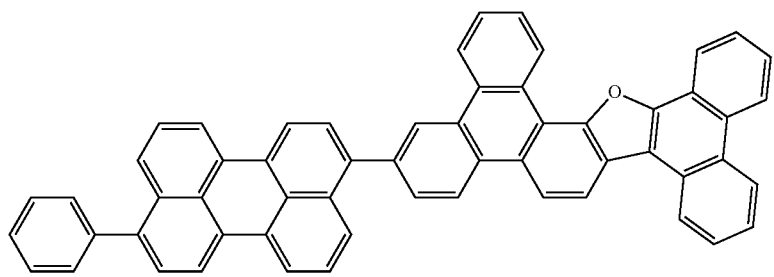
Compound 145
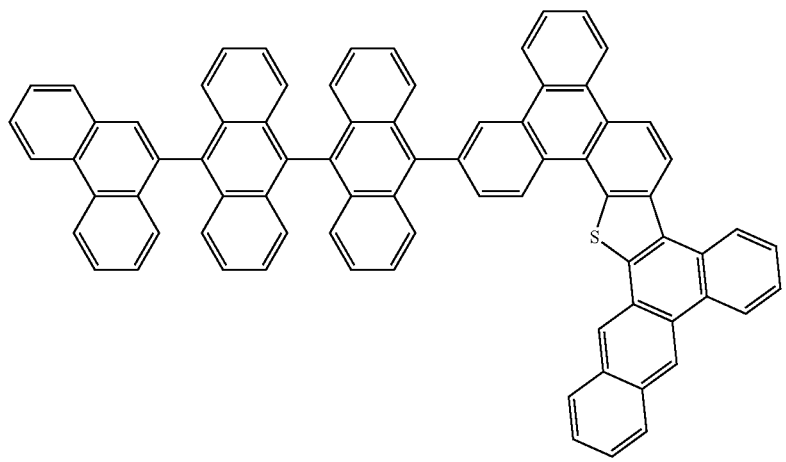
Compound 146
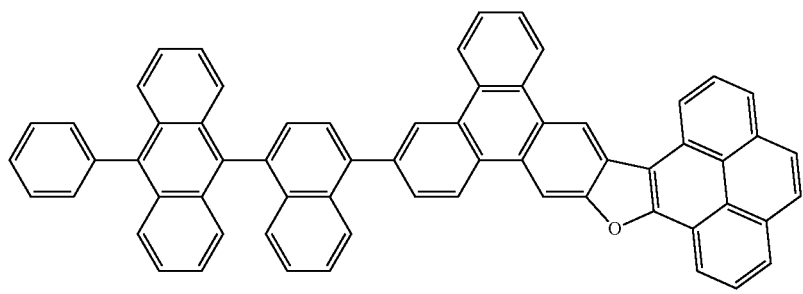
Compound 147
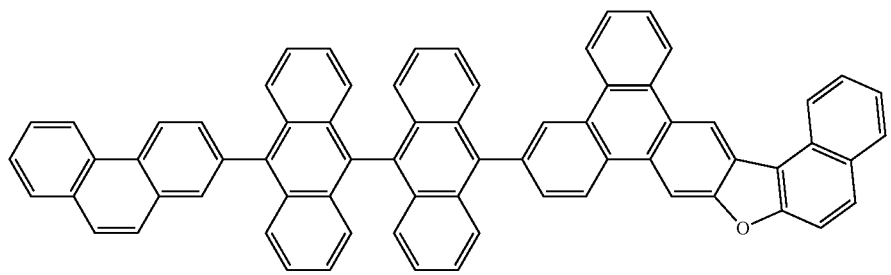
Compound 148
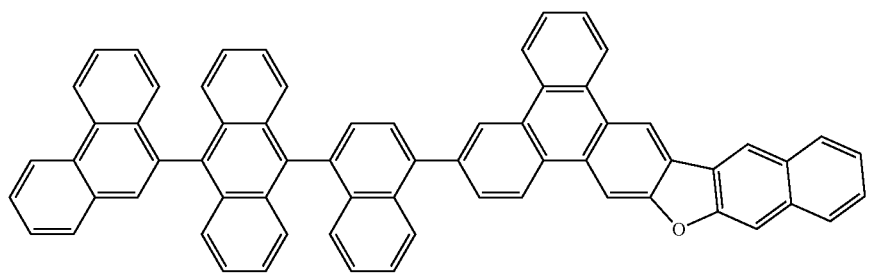
Compound 149

-continued
Compound 150
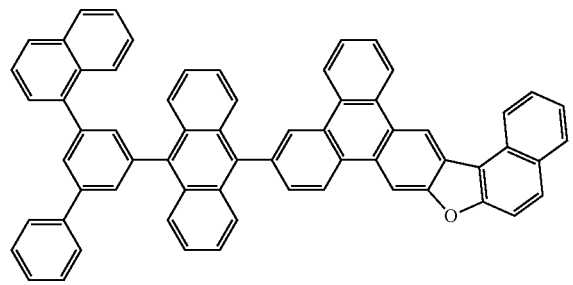
Compound 151
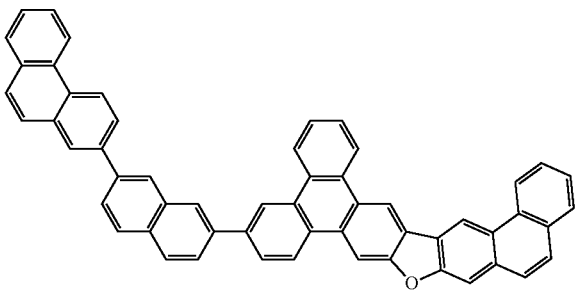
Compound 152
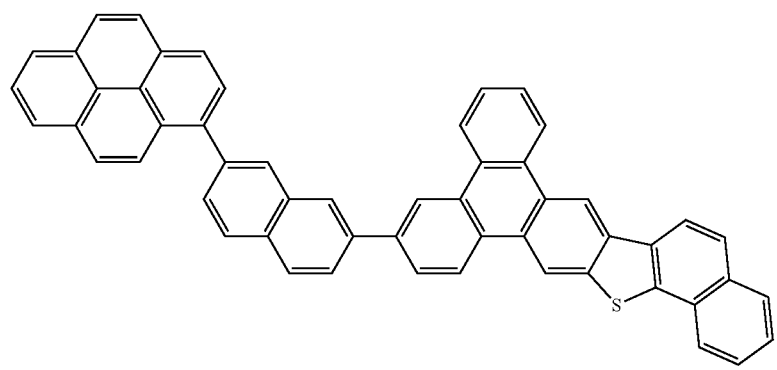
Compound 153
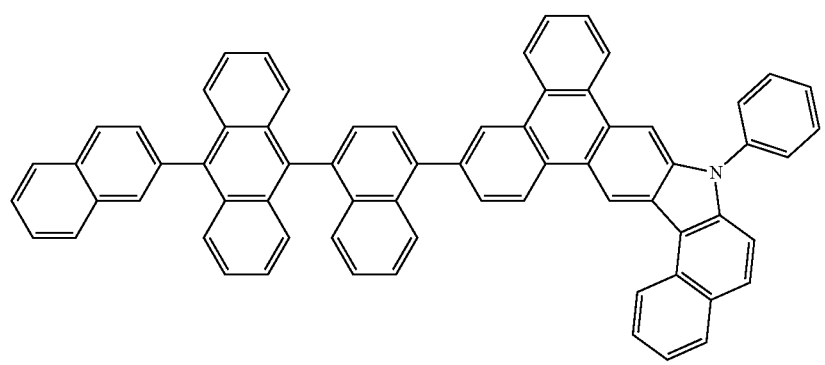
Compound 154
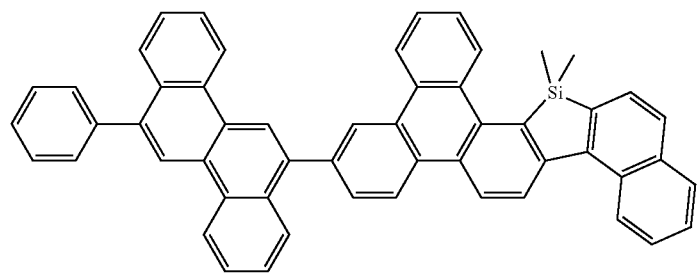

Compound 155
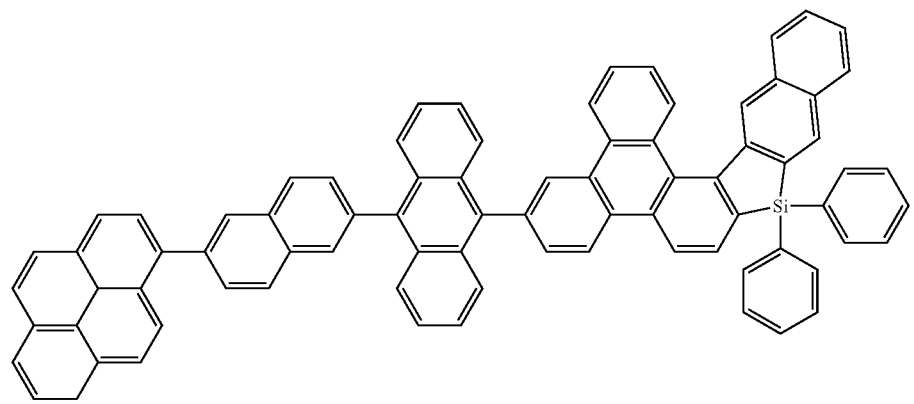
Compound 156
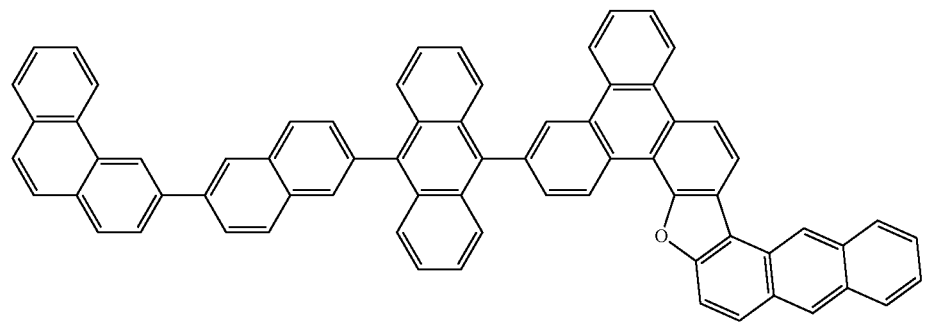
Compound 157
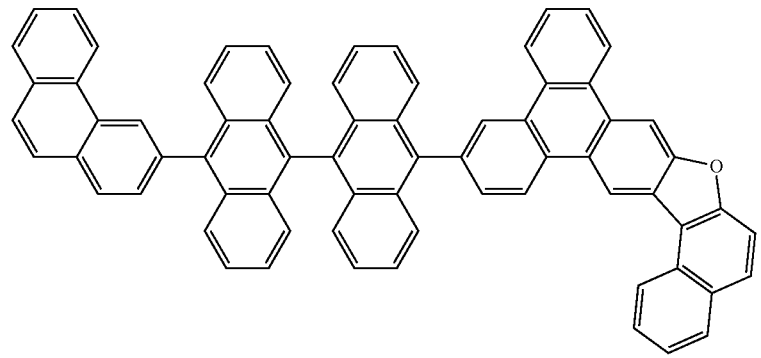
Compound 158
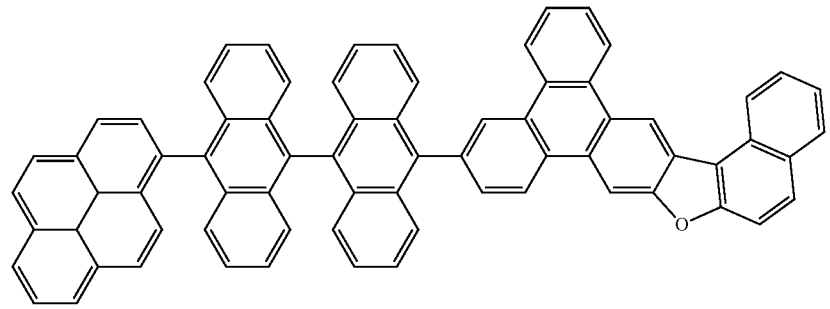

Compound 159
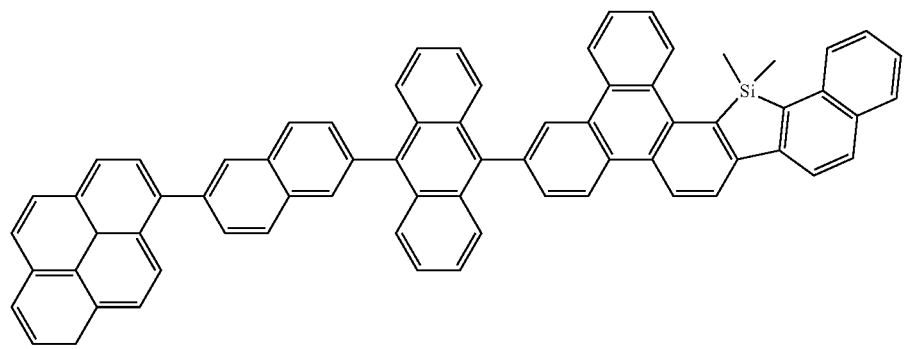
Compound 160
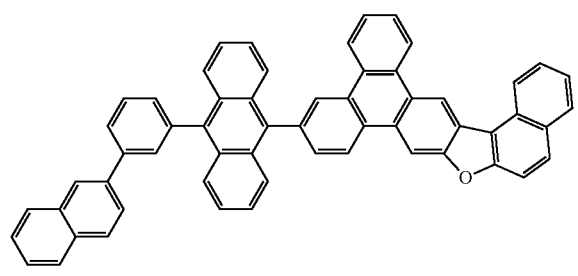
Compound 161
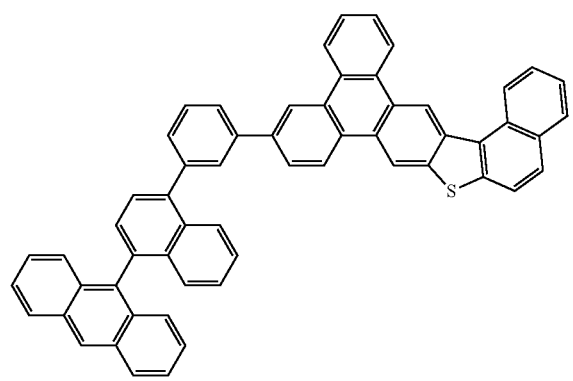
Compound 162
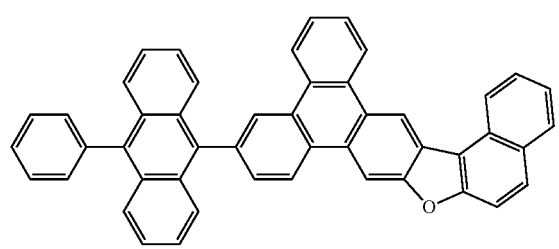
Compound 163
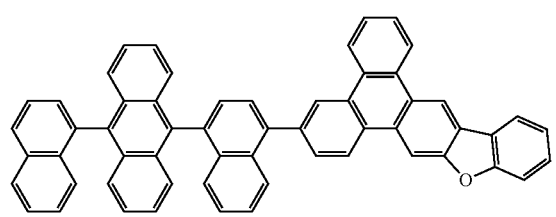
Compound 164
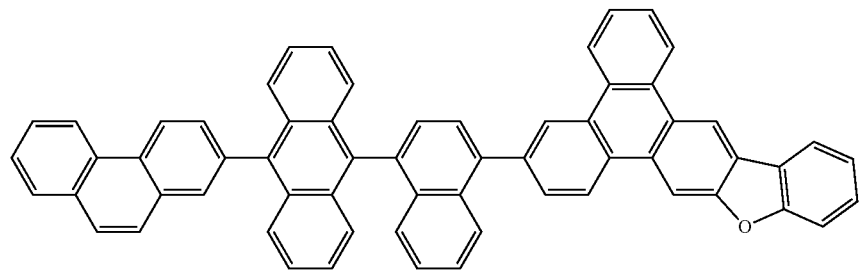
Compound 165
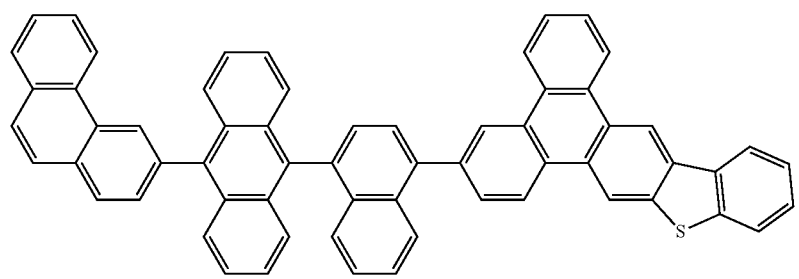

-continued
Compound 166
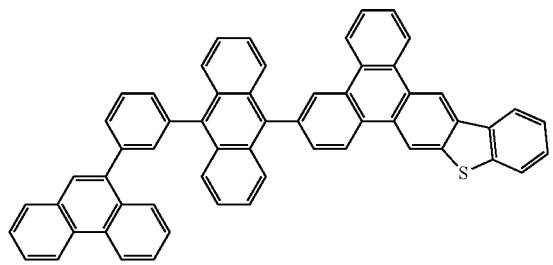
Compound 167
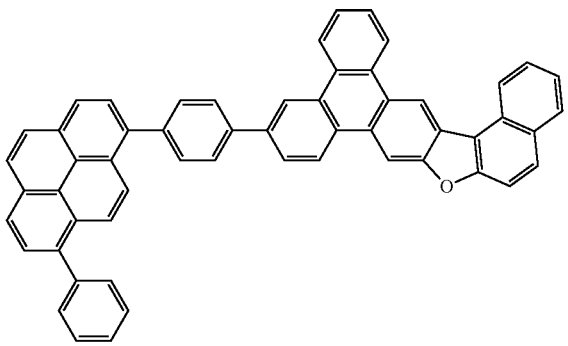
Compound 168
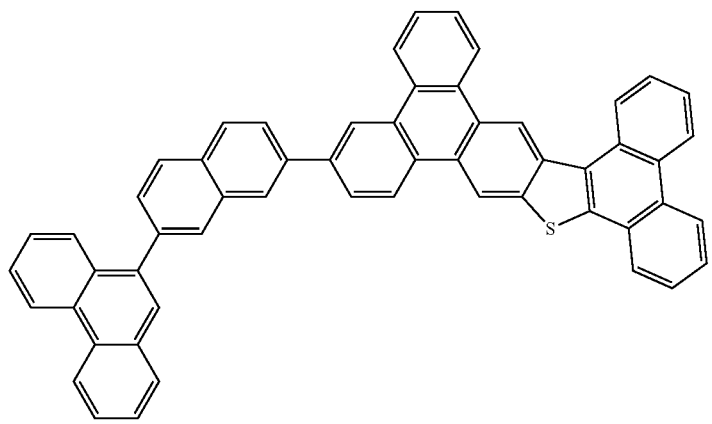
Compound 169
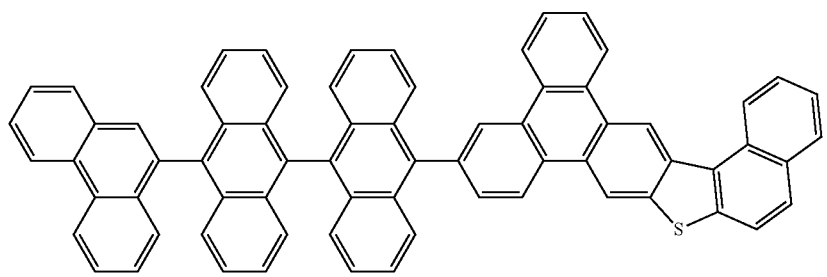
Compound 170
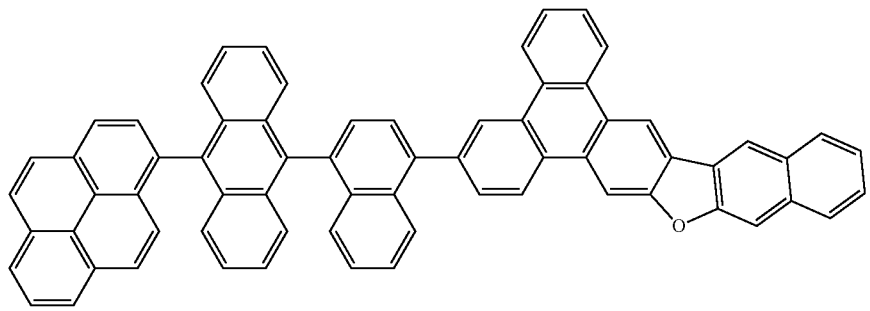

-continued
Compound 171
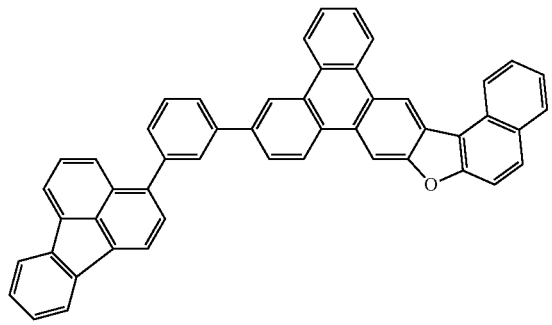
Compound 172
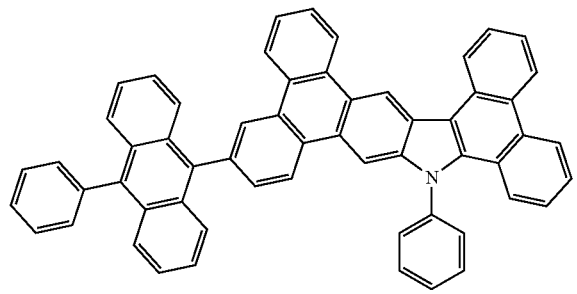
Compound 173
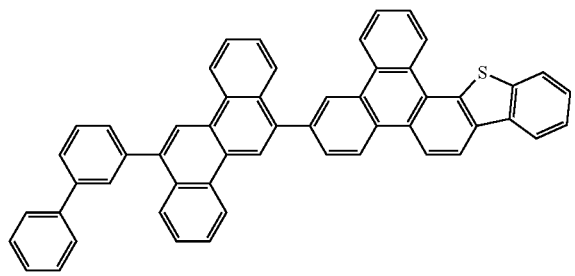
Compound 174
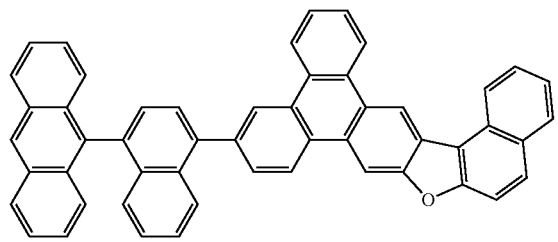
Compound 175
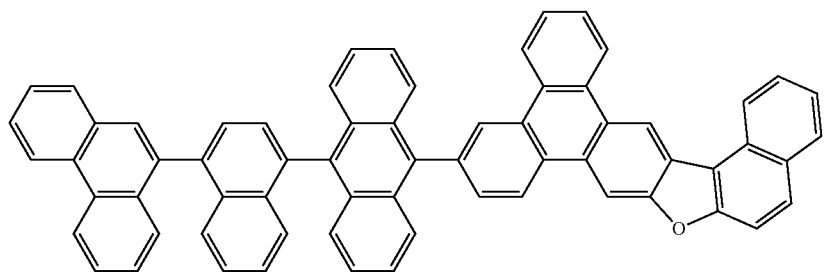
Compound 176
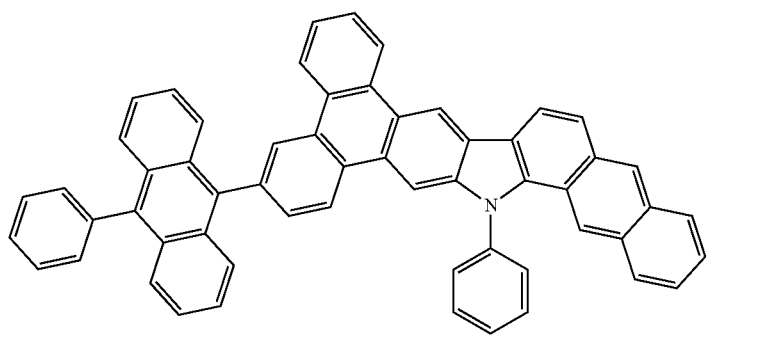
Compound 177
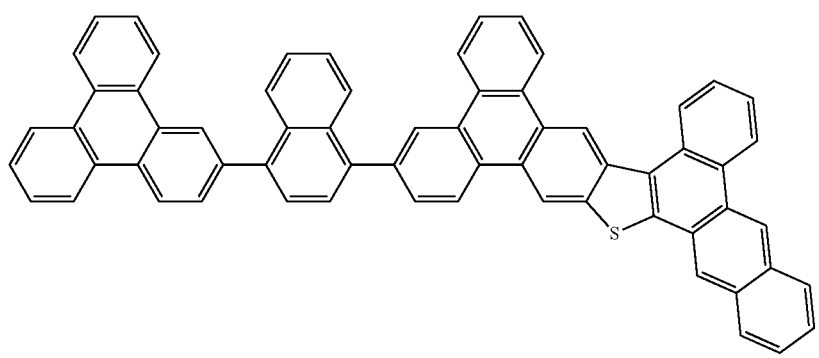

-continued
Compound 178
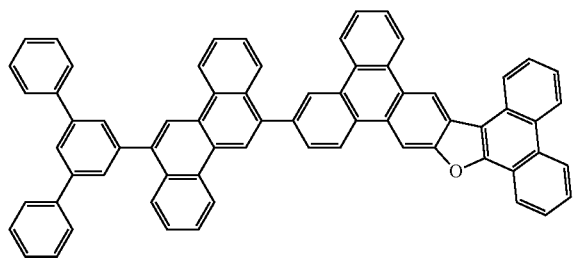
Compound 179
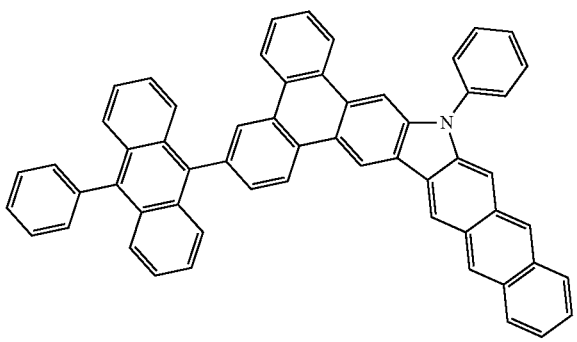
Compound 180
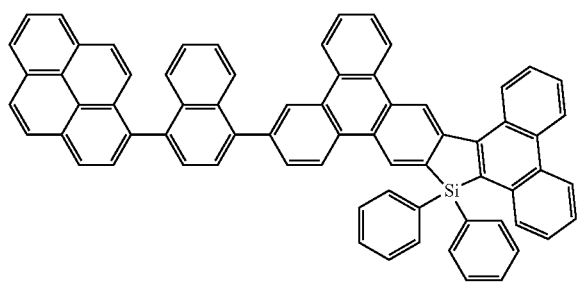
Compound 181
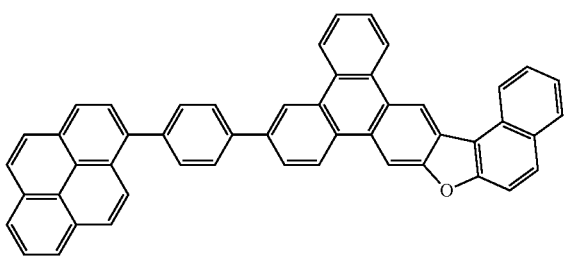
Compound 182
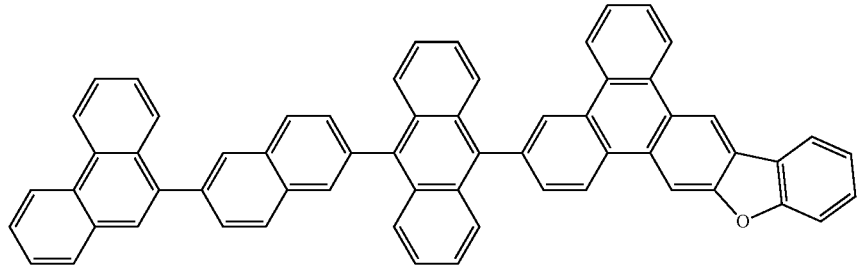
Compound 183
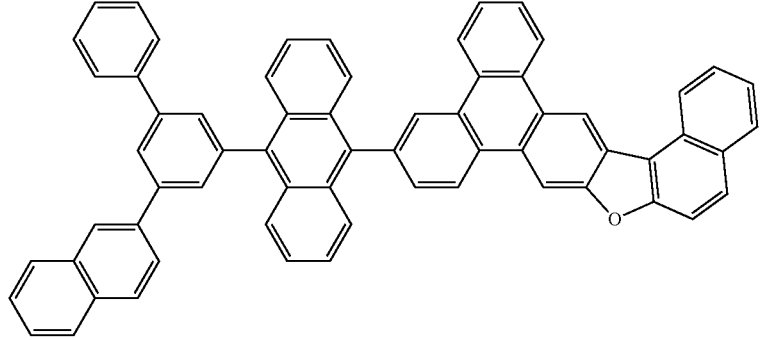
Compound 184
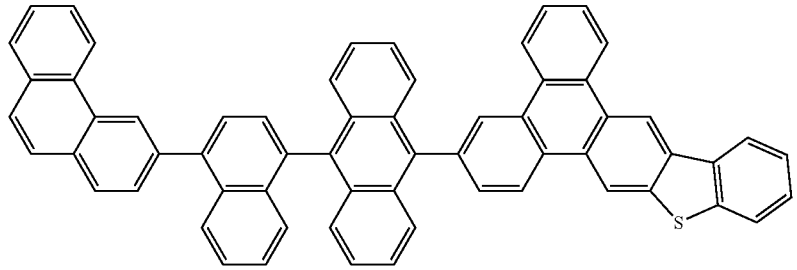

-continued
Compound 185
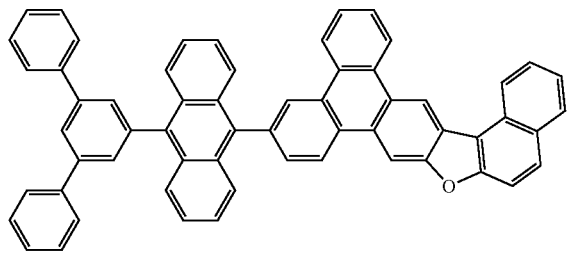
Compound 186
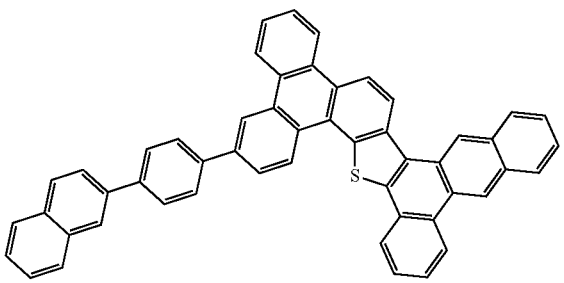
Compound 187
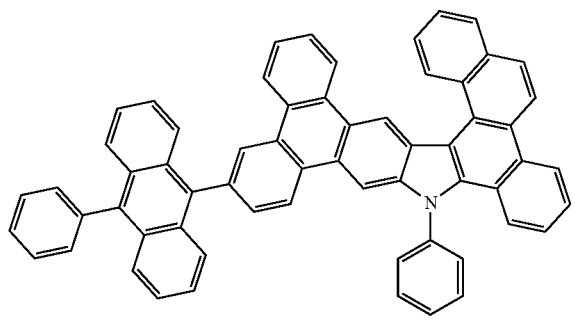
Compound 188
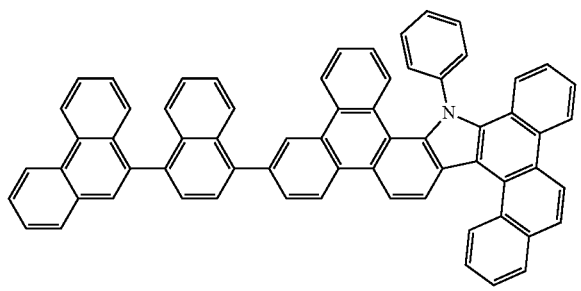
Compound 189
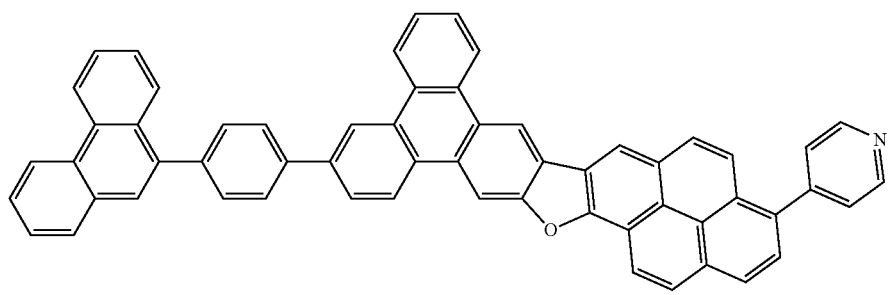
Compound 190
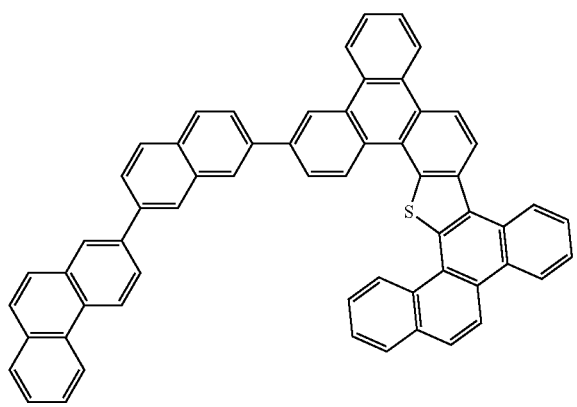
Compound 191
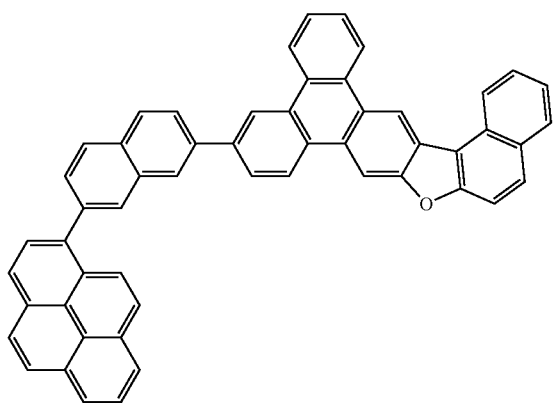

-continued
Compound 192
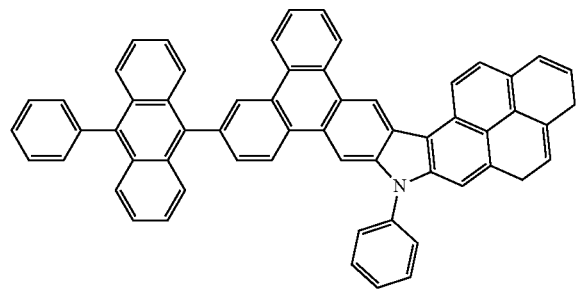
Compound 193
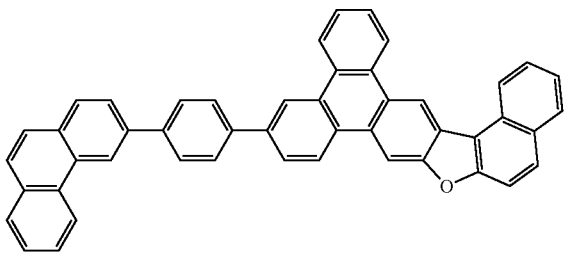
Compound 194
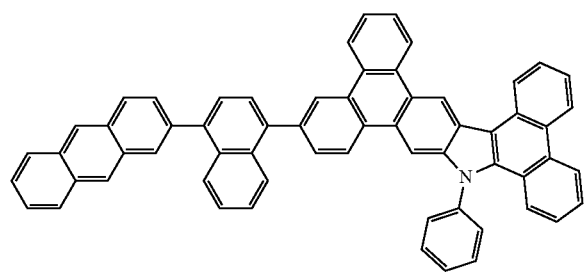
Compound 195
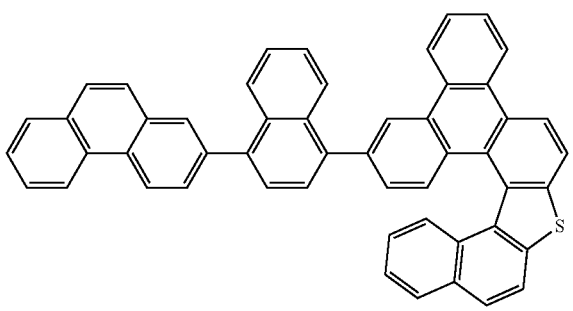
Compound 196
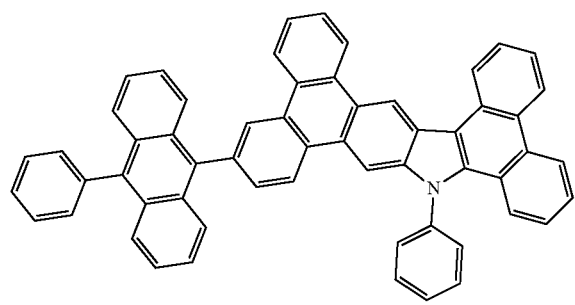
Compound 197
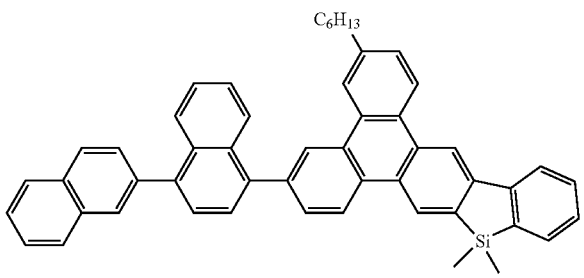
Compound 198
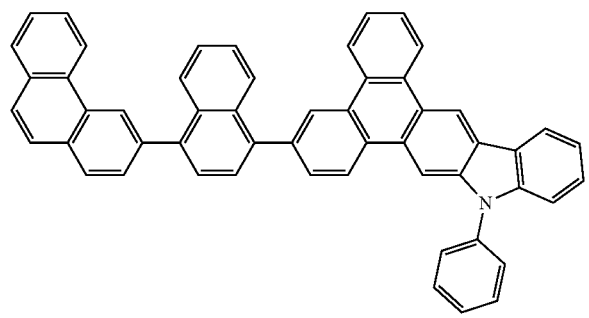
Compound 199
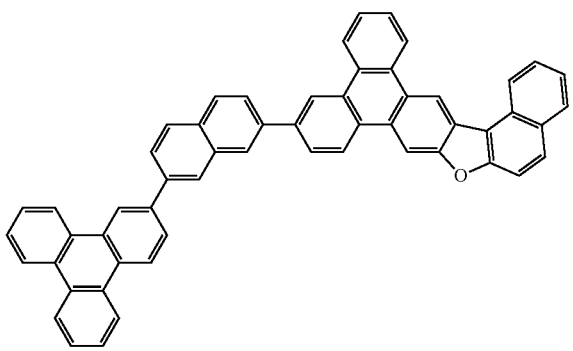

-continued
Compound 200
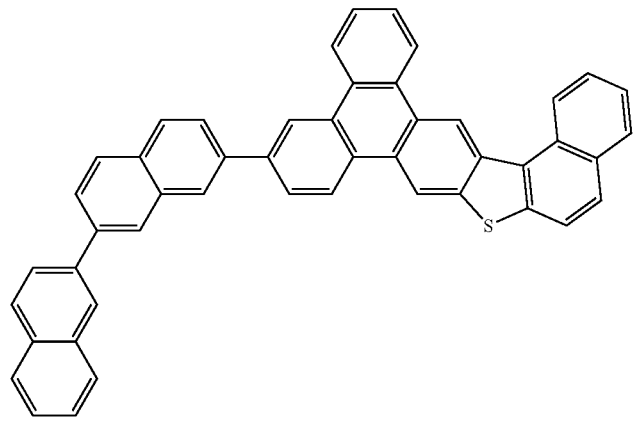
Compound 201
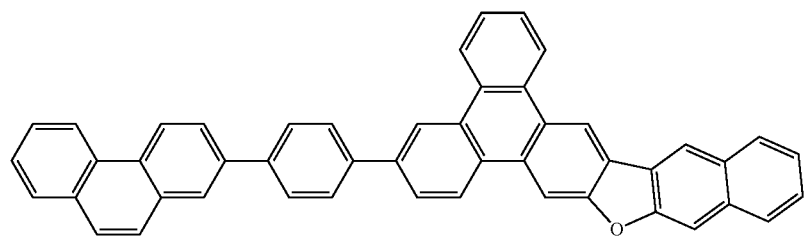
Compound 202
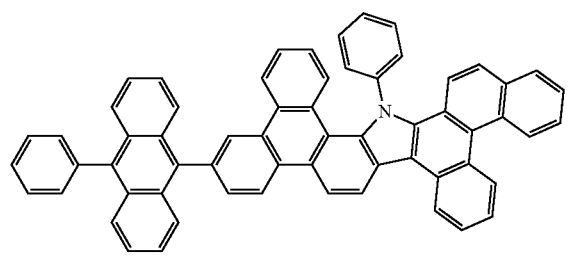
Compound 203
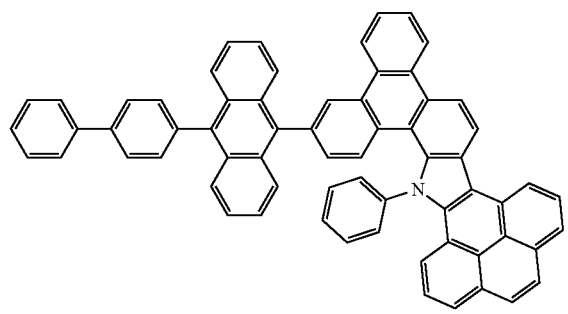
Compound 204
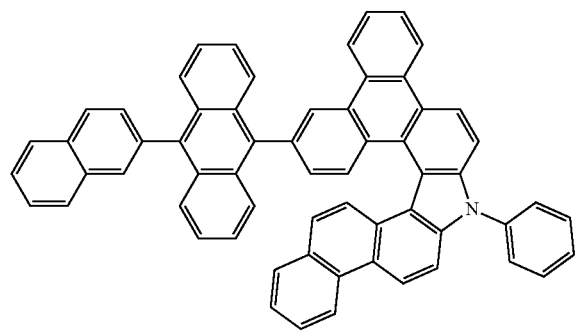
Compound 205
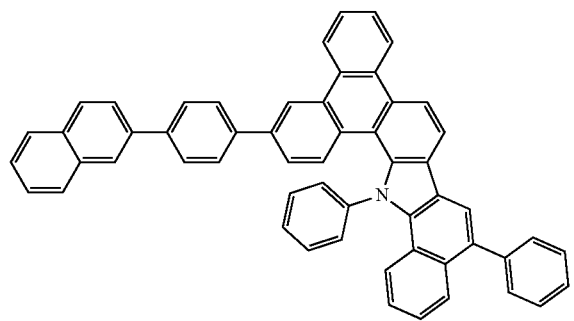
Compound 206
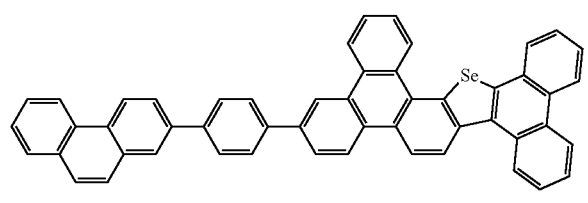
Compound 207
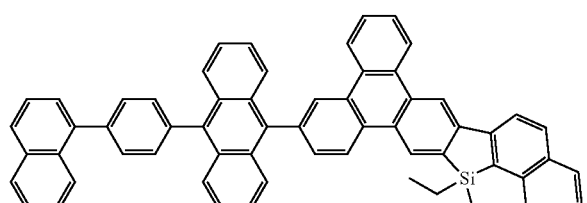

-continued
Compound 208
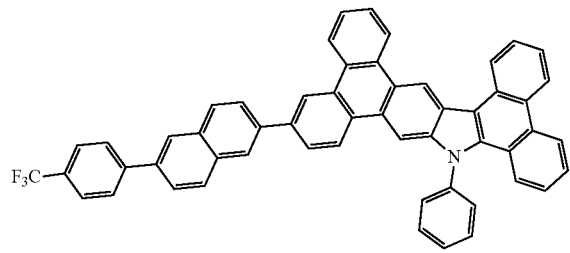
Compound 209
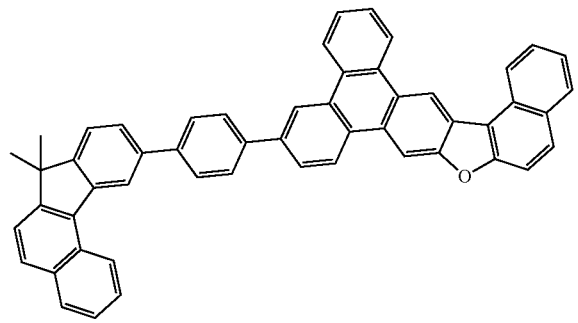
Compound 210
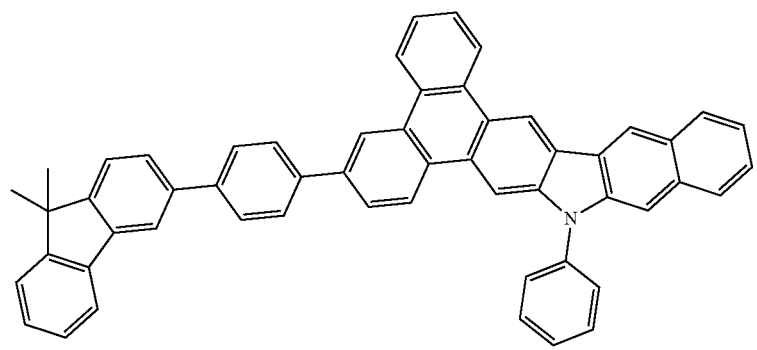
Compound 211
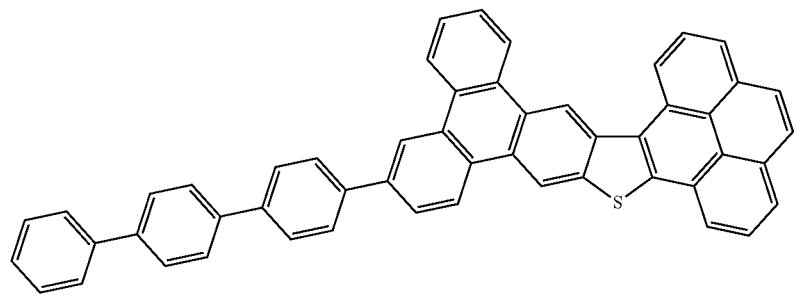
Compound 212
Compound 213
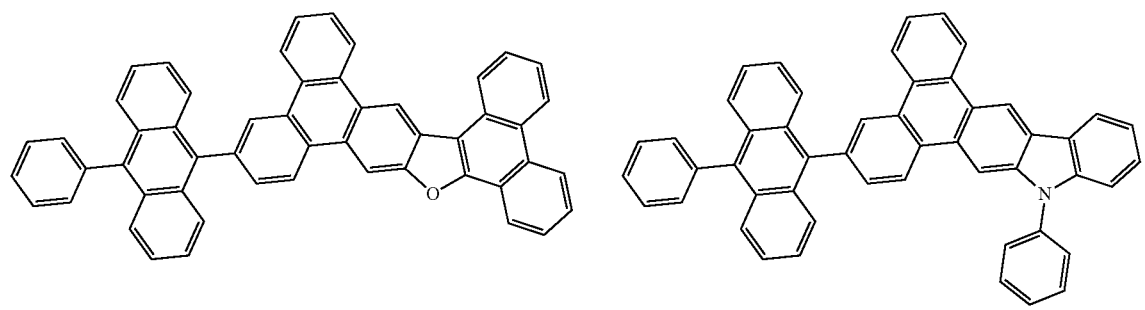
Compound 214
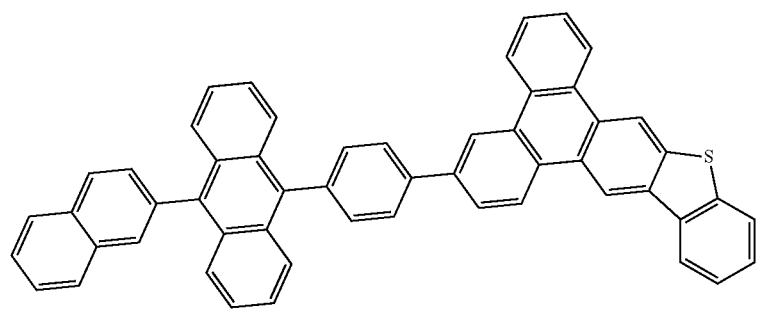

-continued
Compound 215
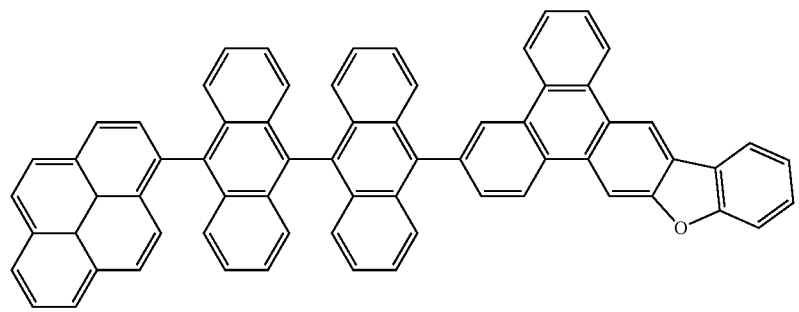
Compound 216
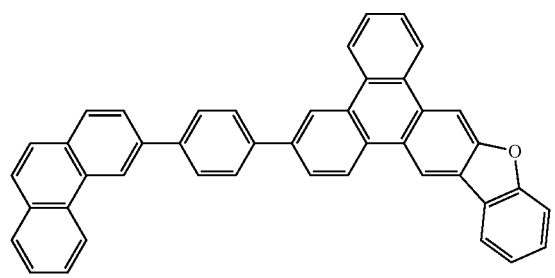
Compound 217
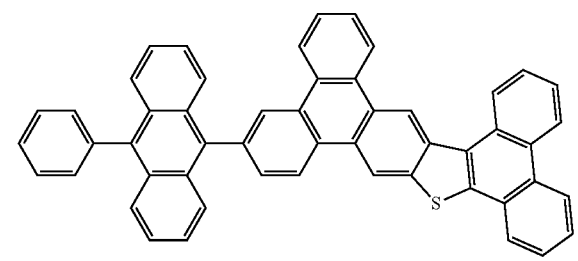
Compound 218
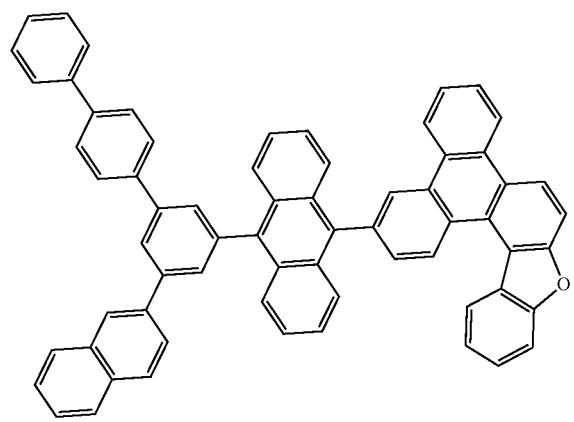
Compound 219
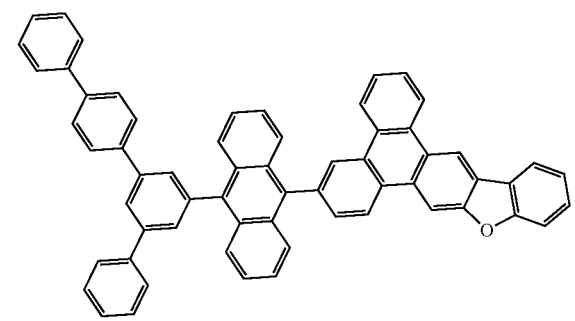
Compound 220
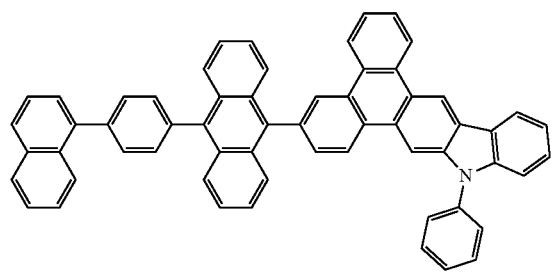
Compound 221
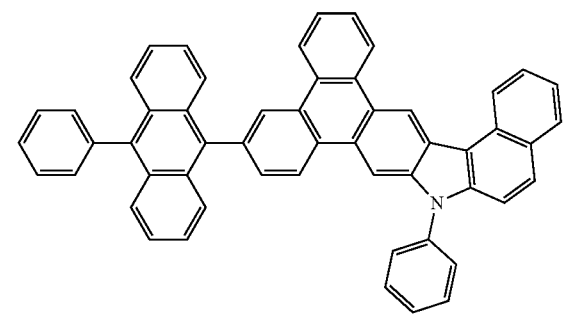

-continued
Compound 222
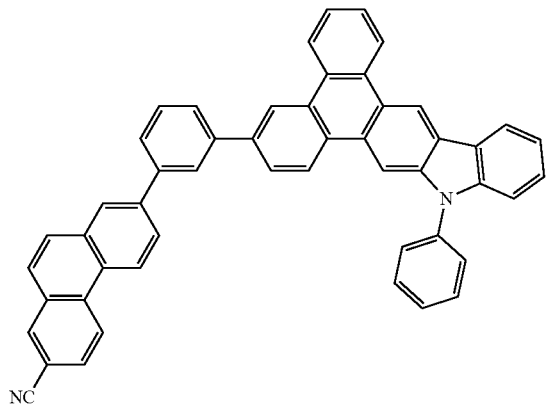
Compound 223
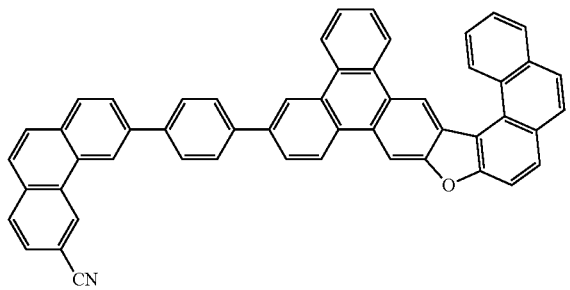
Compound 224
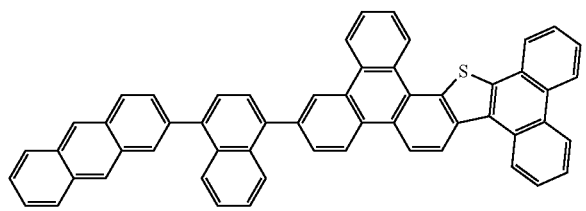
Compound 225
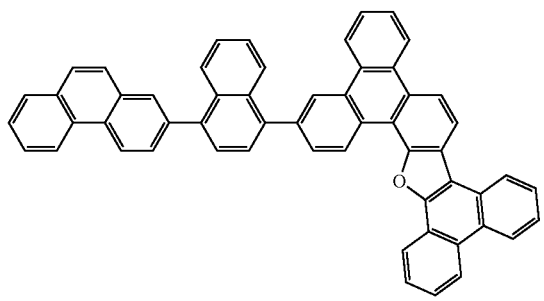
Compound 226
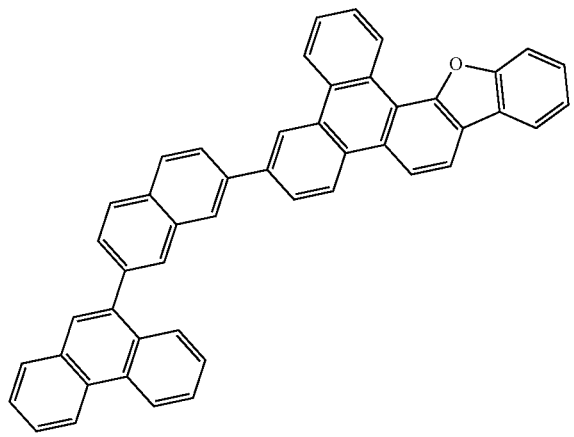
Compound 227
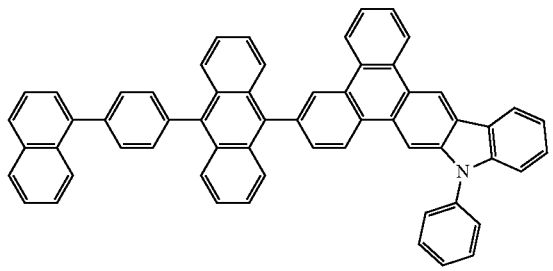
Compound 228
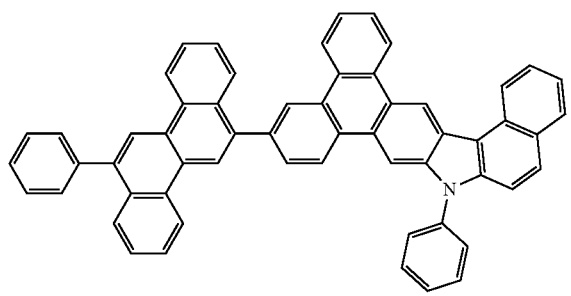
Compound 229
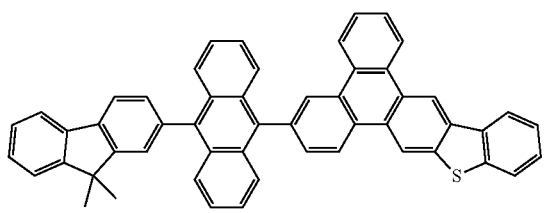

-continued
Compound 230
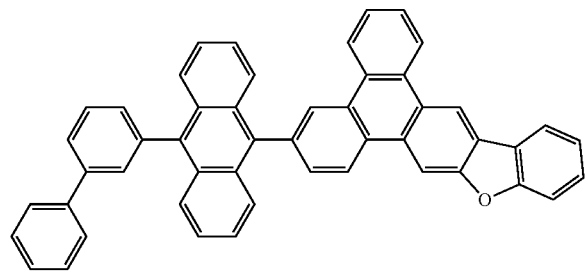
Compound 231
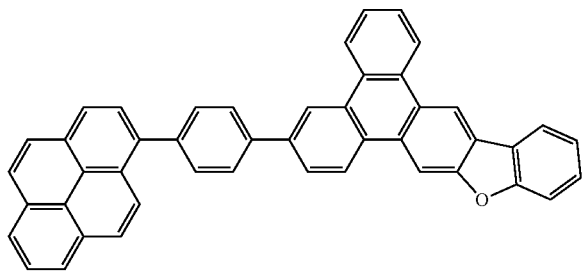
Compound 232
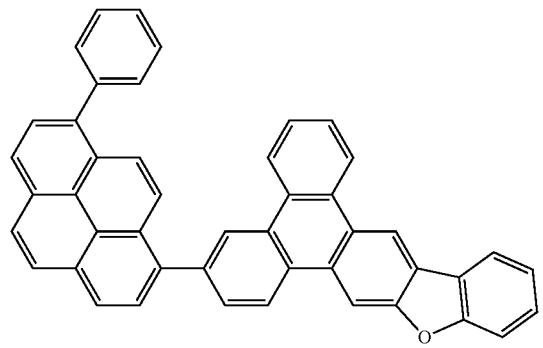
Compound 233
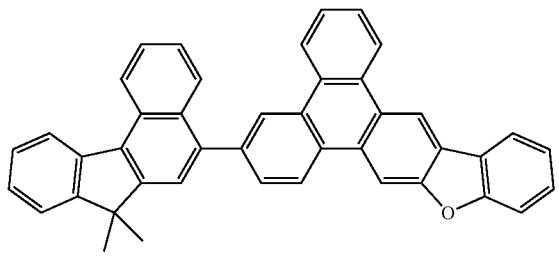
Compound 234
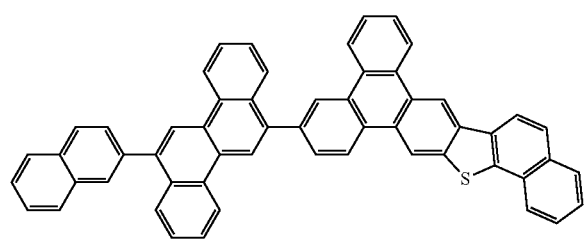
Compound 235
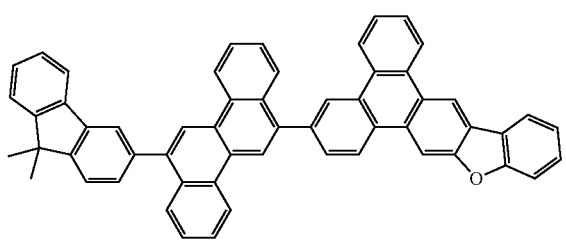
Compound 236
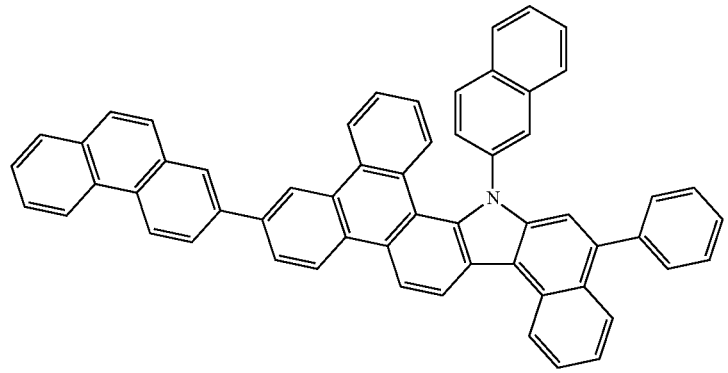
Compound 237
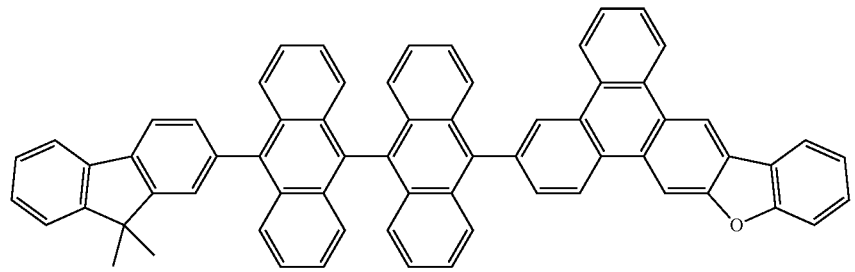

-continued
Compound 238
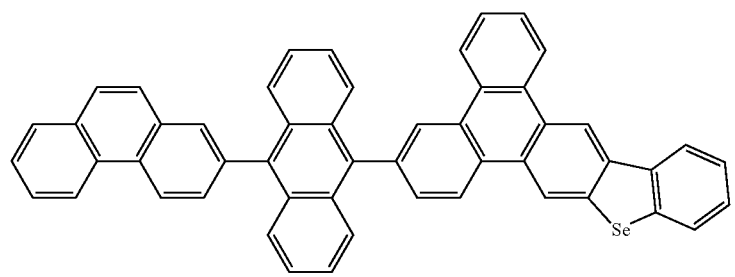
Compound 239
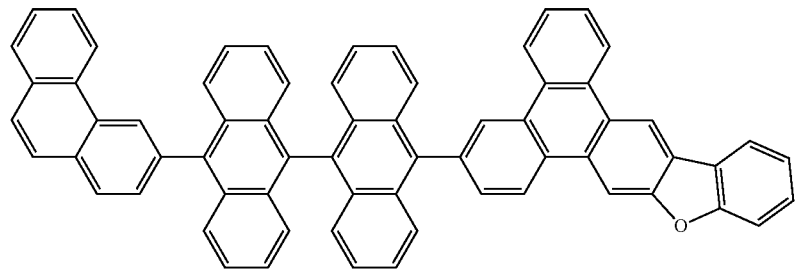
Compound 240
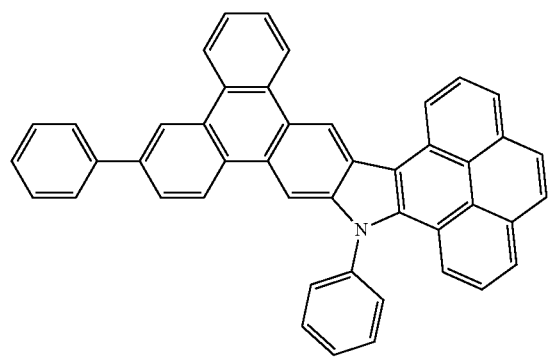
Compound 241
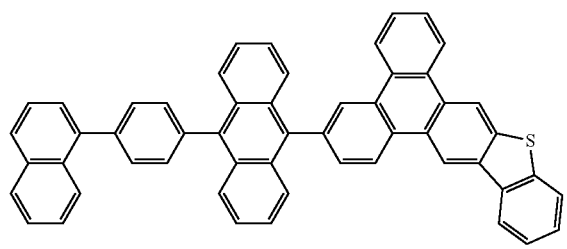
Compound 242
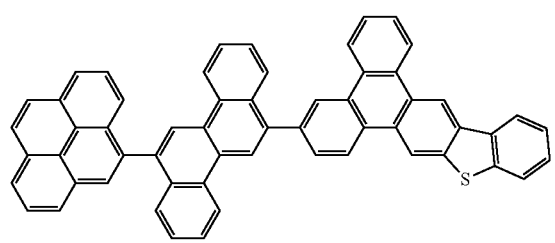
Compound 243
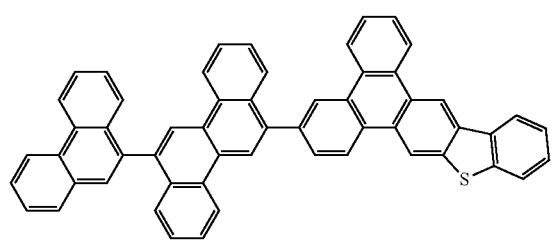
Compound 244
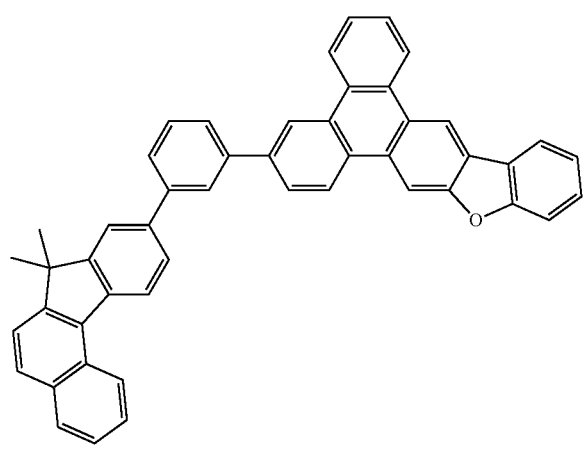
Compound 245
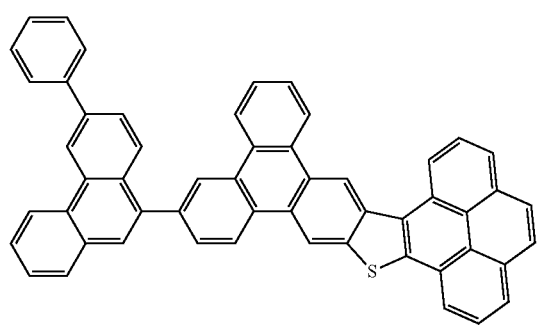

Compound 246
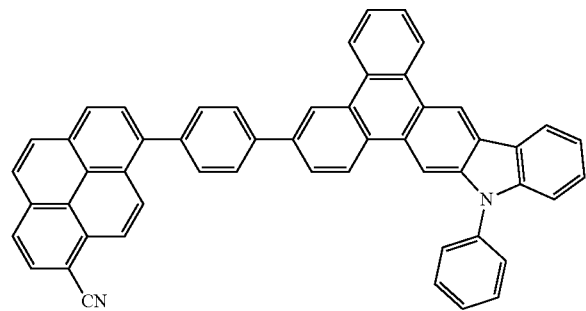
Compound 247
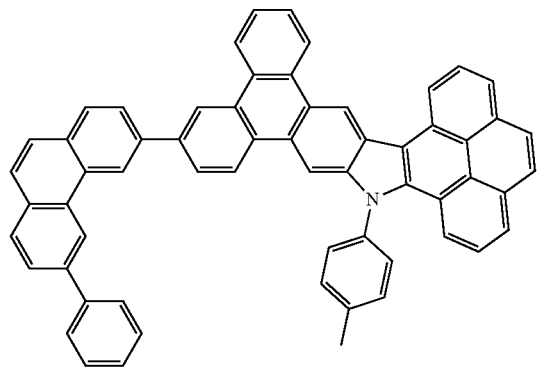
Compound 248
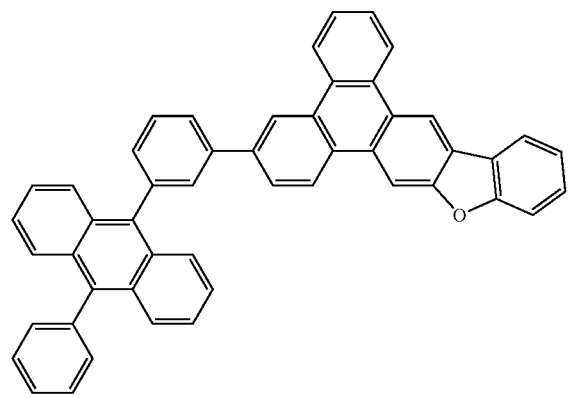
Compound 249
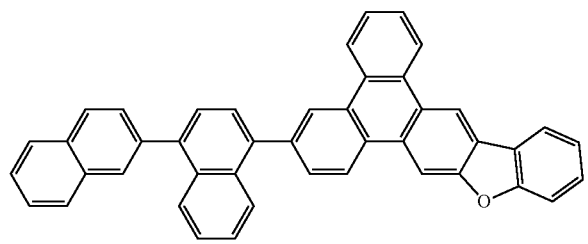
Compound 250
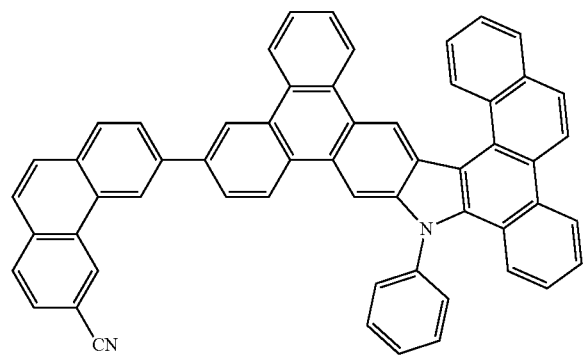
Compound 251
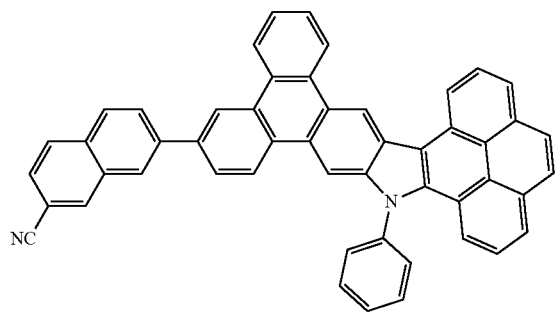
Compound 252
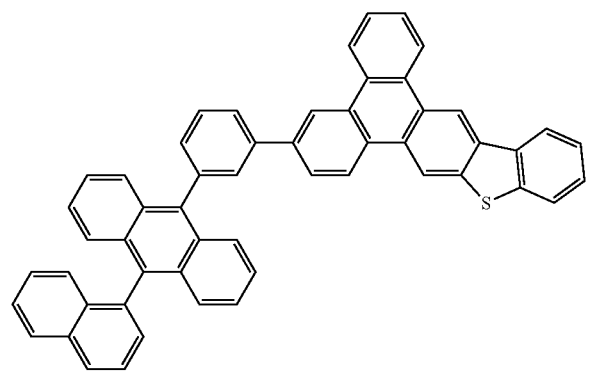
Compound 253
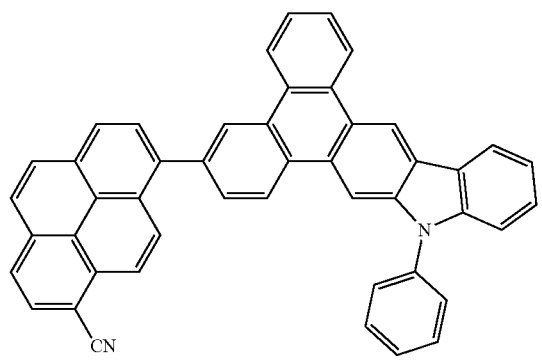

Compound 254
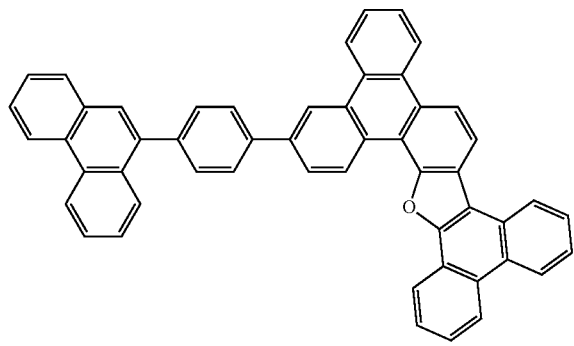
Compound 255
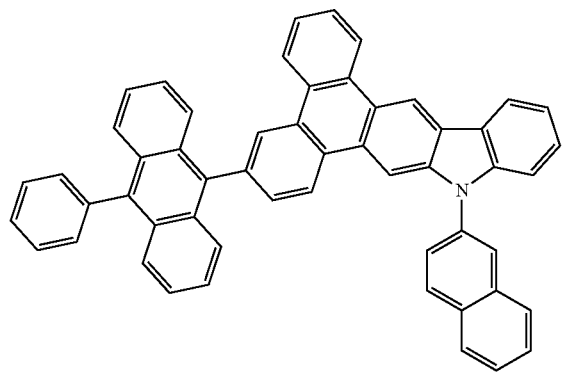
Compound 256
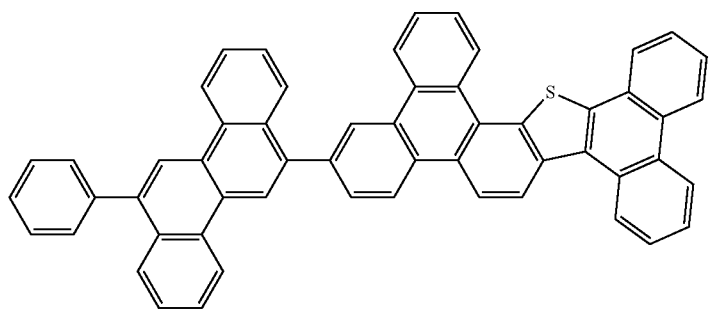
Compound 257
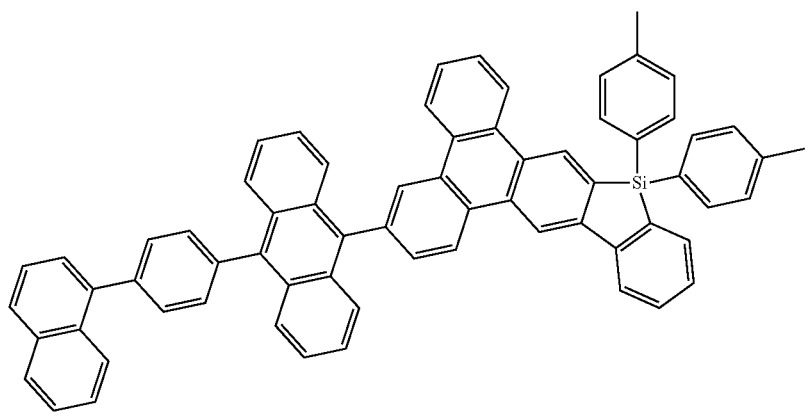
Compound 258
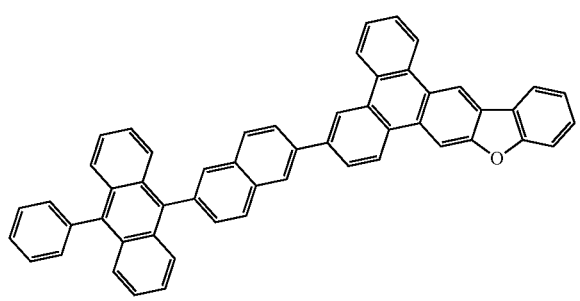
Compound 259
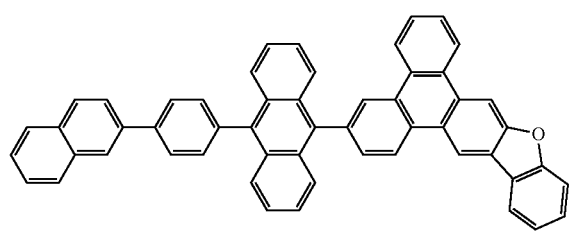

-continued
Compound 260
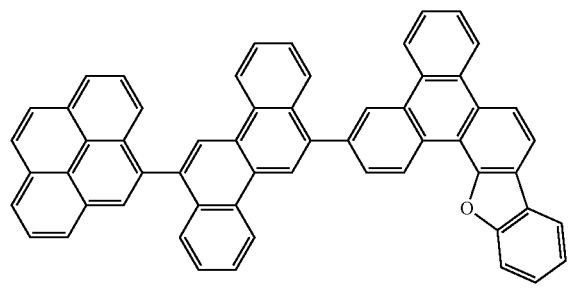
Compound 261
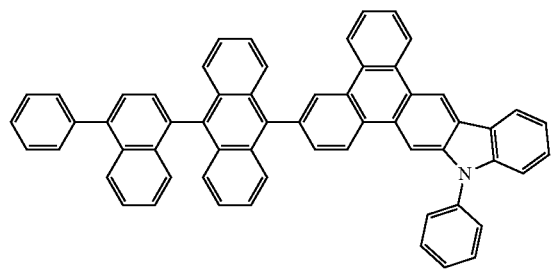
Compound 262
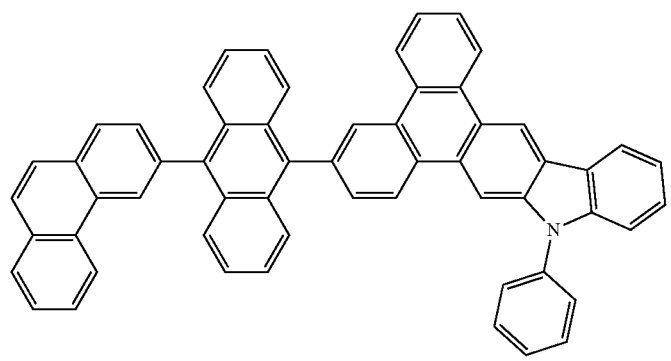
Compound 263
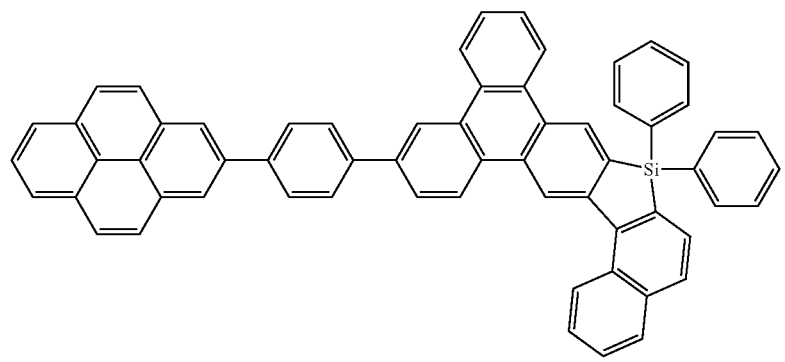
Compound 264
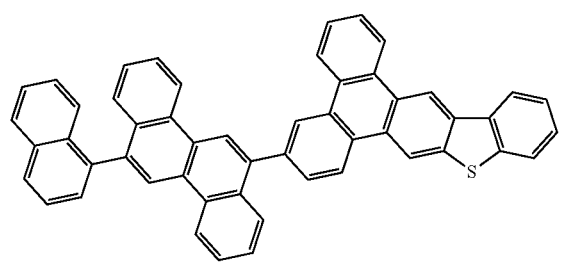
Compound 265
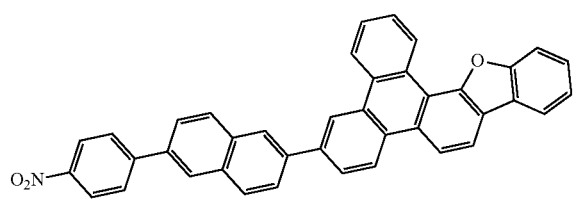

-continued
Compound 266
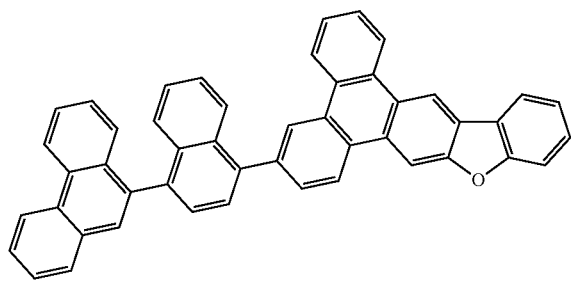
Compound 267
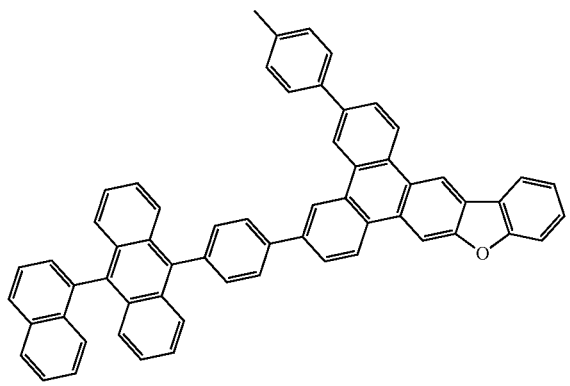
Compound 268
Compound 269
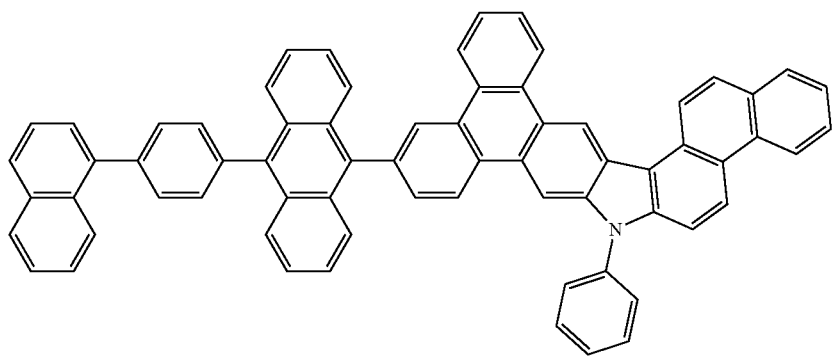
Compound 270
Compound 271
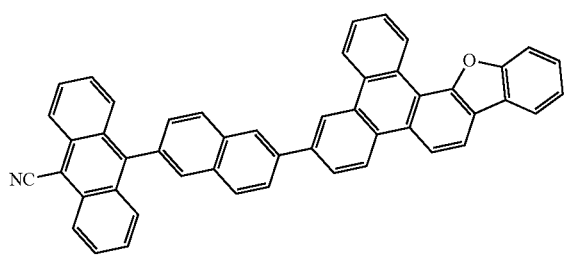
Compound 272
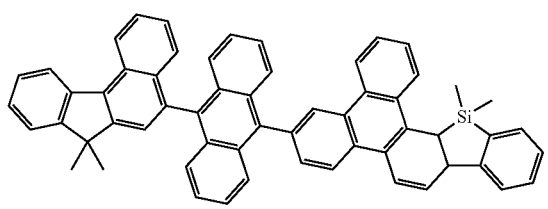
Compound 273
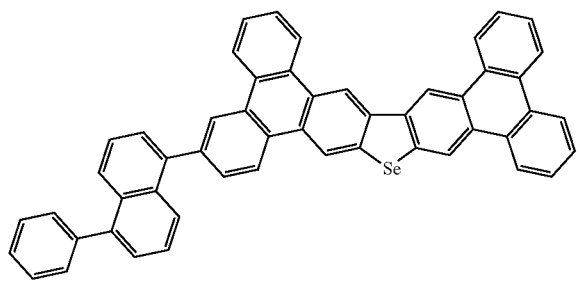
Compound 274
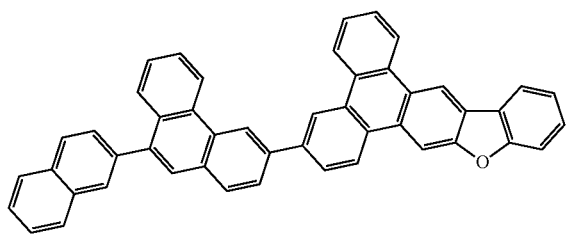
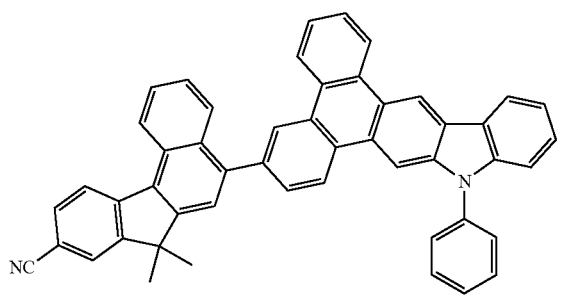
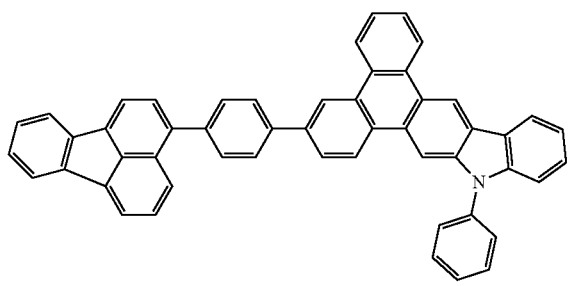

-continued
Compound Compound 275
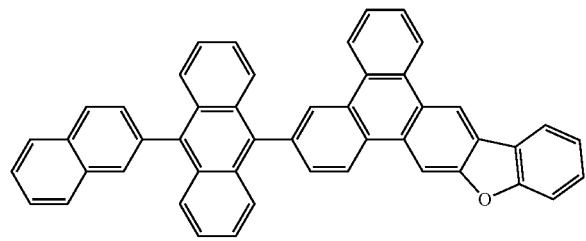
Compound Compound 276
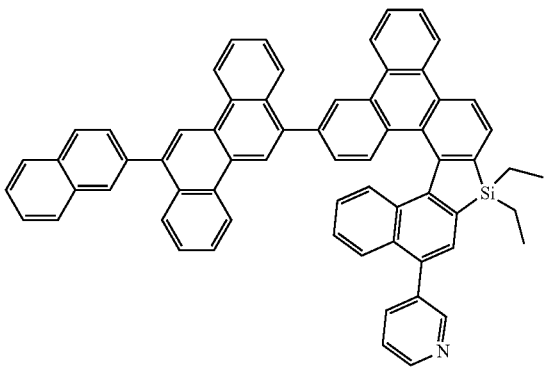
Compound 277
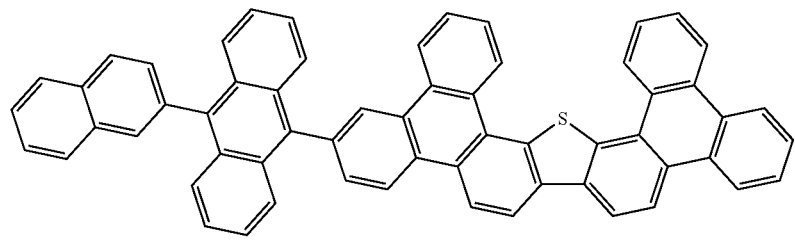
Compound Compound 278
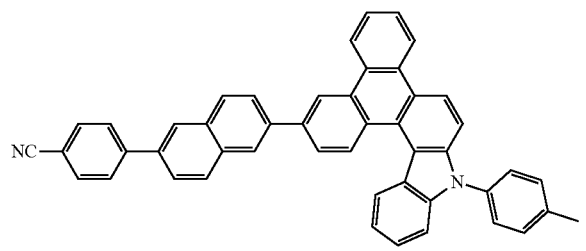
Compound Compound 279
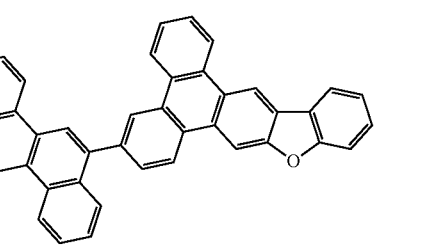
Compound 280
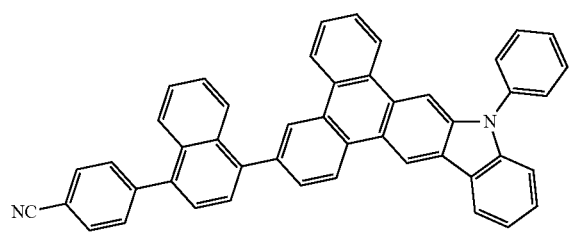
Compound 281
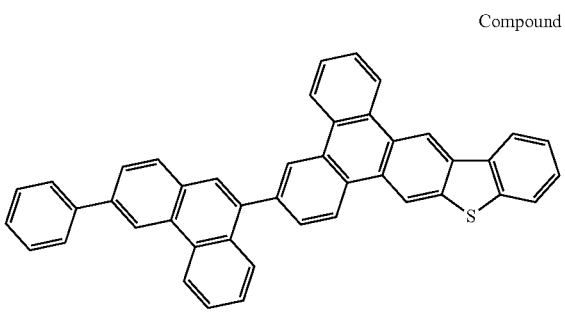
Compound 282
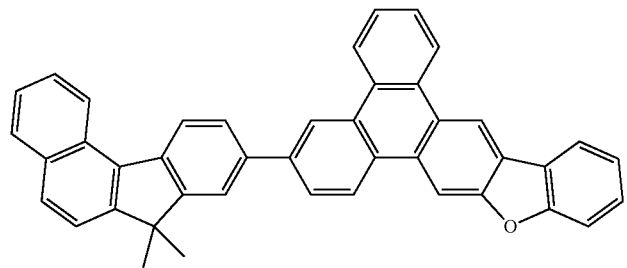

-continued
Compound 283
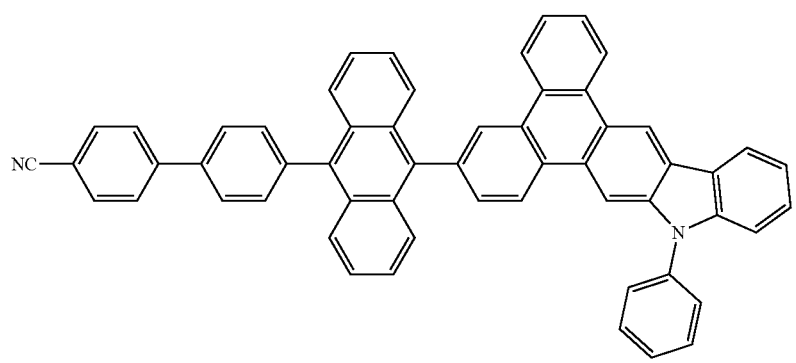
Compound 284
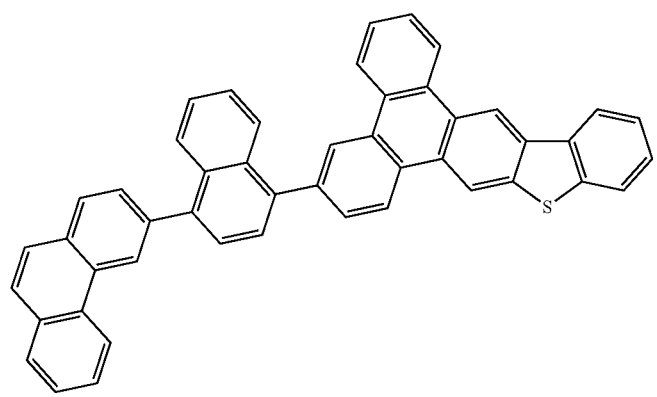
Compound 285
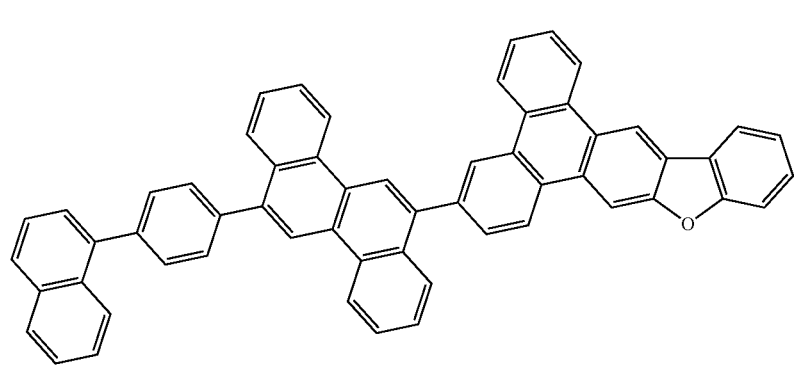
Compound 286
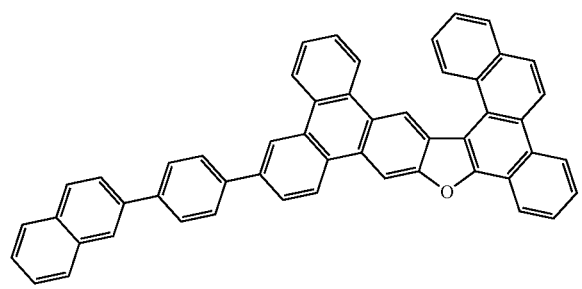
Compound 287
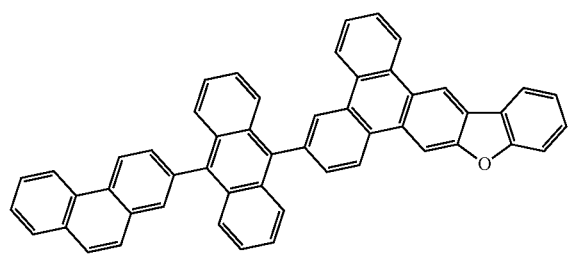

-continued
Compound 288
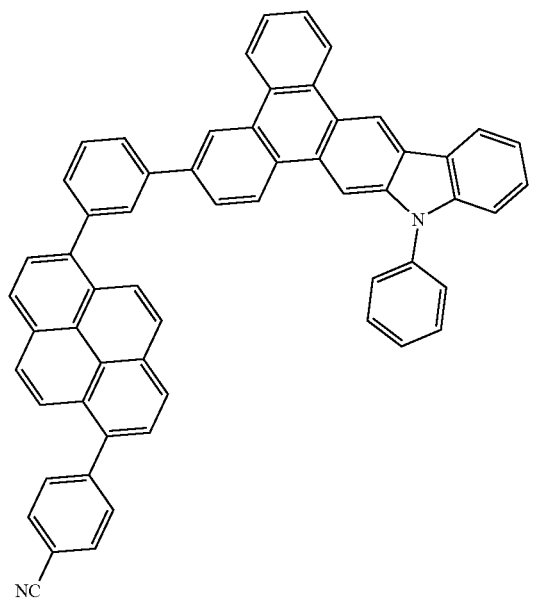
Compound 289
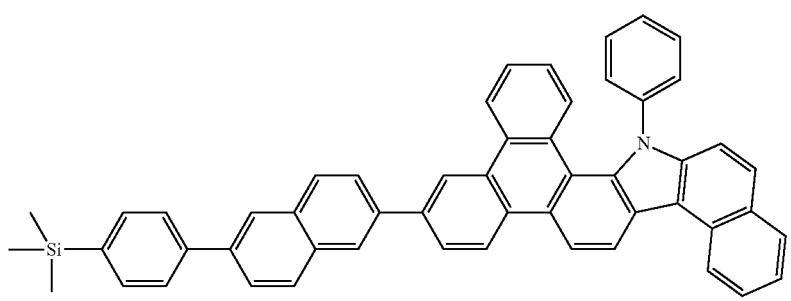
Compound 290
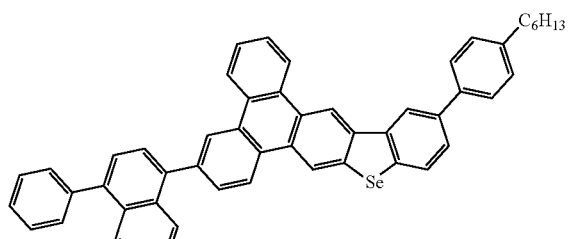
Compound 291
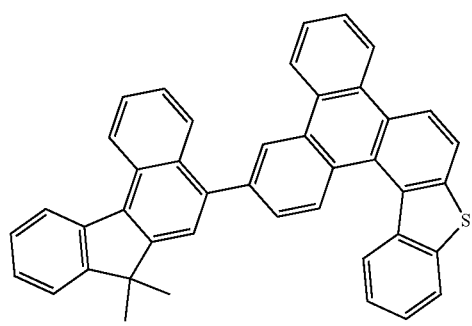
Compound 292
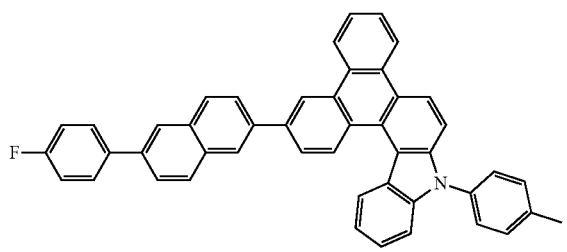
Compound 293
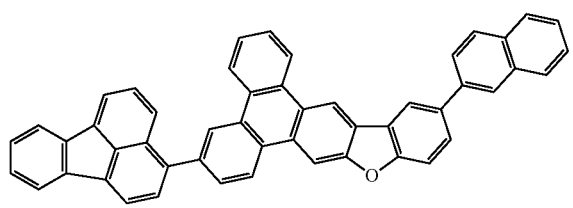

Compound 294
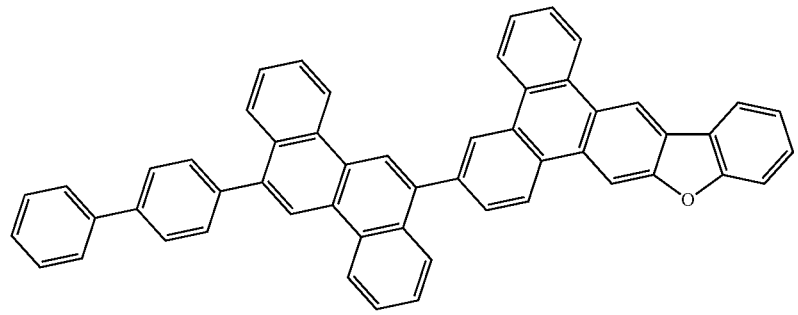
Compound 295
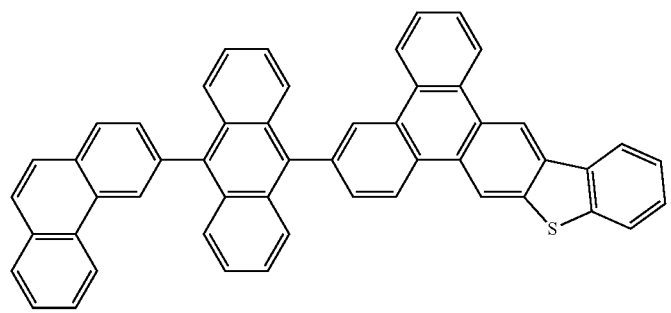
Compound 296
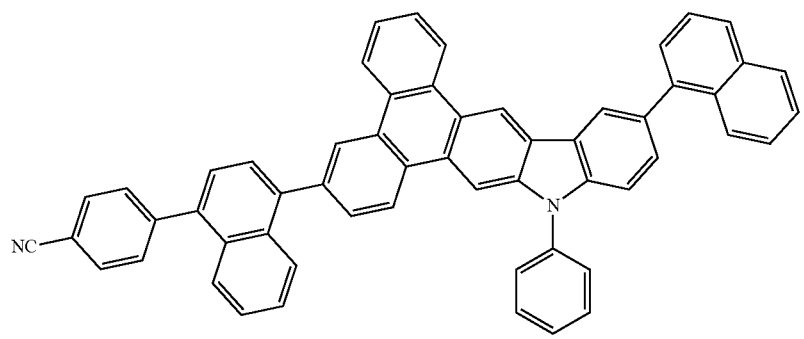
Compound 297
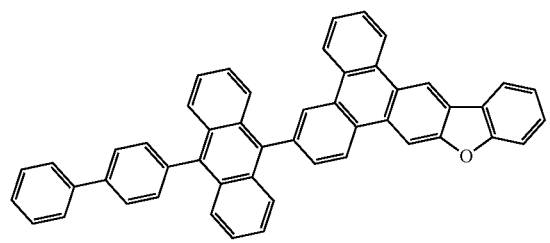
Compound 298
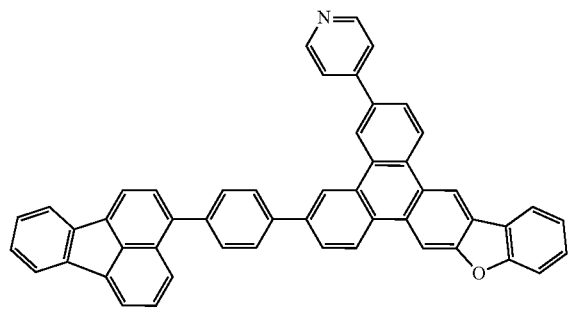

Compound Compound 299

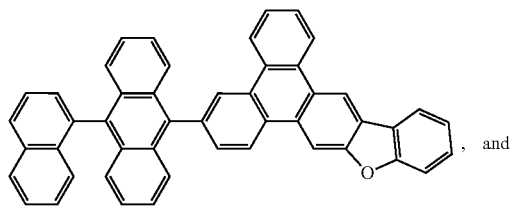

, and

Compound Compound 300

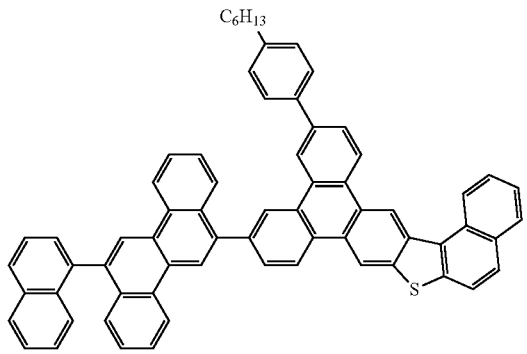

3. An organic electroluminescence device comprising an anode, a cathode and one or more organic layers between the anode and the cathode, wherein at least one of the organic layers comprises an organic compound having the following formula (1):

formula (1)

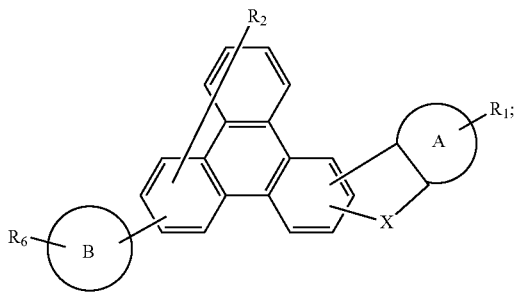

wherein X represents a divalent bridge selected from the group consisting of O, S, Se, $NR_3$ and $SiR_4R_5$;

wherein $R_6$ represents no substitution, mono substitution or di substitutions, and each of the substitutions is selected from the group consisting of halogen, trifluoromethyl, cyano, nitro, silyl, and combinations thereof;

wherein $R_2$ represents mono to the maximum allowable substitution, or no substitution;

wherein ring A represents a monocyclic aromatic hydrocarbyl or a polycyclic aromatic hydrocarbyl having 2, 3 or 4 fused rings;

wherein ring B represents an aromatic linker selected from the group consisting of a monocyclic aromatic hydrocarbyl, a polycyclic aromatic hydrocarbyl having 2, 3, 4 or 5 fused rings, and combinations thereof;

wherein each of $R_1$ to $R_5$ is hydrogen or a substituent selected from the group consisting of alkyl, aryl, aralkyl, heteroaryl, and combinations thereof; and wherein the organic layers comprise an emissive layer having a dopant, and wherein the organic compound is comprised as the dopant.

4. The organic electroluminescence device of claim 3, wherein the organic electroluminescence device is a lighting panel or a backlight panel.

* * * * *